US012441684B2

(12) United States Patent
Ham et al.

(10) Patent No.: US 12,441,684 B2
(45) Date of Patent: Oct. 14, 2025

(54) ORGANIC COMPOUND FOR CAPPING LAYER AND ORGANIC LIGHT EMITTING DIODE COMPRISING THE SAME

(71) Applicant: Dongjin Semichem Co., Ltd., Incheon (KR)

(72) Inventors: Ho Wan Ham, Hwaseong-si (KR); Hyun Cheol An, Hwaseong-si (KR); Hee Joo Kim, Hwaseong-si (KR); Dong Jun Kim, Hwaseong-si (KR); Jeong Woo Han, Hwaseong-si (KR); Ja Eun Ann, Hwaseong-si (KR); Dong Yuel Kwon, Hwaseong-si (KR); Sung Kyu Lee, Hwaseong-si (KR); Tae Min Kim, Hwaseong-si (KR)

(73) Assignee: Dongjin Semichem Co., Ltd., Incheon (KR)

( * ) Notice: Subject to any disclaimer, the term of this patent is extended or adjusted under 35 U.S.C. 154(b) by 937 days.

(21) Appl. No.: 17/385,218

(22) Filed: Jul. 26, 2021

(65) Prior Publication Data

US 2022/0127277 A1 Apr. 28, 2022

(30) Foreign Application Priority Data

Oct. 28, 2020 (KR) ........................ 10-2020-0141337

(51) Int. Cl.
*C07D 493/00* (2006.01)
*C07D 209/86* (2006.01)
(Continued)

(52) U.S. Cl.
CPC ......... *C07D 209/86* (2013.01); *C07D 493/00* (2013.01); *C07D 495/00* (2013.01);
(Continued)

(58) Field of Classification Search
None
See application file for complete search history.

(56) References Cited

U.S. PATENT DOCUMENTS

2012/0138918 A1* 6/2012 Naraoka ................ H05B 33/14
257/E51.026

FOREIGN PATENT DOCUMENTS

| | | | |
|---|---|---|---|
| JP | 2001354668 A | * | 12/2001 |
| KR | 10-2017-0031614 | * | 3/2017 |
| WO | WO-2011/043083 A1 | * | 4/2011 |

OTHER PUBLICATIONS

Machine English translation of Fujishita et al. (JP 2001-354668 A). Mar. 27, 2024.*

(Continued)

*Primary Examiner* — Jay Yang
(74) *Attorney, Agent, or Firm* — United One Law Group LLC; Kongsik Kim; Jhongwoo Peck

(57) ABSTRACT

As a compound for a capping layer for an organic light emitting device, disclosed is a capping layer compound represented by Formula 1 below. In addition, an organic light emitting device including the capping layer compound is also disclosed.

<Formula 1>

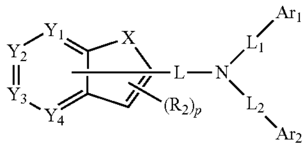

15 Claims, 2 Drawing Sheets

(51) Int. Cl.
*C07D 495/00* (2006.01)
*H01L 51/00* (2006.01)
*H10K 50/858* (2023.01)
*H10K 85/60* (2023.01)
*H10K 50/80* (2023.01)
*H10K 71/00* (2023.01)
*H10K 101/00* (2023.01)

(52) U.S. Cl.
CPC ......... *H10K 50/858* (2023.02); *H10K 85/622* (2023.02); *H10K 85/626* (2023.02); *H10K 85/636* (2023.02); *H10K 85/6572* (2023.02); *H10K 85/6574* (2023.02); *H10K 50/80* (2023.02); *H10K 71/00* (2023.02); *H10K 2101/00* (2023.02)

(56) References Cited

OTHER PUBLICATIONS

Machine English translation of Ham et al. (KR-10-2017-0031614). Jan. 9, 2025.*

* cited by examiner

ORGANIC COMPOUND FOR CAPPING LAYER AND ORGANIC LIGHT EMITTING DIODE COMPRISING THE SAME

CROSS-REFERENCE TO RELATED APPLICATION

This application claims priority to Korean Application No. KR 10-2020-0141337 filed on Oct. 28, 2020, which application is incorporated herein by reference in its entirety.

BACKGROUND

1. Field of the Invention

The present invention relates to a novel organic compound for a capping layer and an organic light emitting device including the same.

2. Description of the Related Art

Materials used for organic layers in an organic light emitting device can be classified into light emitting materials, hole injection materials, hole transport materials, electron transport materials, electron injection materials, and the like, according to the functions thereof.

In addition, the light emitting materials can be classified into a fluorescent material derived from a singlet excited state of an electron and a phosphorescent material derived from a triplet excited state of an electron according to light emitting mechanisms and also classified into blue, green, and red light emitting materials according to the emission colors.

A typical organic light emitting device may have a structure in which an anode is disposed on a substrate, and a hole transport layer, a light emitting layer, an electron transport layer, and a cathode are sequentially stacked on the anode. Here, the hole transport layer, the light emitting layer, and the electron transport layer are organic thin films made of organic compounds.

The principle for driving such an organic light emitting diode having the above-described structure will be described below.

When a voltage is applied between the anode and the cathode, holes injected from the anode move to the emission layer through the hole transport layer, and electrons injected from the cathode move to the emission layer through the electron transport layer. The holes and electrons recombine in the emission layer to generate excitons.

Light is generated as the excitons change from an excited state to a ground state. Regarding to the efficiency of the organic light emitting device, internal luminous efficiency and external luminous efficiency are considered. The internal luminous efficiency is related to how efficiently excitons are generated and photoconverted in organic material layers, such as the hole transport layer, the light emitting layer, and the electron transport layer, interposed between the first and second electrodes. It is known that the internal luminous efficiency is 25% for the fluorescence 100% for the phosphorescence.

On the other hand, the external luminous efficiency refers to how efficiently the light generated in the organic material layers exits the organic light emitting device, and it is known that the level of the external luminous efficiency is about 20% of level of the internal luminous efficiency. As a method of increasing the light extraction from the organic lighting emitting device, various organic compounds having a refractive index of 1.7 or higher have been used as an application for a capping layer to prevent the total reflection and loss of light going out to the outside. Thus, to increase the external luminous efficiency of the organic light emitting device, efforts have been made to develop organic compounds having high refractive index and thin film stability.

DOCUMENT OF RELATED ART

Patent Document (Patent Document 1) Korean Patent Application Publication No. 10-2004-0098238

SUMMARY

An objective of the present invention is to provide a capping layer compound a having high refractive index and excellent thin film stability and an organic light emitting device including the same capping layer compound, the compound having a structure in which a fused ring formed by two or more rings including a 5-membered cyclic ring and a 6-membered cyclic ring fused to each other with or without a heteroatom of N, O, S, Se, or Te is directly linked to or indirectly linked to a nitrogen atom of one arylamine via a linker.

Another objective of the present invention is to provide a capping layer compound and an organic light emitting device including a structure in which the fused ring of the 5-membered cyclic ring and the 6-membered cyclic ring is linked to the nitrogen atom of the arylamine, in which the 5-membered cyclic ring is a heterocyclic 5-membered cyclic ring containing 0, S, Se, or Te or the 6-membered cyclic ring is a heterocyclic 6-membered cyclic ring containing N, the compound having a large band gap not to be able to absorb a visible light region and high refractive index and having an increased absorption wavelength range for the visible light region, thereby enabling an organic light emitting device having high efficiency and long lifespan.

A further objective of the present invention is to provide a capping layer compound and an organic light emitting device including the same, the compound minimizing the bulky characteristic of an end portion of the arylamine or an end portion of the fused ring to improve an intermolecular reaction characteristic, thereby improving both the refractive index and stability against external air and moisture. The compound also has a high glass transition temperature (Tg) and a high deposition temperature (Td), thereby preventing recrystallization of molecules and enabling a stable thin film that is durable against heat generated during an operation of an organic light emitting device so that organic material layer organic light emitting device has increased efficiency and improved lifespan.

The above objectives and other objectives will be described in detail below.

As a means for achieving the objectives, the present invention provides a capping layer compound represented by Formula 1 shown below as a compound for a capping layer for an organic light emitting device.

<Formula 1>

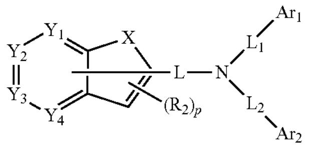

In Formula 1,

X is O, S, Se, Te, or CRR';

R and R' are each independently hydrogen, deuterium, halogen, a nitro group, a nitrile group, a substituted or unsubstituted C1-C30 alkyl group, a substituted or unsubstituted C2-C30 alkenyl group, a substituted or unsubstituted C1-C30 alkoxy group, a substituted or unsubstituted C1-C30 sulfide, a substituted or unsubstituted C6-C50 aryl group, or a substituted or unsubstituted C2-C50 heteroaryl group, in which R and R' that are adjacent to each other may or may not form a ring by combining with each other, $Y_1$ to $Y_4$ are each independently C, $CR_1$, or N, $R_1$s are each independently hydrogen, deuterium, halogen, a nitro group, a nitrile group, a substituted or unsubstituted C1-C30 alkyl group, a substituted or unsubstituted C2-C30 alkenyl group, a substituted or unsubstituted C1-C30 alkoxy group, a substituted or unsubstituted C1-C30 sulfide group, or a substituted or unsubstituted C6-C50 aryl group, in which the $R_1$'s adjacent to each other may or may not form a ring by combining with each other, $Ar_1$ and $Ar_2$ are each independently a substituted or unsubstituted C6-C50 aryl group, or a substituted or unsubstituted C2-C50 heteroaryl group, $R_2$s are each independently hydrogen, deuterium, halogen, a nitro group, a nitrile group, a substituted or unsubstituted C1-C30 alkyl group, a substituted or unsubstituted C2-C30 alkenyl group, a substituted or unsubstituted C1-C30 alkoxy group, a substituted or unsubstituted C1-C30 sulfide group, a substituted or unsubstituted C6-C50 aryl group, or a substituted or unsubstituted heteroaryl group, L, $L_1$, and $L_2$ are each independently a directly-linked, substituted or unsubstituted C6-C50 arylene group, or a substituted or unsubstituted C2-C50 heteroarylene group, and p is an integer in a range of from 0 to 2.

In addition, the present invention provides an organic light emitting device including the capping layer containing the compound.

In addition, the organic light emitting device may further include first and second electrodes and an organic material layer disposed between the first and second electrodes, in which the capping layer is disposed on an outer surface of either one or both of the first and second electrodes.

The capping layer compound and the organic light emitting device according to the embodiments of the present invention feature that a fused ring in which two or more rings such as a 5-membered cyclic ring and a 6-membered cyclic ring are fused to each other with or without a heteroatom selected from among N, O, S, Se, or Te is directly linked to or indirectly linked to the nitrogen atom of one arylamine via a linker. Therefore, the capping layer compound has the advantages of high refractive index and excellent thin film stability.

According to the present invention, the compound has a structure in which the fused ring of the 5-membered cyclic ring and the 6-membered cyclic ring is linked to the nitrogen atom of the arylamine, in which the 5-membered cyclic ring is a heterocyclic 5-membered cyclic ring containing O, S, Se, or Te or the 6-membered cyclic ring is a heterocyclic 6-membered cyclic ring containing N. Therefore, the compound has a large band gap not to be able to absorb a visible light region and high refractive index and can absorb a broader range of UV rays, thereby enabling an organic light emitting device having high color purity, high efficiency, and long lifespan.

In addition, the present invention minimizes the bulky characteristic of the end portion of the arylamine or the end portion of the fused ring, thereby improving the intermolecular reaction characteristic, resulting in improvement in the refractive index and in stability against external air and moisture. In addition, since the compound of the present invention has a high glass transition temperature (Tg) and a high deposition temperature (Td), recrystallization of molecules is prevented so that a stable thin film resisting heat generated during operation of an organic light emitting device can be maintained. Therefore, external quantum efficiency and lifespan are improved.

The above objectives and other objectives will be described in detail below.

BRIEF DESCRIPTION OF THE DRAWINGS

The above and other objectives, features, and other advantages of the present invention will be more clearly understood from the following detailed description taken in conjunction with the accompanying drawings, in which.

DETAILED DESCRIPTION

Figure 1:
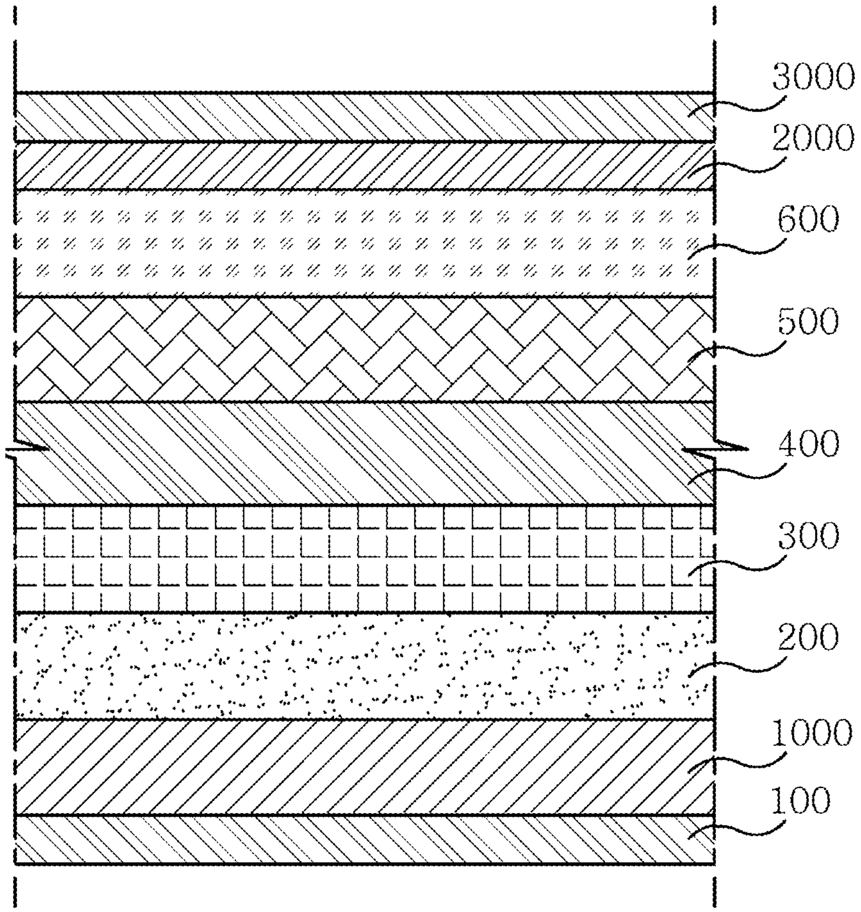
FIG. 1 is a cross-sectional view schematically illustrating the layered structure of an organic light emitting device.

Prior to a description of the present invention, it should be noted that the terms used in the present specification are used only to describe specific examples and are not intended to limit the scope of the present invention which will be defined only by the appended claims. Unless otherwise defined herein, all terms including technical and scientific terms used herein have the same meaning as commonly understood by those who are ordinarily skilled in the art to which this invention pertains.

Unless otherwise stated herein, it will be further understood that the terms "comprise", "comprises", and "comprising", when used in this specification, specify the presence of stated features, regions, integers, steps, operations, elements and/or components but do not preclude the presence or addition of one or more other features, regions, integers, steps, operations, elements, components and/or groups thereof.

Throughout this specification and claims, the term "aryl" refers to a functional group having a C5-50 aromatic hydrocarbon ring such as phenyl, benzyl, naphthyl, biphenyl, terphenyl, fluorene, phenanthrenyl, triphenylenyl, perylenyl, chrysenyl, fluoranthenyl, benzofluorenyl, benzotriphenylenyl, benzochrysenyl, anthracenyl, stilbenyl, or pyrenyl. The term "heteroaryl" refers to a C2-50 aromatic ring containing at least one heteroatom. For example, it includes a heterocyclic ring such as pyrrolyl, pyrazinyl, pyridinyl, indolyl, isoindolyl, furyl, benzofuranyl, isobenzofuranyl, dibenzofuranyl, benzothiophenyl, dibenzothiophenyl, quinolyl group, isoquinolyl, quinoc Salinyl, carbazolyl, phenanthridinyl, acridinyl, phenanthrolinyl, thienyl, and pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzofuran ring, thiazole Ring, thiadiazole ring, benzothiophene ring, triazole ring, imidazole ring, benzoimidazole ring, pyran ring, and dibenzofuran ring.

Throughout the present specification and claims, the term "substituted or unsubstituted" means that a portion is substituted or unsubstituted with at least one selected from the group consisting of deuterium, halogen, amino groups, cyano groups, nitrile groups, nitro groups, nitroso groups, sulfamoyl groups, isothiocyanate groups, thiocyanate groups, carboxyl groups, C1-C30 alkyl groups, C1-C30 alkylsulfinyl groups, C1-C30 alkylsulfonyl groups, C1-C30 alkylsulfanyl groups, C1-C12 fluoroalkyl groups, C2-C30 alkenyl groups, C1-C30 alkoxy groups, C1-C12 N-alkylamino groups, C2-C20 N,N-dialkylamino groups, C1-C6 N-alkylsulfamoyl groups, C2-C12 N,N-dialkylsulfamoyl groups, C3-C30 silyl groups, C3-C20 cycloalkyl groups, C3-C20 heterocycloalkyl groups, C6-C50 aryl groups, C3-C50 heteroaryl groups, etc. In addition, the same symbols throughout the present specification may have the same meaning unless otherwise specified.

All or some embodiments described herein may be selectively combined and configured so that the embodiments may be modified in various ways unless the context clearly indicates otherwise.

Hereinafter, embodiments of the present invention and the effects thereof will be described in detail below.

Hereinafter, the present invention will be described in detail.

An organic light emitting device according to an embodiment of the present invention may be an organic light emitting device including a capping layer. Specifically, the organic light emitting device may include: an organic material layer interposed between a first electrode and a second electrode; and a capping layer disposed on an outer surface of either the first electrode or the second electrode and made of a capping layer compound.

Specific examples of the capping layer compound of the present invention include compounds represented Formula 1 shown below.

<Formula 1>

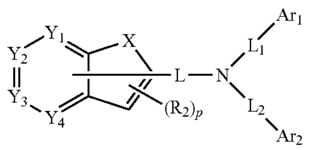

In Formula 1,

X is O, S, Se, Te, or CRR';

R and R' are each independently hydrogen, deuterium, halogen, a nitro group, a nitrile group, a substituted or unsubstituted C1-C30 alkyl group, a substituted or unsubstituted C2-C30 alkenyl group, a substituted or unsubstituted C1-C30 alkoxy group, a substituted or unsubstituted C1-C30 sulfide, a substituted or unsubstituted C6-C50 aryl group, or a substituted or unsubstituted C2-C50 heteroaryl group, in which R and R' that are adjacent to each other may or may not form a ring by combining with each other, $Y_1$ to $Y_4$ are each independently C, $CR_1$, or N, $R_1$s are each independently hydrogen, deuterium, halogen, a nitro group, a nitrile group, a substituted or unsubstituted C1-C30 alkyl group, a substituted or unsubstituted C2-C30 alkenyl group, a substituted or unsubstituted C1-C30 alkoxy group, a substituted or unsubstituted C1-C30 sulfide group, or a substituted or unsubstituted C6-C50 aryl group, in which the $R_1$'s adjacent to each other may or may not form a ring by combining with each other, $Ar_1$ and $Ar_2$ are each independently a substituted or unsubstituted C6-C50 aryl group, or a substituted or unsubstituted C2-C50 heteroaryl group, $R_2$s are each independently hydrogen, deuterium, halogen, a nitro group, a nitrile group, a substituted or unsubstituted C1-C30 alkyl group, a substituted or unsubstituted C2-C30 alkenyl group, a substituted or unsubstituted C1-C30 alkoxy group, a substituted or unsubstituted C1-C30 sulfide group, a substituted or unsubstituted C6-C50 aryl group, or a substituted or unsubstituted heteroaryl group, L, $L_1$, and $L_2$ are each independently a directly-linked, substituted or unsubstituted C6-C50 arylene group, or a substituted or unsubstituted C2-C50 heteroarylene group, and p is an integer in a range of from 0 to 2.

In addition, as specific examples of the capping layer compound of the present invention, Formula 1 refers to capping layer compounds represented by Formula 2 shown below.

<Formula 2>

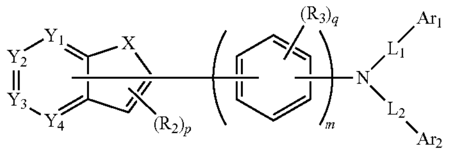

In Formula 2,

X, $Y_1$ to $Y_4$, $Ar_1$, $Ar_2$, $R_2$, $L_1$, $L_2$ and p are the same as defined in Formula 1 above, $R_3$ is defined in the same way as $R_2$ in Formula 1 (provided that the number of carbon atoms in $R_3$ satisfies the carbon number range defined for L), p is an integer in a range of from 0 to 4, and m is an integer in a range of from 1 to 5.

The capping layer compound represented by Formula 2 has a structure in which a fused ring including X formed by fusing a 5-membered cyclic ring and a 6-membered cyclic ring is linked to the nitrogen of an arylamine via a phenylene group, thereby minimizing the absorption of wavelengths in a blue region and improving the refractive index.

In addition, as specific examples of the capping layer compound of the present invention, Formula 1 refers to capping layer compounds represented by Formula 3 shown below.

<Formula 3>

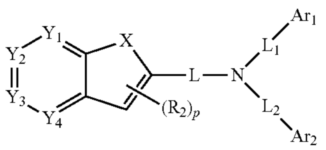

In Formula 3,

X, $Y_1$ to $Y_4$, $Ar_1$, $Ar_2$, $R_2$, L, $L_1$, and $L_2$ are the same as defined in Formula 1 above, and p is 0 or 1.

The capping layer compound represented by Formula 3 has a structure in which a fused ring including X formed by fusing a 5-membered cyclic ring and a 6-membered cyclic ring is linked to the nitrogen of an arylamine, and the nitrogen bonding position is linked to a carbon atom of the 5-membered cyclic ring. Specifically, the nitrogen bonding position is linked to the carbon atom that is closest to X. This structure further increases the refractive index.

Here, when X is O, S, Te, or Se, the position closest to X may mean Position 2 of the fused ring while when X is CRR', the position may mean Position 6.

In addition, as specific examples of the capping layer compound of the present invention, Formula 1 refers to capping layer compounds represented by Formula 4 shown below.

<Formula 4>

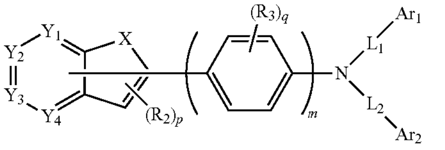

In Formula 4,

X, $Y_1$ to $Y_4$, $Ar_1$, $Ar_2$, $R_2$, $L_1$, $L_2$ and p are the same as defined in Formula 1 above, $R_3$ is defined in the same way as $R_2$ in Formula 1 (provided that the number of carbon atoms in $R_3$ satisfies the carbon number range defined for L), q is an integer in a range of from 0 to 4, and m is an integer in a range of from 1 to 5.

The capping layer compound represented by Formula 4 has a structure in which a fused ring including X formed by fusing a 5-membered cyclic ring and a 6-membered cyclic ring is linked to the nitrogen of an arylamine by a 1,4-phenylene group of a para bond. This structure increases a refractive index and an absorbable wavelength range in a visible light region, so that the compound has improved stability against external UV exposure.

In addition, as specific examples of the capping layer compound of the present invention, Formula 1 refers to capping layer compounds represented by Formula 5 shown below.

<Formula 5>

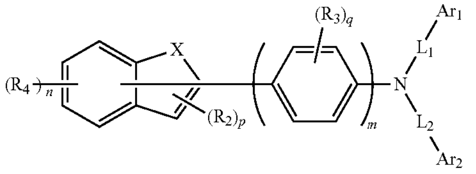

In Formula 5,

X, $Ar_1$, $Ar_2$, $R_2$, $L_1$, and $L_2$ are the same as defined in Formula 1 above, $R_3$s are each independently defined in the same way as $R_2$ in Formula 1 (provided that the number of carbon atoms in $R_3$ satisfies the carbon number range defined for L), $R_4$s are each independently defined in the same way as $R_1$ in Formula 1 above, p is 0 or 1, q is an integer in a range of from 0 to 4, m is an integer in a range of from 1 to 5, and n is an integer in a range of from 0 to 4.

In the capping layer compound represented by Formula 5, $Y_1$ to $Y_4$ of the 6-membered cyclic ring are all carbon, the nitrogen of the arylamine is linked to the fused ring including X formed by fusing the 5-membered cyclic ring and the 6-membered cyclic ring, the nitrogen is linked to a carbon atom of the 5-membered cyclic ring, and the 5-membered cyclic ring and the nitrogen are linked by a 1,4-phenylene group of a para bond. This structure minimizes the twist angle between the core (fused ring) and the linker. Therefore, an excellent molecular arrangement can be achieved, and the refractive index can be improved.

In addition, as specific examples of the capping layer compound of the present invention, Formula 1 refers to capping layer compounds represented by Formula 6 shown below.

<Formula 6>

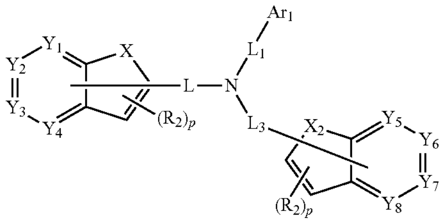

In Formula 6,

X, $Y_1$ to $Y_4$, $Ar_1$, $R_2$, L, $L_1$, and p are the same as defined in Formula 1 above, $L_3$ is defined in the same way as L, $L_1$ and $L_2$ in Formula 1 above, $X_2$ is defined in the same way as X in Formula 1, and $Y_5$ to $Y_8$ are each independently defined in the same way as $Y_1$ to $Y_4$ in Formula 1 (provided that the number of carbon atoms in $Y_5$ to $Y_8$ satisfies the carbon number range defined for $Ar_2$).

The capping layer compound represented by Formula 6 has a structure in which two fused rings each formed by fusing a 5-membered cyclic ring and a 6-membered cyclic ring are linked to the nitrogen atoms of an arylamine, respectively. Since the compound has two or more fused rings, the compound has a high refractive index and minimize the adsorption of a blue wavelength range.

In addition, as specific examples of the capping layer compound of the present invention, Formula 1 refers to capping layer compounds represented by Formula 7 shown below.

<Formula 7>

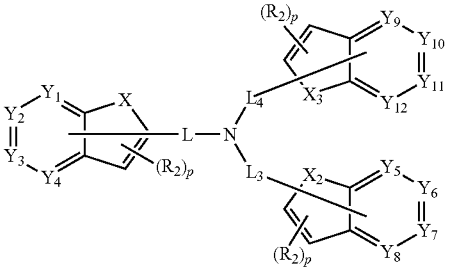

In Formula 7,

X, $Y_1$ to $Y_4$, $R_2$, L, and p are defined each independently in the same way as in Formula 1 above, $L_3$ and $L_3$ are each independently defined in the same way as $L_1$ and $L_2$ in Formula 1 above, $X_2$ and $X_3$ are each independently defined in the same way as X in Formula 1 above, and $Y_5$ to $Y_{12}$ are each independently defined in the same way as $Y_1$ to $Y_4$ in Formula 1 (provided that the number of carbon atoms in $Y_5$ to $Y_{12}$ satisfies the carbon number range defined for $Ar_1$ or $Ar_2$).

The capping layer compound represented by Formula 7 has a structure in which three fused rings, each formed by fusing a 5-membered cyclic ring and a 6-membered cyclic ring are linked to the nitrogen atoms of an arylamine, respectively. This structure is effective in maximally increasing the refractive index and the absorption intensity for a ultraviolet (UV) region.

In Formulas 1 to 7, X, $X_2$, and $X_3$ may each independently be 0 or S, thereby minimizing the bond length of heteroatoms, thereby reducing bulky properties.

More specifically, when X is O, a high refractive index can be maintained and the deposition temperature can be lowered because the molecular weight is reduced. In addition, when X is S, the compound has a high refractive index and has the advantage of forming a stable thin film because the compound has a high deposition temperature.

In addition, in Formulas 1 to 7, $R_1$ and $R_2$ may be each independently selected from among hydrogen, deuterium, a methyl group, a methoxy group, a phenyl group, and combinations thereof. This minimizes the bulky properties of the ring structure adjacent to the amine, thereby effectively improving the refractive index. More specifically, $R_1$ and $R_2$ may be each independently selected from among hydrogen, a phenyl group, a biphenyl group, and combinations thereof.

In addition, in Formulas 1 to 7, all of L, $L_1$, $L_2$, $L_3$, and $L_4$, which are intermediate linkers, may not be direct bonds. That is, the fused ring including X, $X_2$, or $X_3$, $Ar_1$, and $Ar_2$ may not be directly linked but may be linked by a nitrogen atom. In this case, it is possible to improve the refractive index and the absorption intensity.

In Formulas 2, 4, and 5, m may be 1 or 2. That is, the fused ring including X and the nitrogen may be linked by a phenylene group or a biphenylene group. More specifically, the fused ring including X and the nitrogen may be linked by a 1,4-phenylene group or 1,4-biphenylene group having a para bond. In this case, the absorption for the visible light region can be minimized.

In addition, in Formulas 1 to 6, $Ar_1$ and $Ar_2$ may be each independently selected from among a phenyl group, a biphenyl group, a terphenyl group, a naphthyl group, a phenanthrenyl group, a triphenylenyl group, a benzofuran group, a benzothiophene group, and combinations thereof. More specifically, they may include a terphenyl group, a naphthyl group, a benzofuran group, or a benzothiophene group. In this case, the refractive index is increased and the deposition temperature is lowered. Therefore, the thermal stability of the compound can be effectively improved.

As such, the capping layer compound of the present invention minimizes the bulky characteristic of a substituent, thereby having a high refractive index. In addition, the ability to absorb UV rays is improved, and the refractive index is improved due to an improved intermolecular reaction characteristic in a thin film.

In the definitions of Formulas 1 to 4, when one element is expressed as "being substituted", a substituent to replace the element may be hydrogen. However, in the present invention, the substituent may not be limited thereto. Alternatively, any other one among the substituents mentioned above may be used.

The compounds described below are specific examples of the compounds according to the present invention. The examples described below are presented only to help understanding of the present invention, and the scope of the present invention is not limited thereto.

1

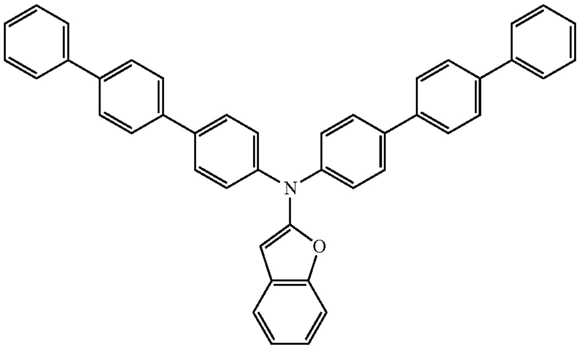

2

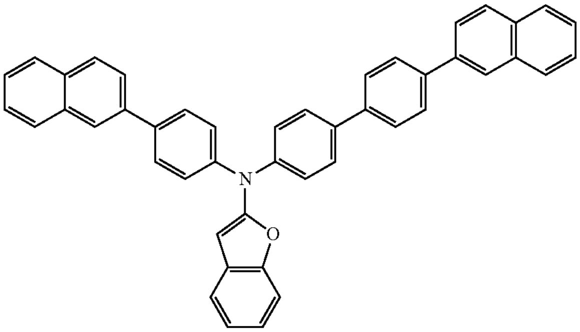

3

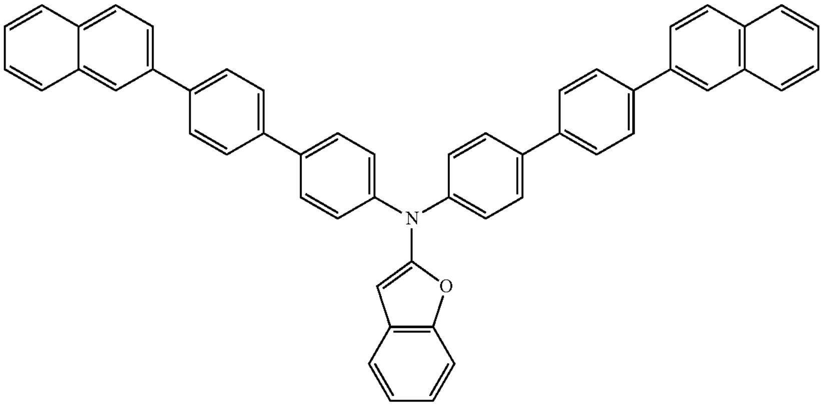

-continued
4
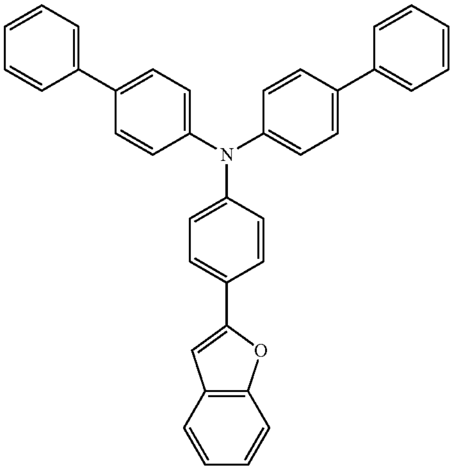
5
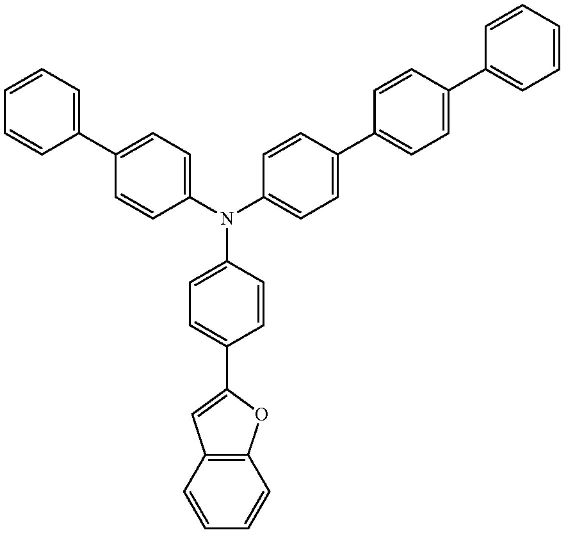
6
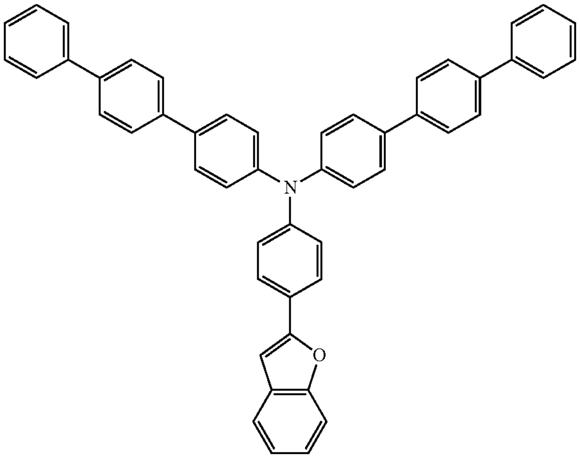
7
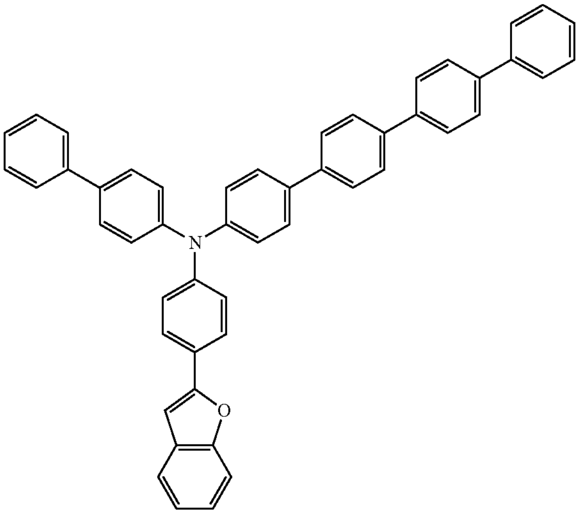
8
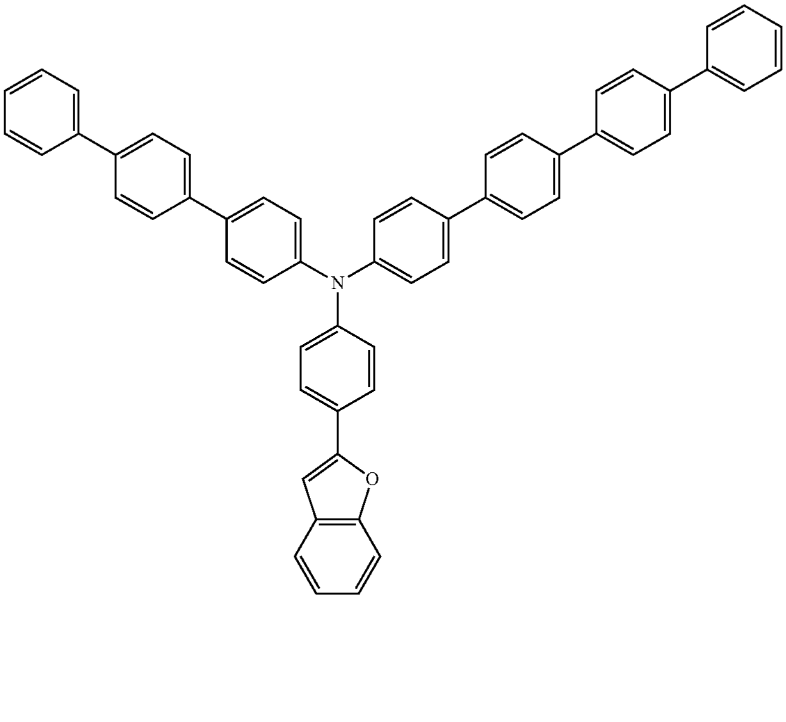

-continued
9
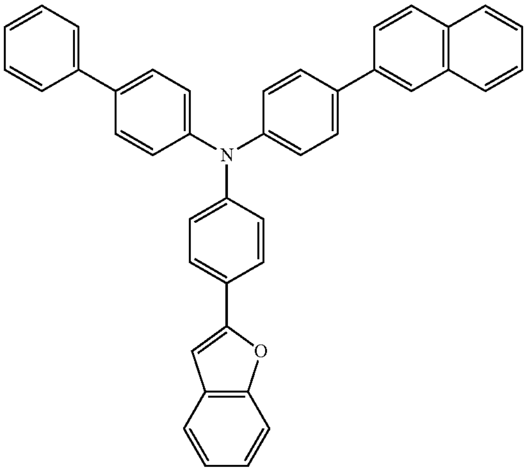
10
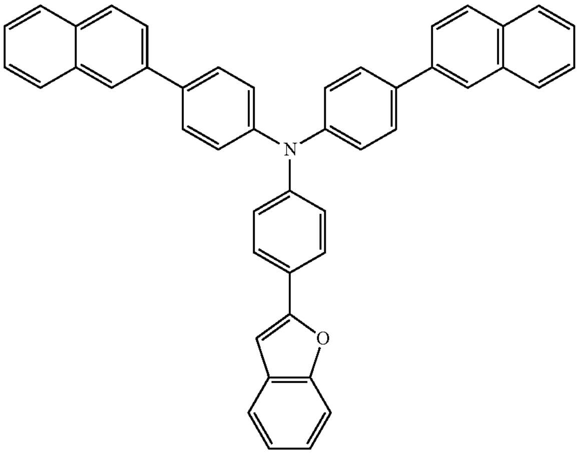
11
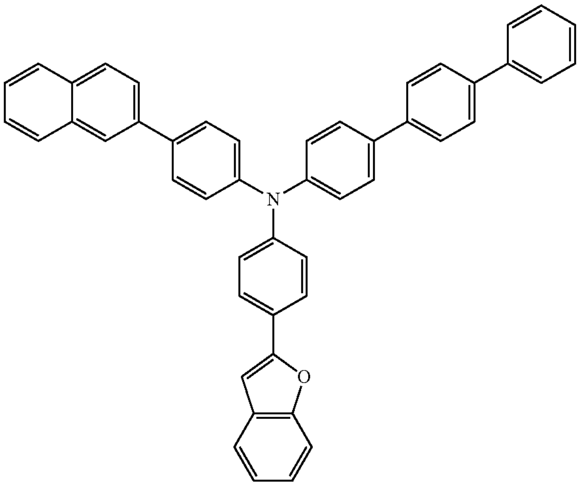
12
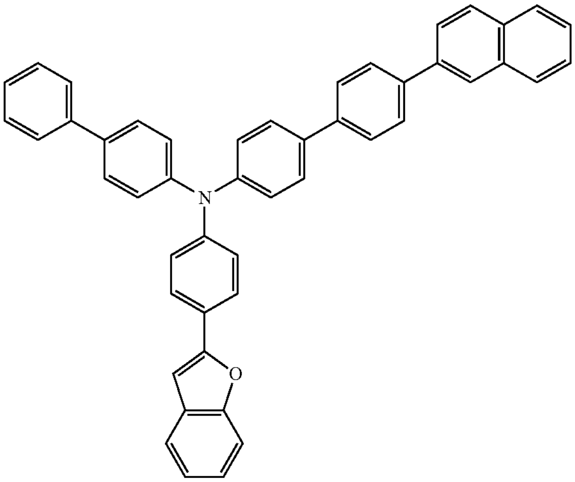
13
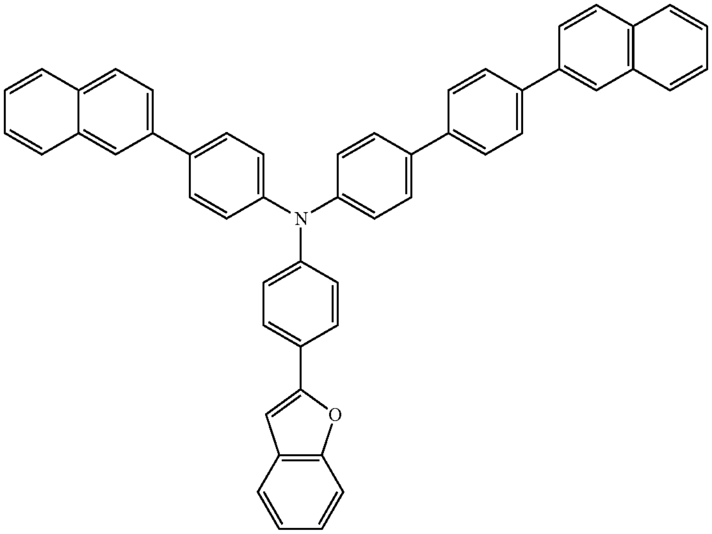

-continued
14
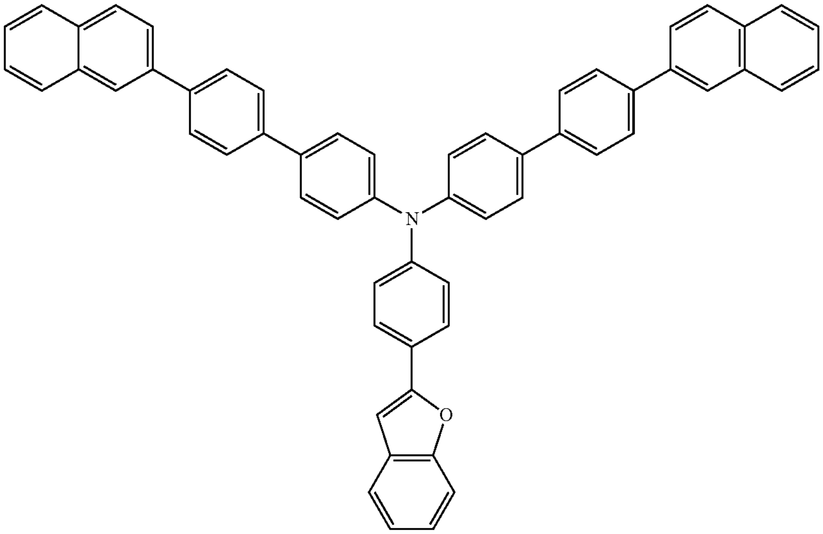
15
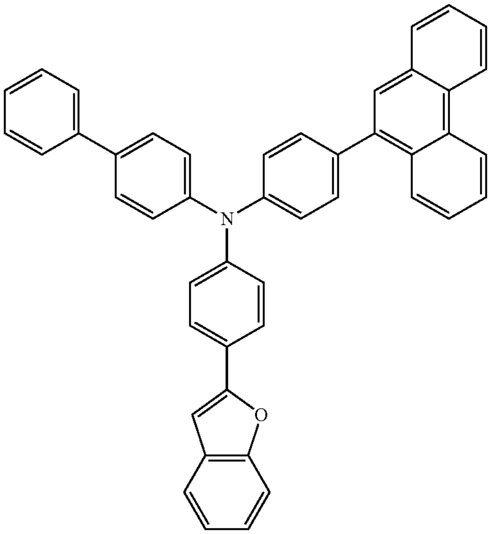
16
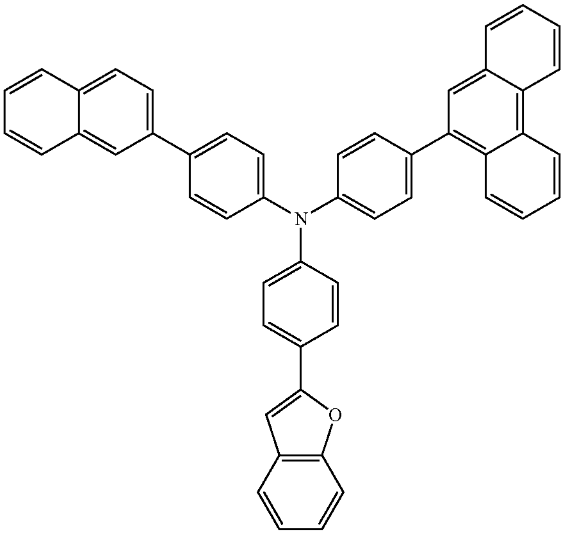
17
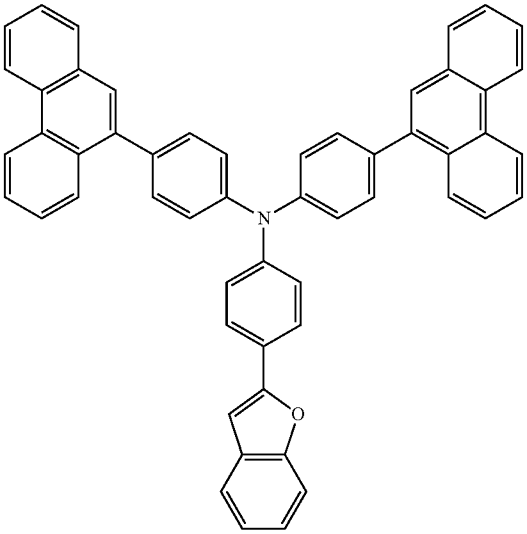
18
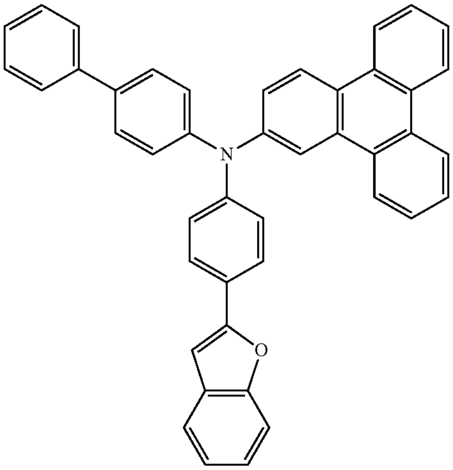

-continued
19
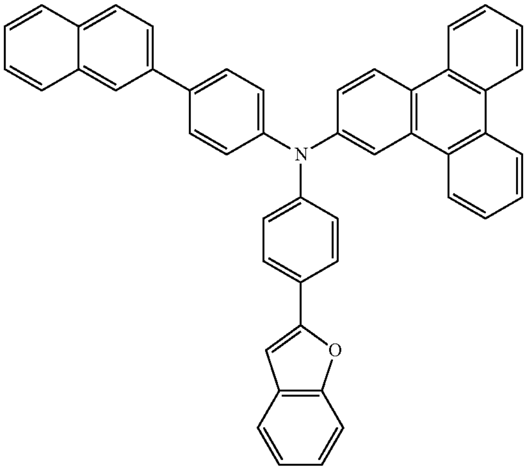
20
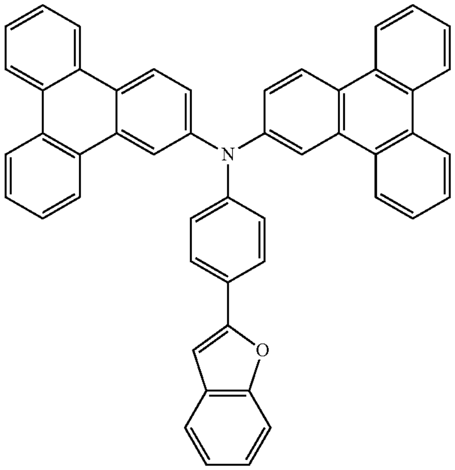
21
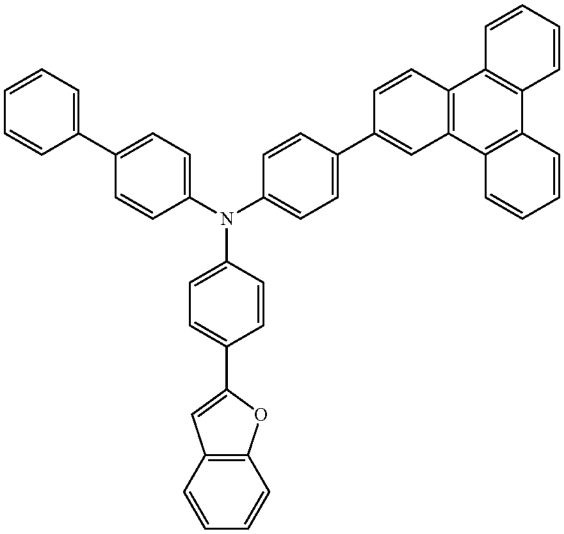
22
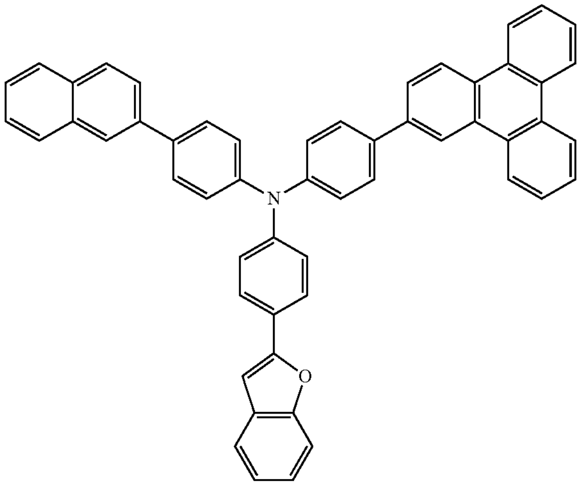
23
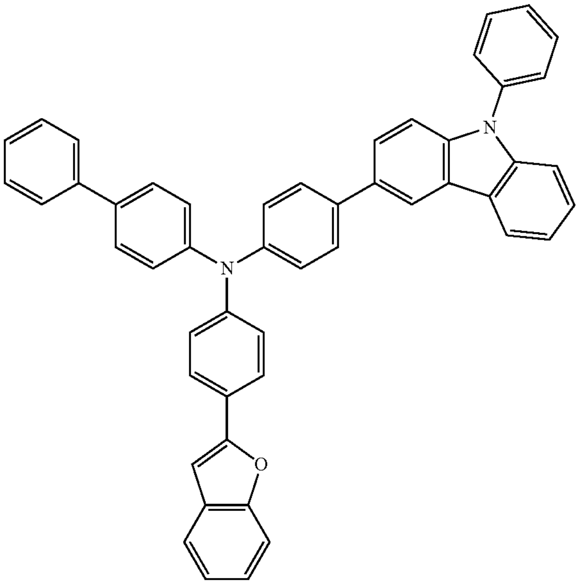
24
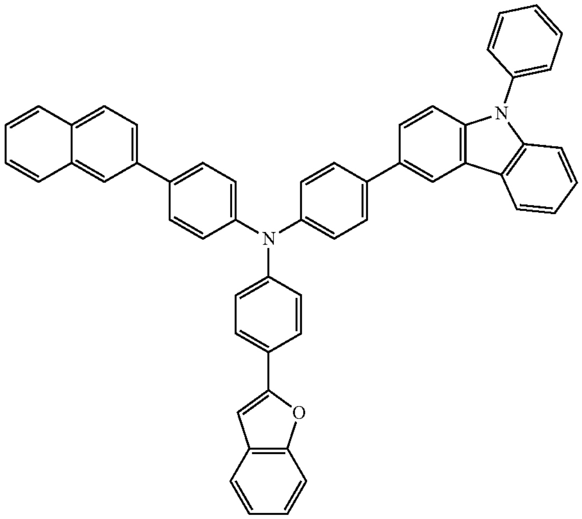

-continued
25
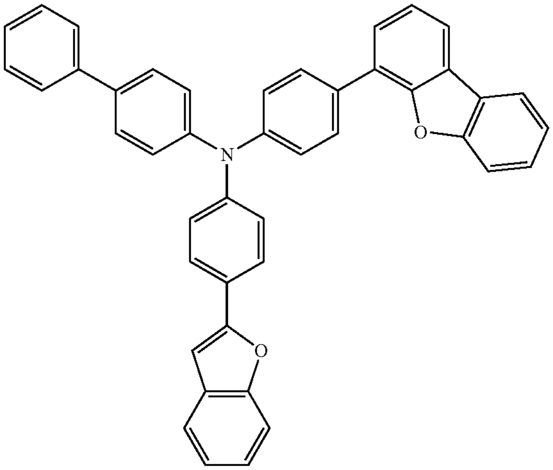
26
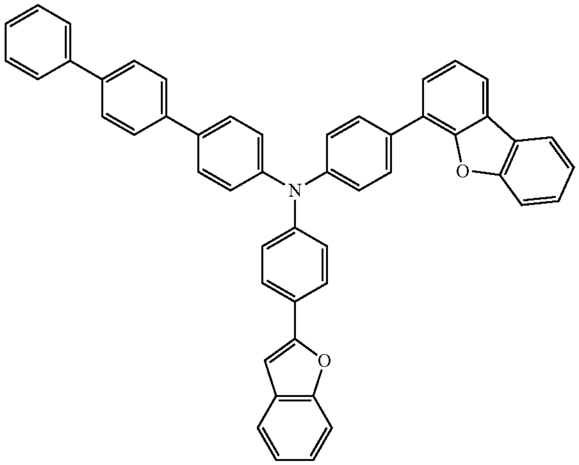
27
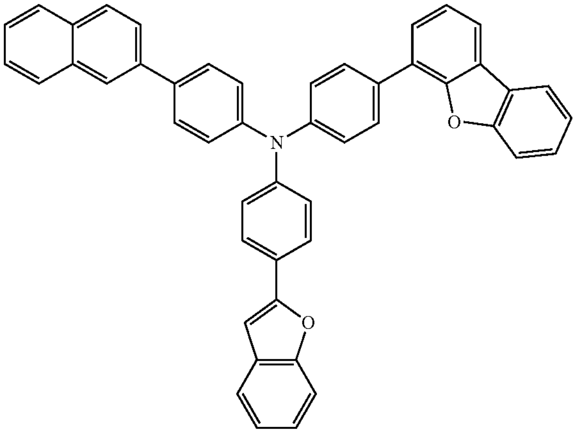
28
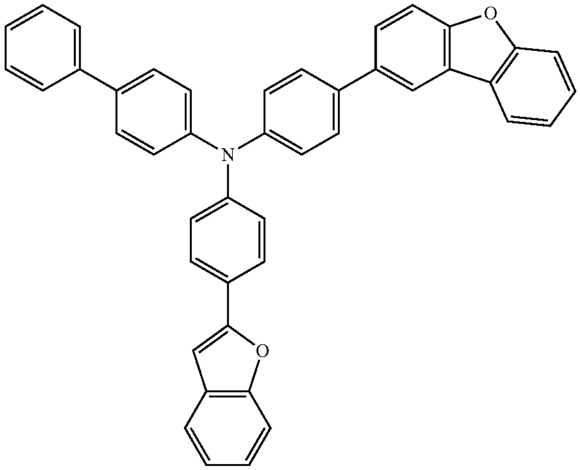
29
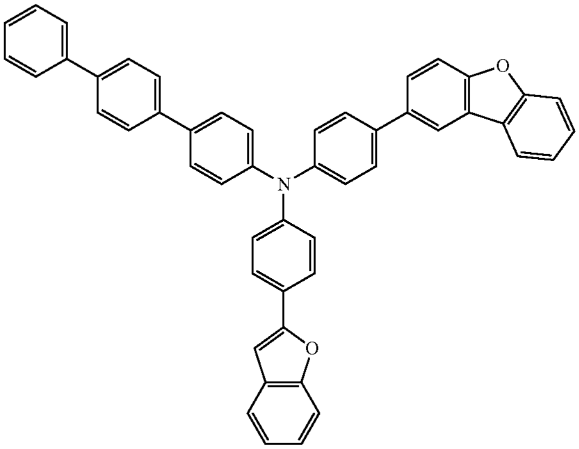
30
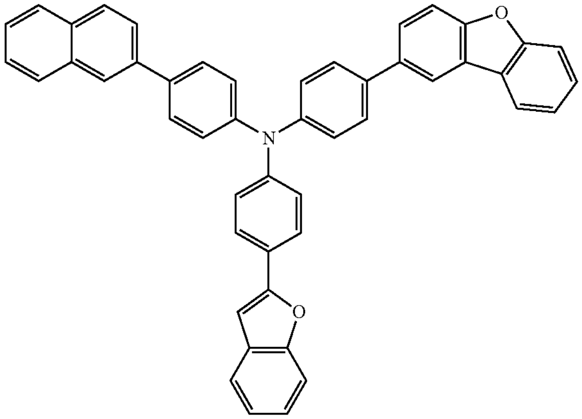

-continued
31
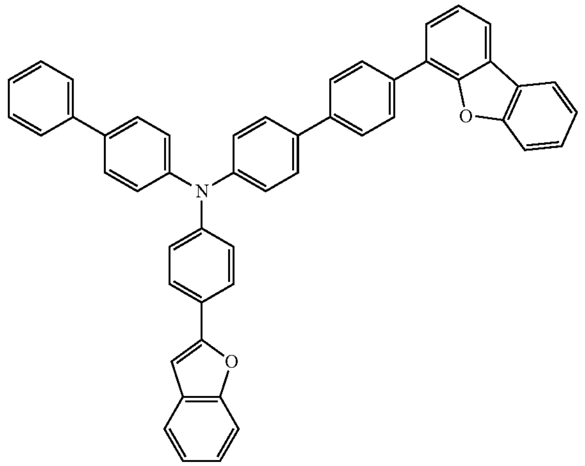
32
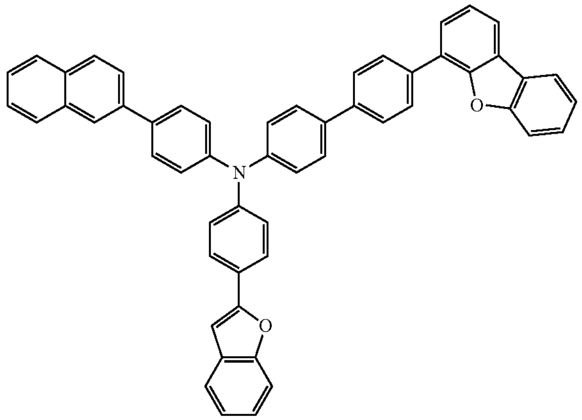
33
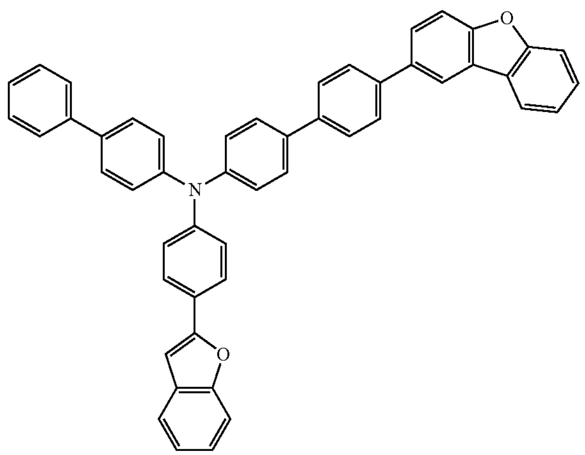
34
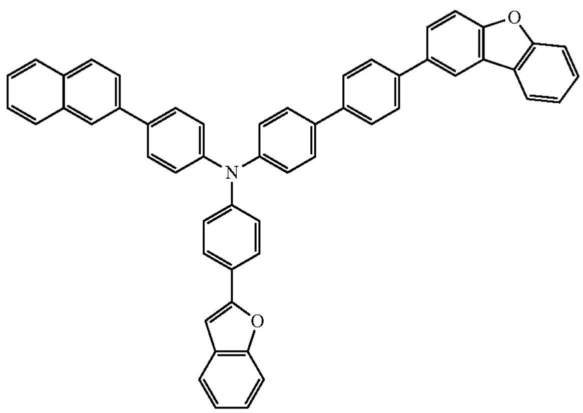
35
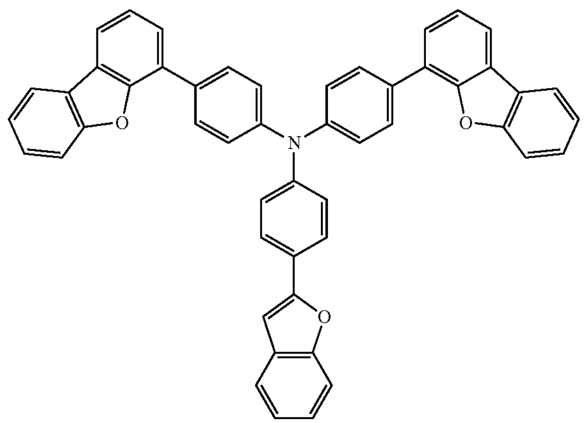
36
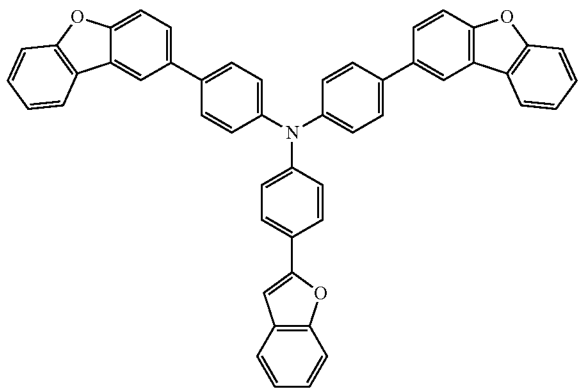

-continued
37
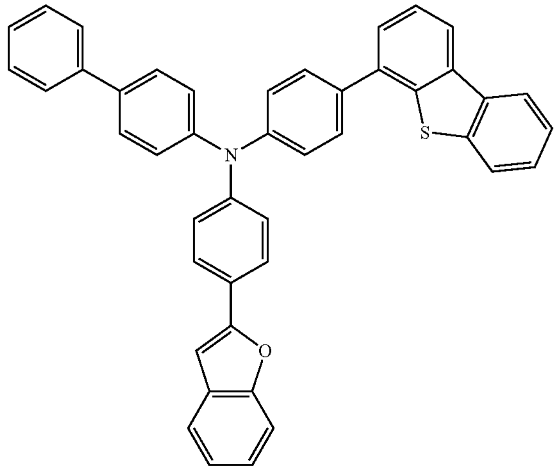
38
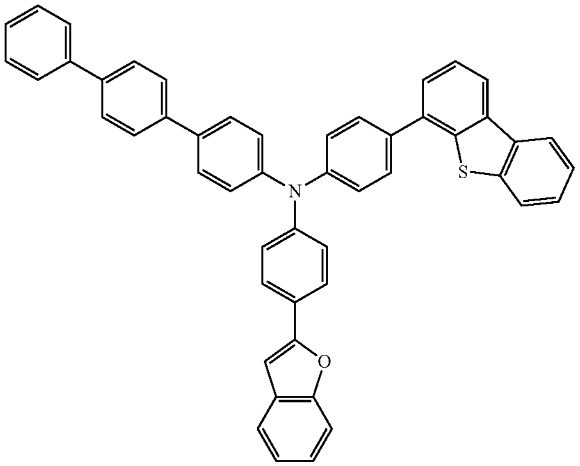
39
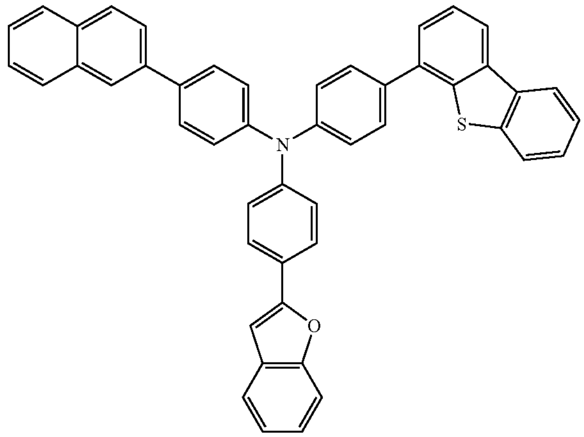
40
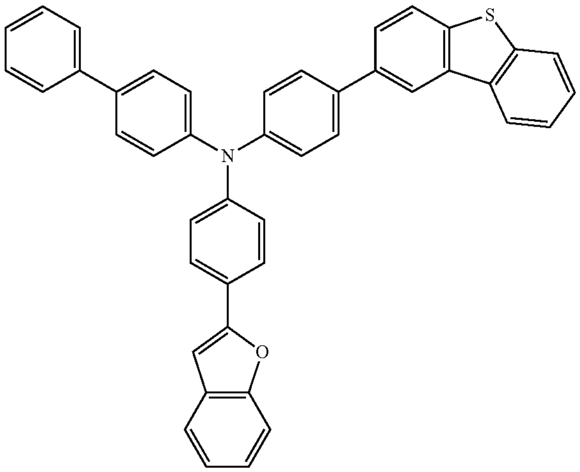
41
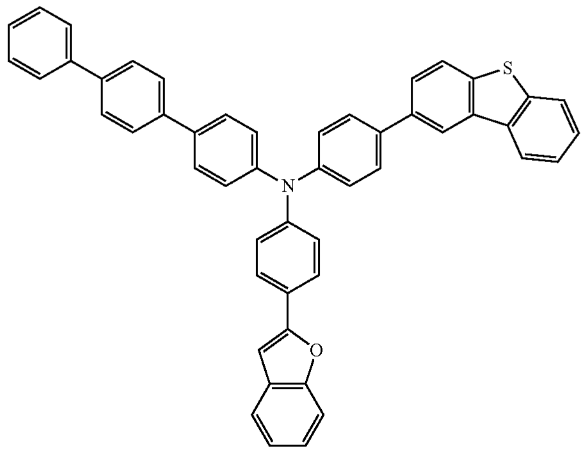
42
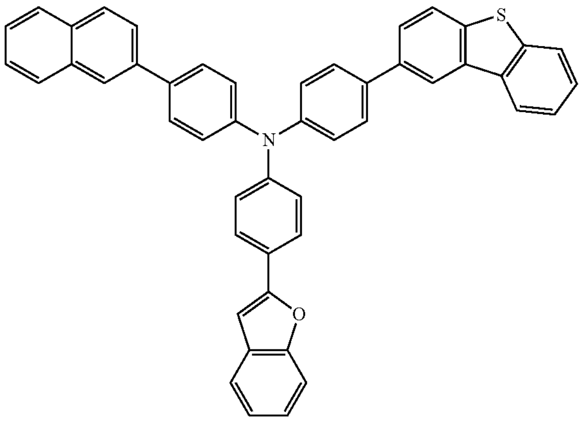

-continued
43
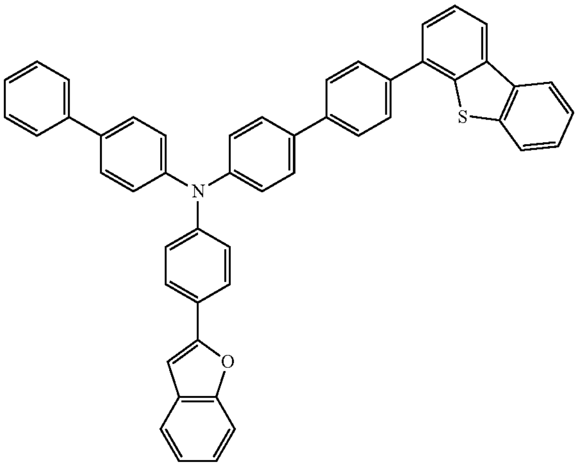
44
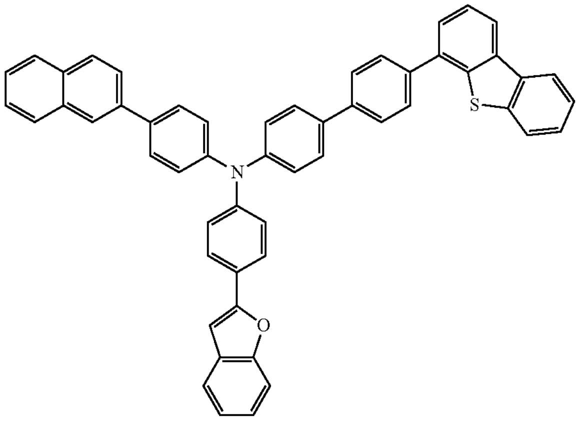
45
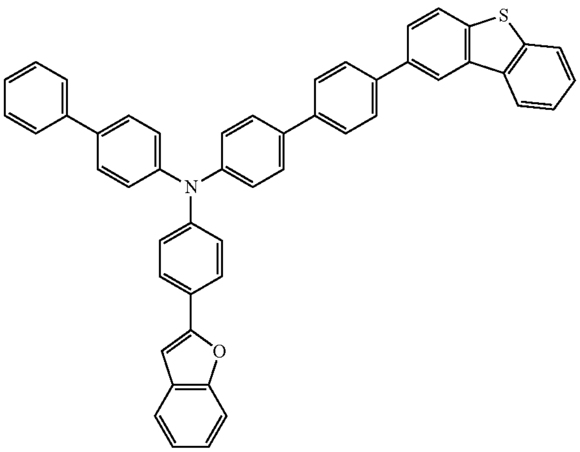
46
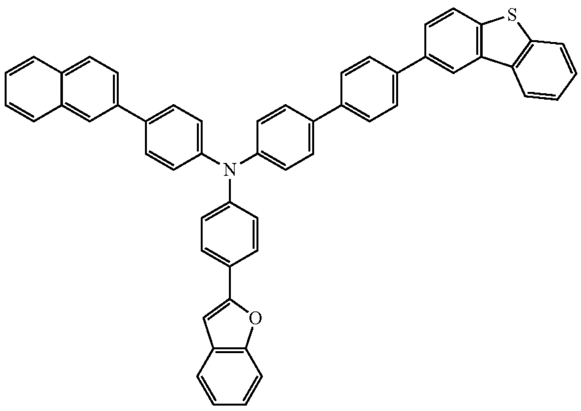
47
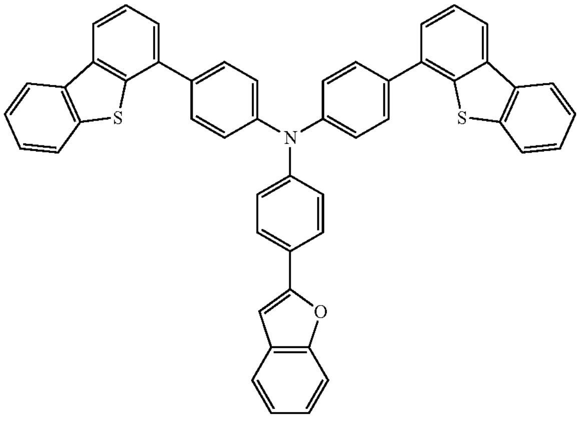
48
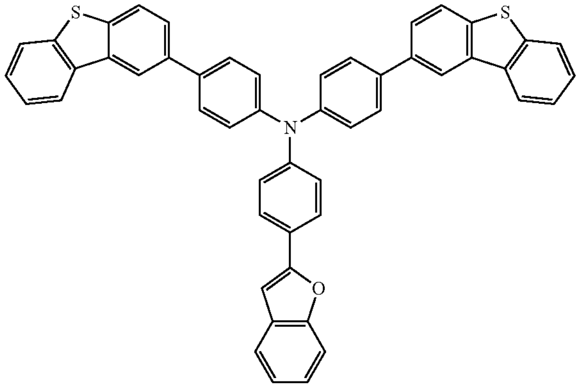

-continued
49
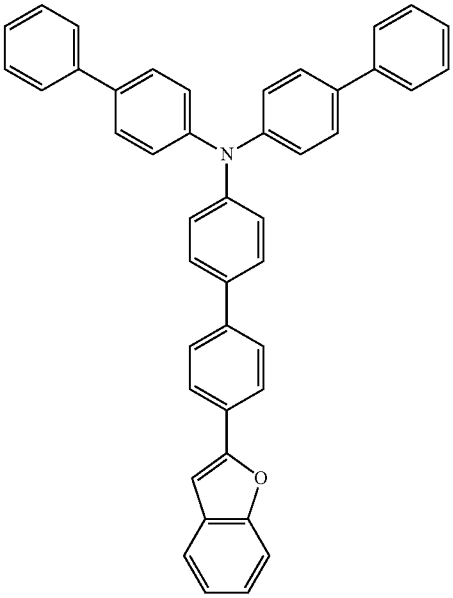
50
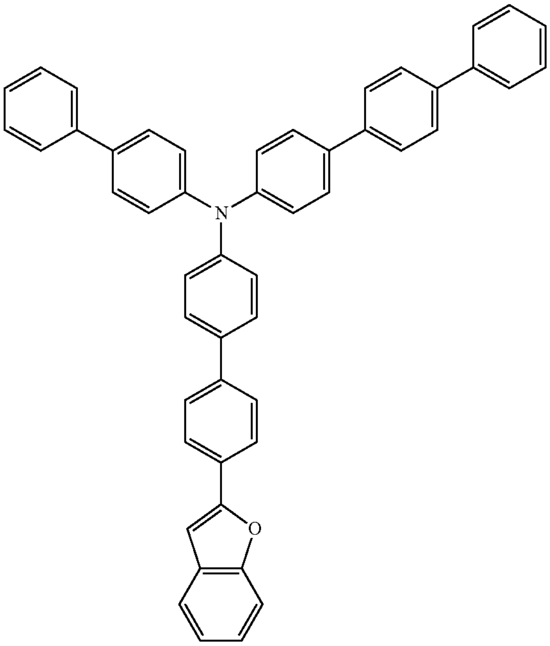
51
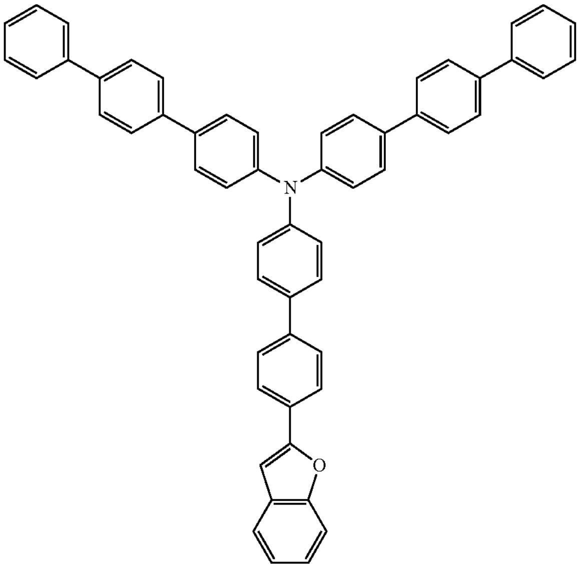
52
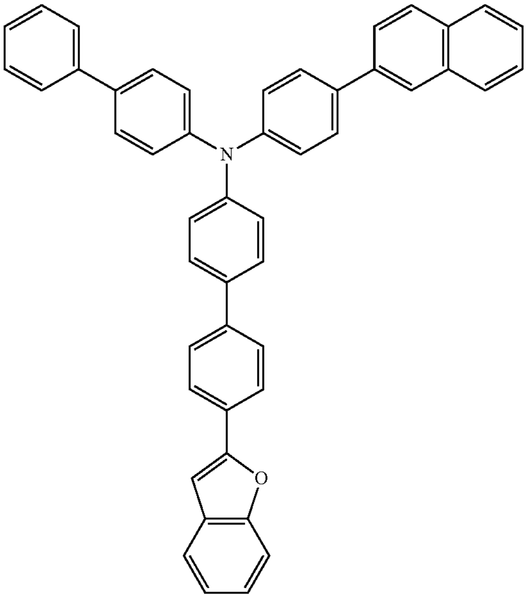

-continued
53
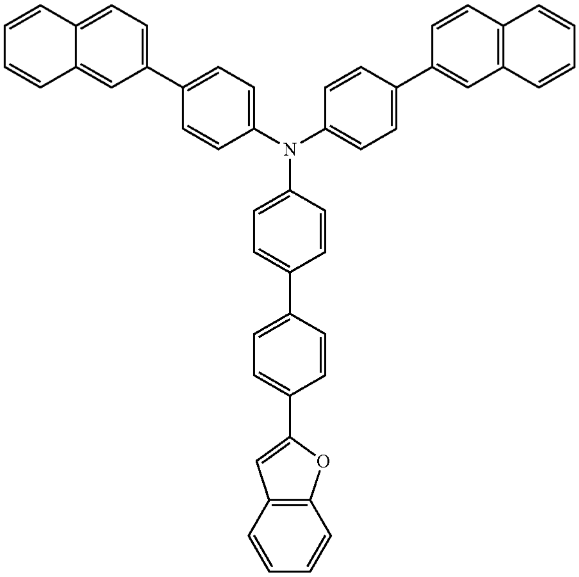
54
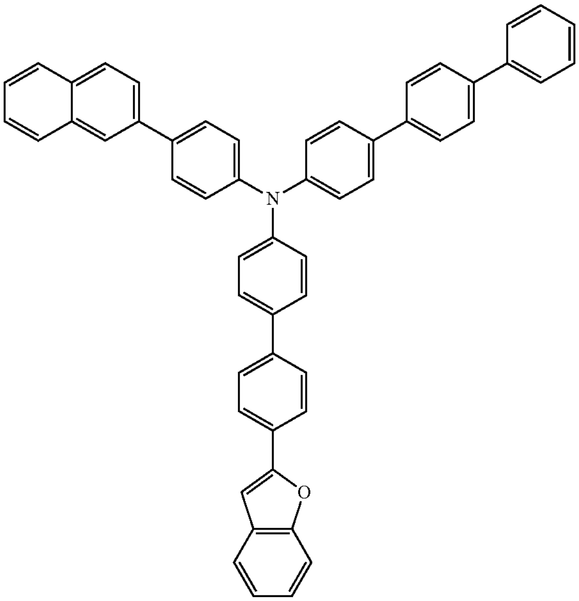
55
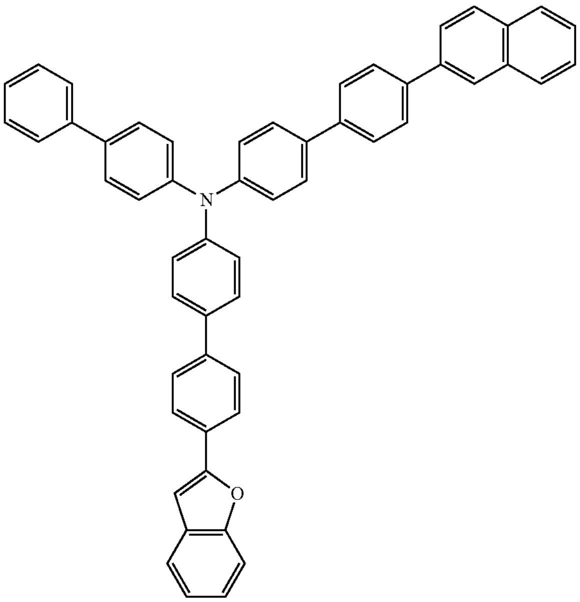
56
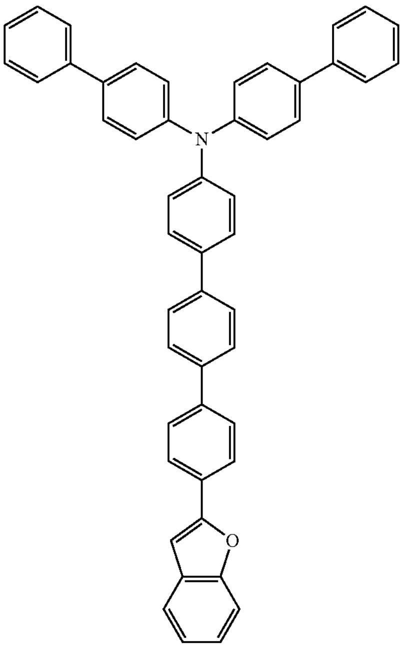

-continued
57
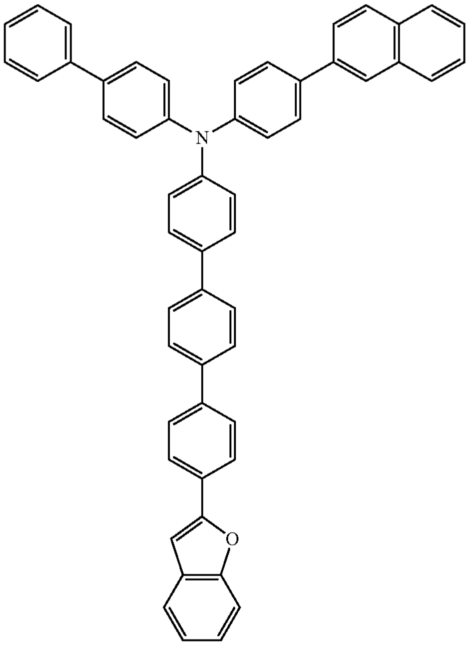
58
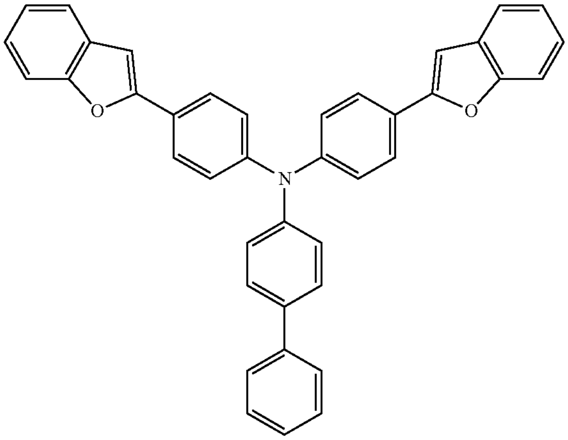
59
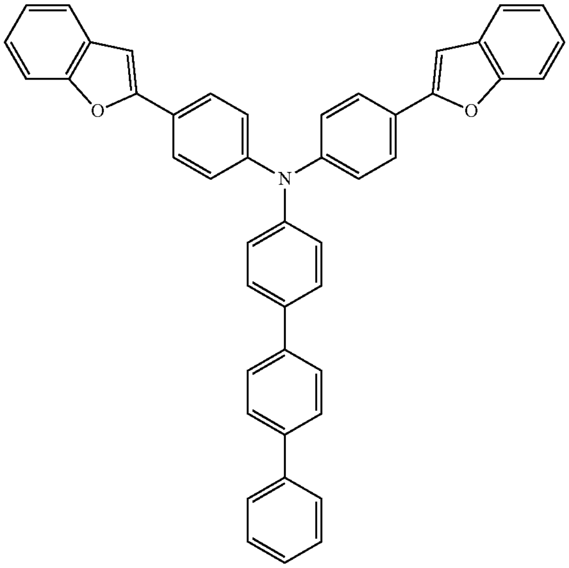
60
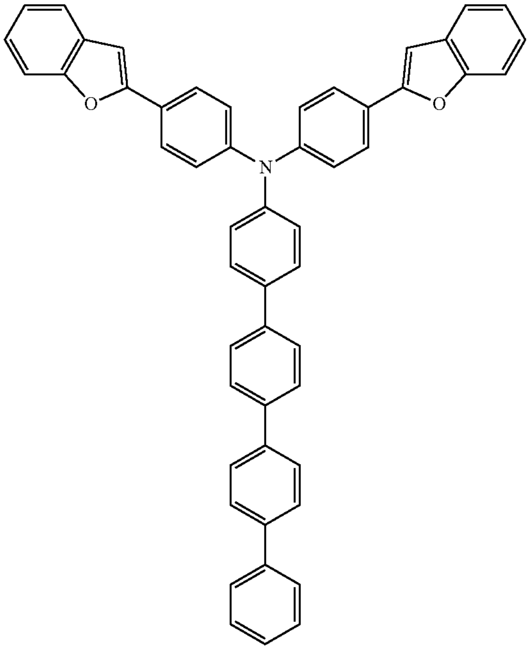

-continued
61
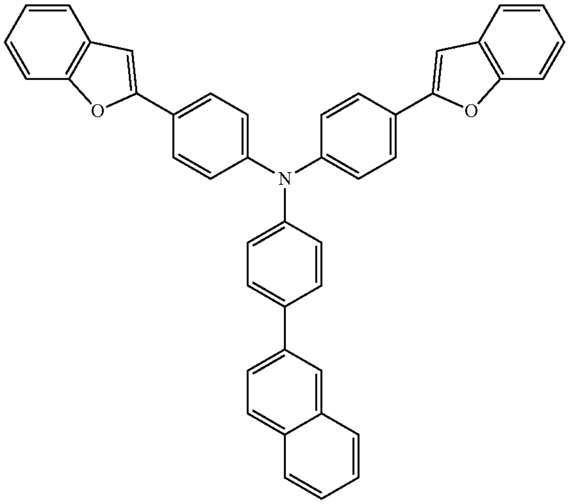
62
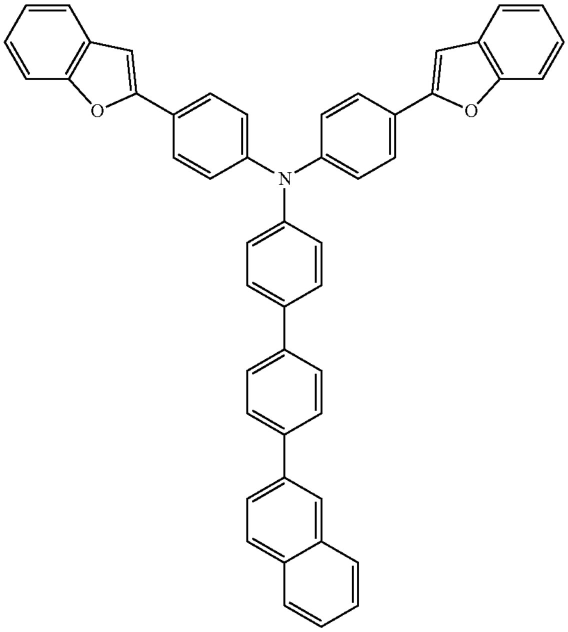
63
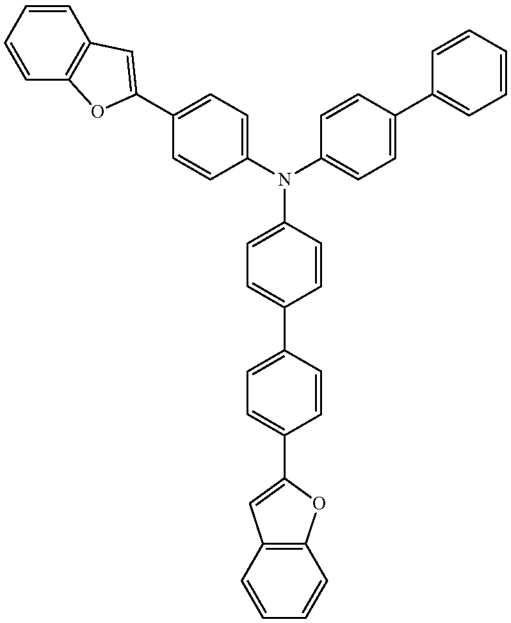
64
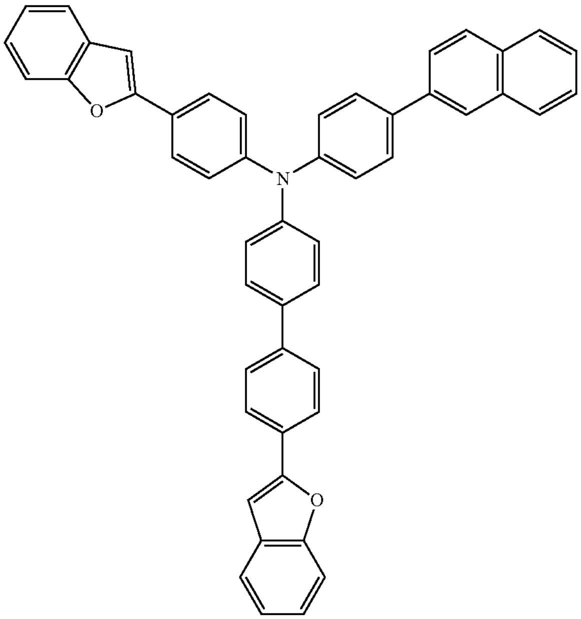

-continued
65
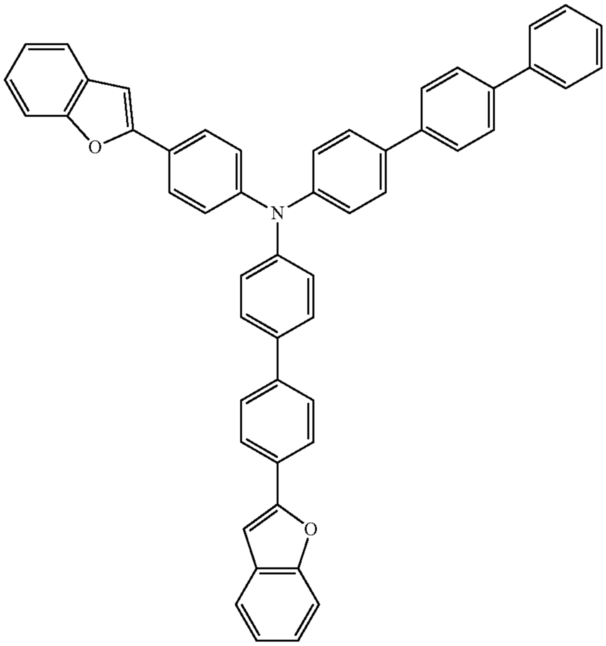
66
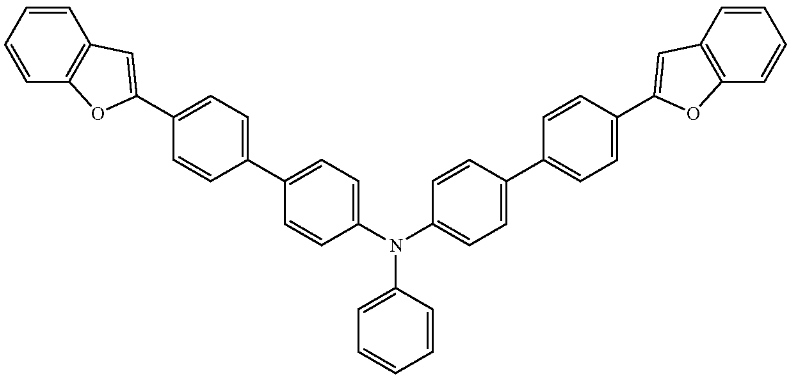
67
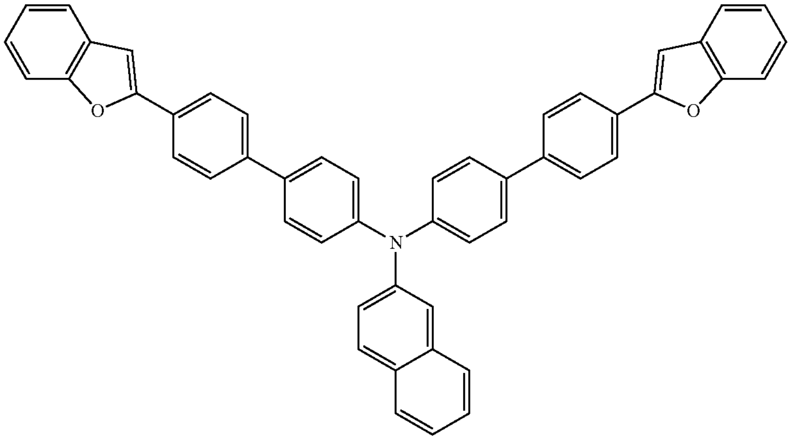

-continued
68
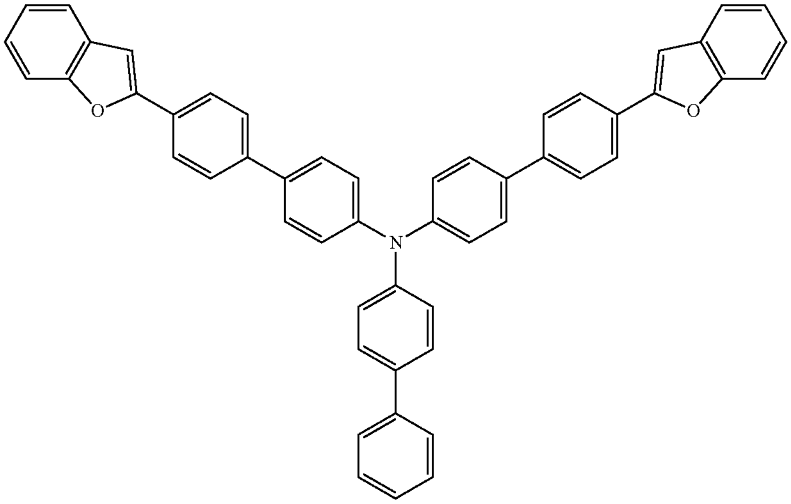
69
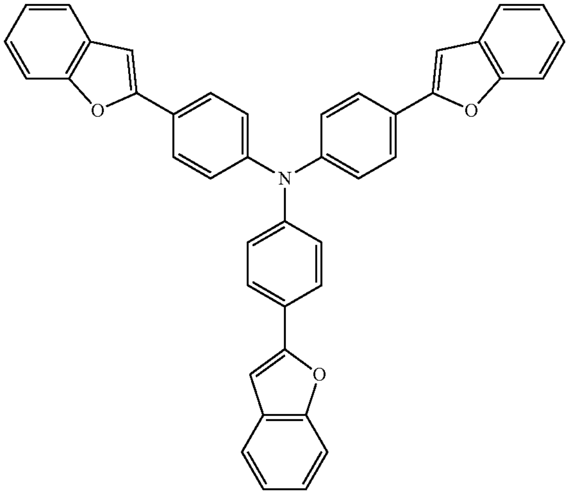
70
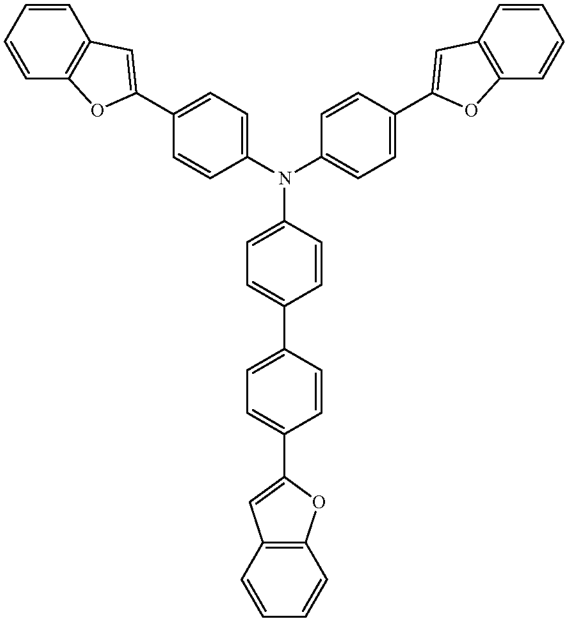

-continued
71
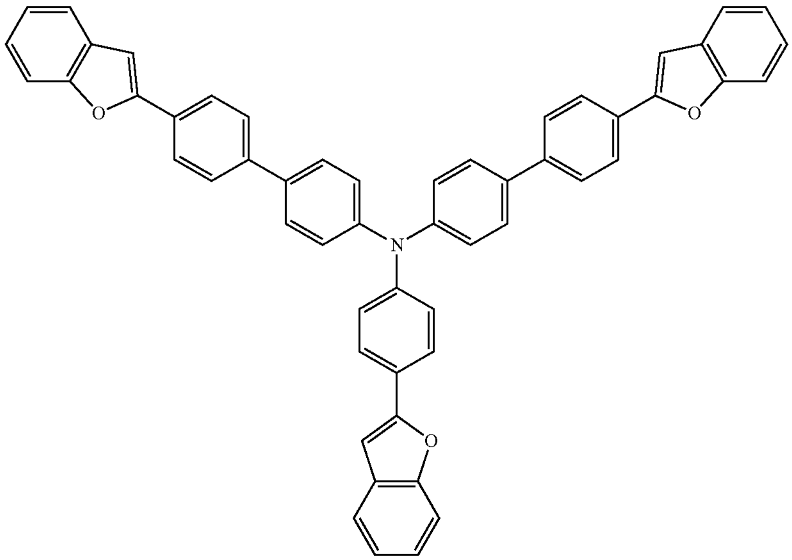
72
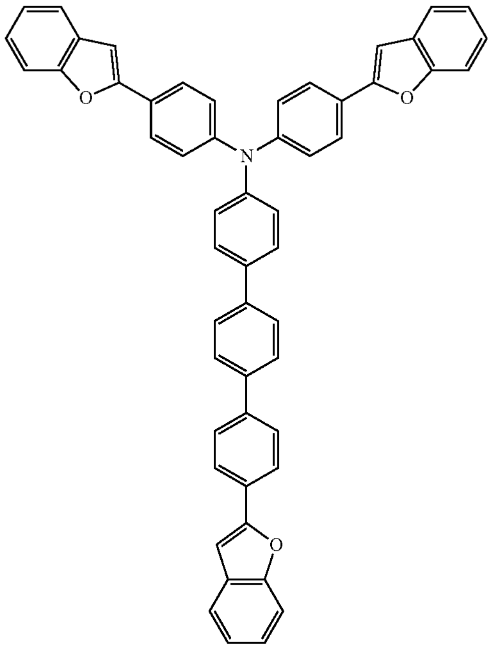
73
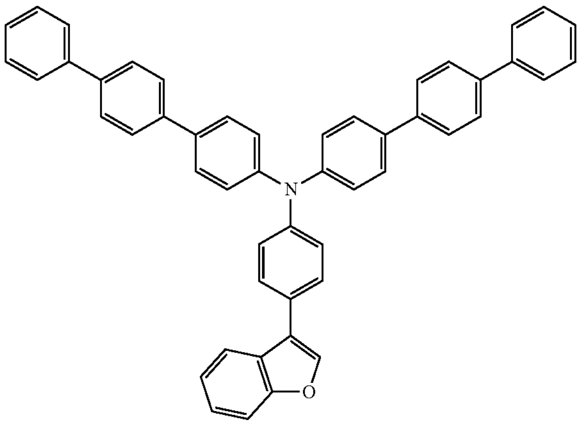

-continued
74
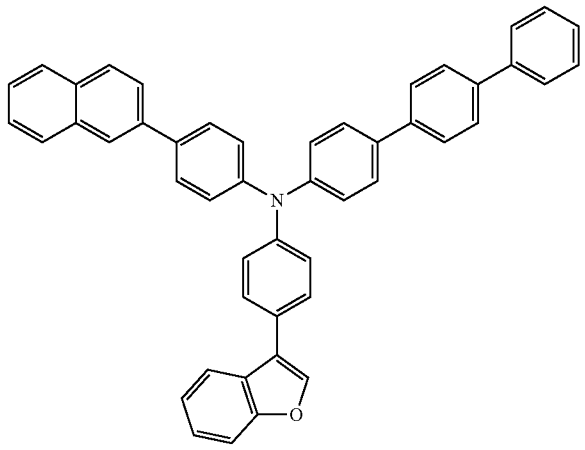
75
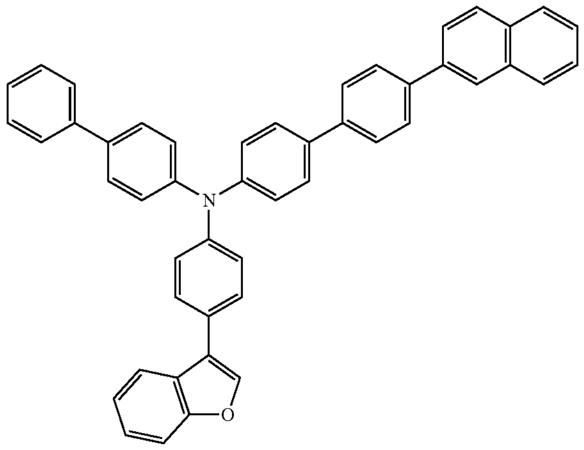
76
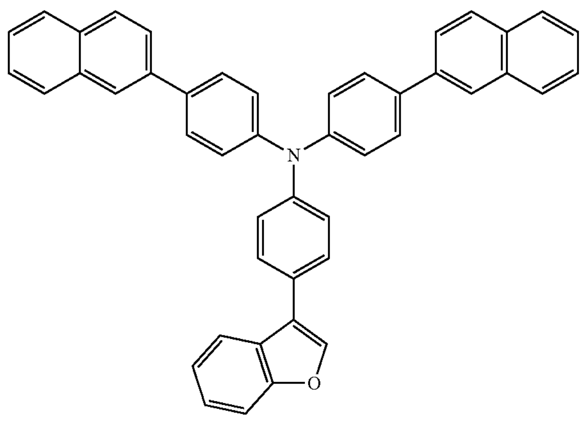
77
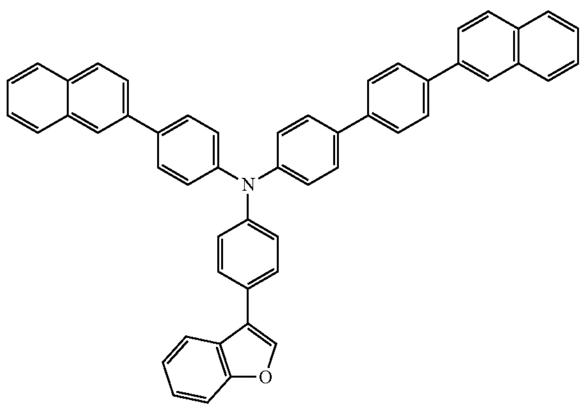
78
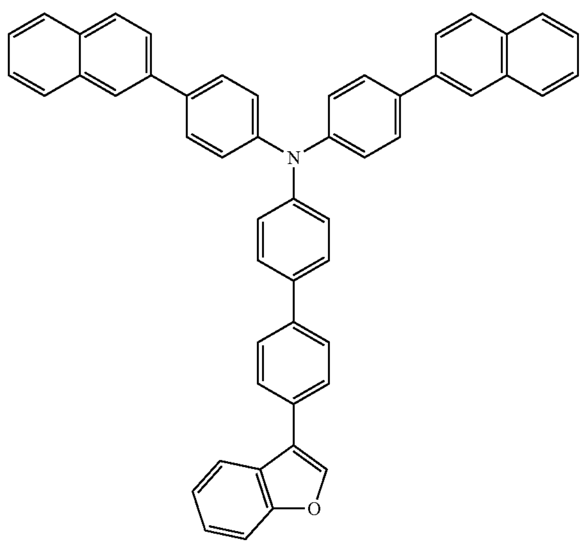
79
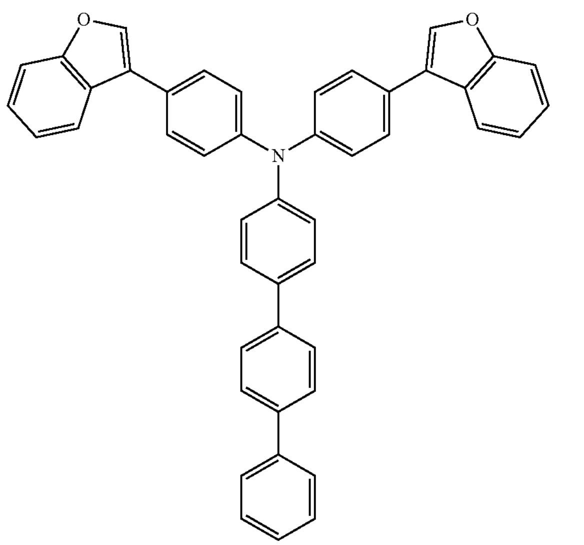

-continued
80
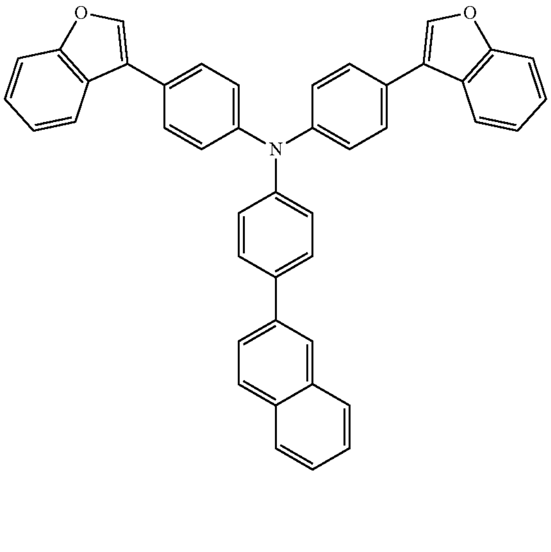
81
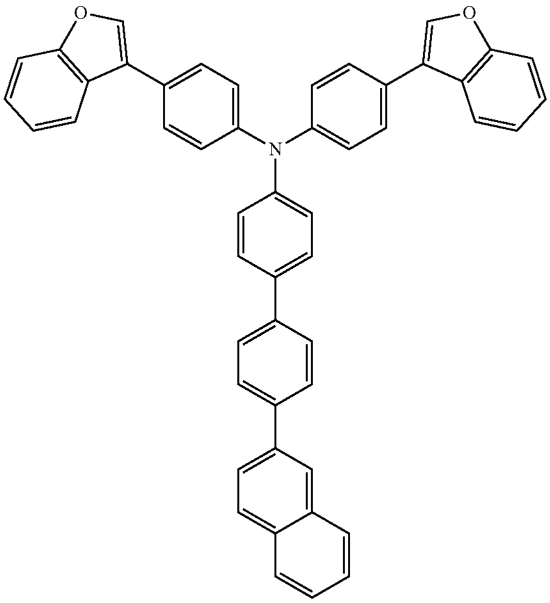
82
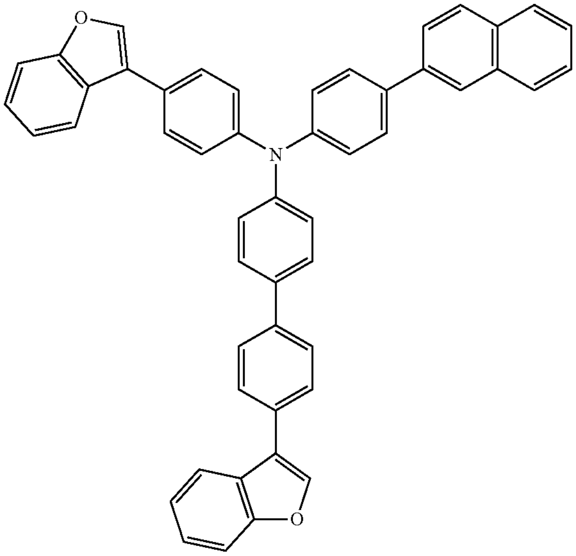
83
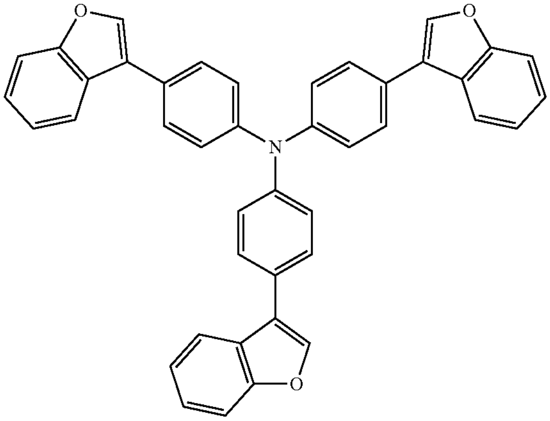

-continued
84
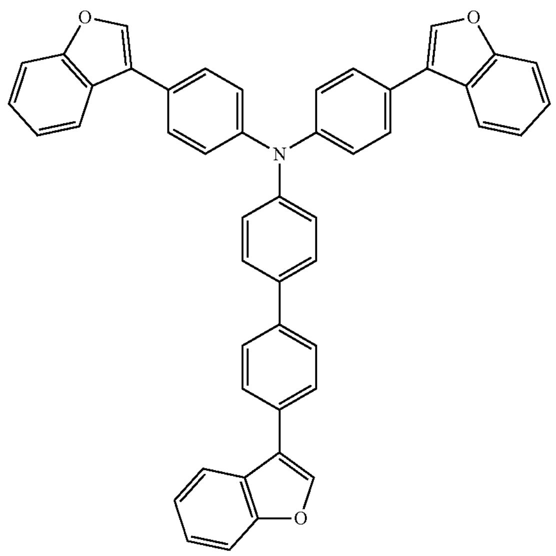
85
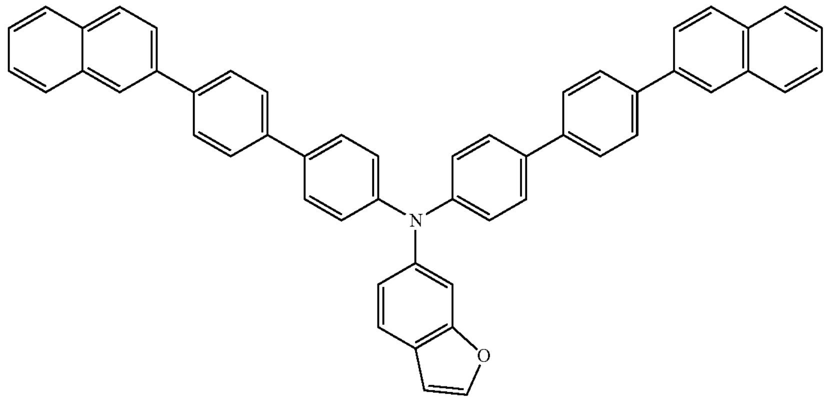
86
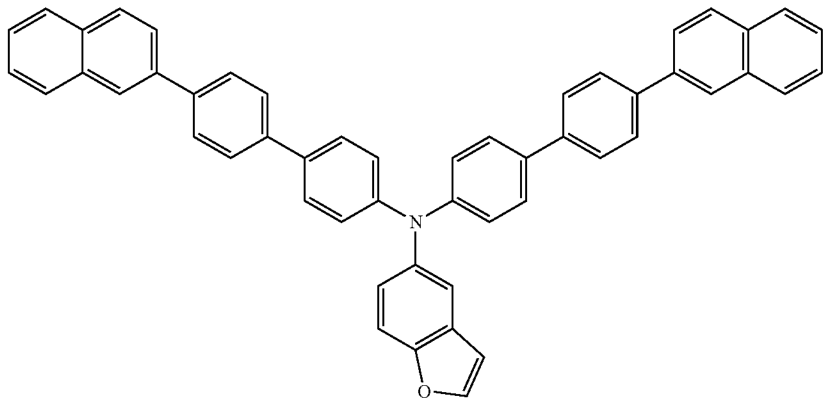

-continued
87
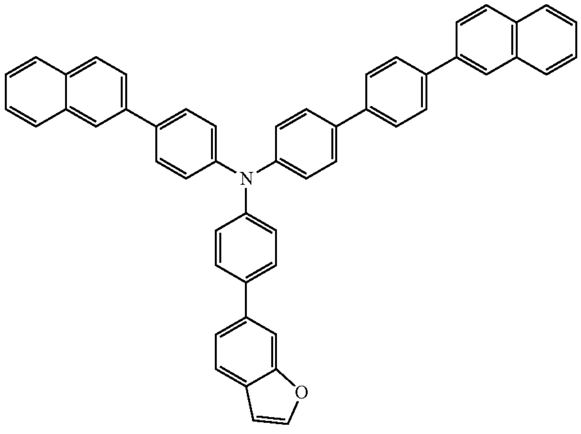
88
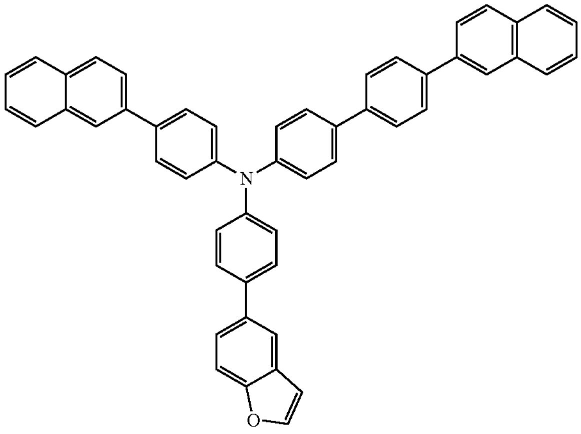
89
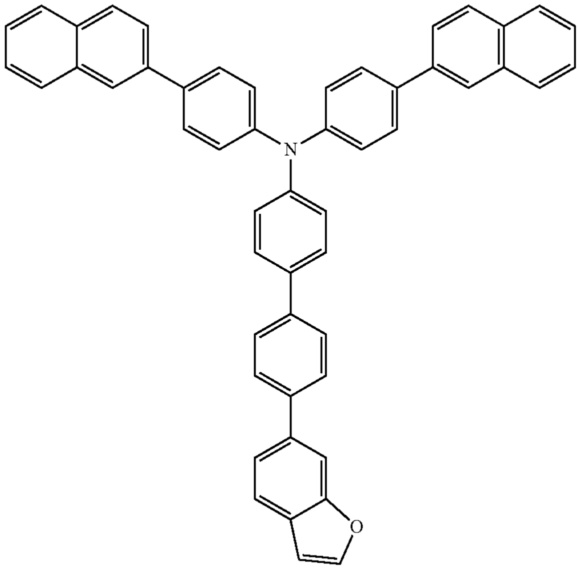
90
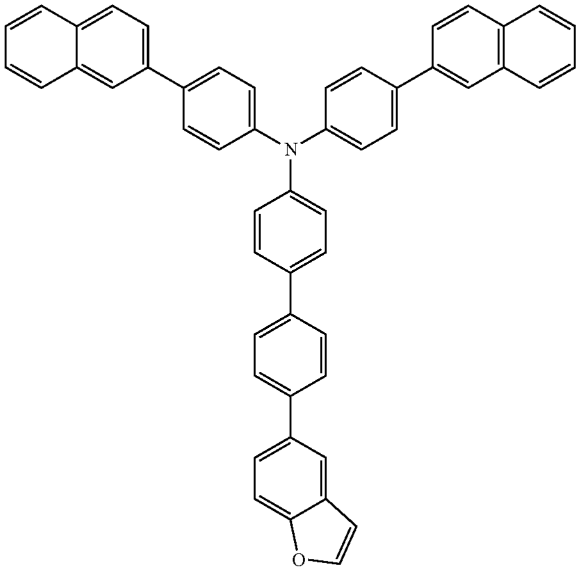
91
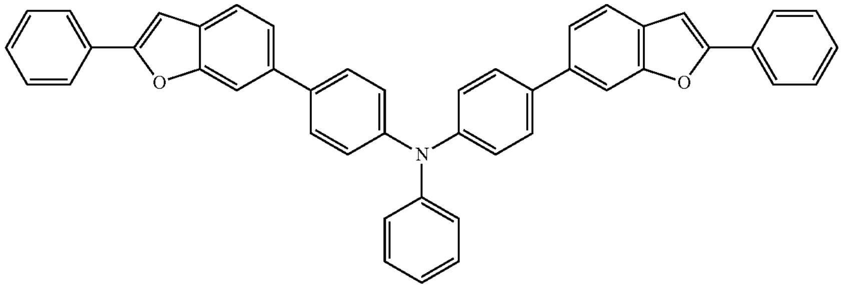

-continued
92
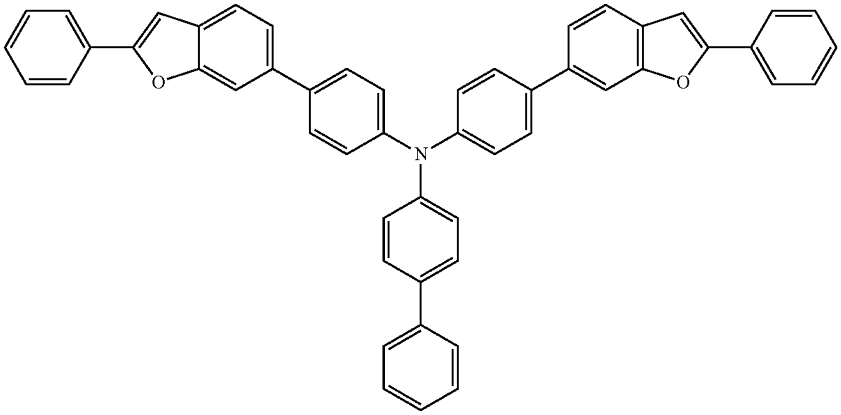
93
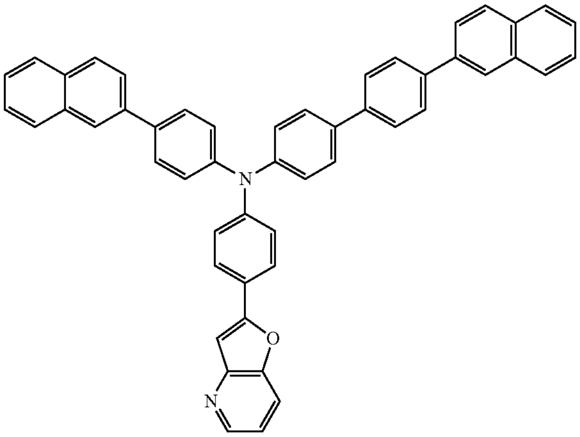
94
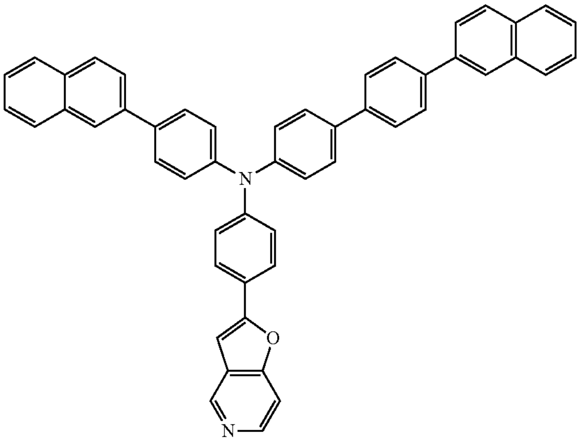
95
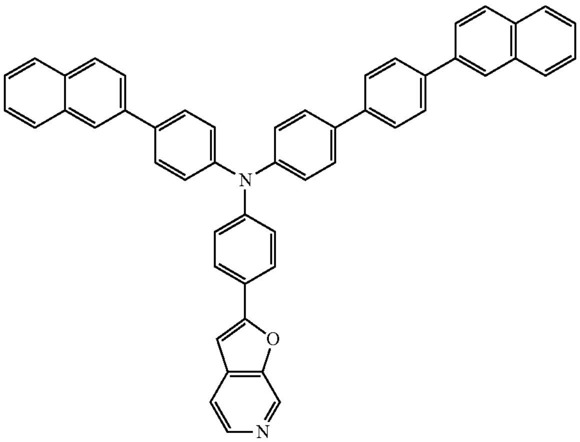
96
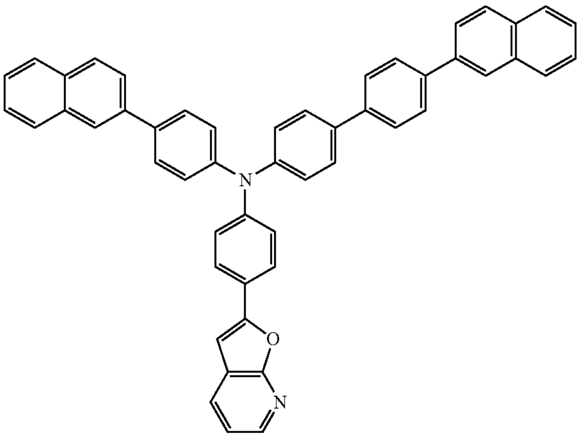

-continued
97
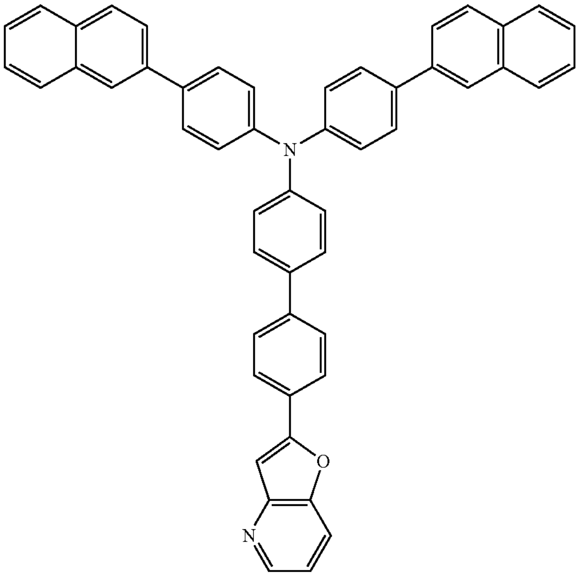
98
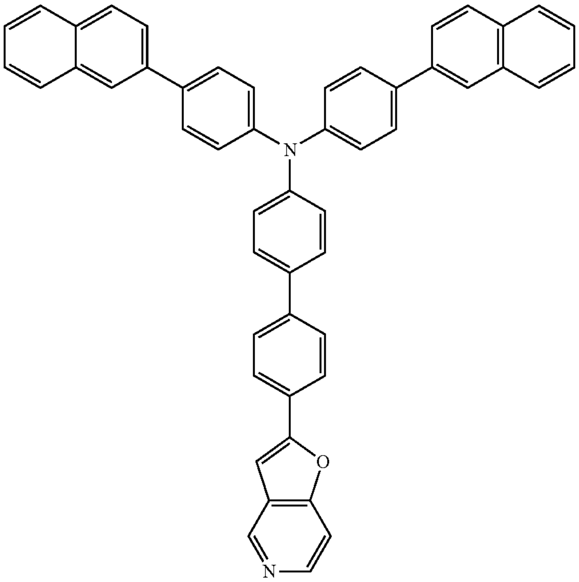
99
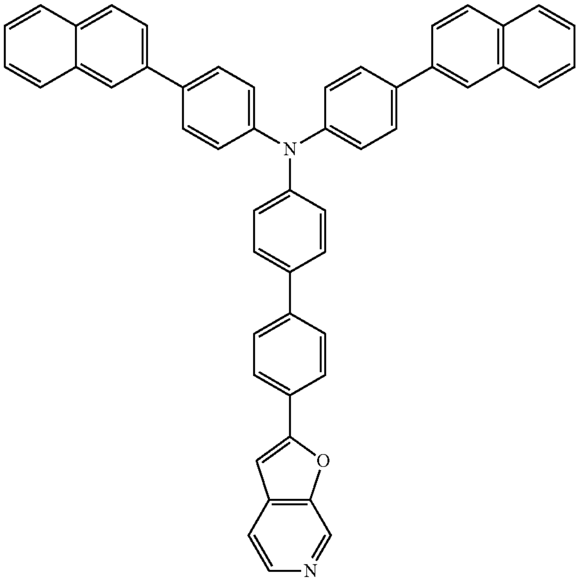
100
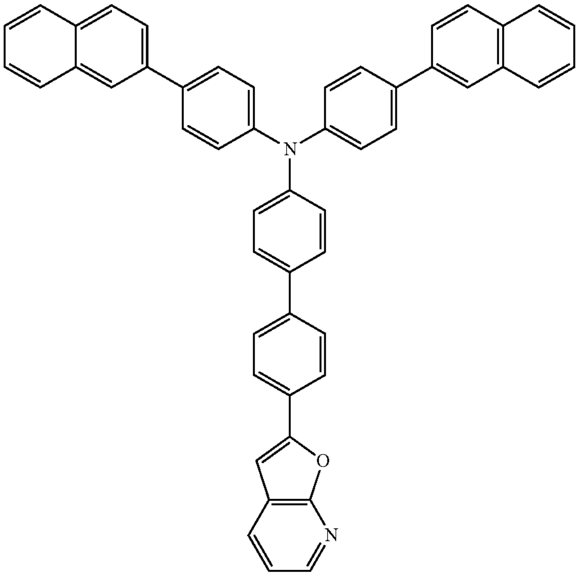
101
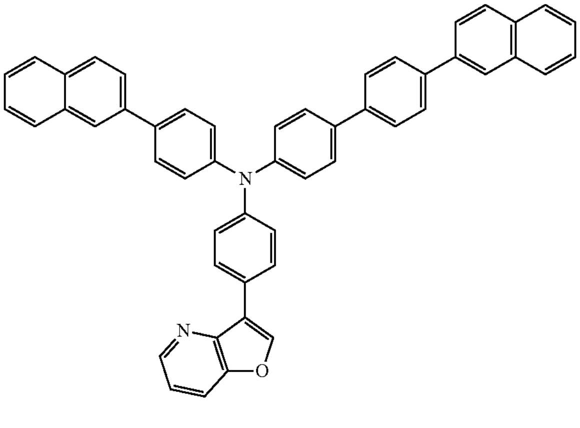
102
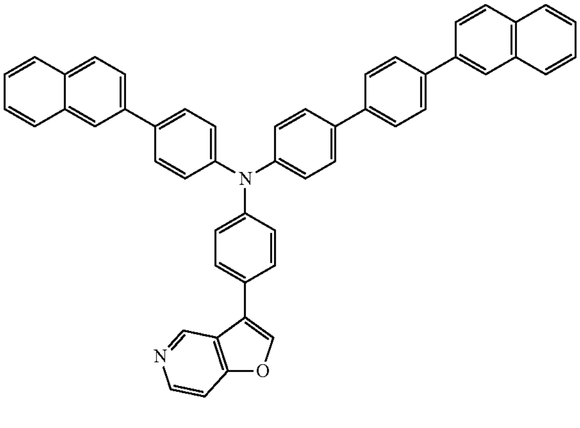

-continued
103
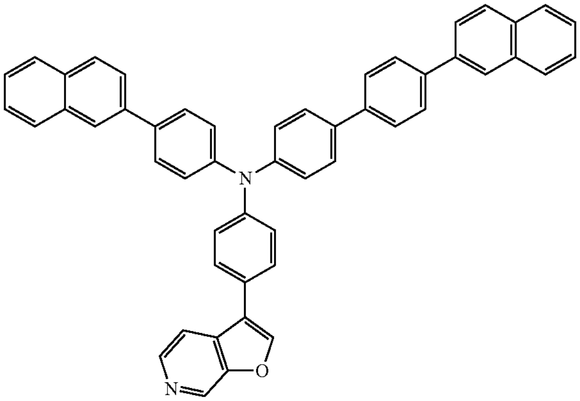
104
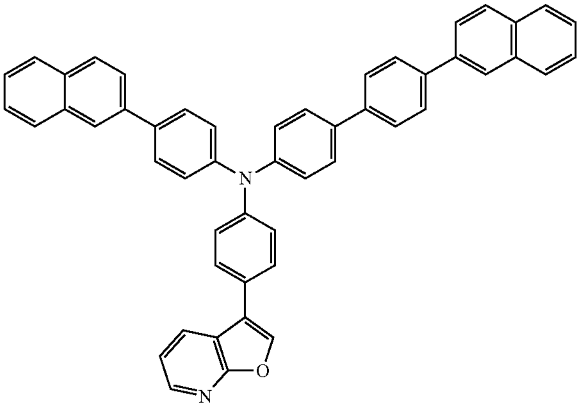
105
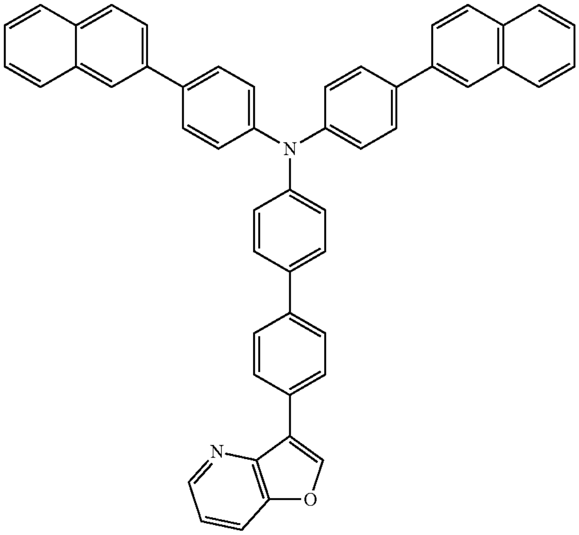
106
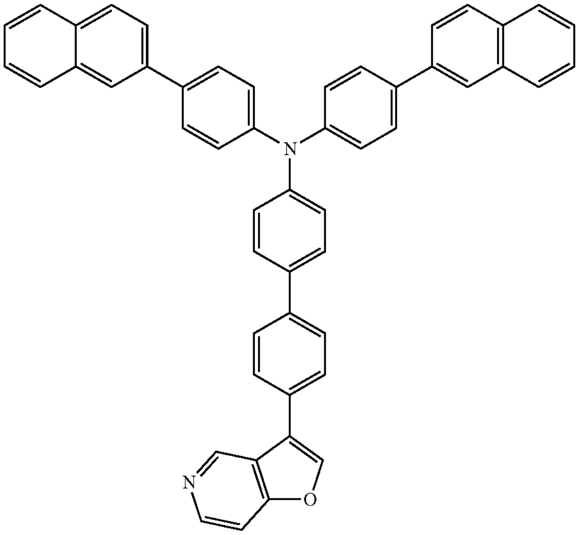
107
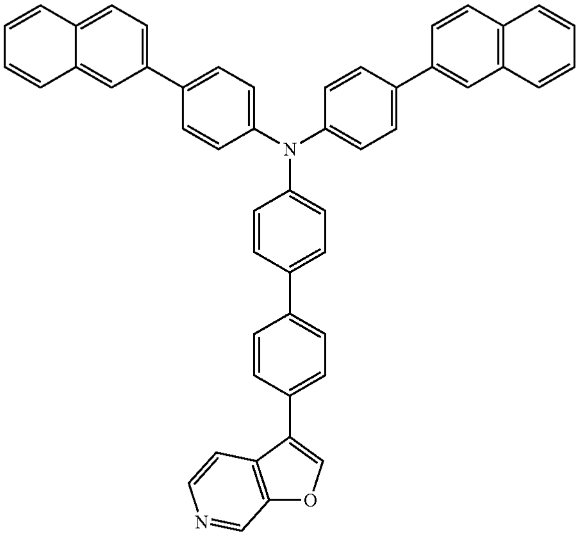
108
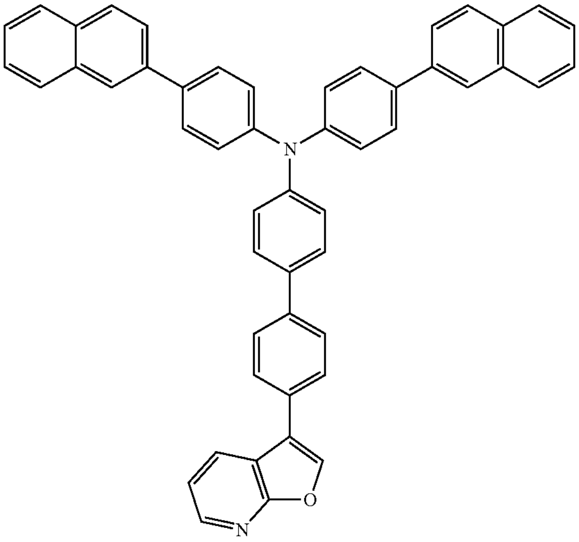

-continued
109
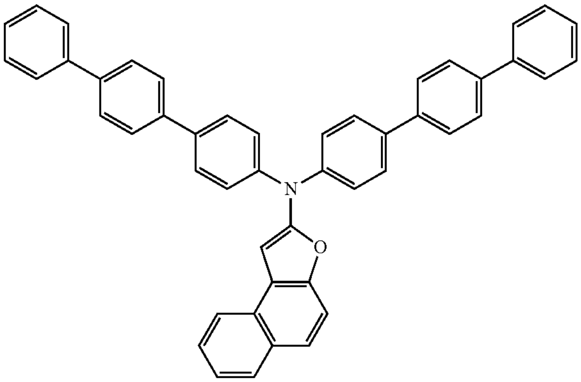
110
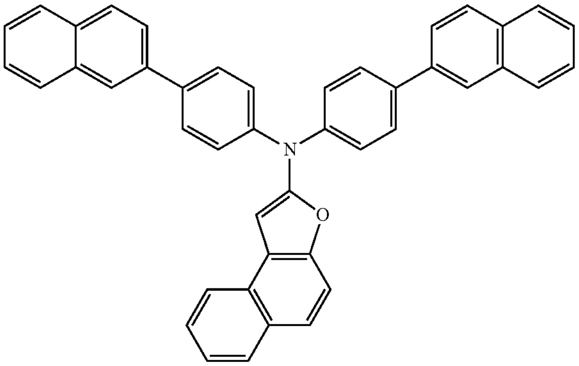
111
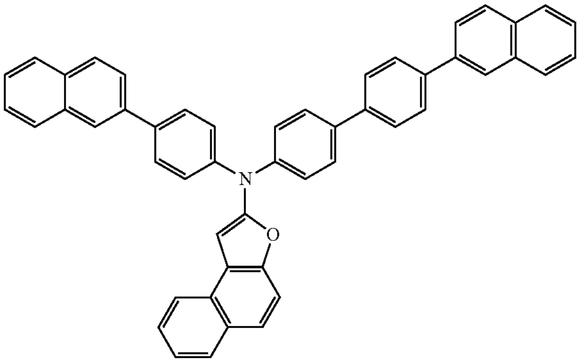
112
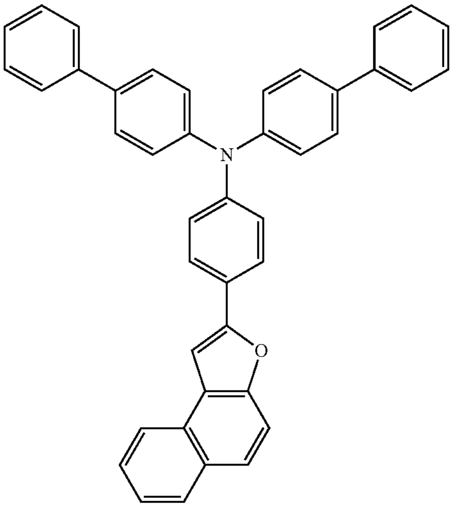
113
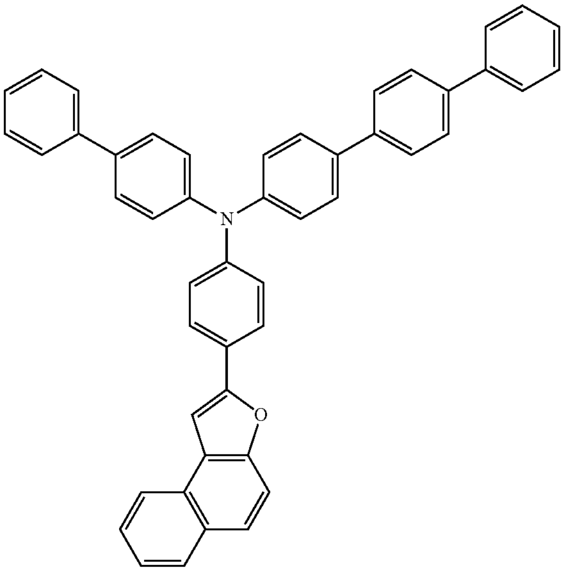
114
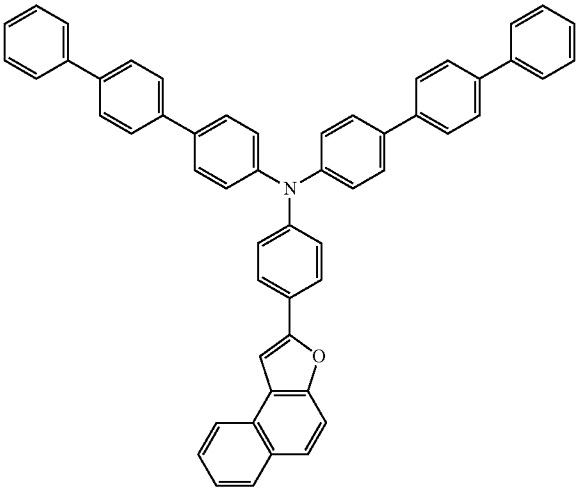

-continued
115
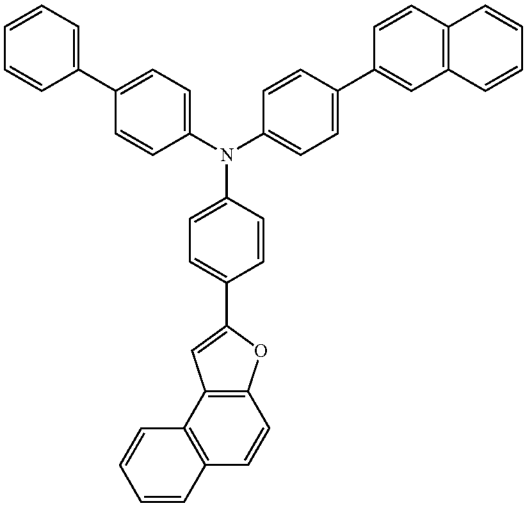
116
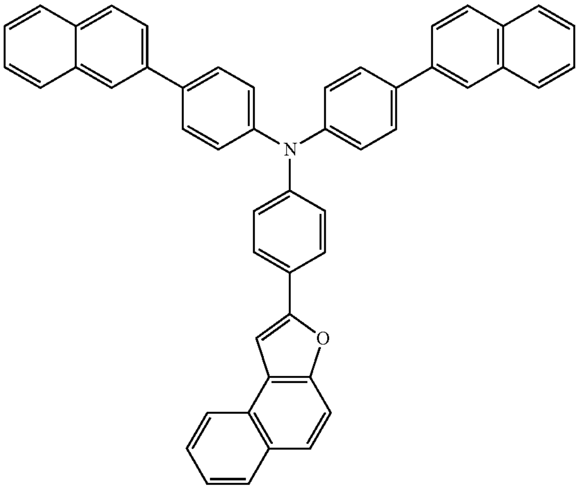
117
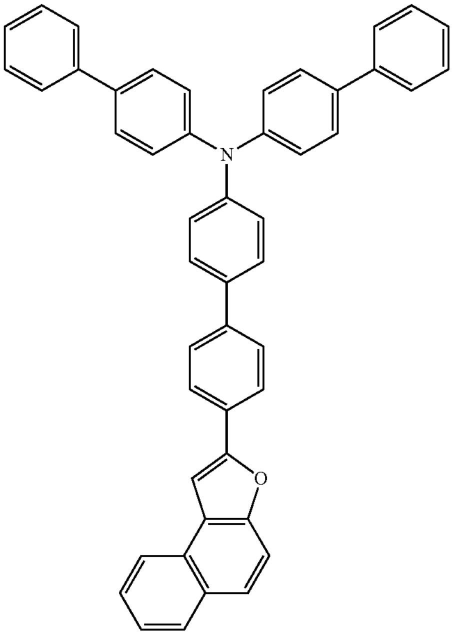
118
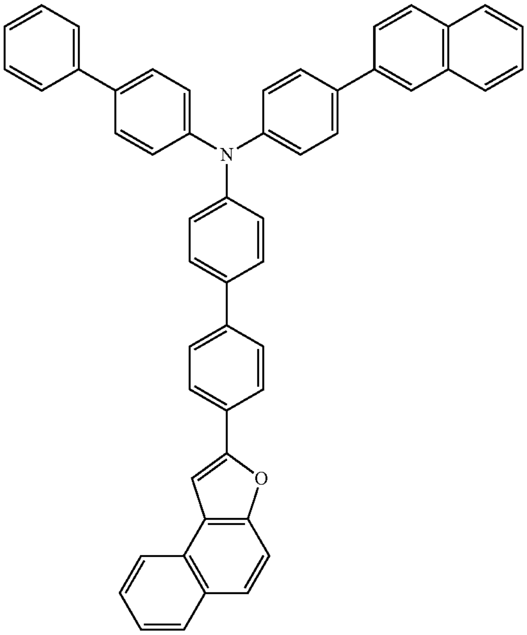
119
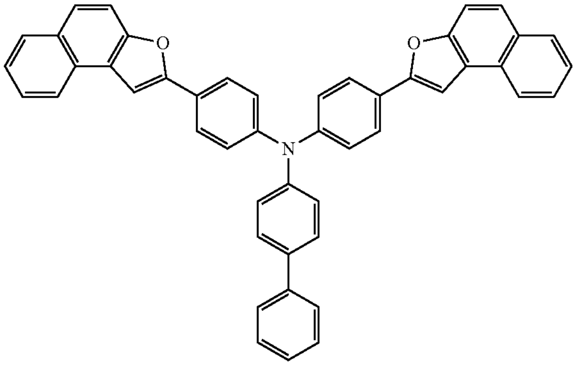
120
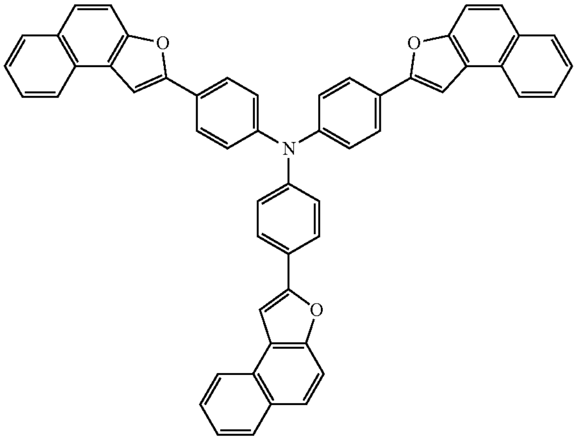

-continued
121
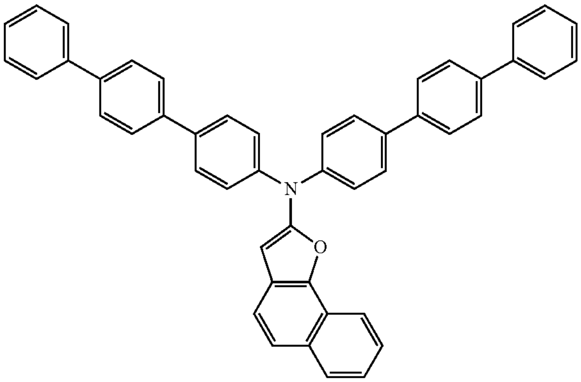
122
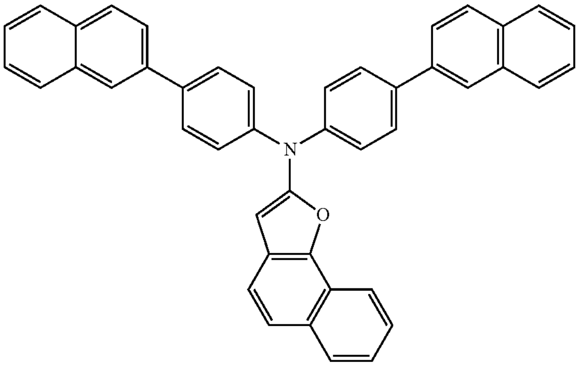
123
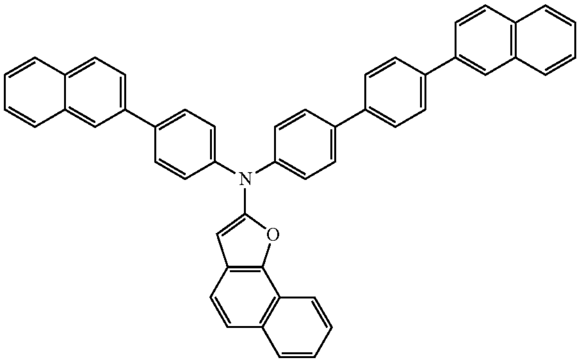
124
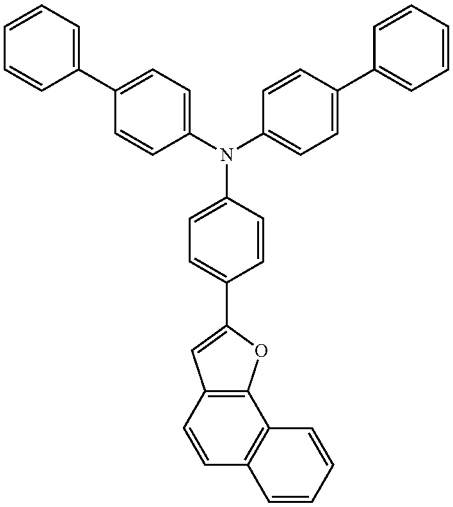
125
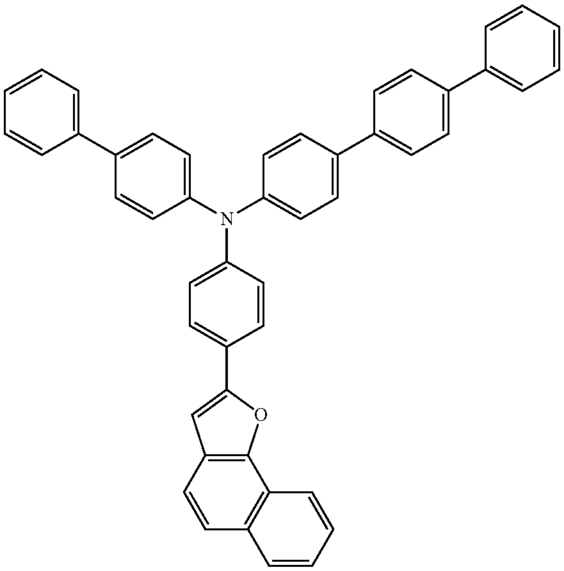
126
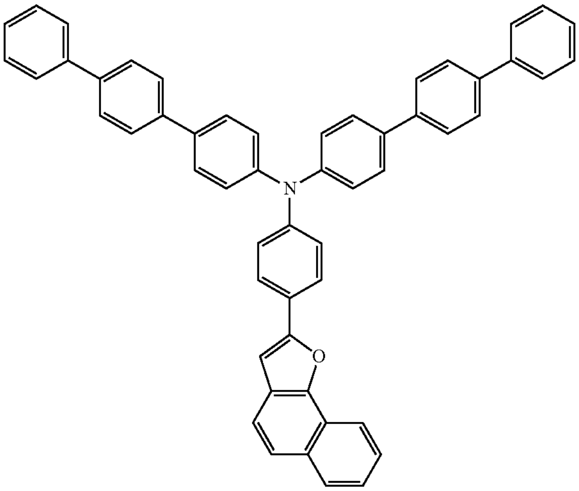

-continued
127
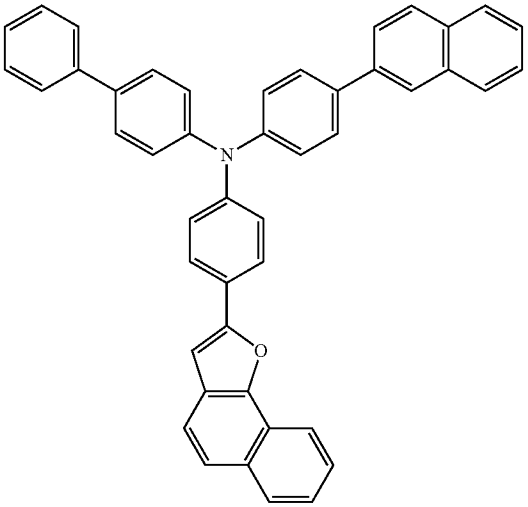
128
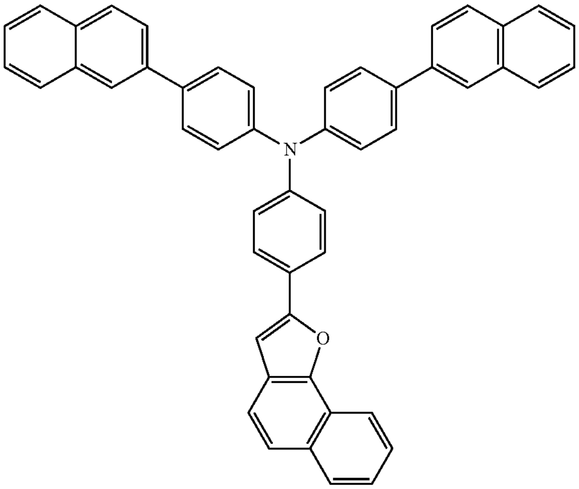
129
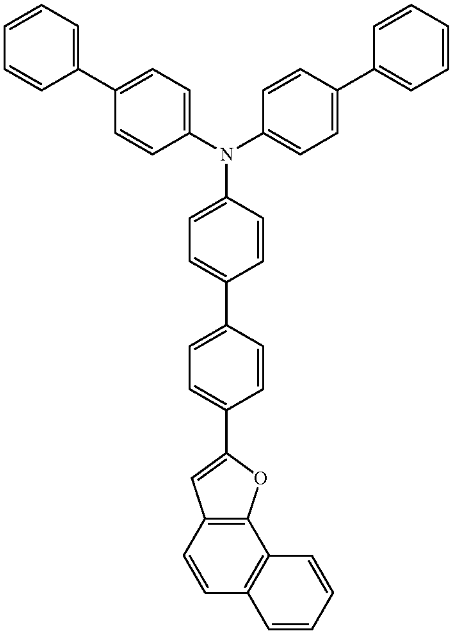
130
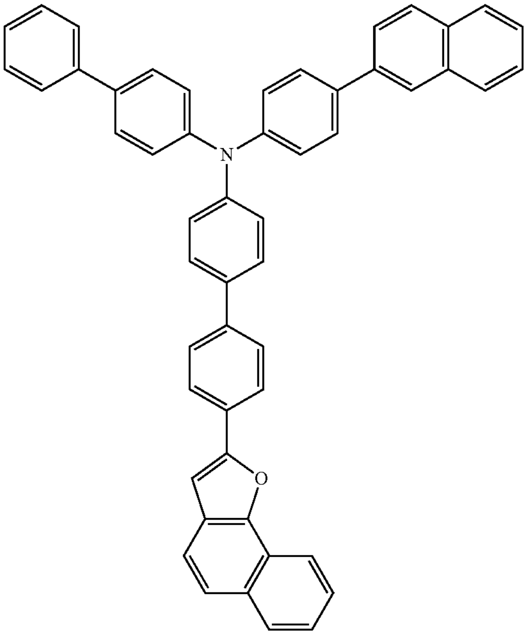
131
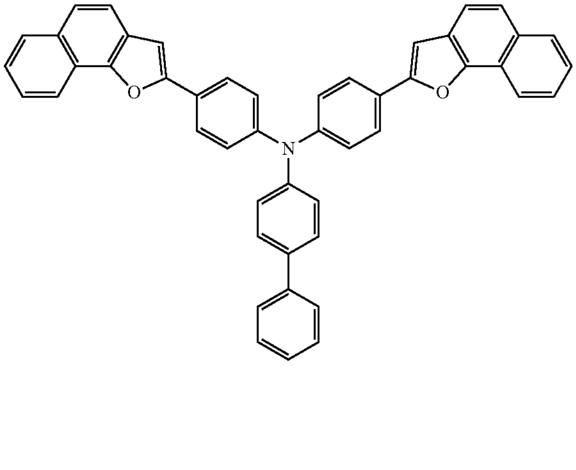
132
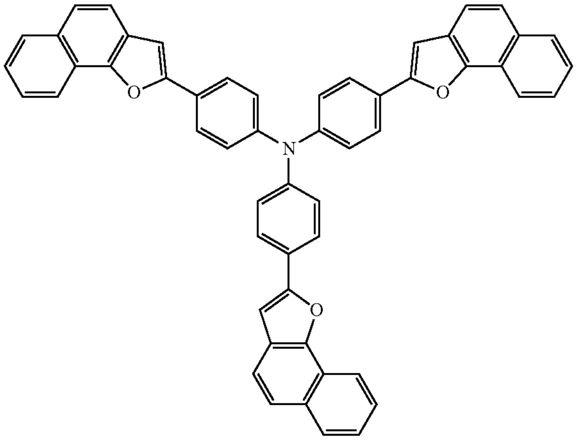

-continued
133
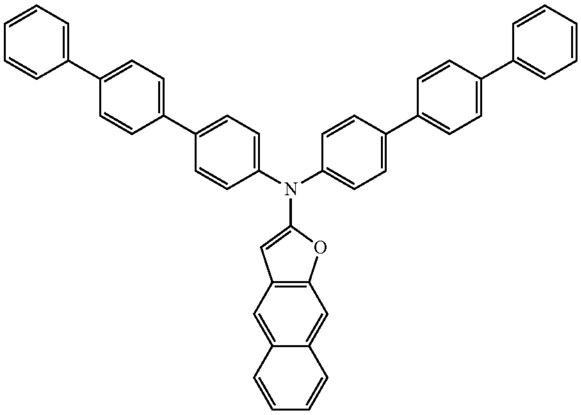
134
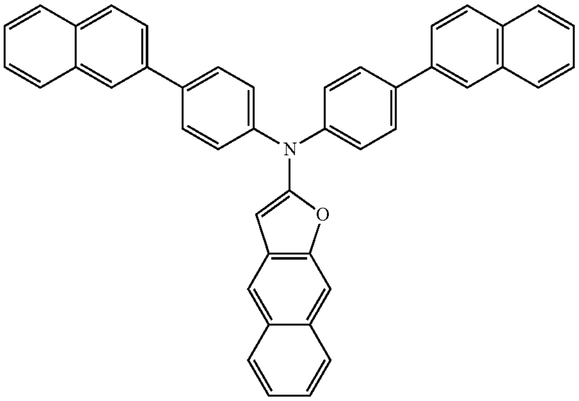
135
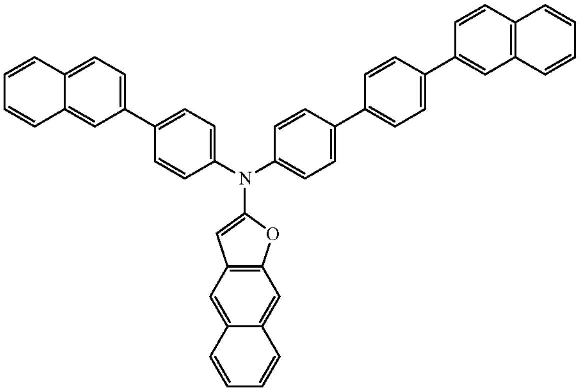
136
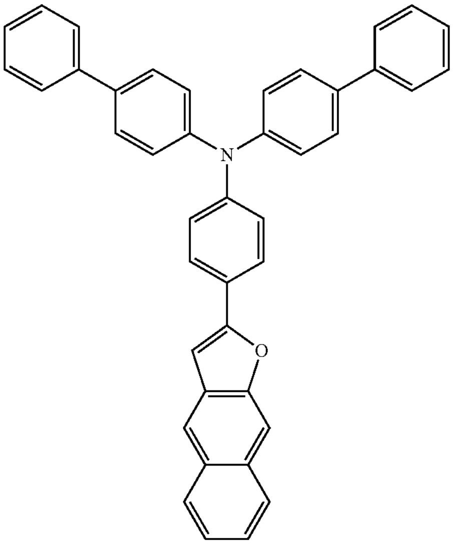
137
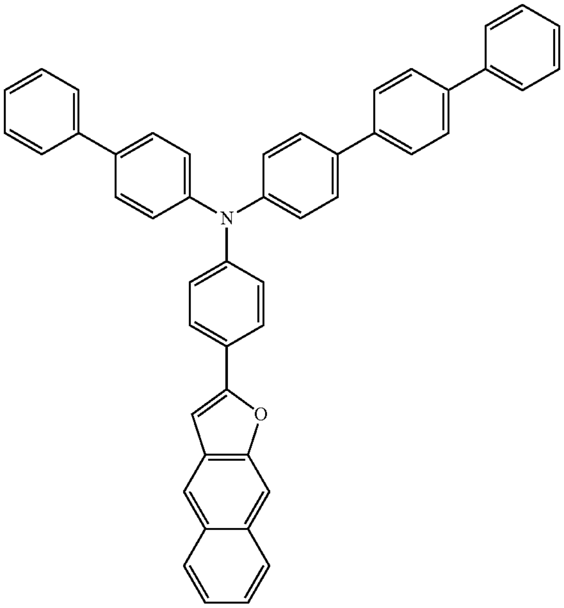
138
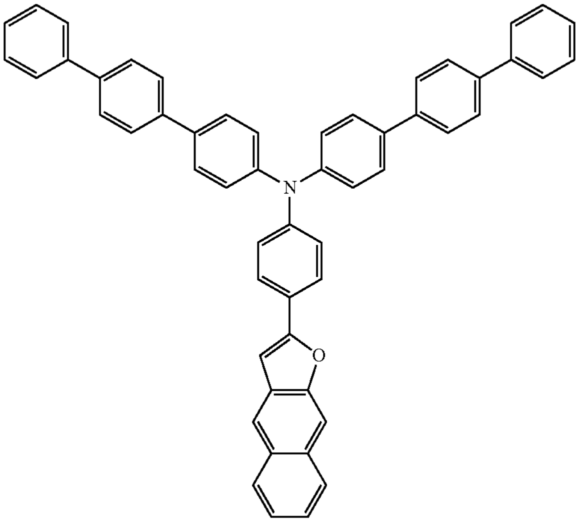

-continued
139
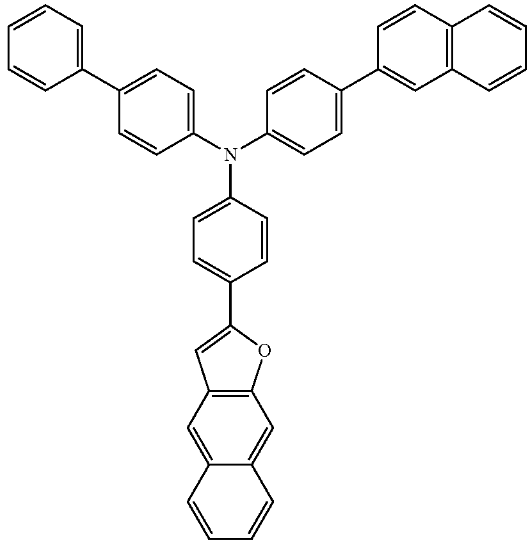
140
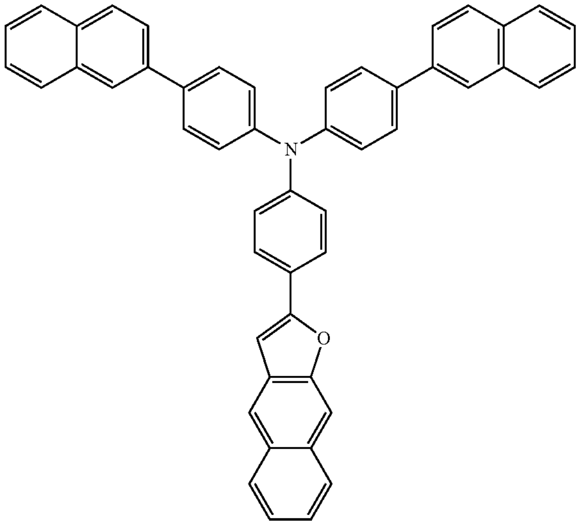
141
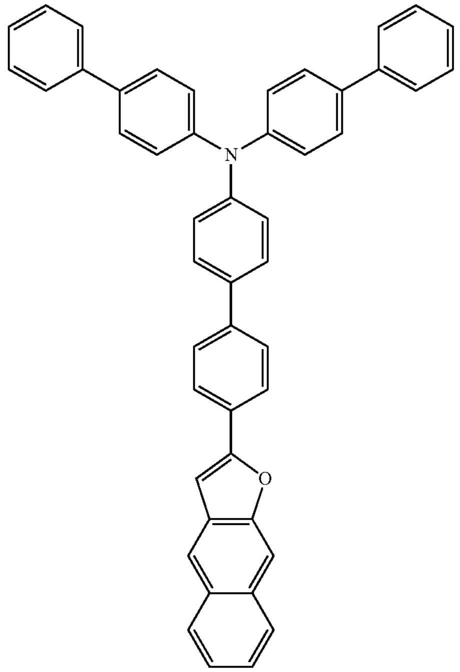
142
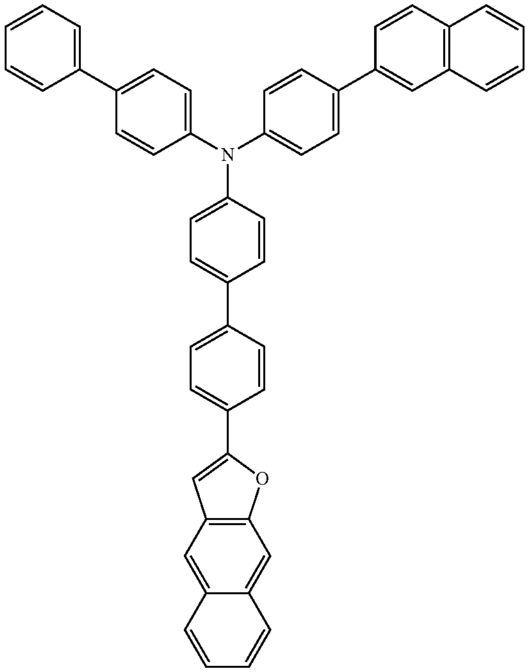

-continued
143
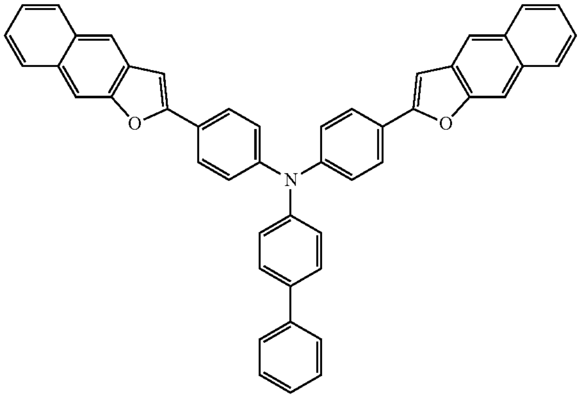
144
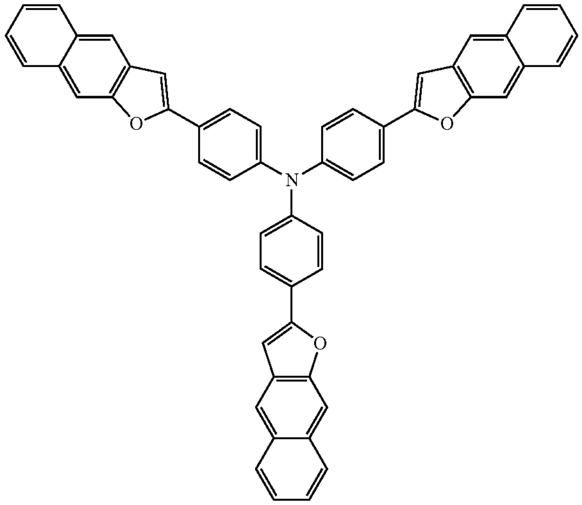
145
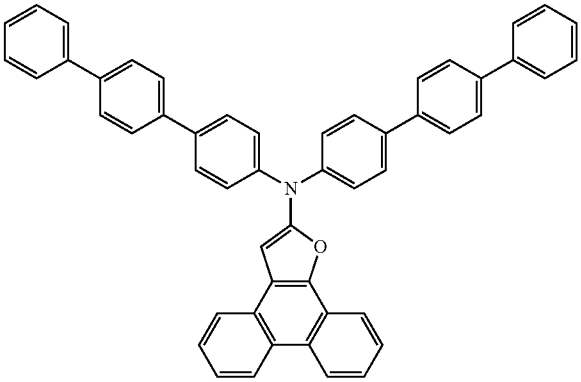
146
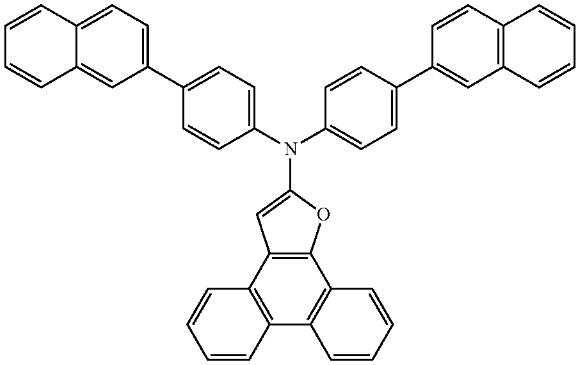
147
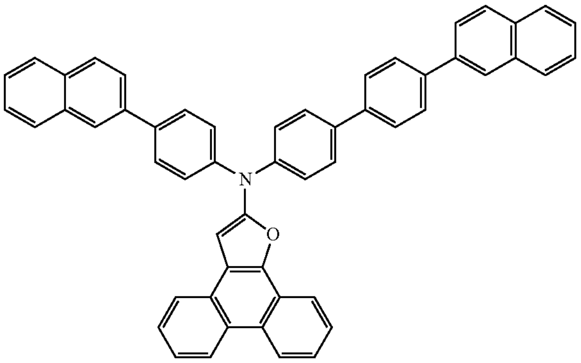
148
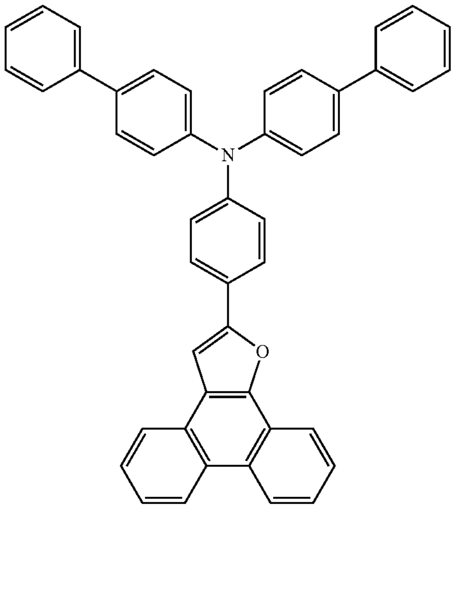

-continued
149
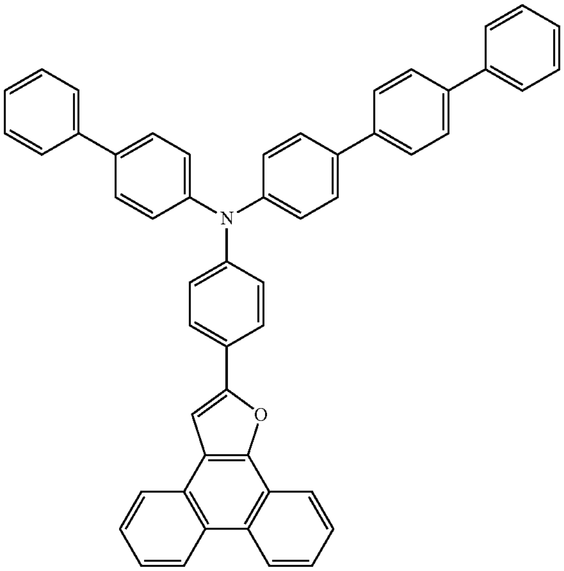
150
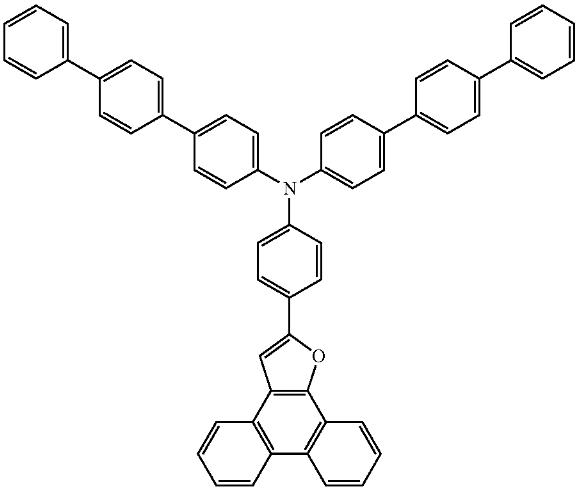
151
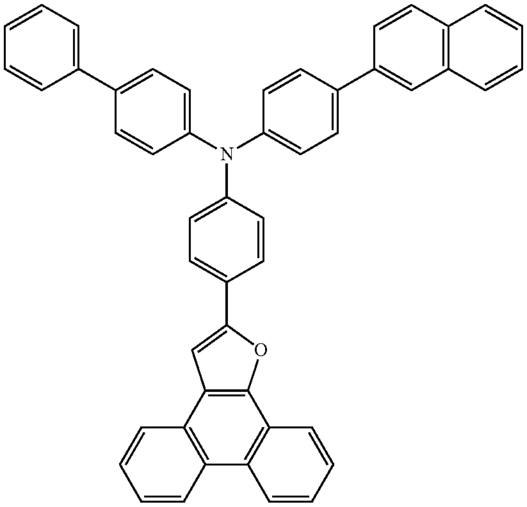
152
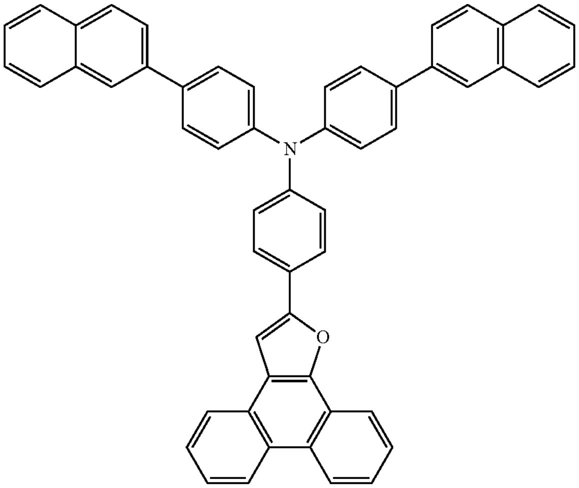

-continued
153
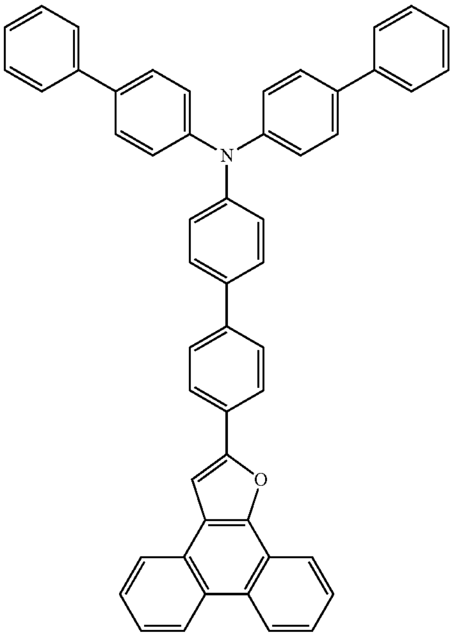
154
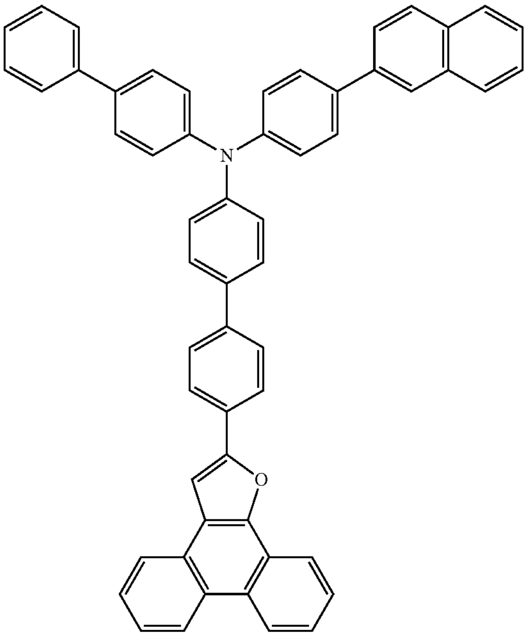
155
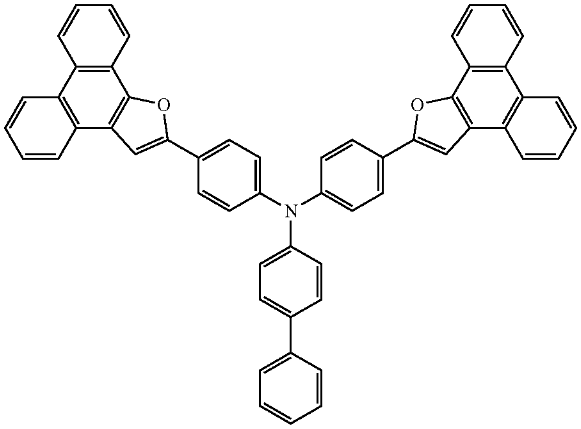
156
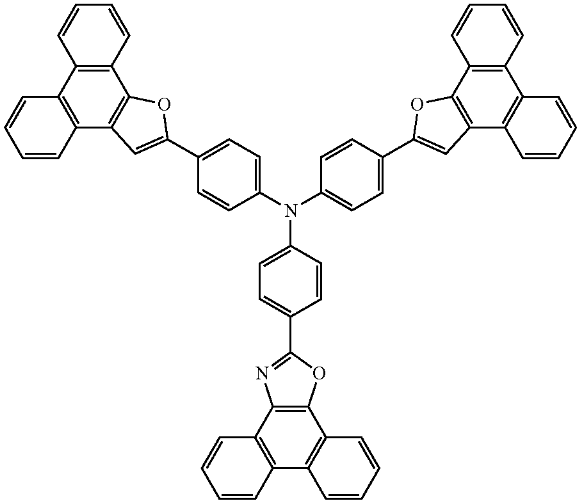
157
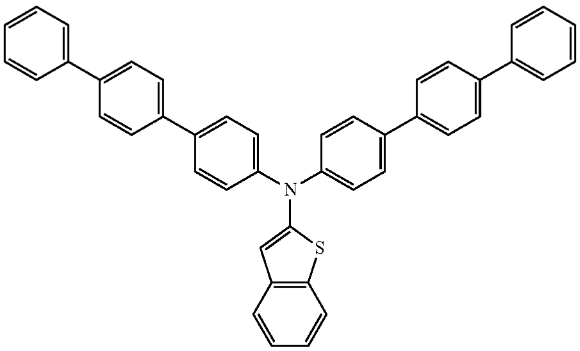
158
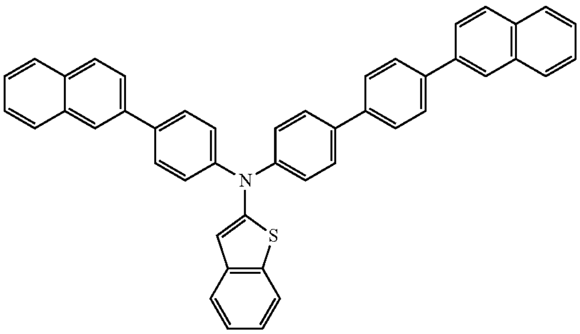

-continued
159
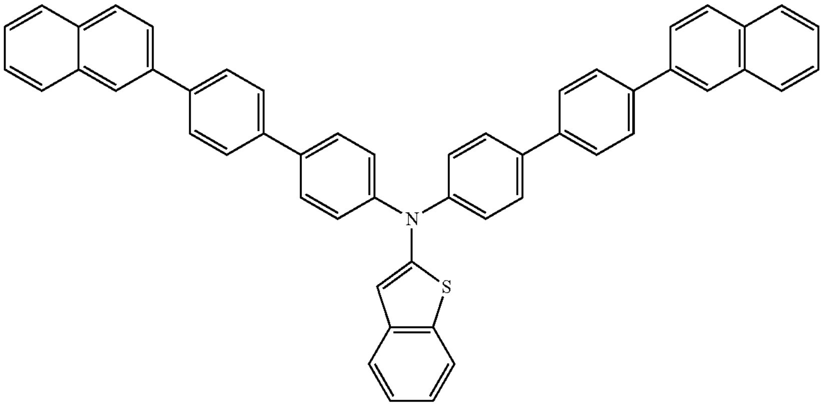
160
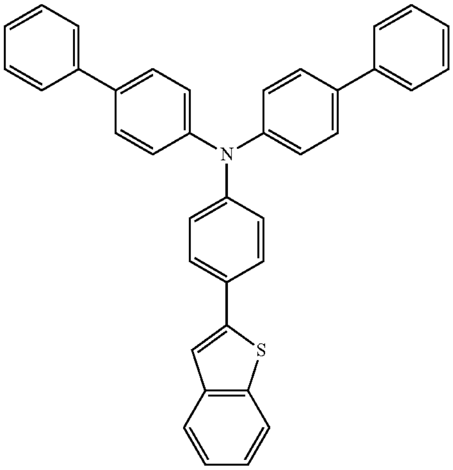
161
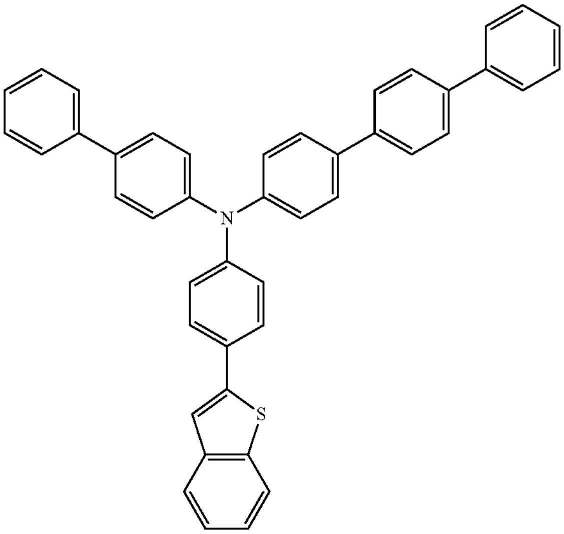
162
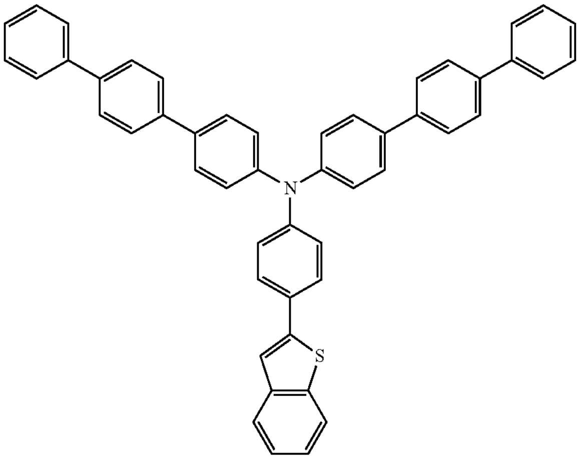
163
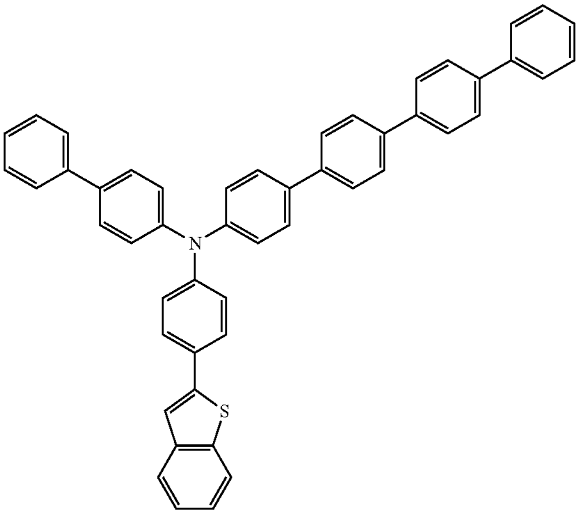

-continued
164
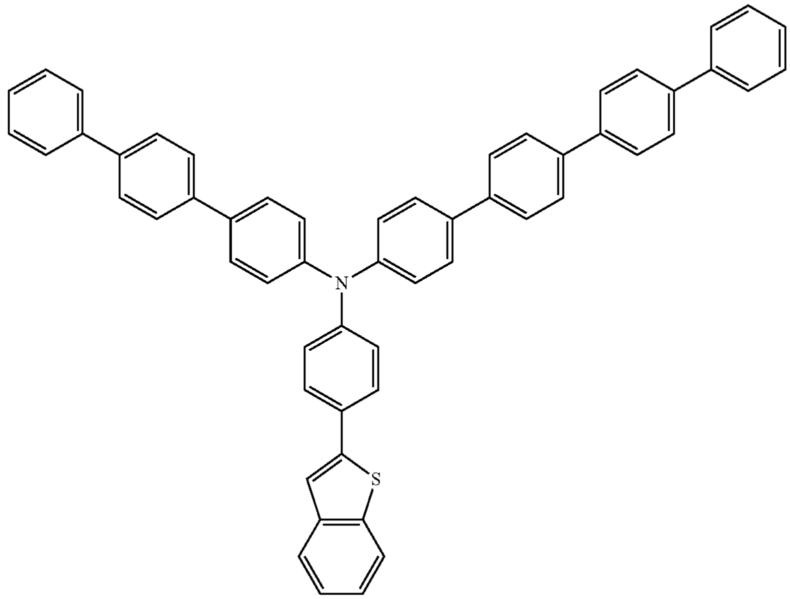
165
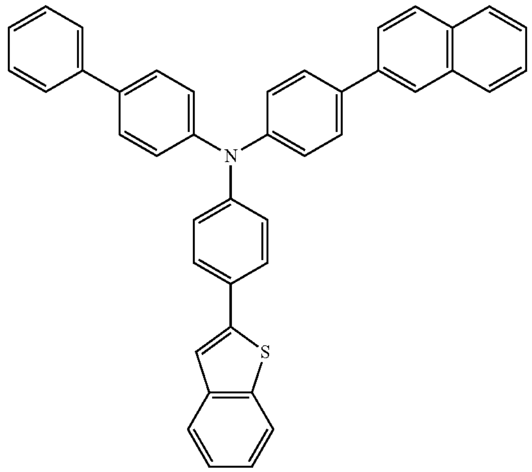
166
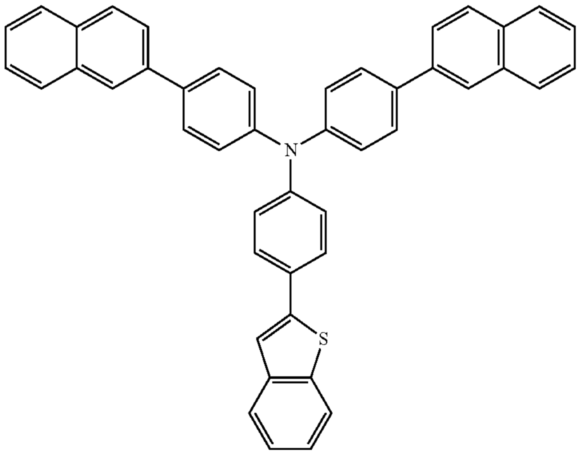
167
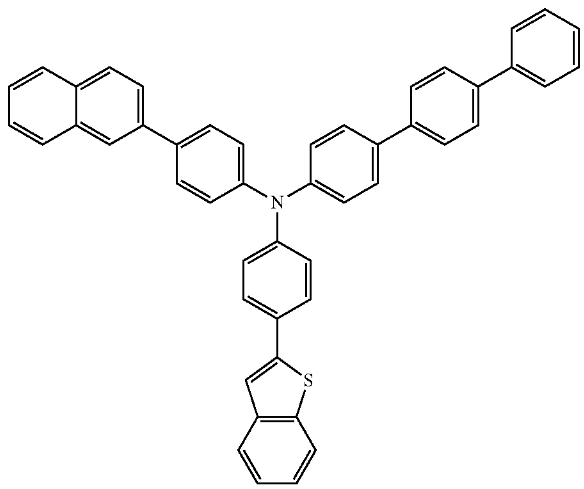
168
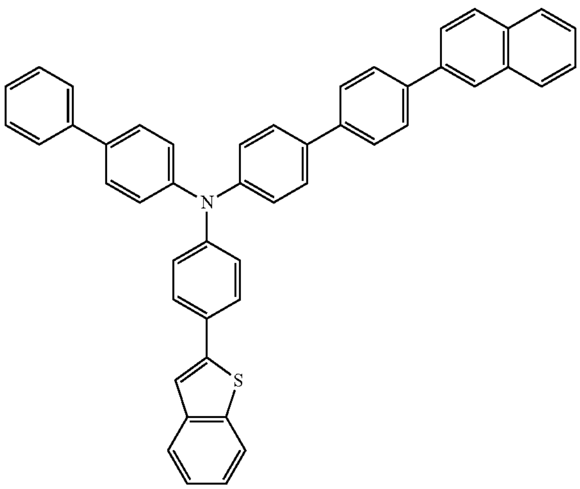

-continued
169
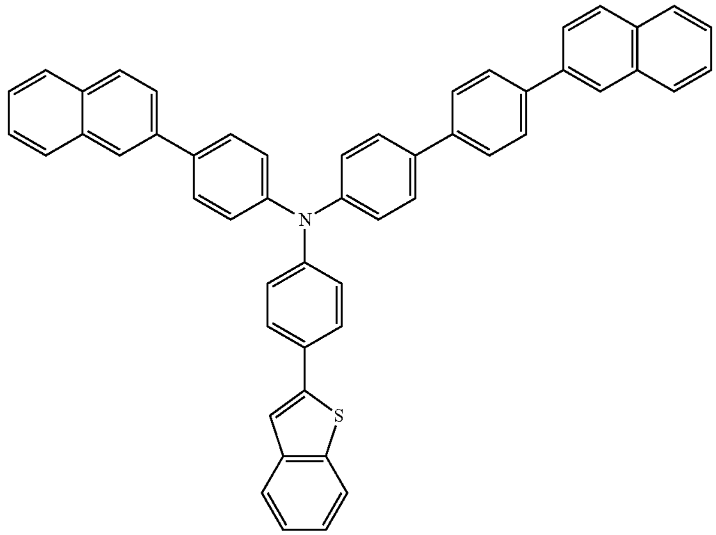
170
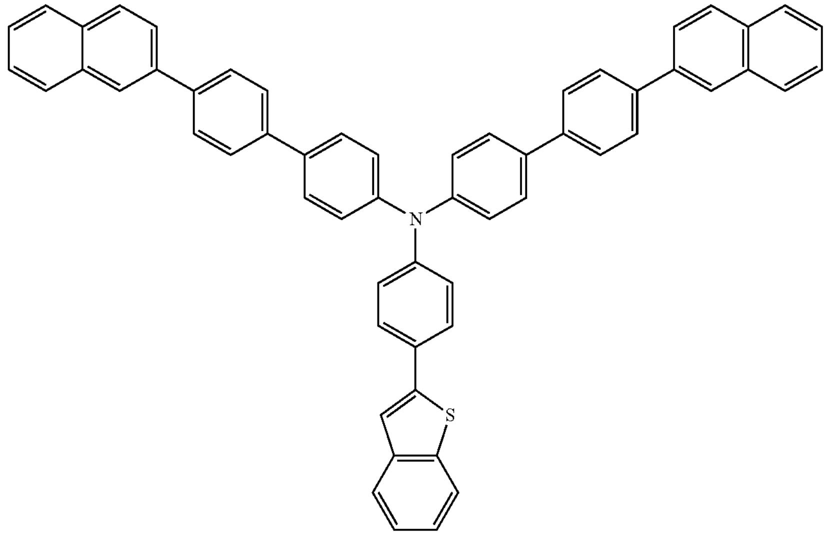
171
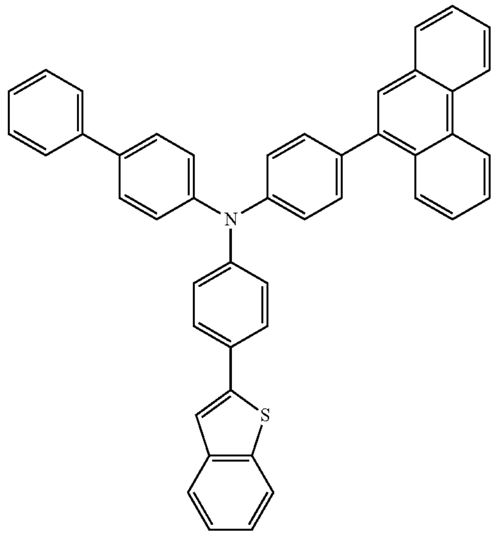
172
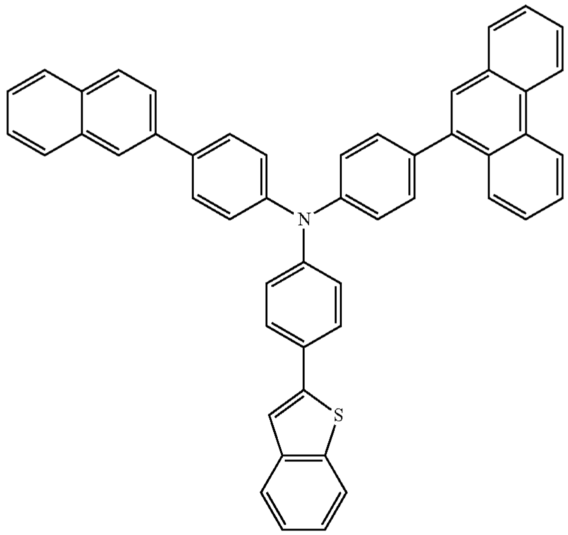

-continued
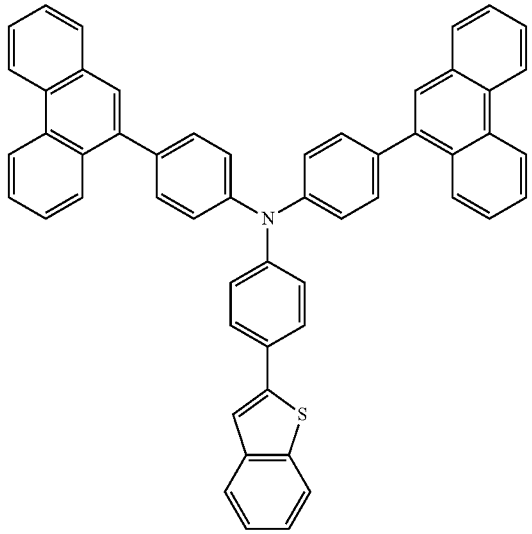
173
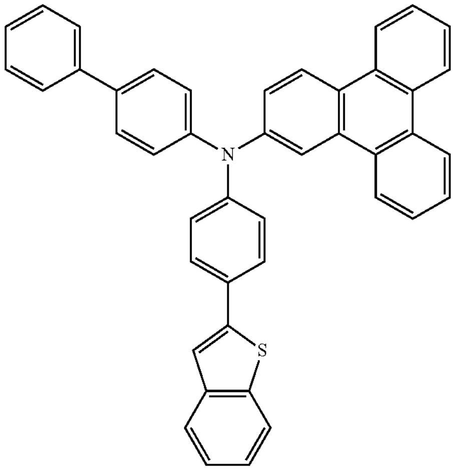
174
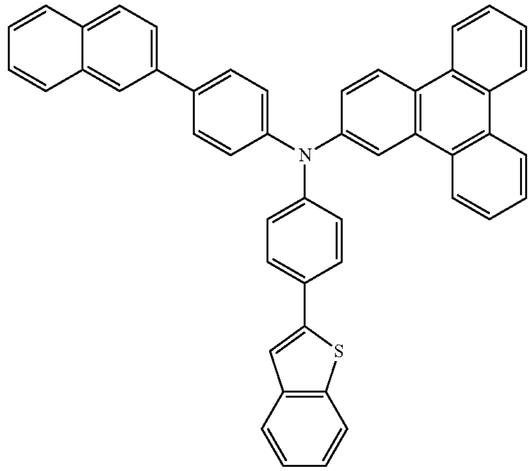
175
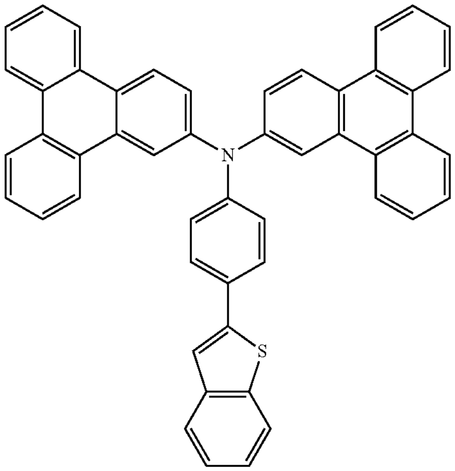
176
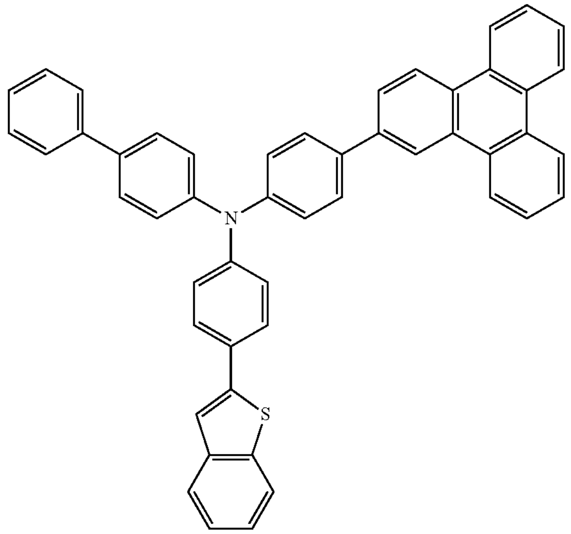
177
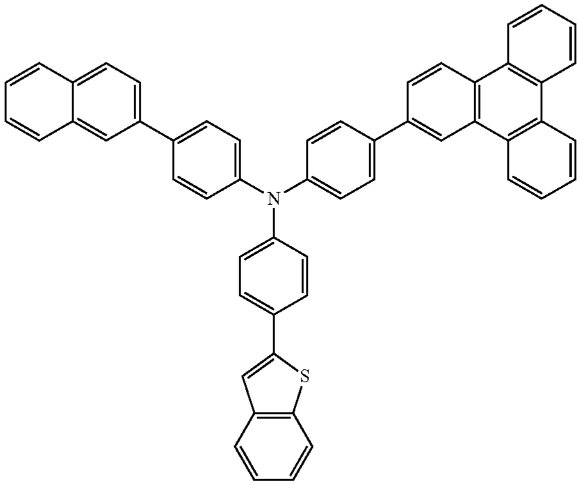
178

-continued
179
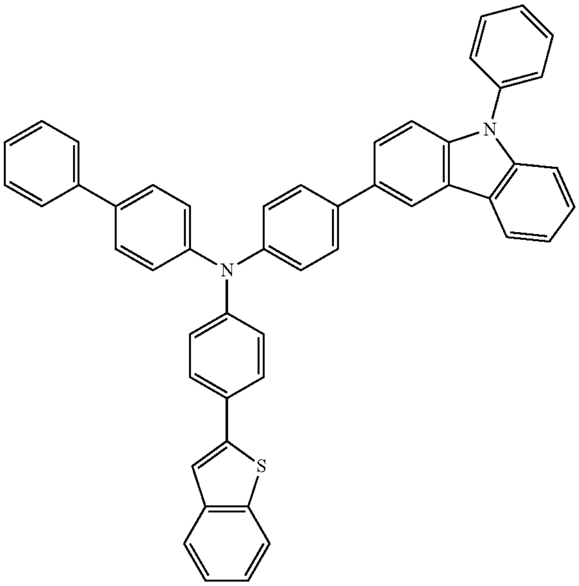
180
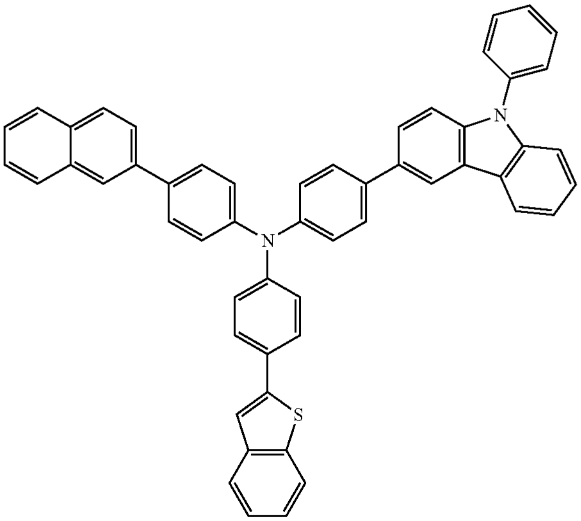
181
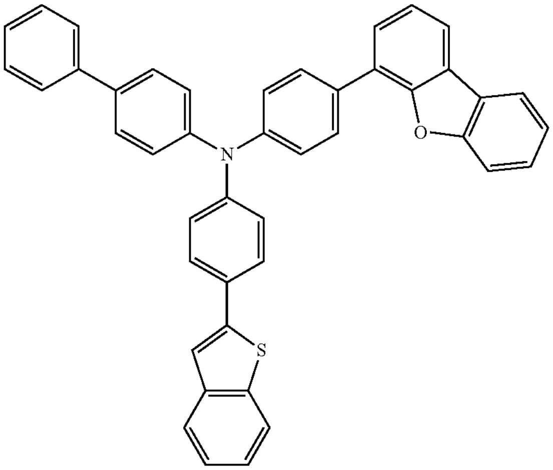
182
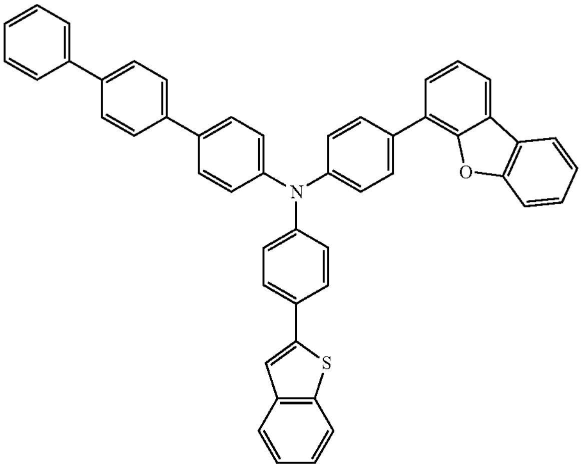
183
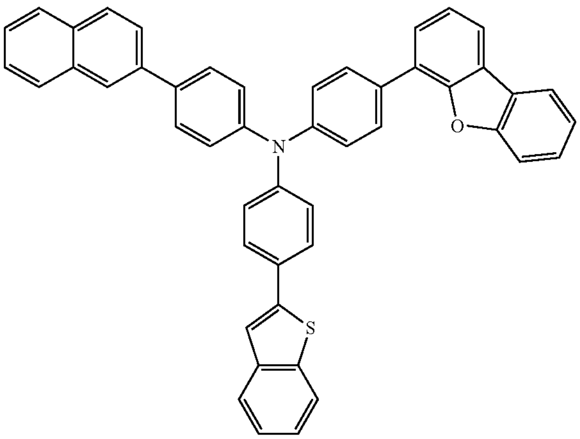
184
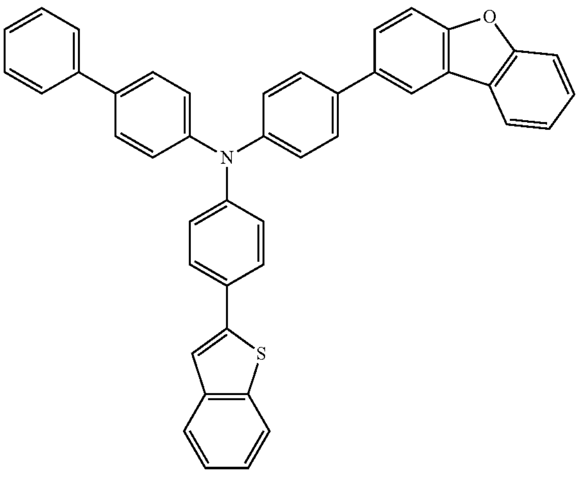

-continued
185
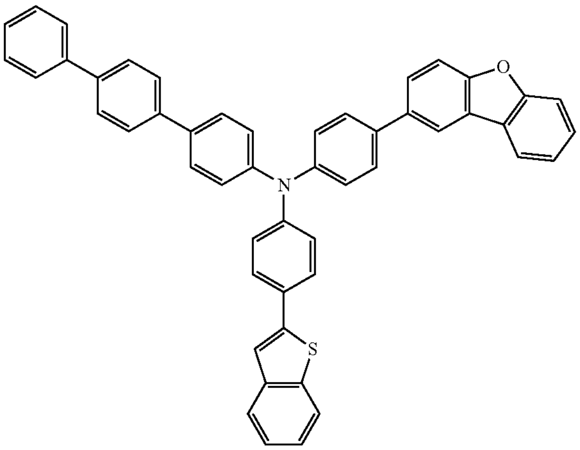
186
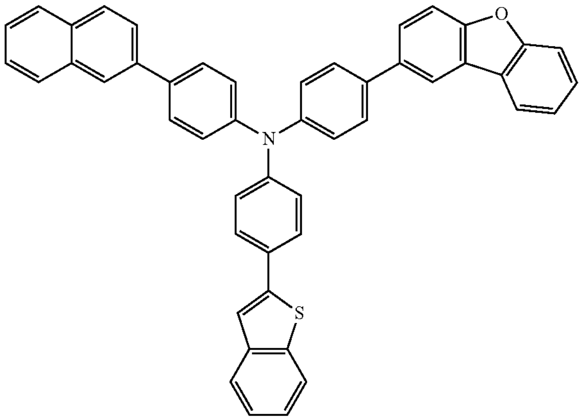
187
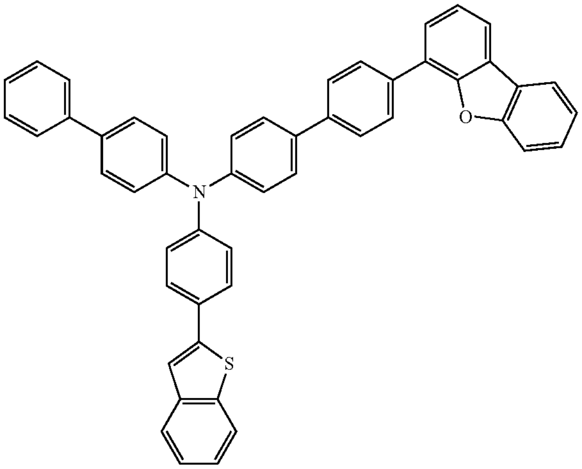
188
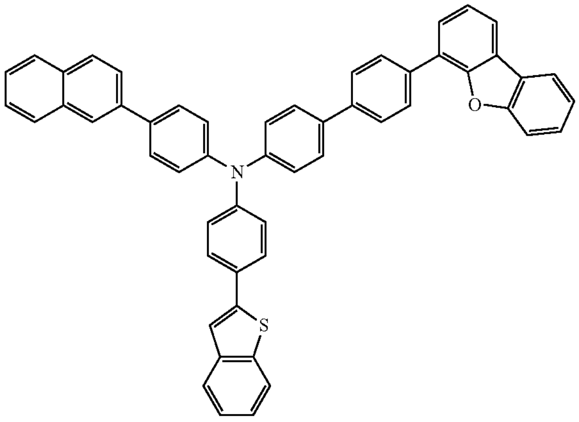
189
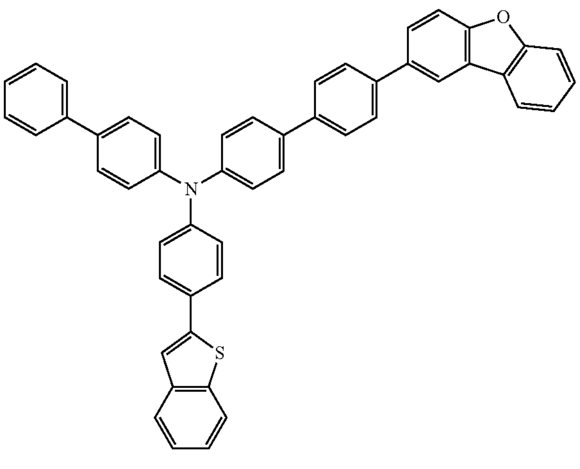
190
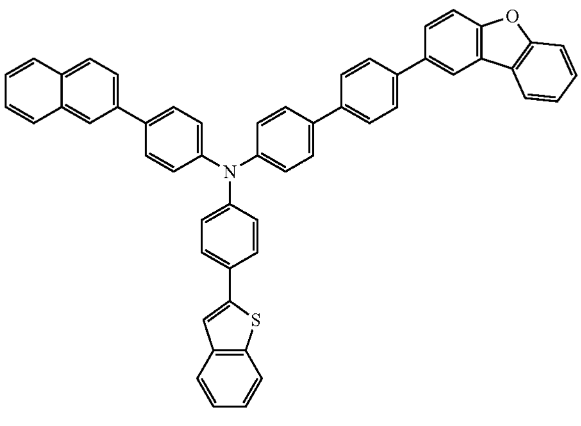

-continued
191
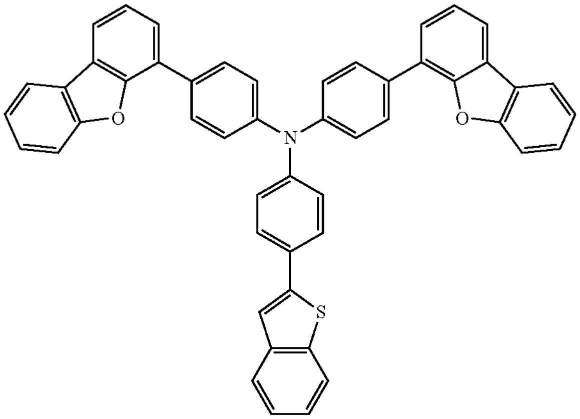
192
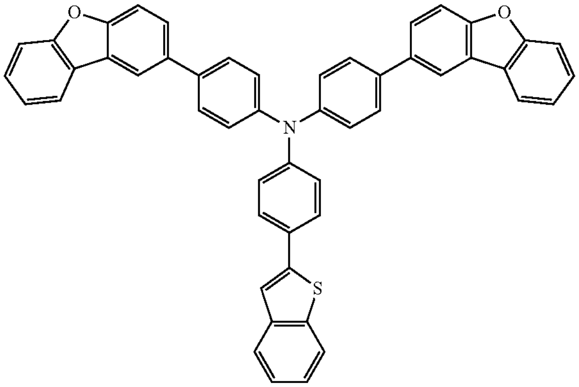
193
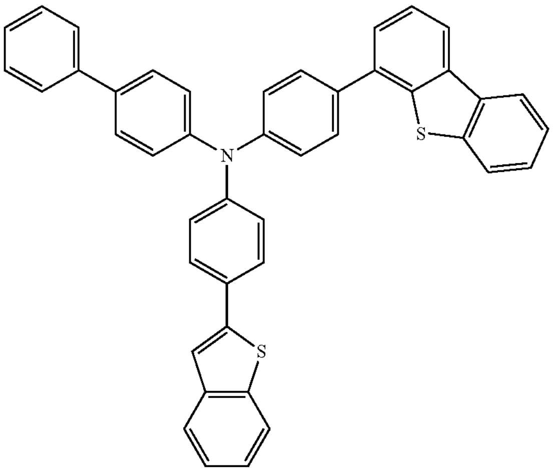
194
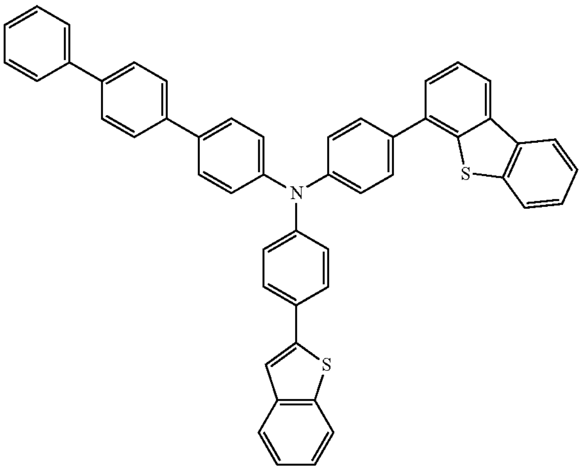
195
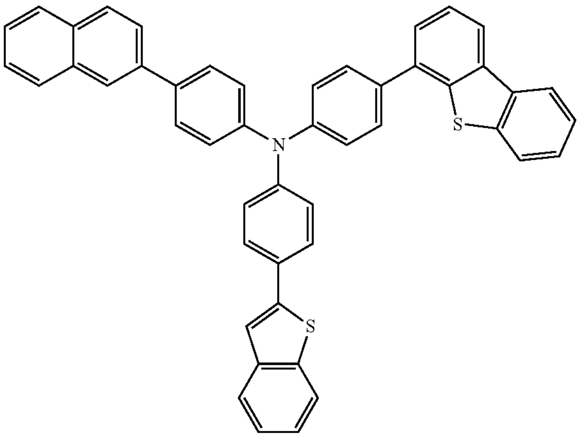
196
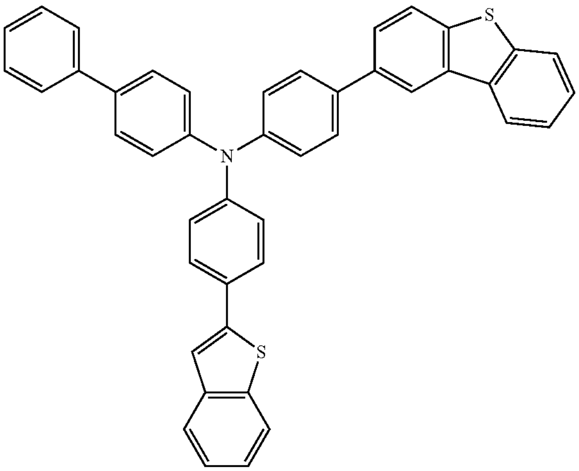

-continued
197
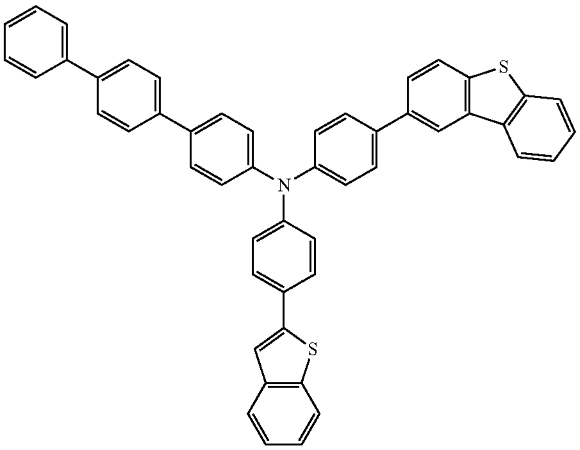
198
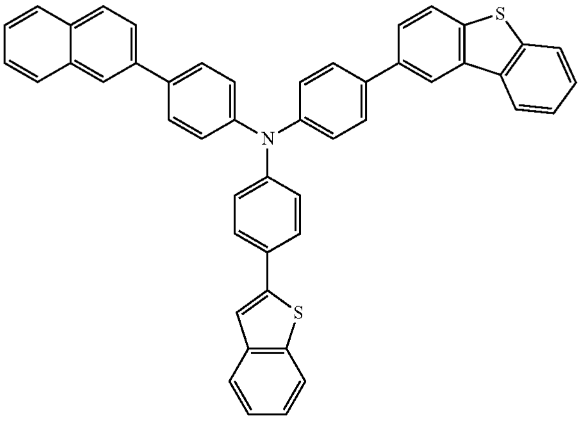
199
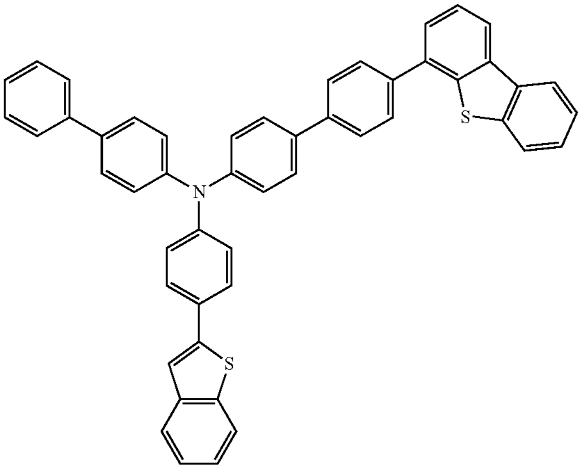
200
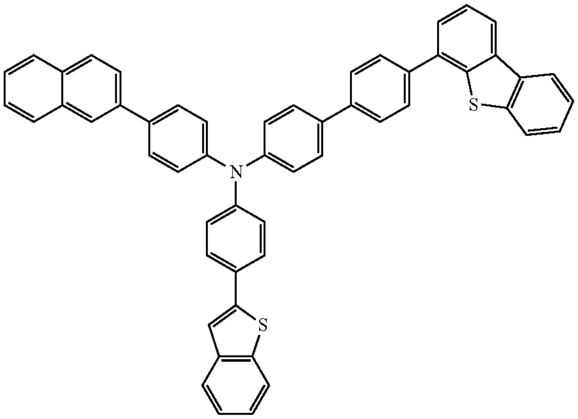
201
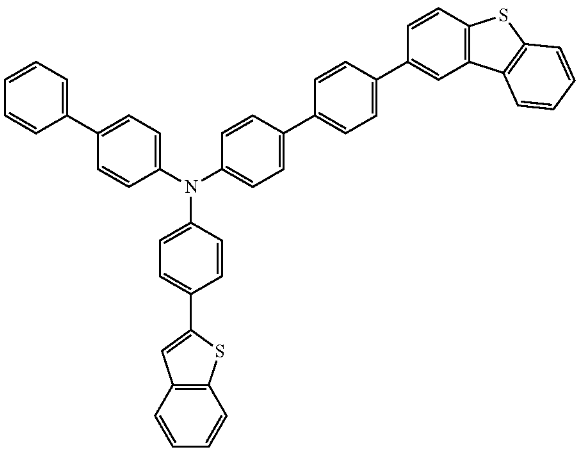
202
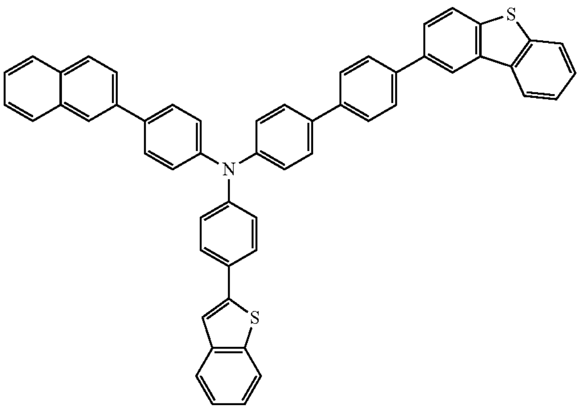

-continued
203
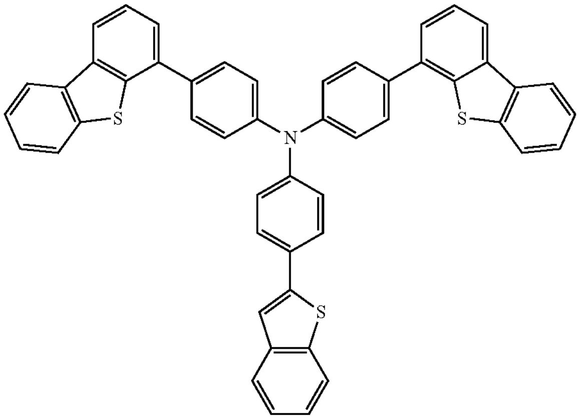
204
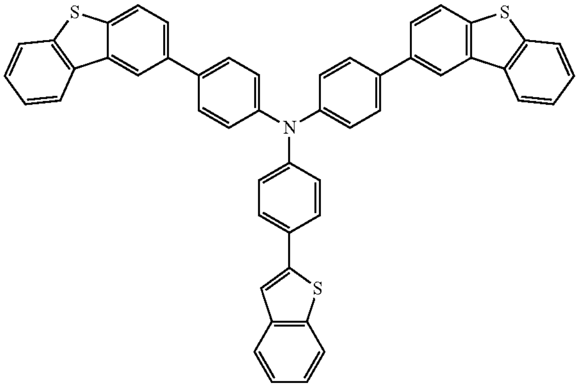
205
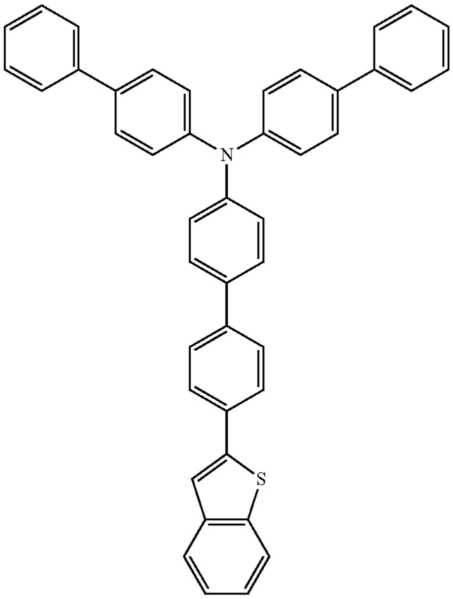
206
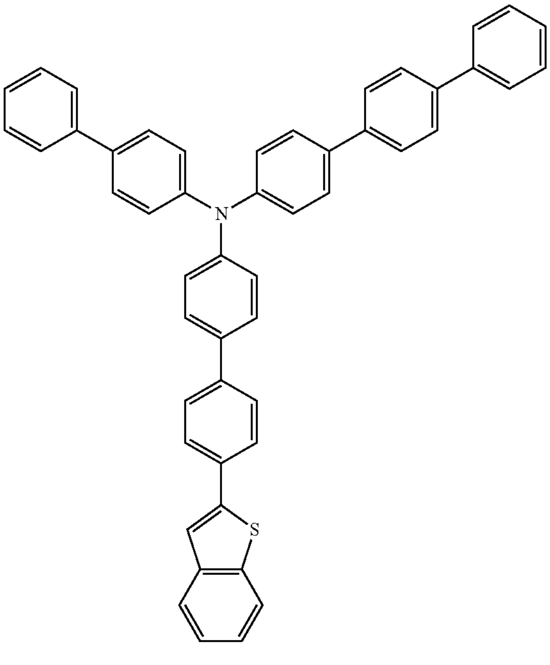

-continued
207
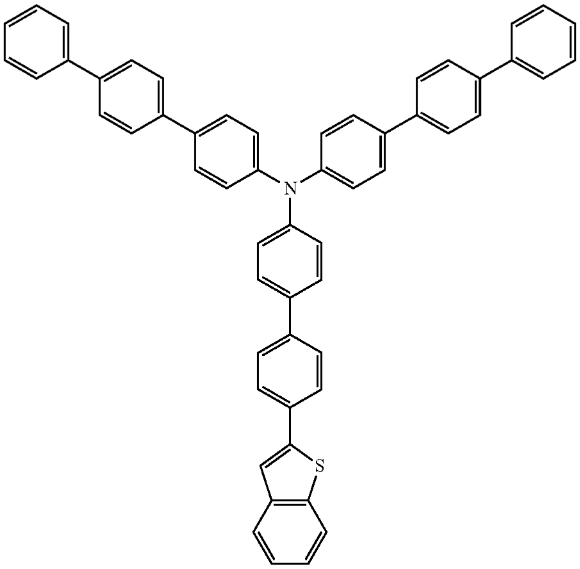
208
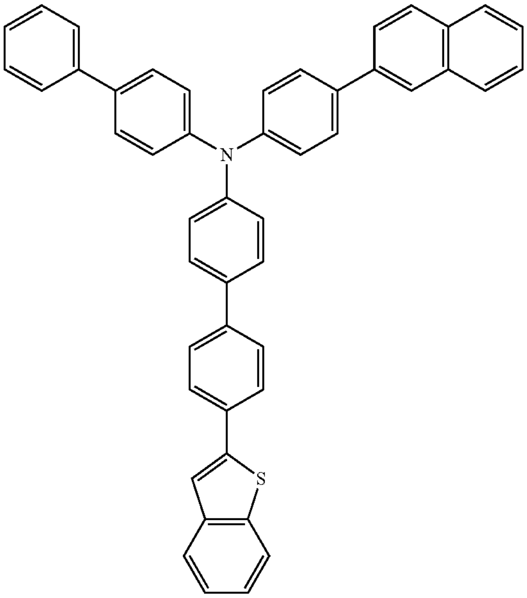
209
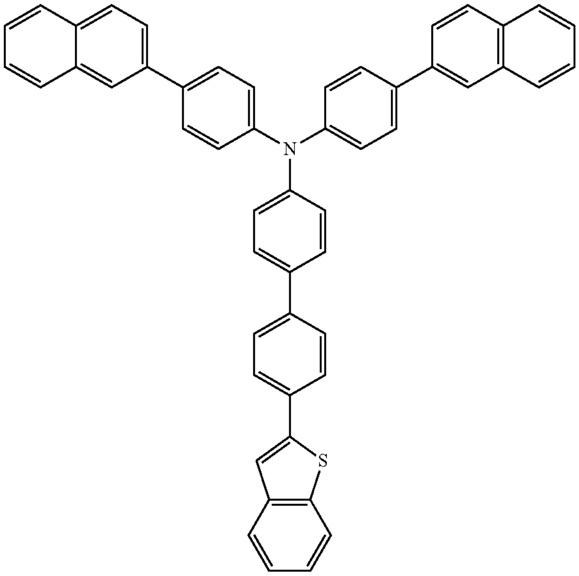
210
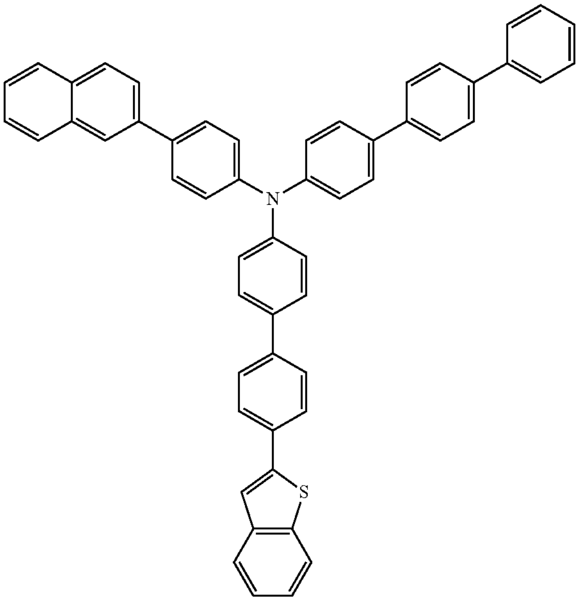

-continued
211
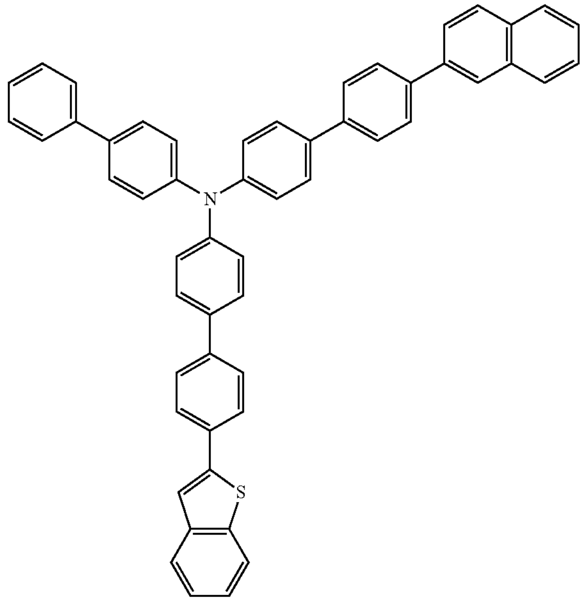
212
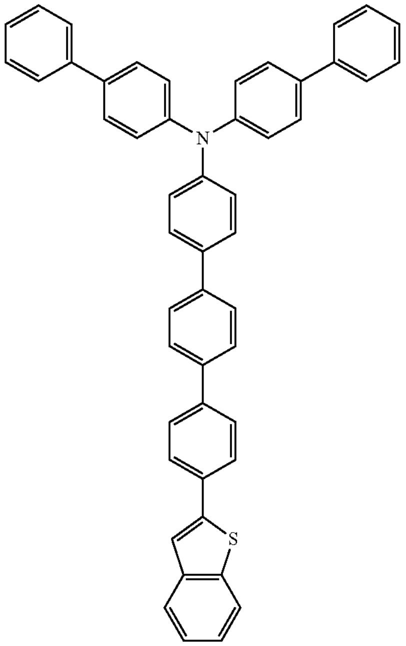
213
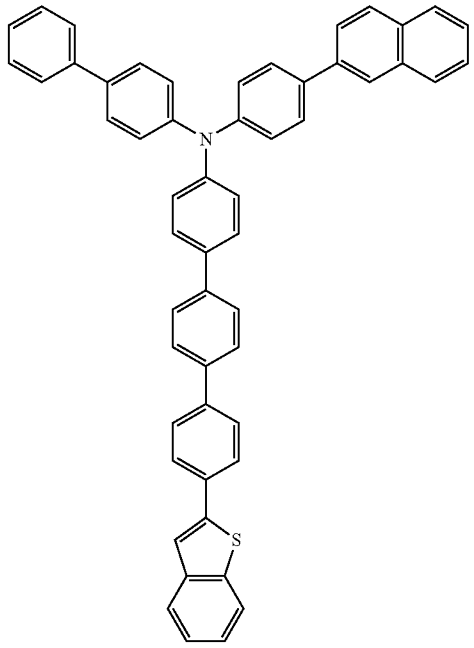
214
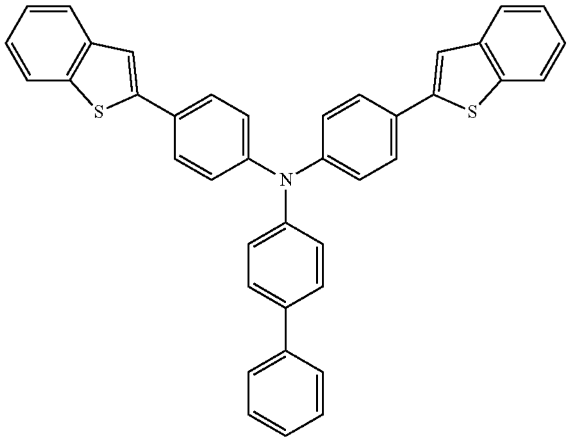

-continued
215
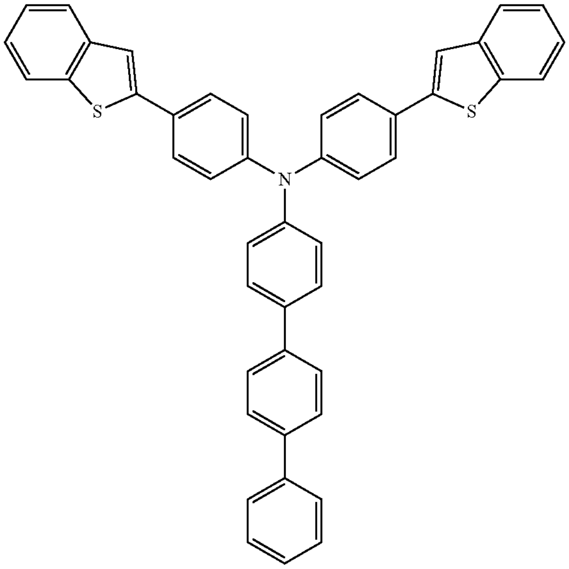
216
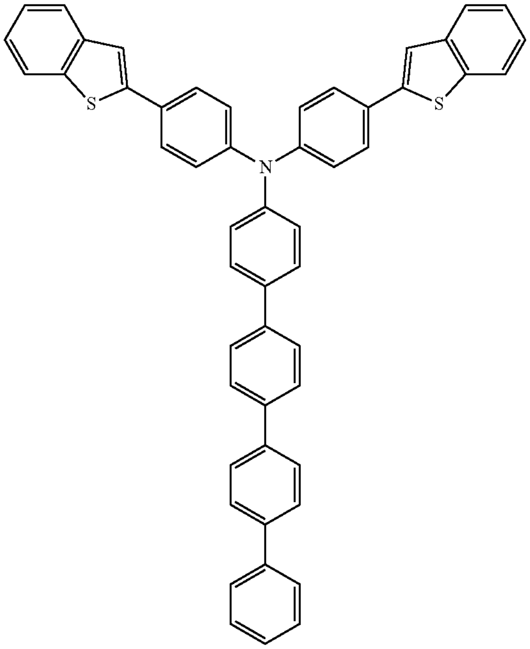
217
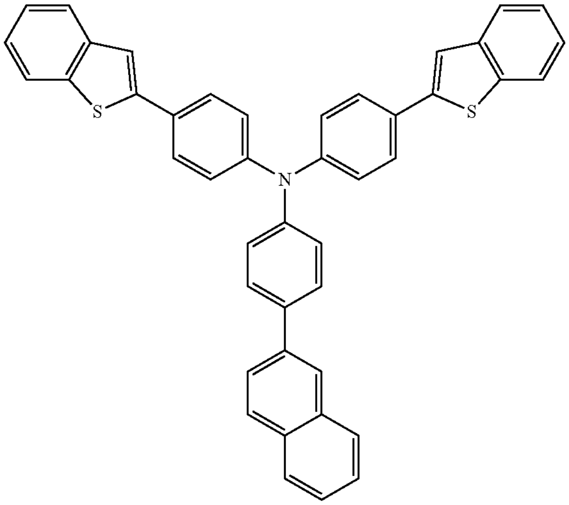
218
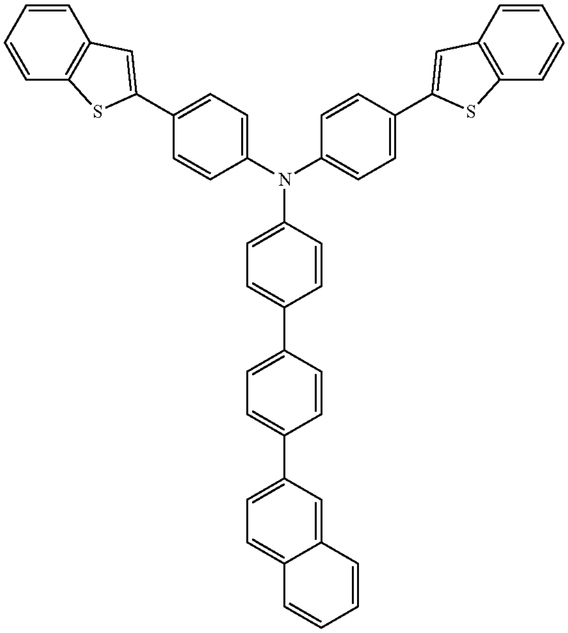

-continued
219
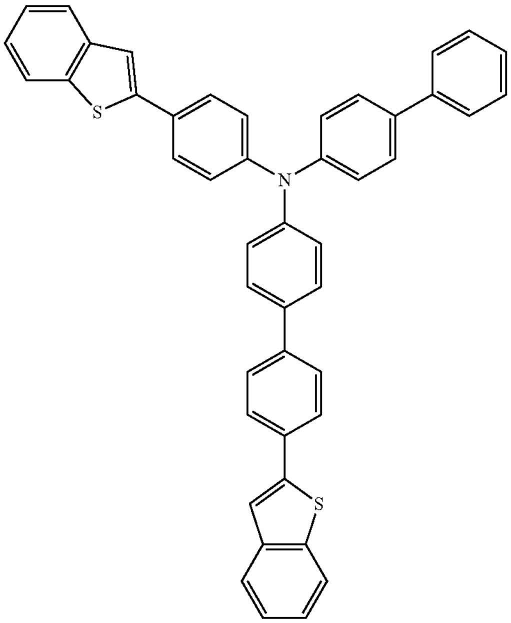
220
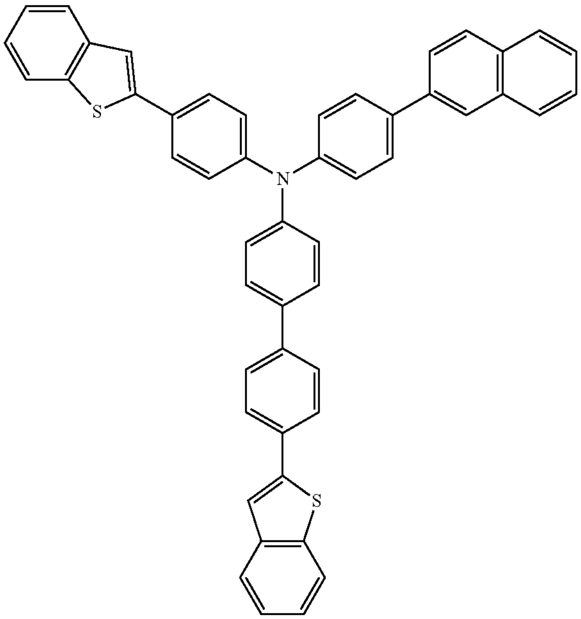
221
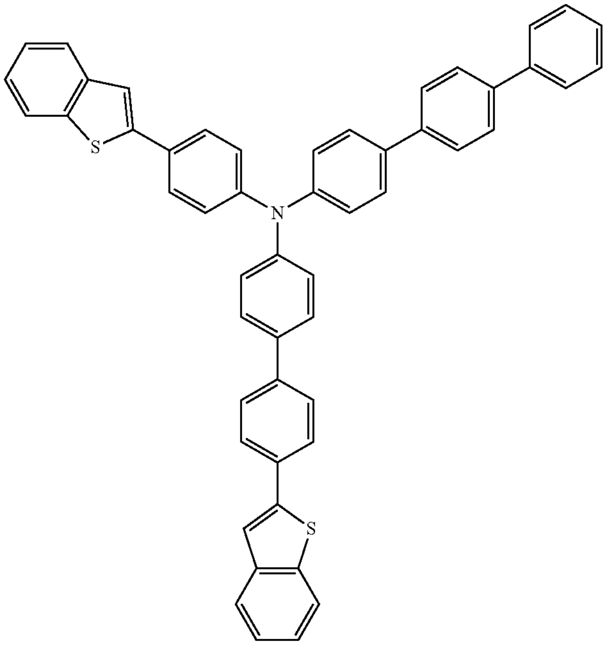
222
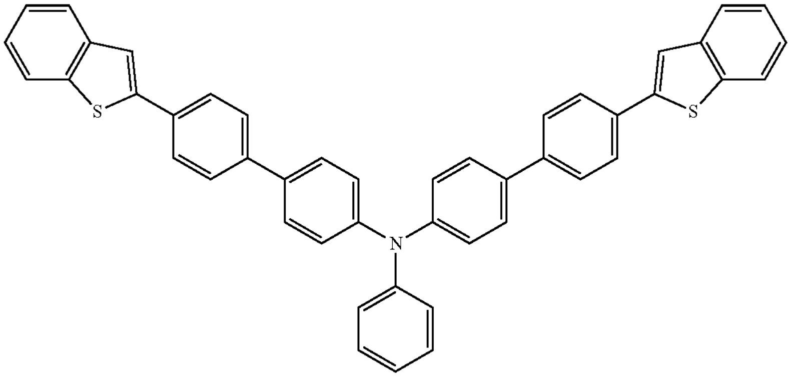

-continued
223
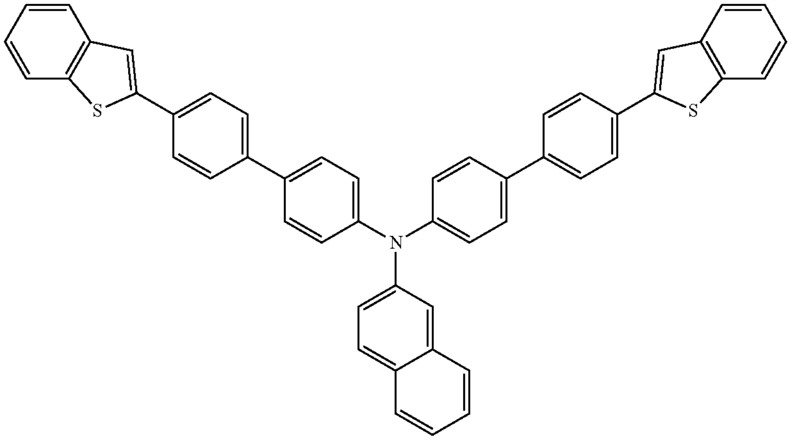
224
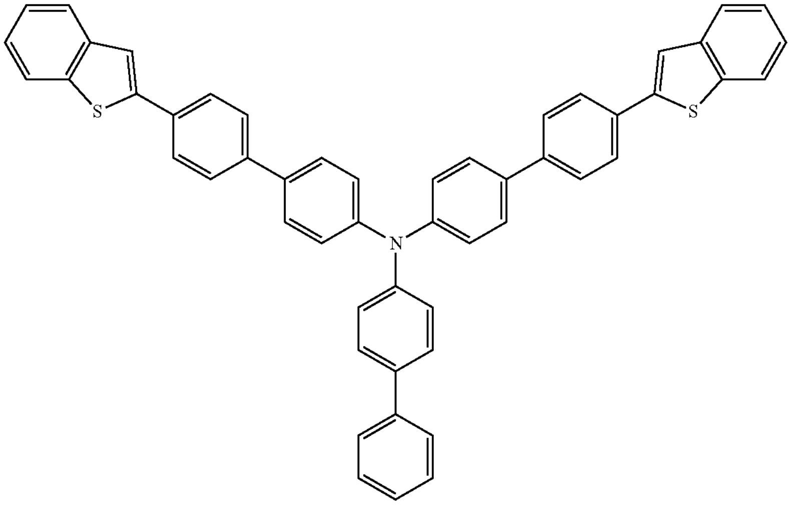
225
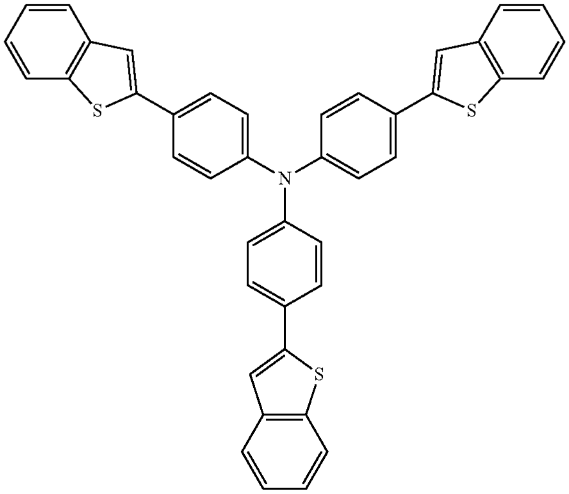
226
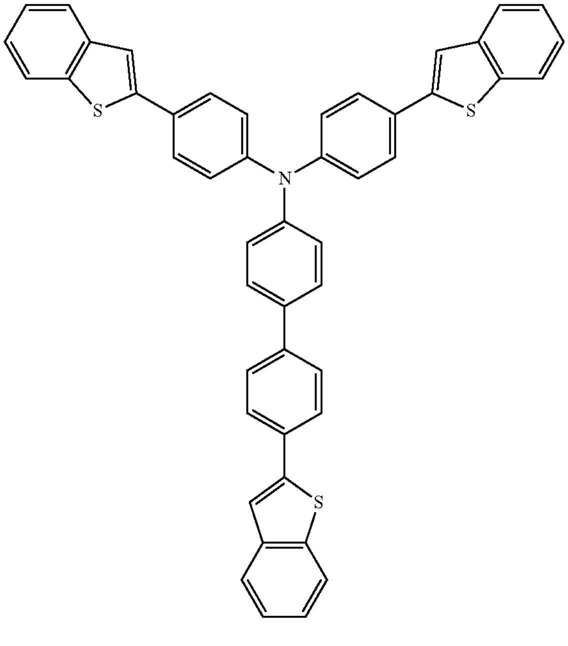

-continued
227
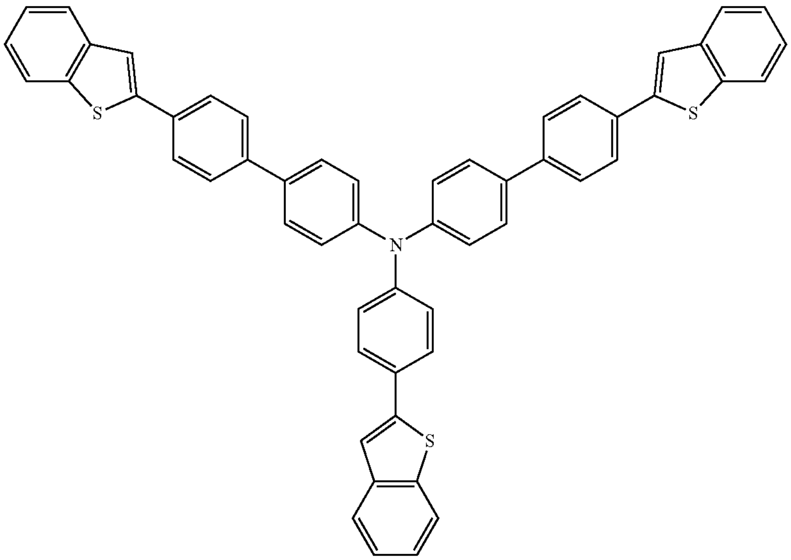
228
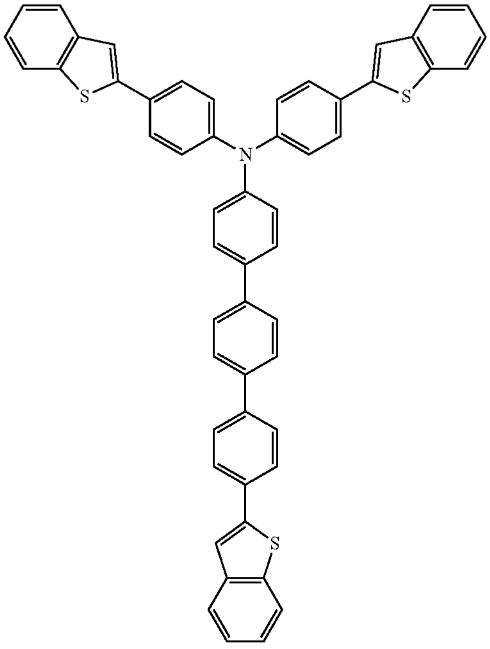
229
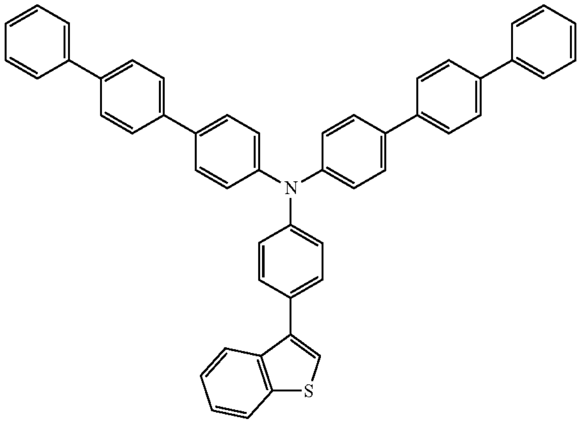

-continued
230
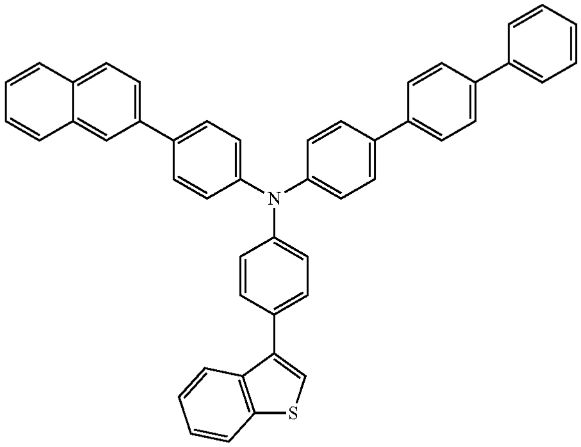
231
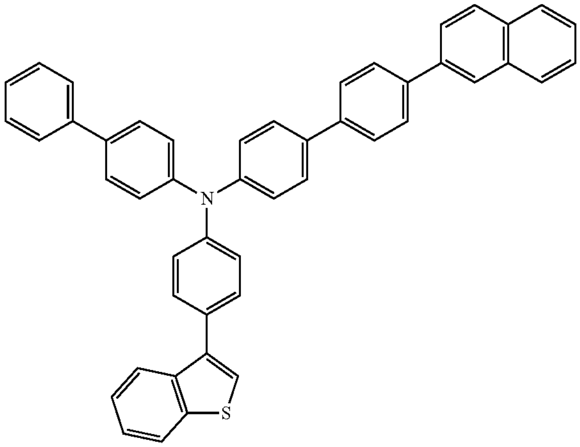
232
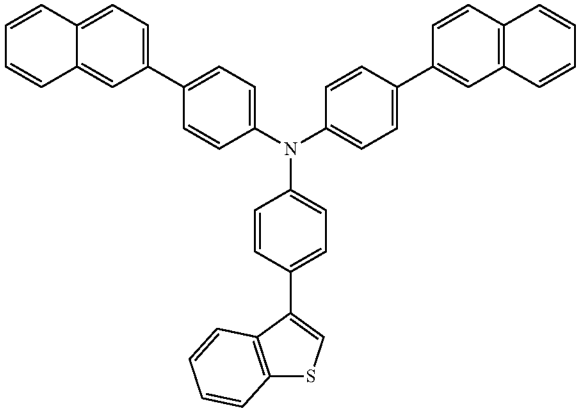
233
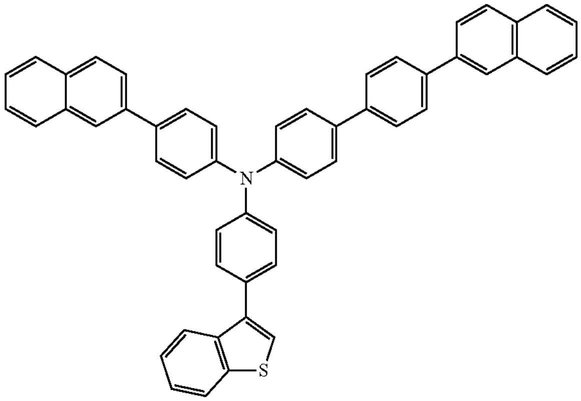
234
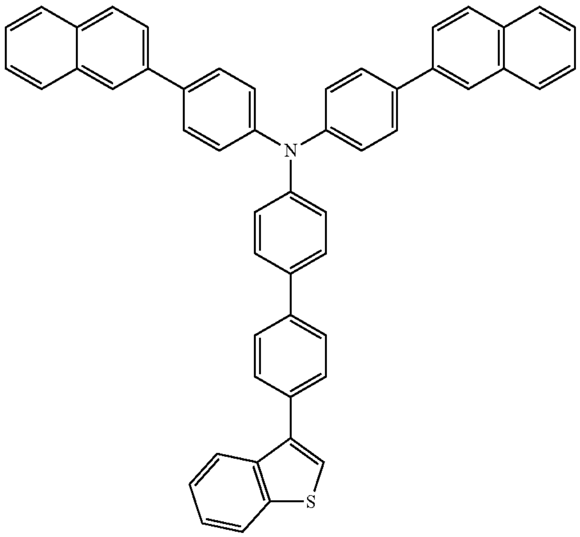
235
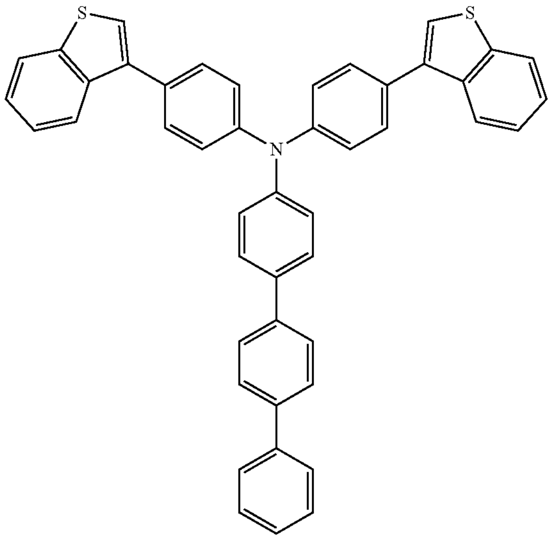

-continued
236
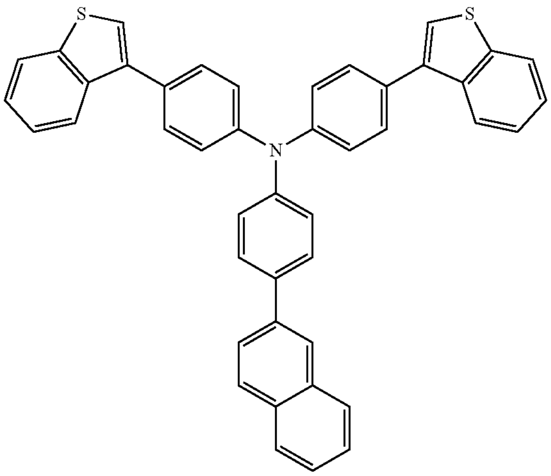
237
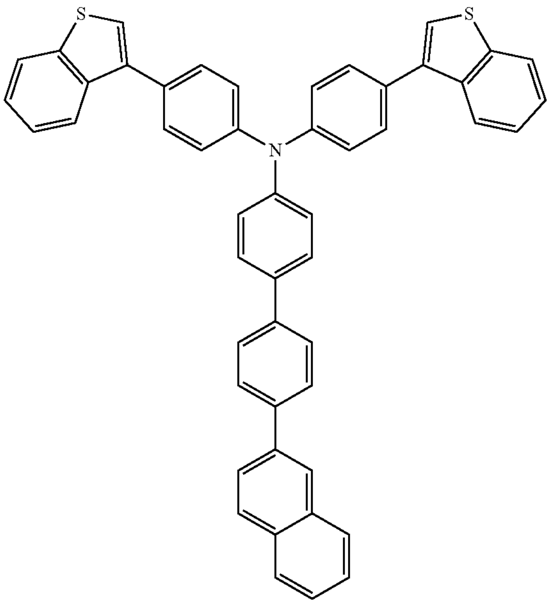
238
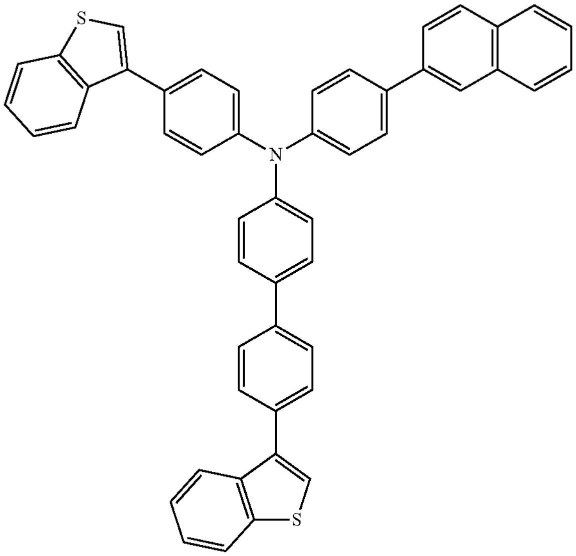
239
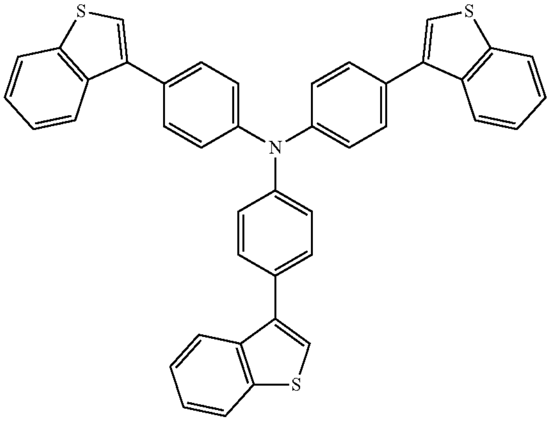

-continued
240
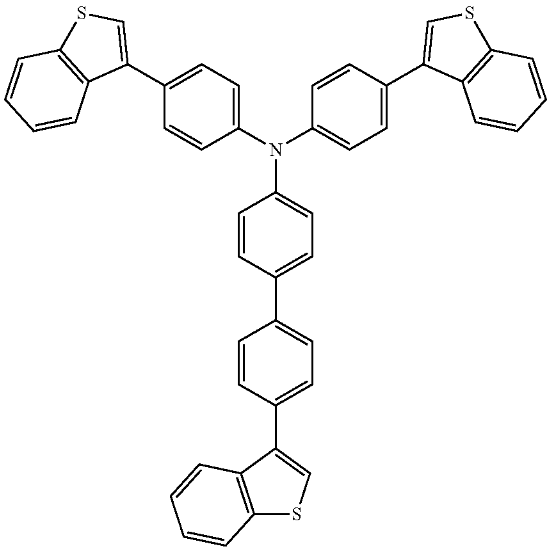
241
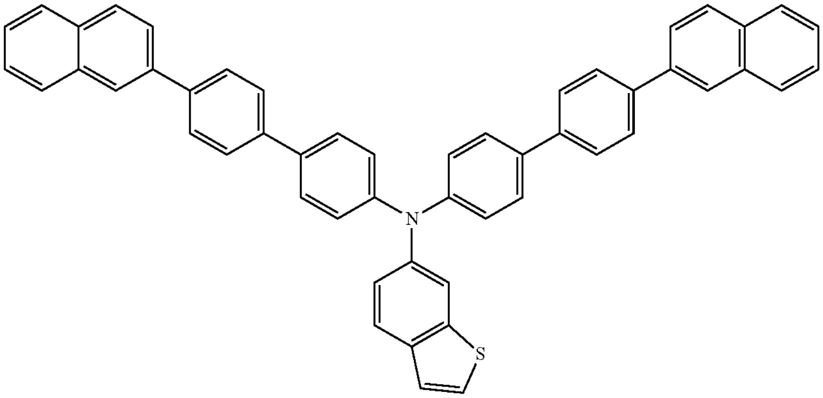
242
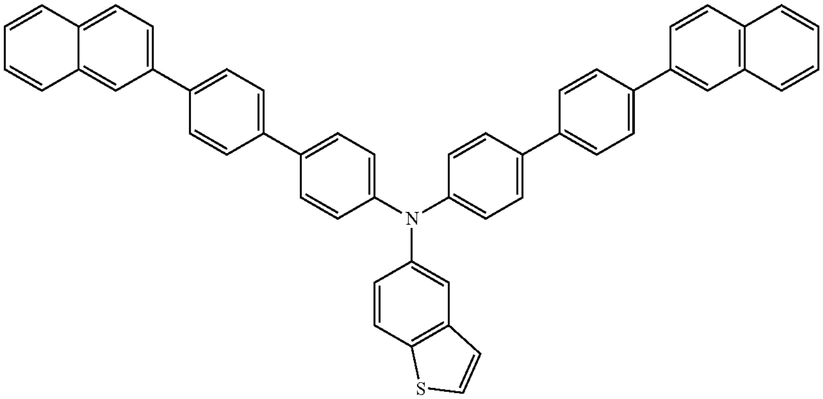

-continued
243
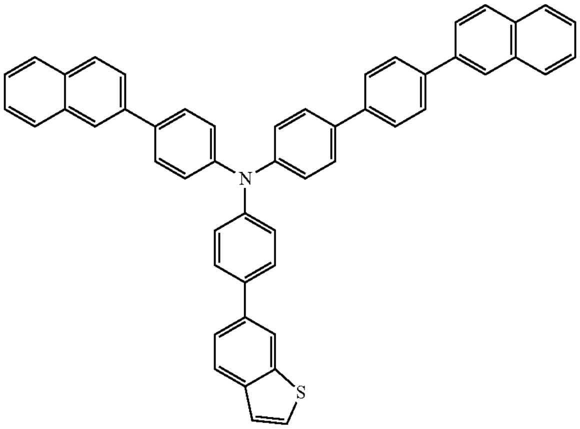
244
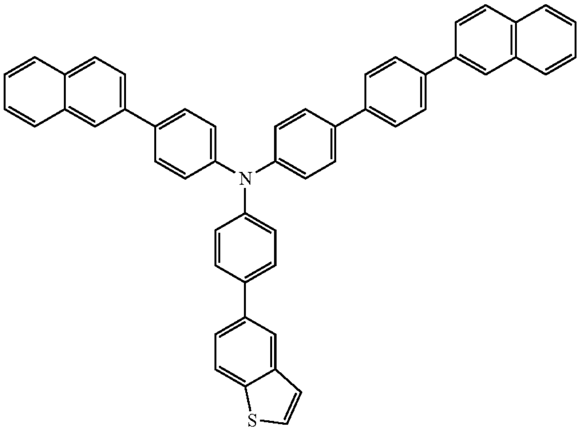
245
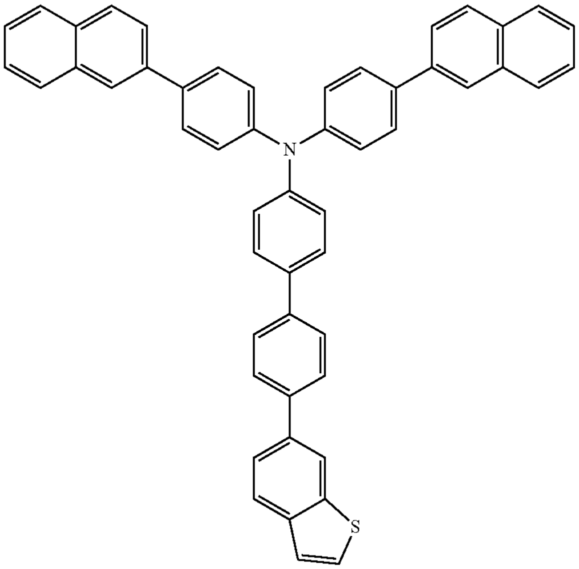
246
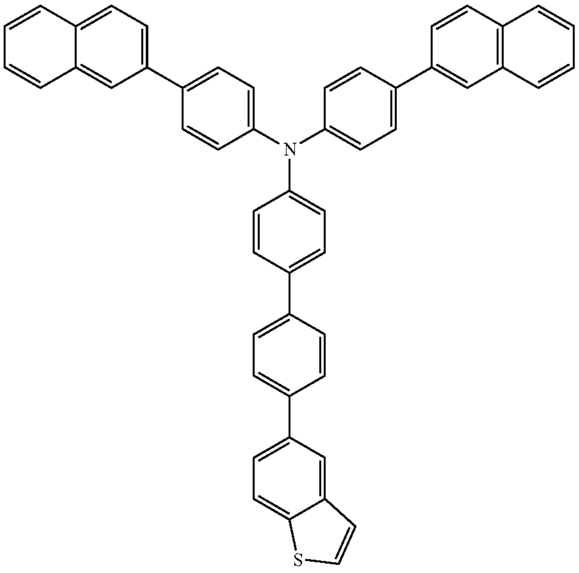
247
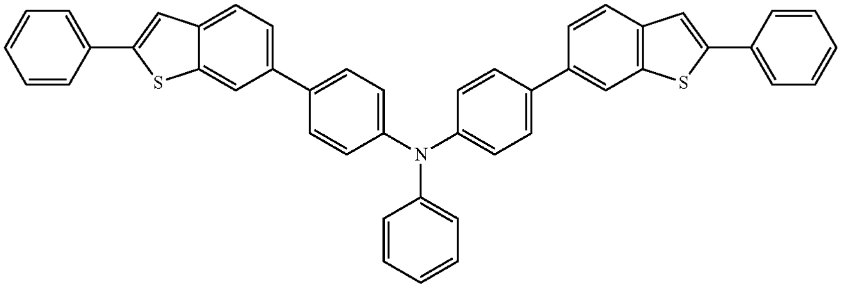

-continued
248
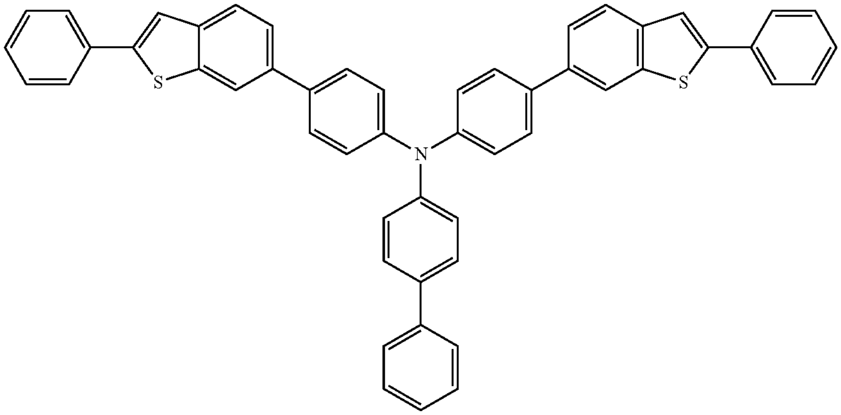
249
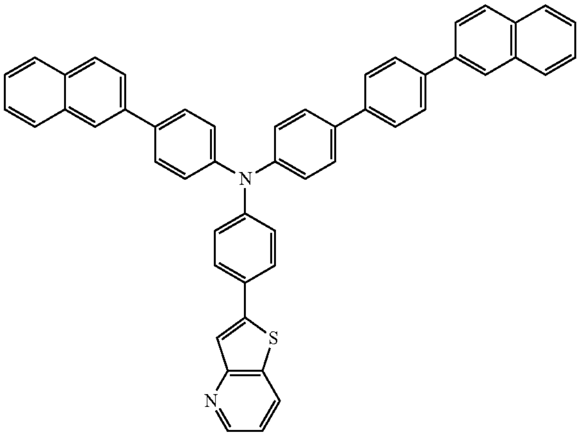
250
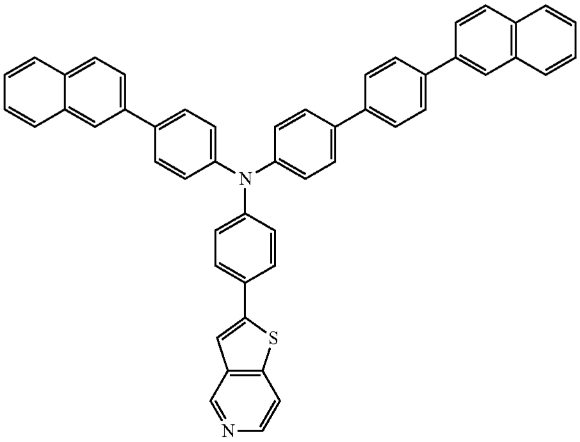
251
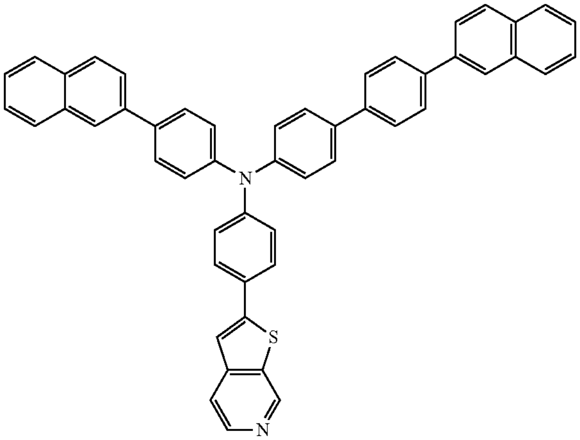
252
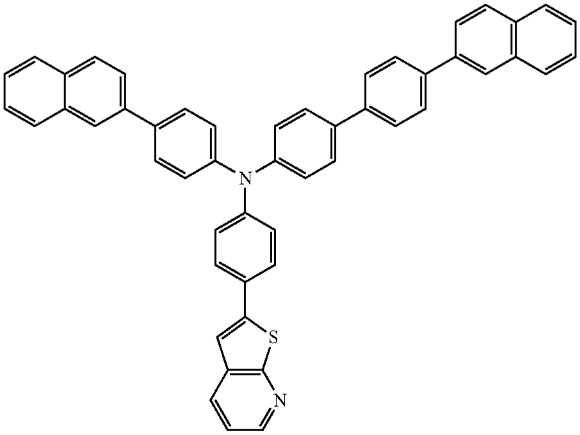

253
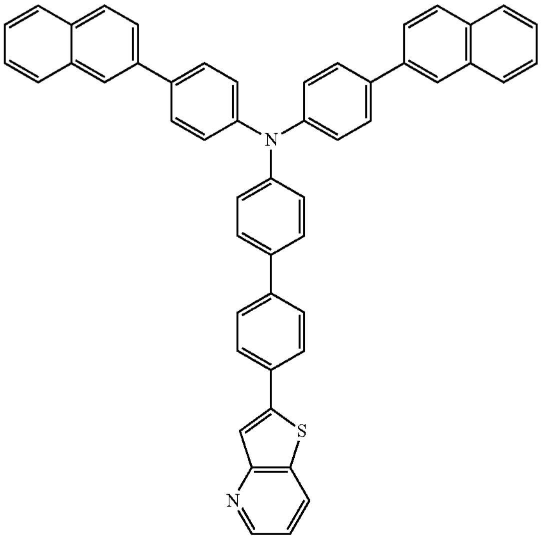
254
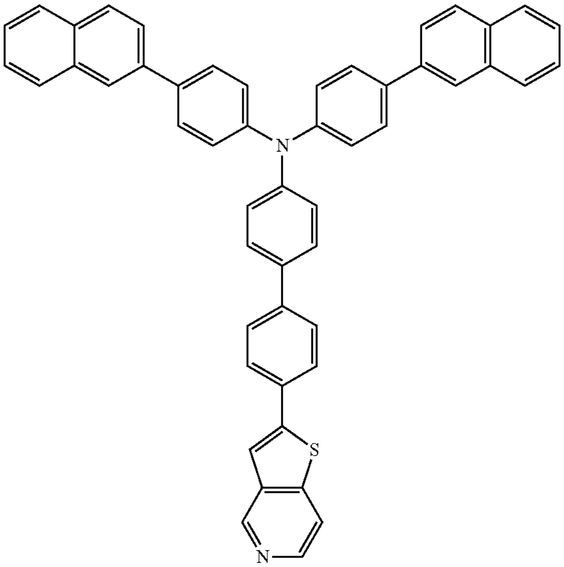
255
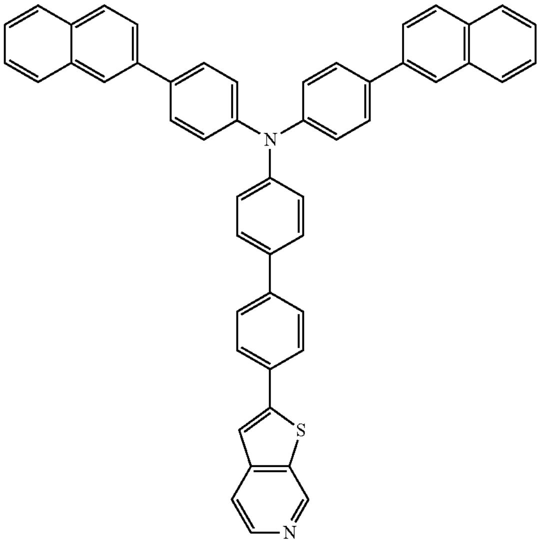
256
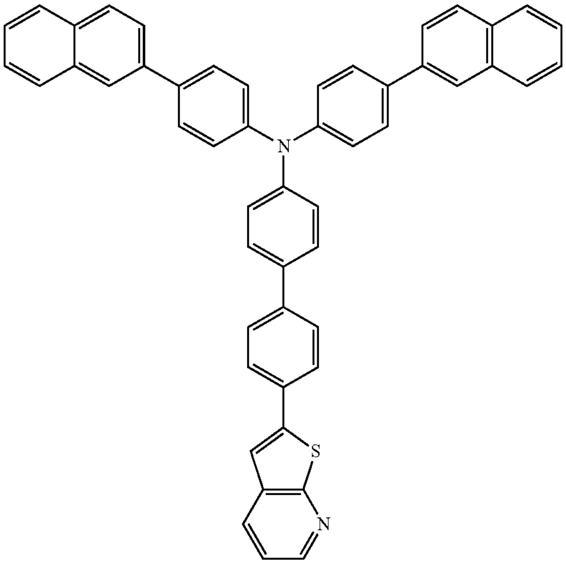
257
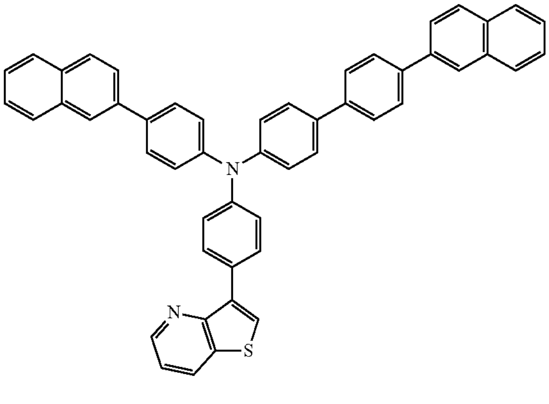
258
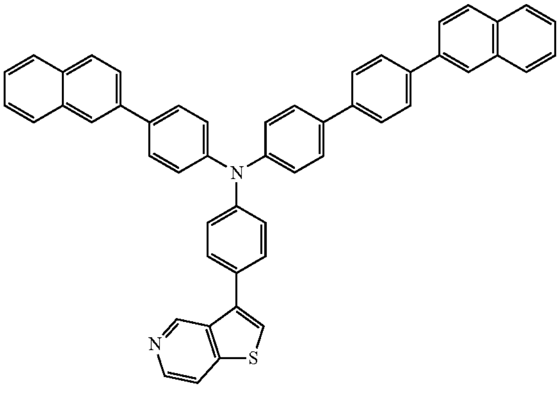

-continued
259
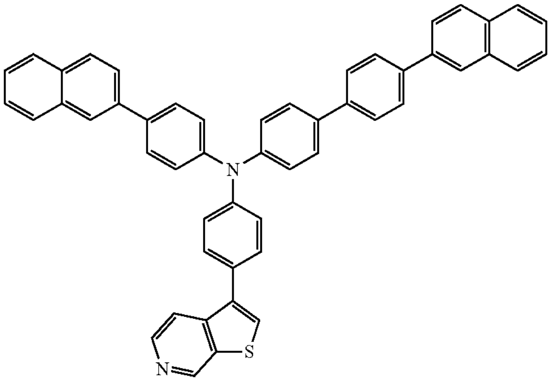
260
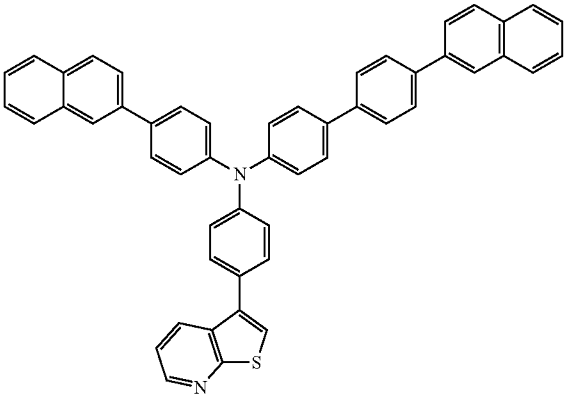
261
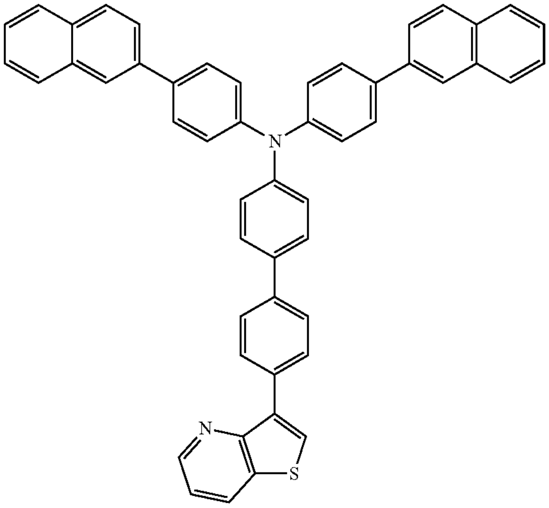
262
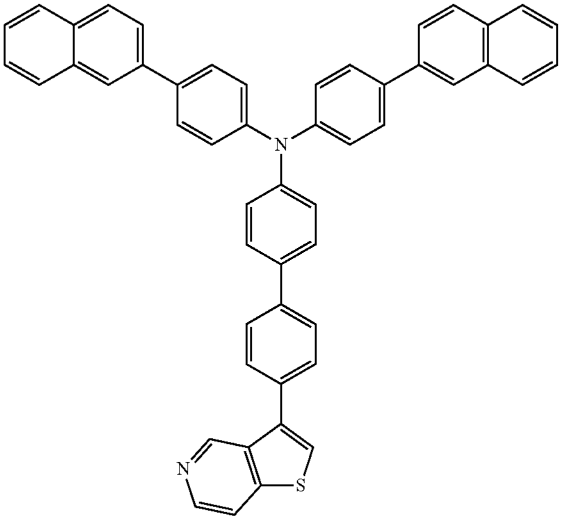
263
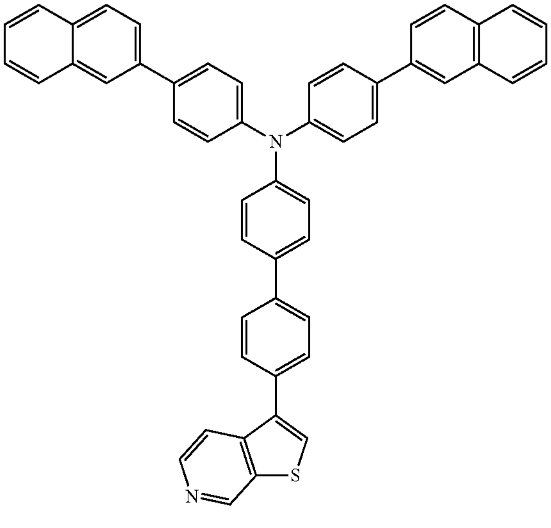
264
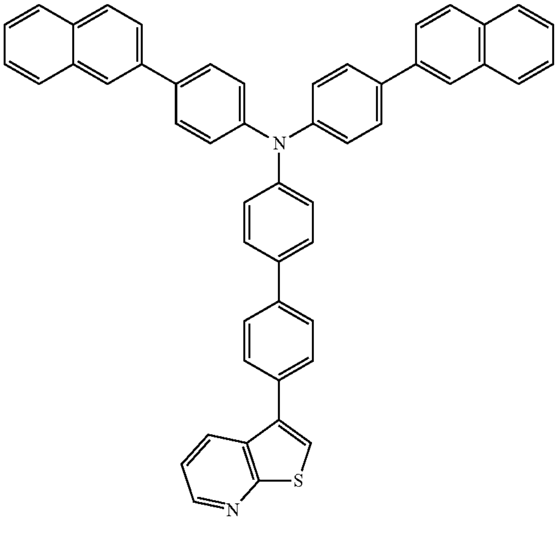

-continued
265
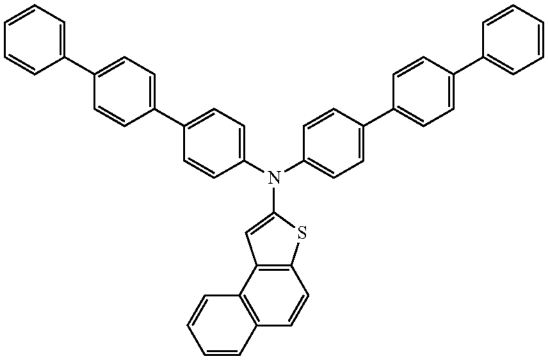
266
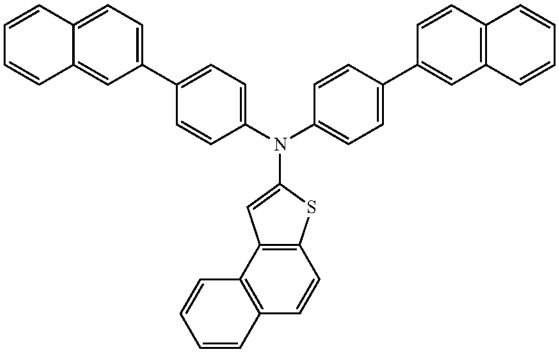
267
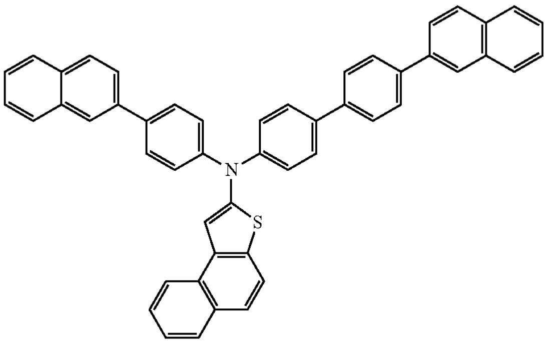
268
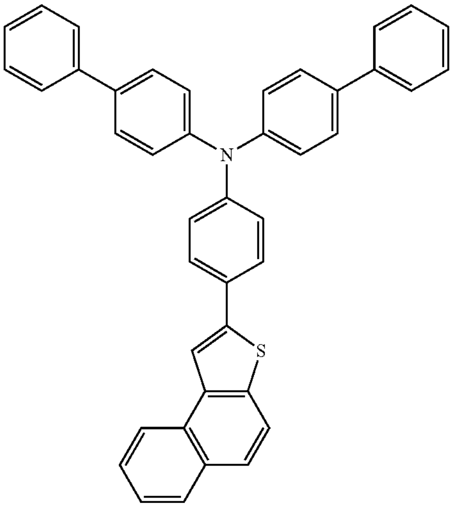
269
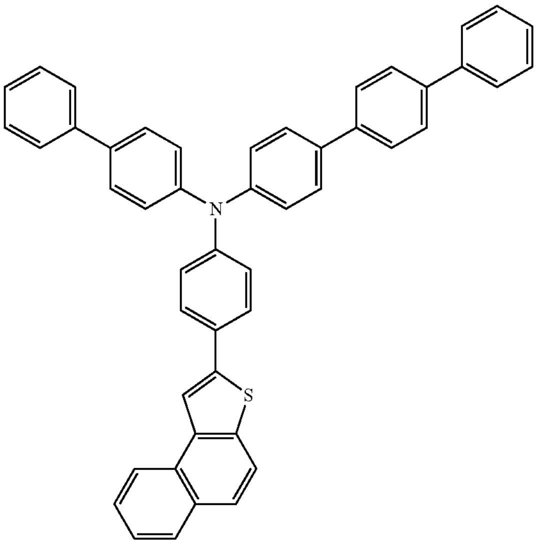
270
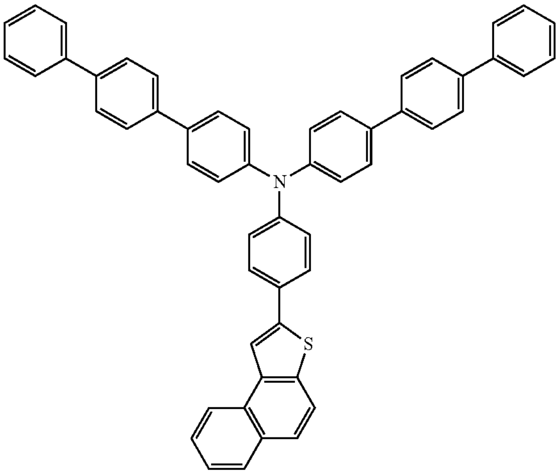

-continued
271
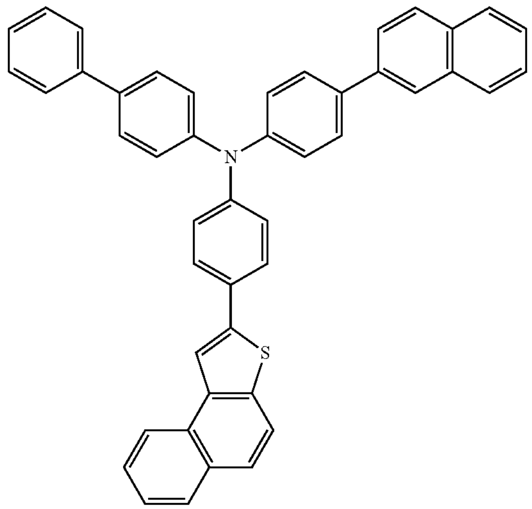
272
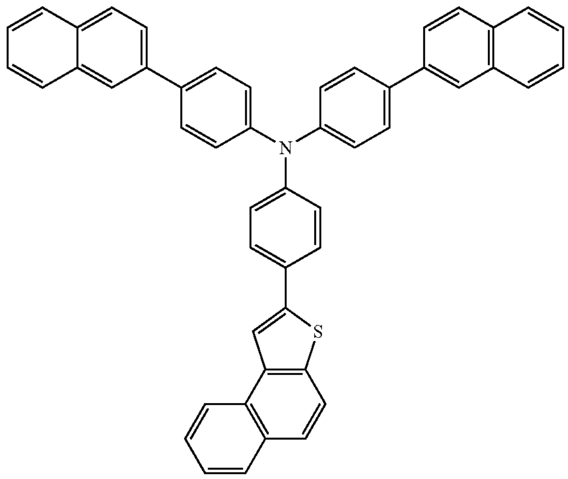
273
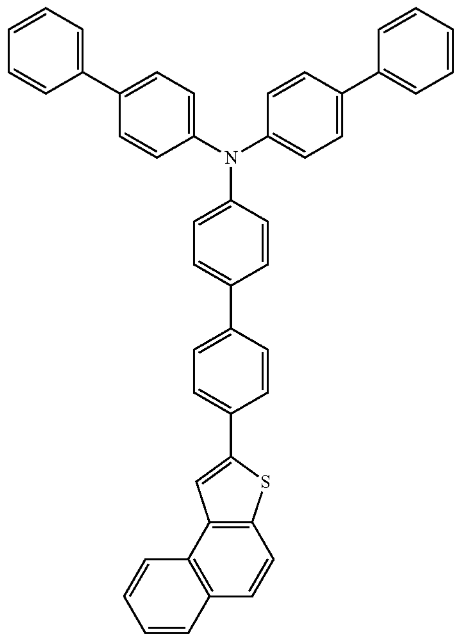
274
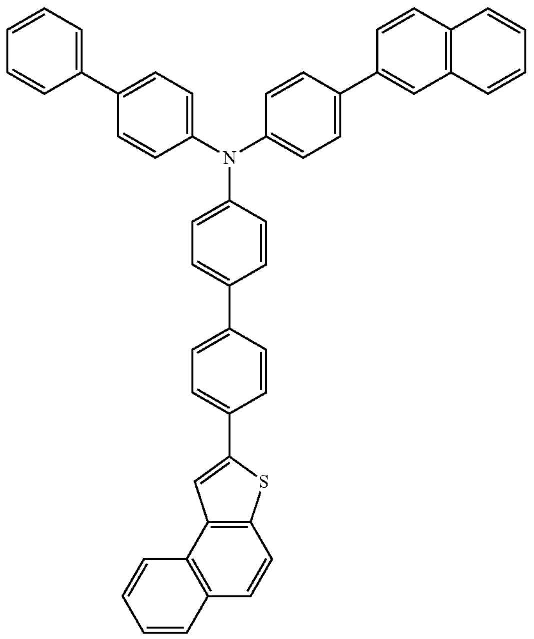
275
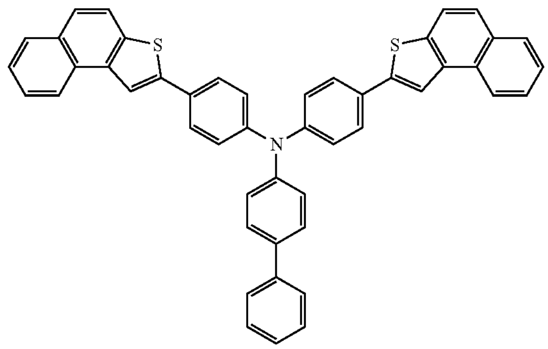
276
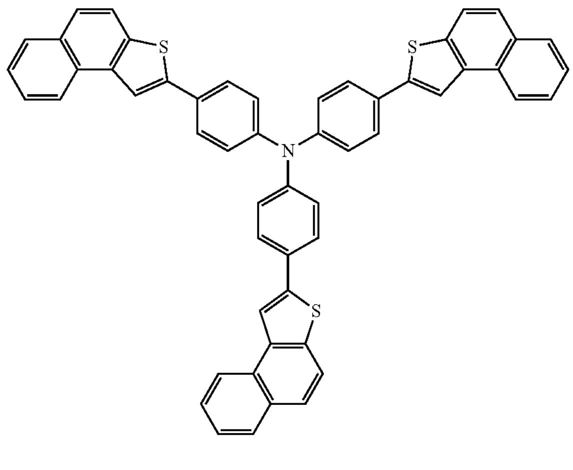

-continued
277
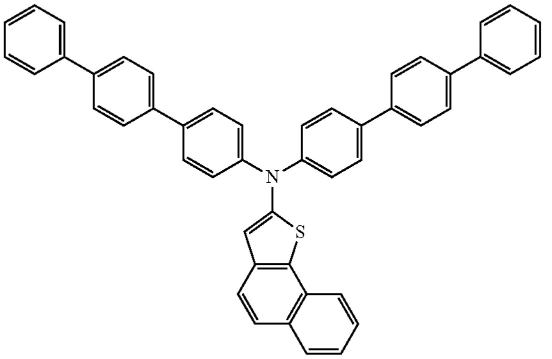
278
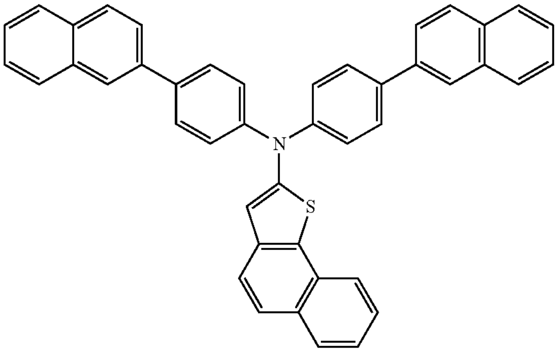
279
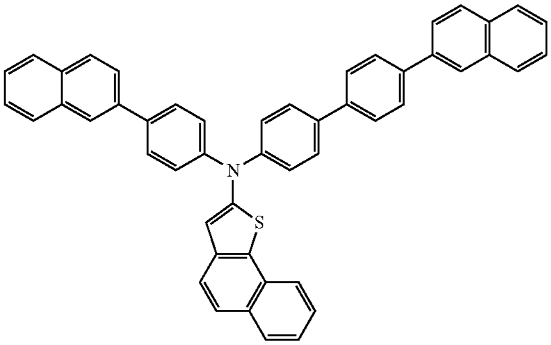
280
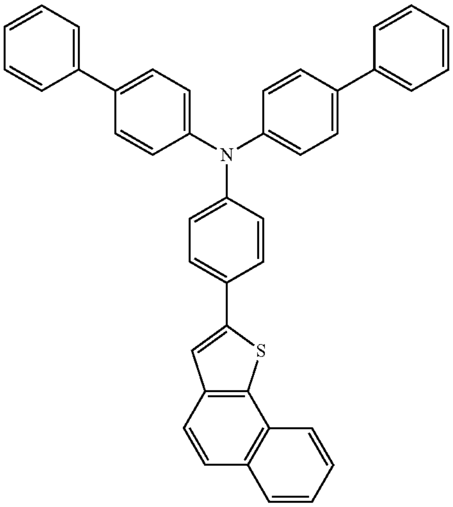
281
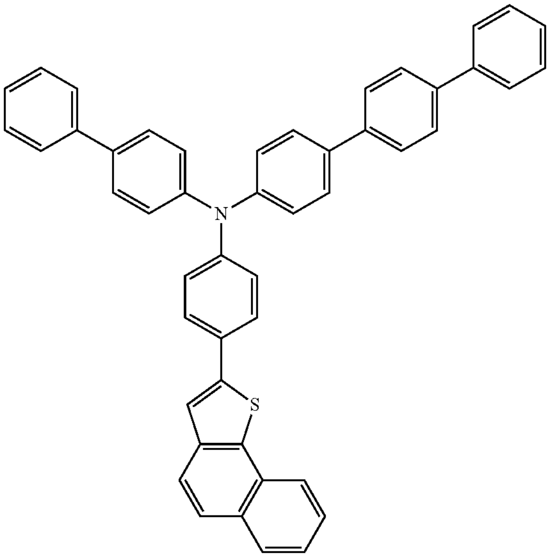
282
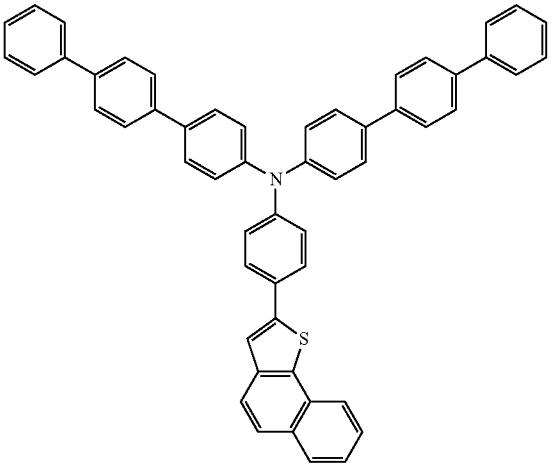

-continued
283
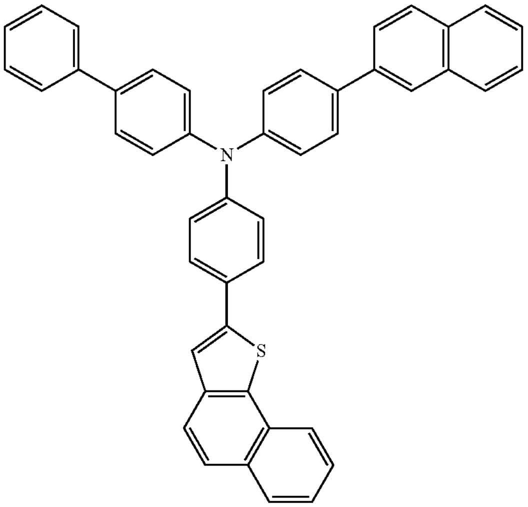
284
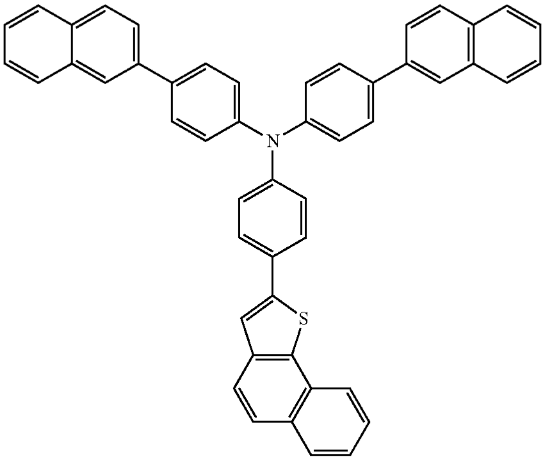
285
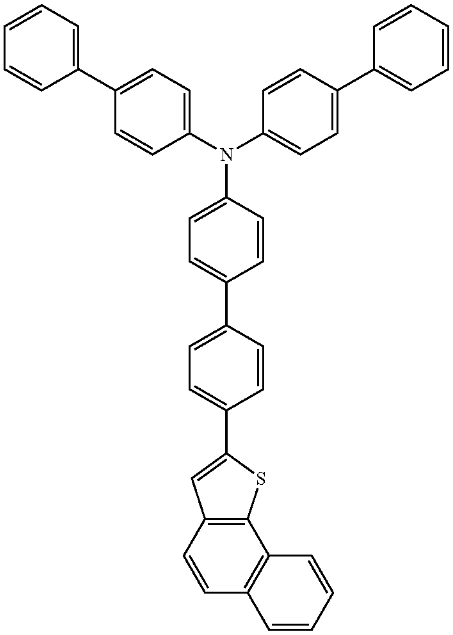
286
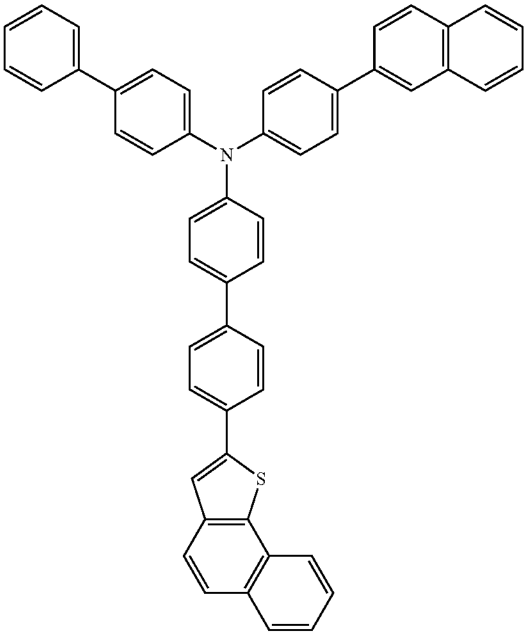
287
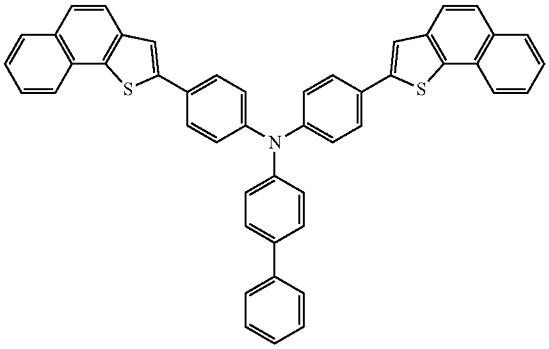
288
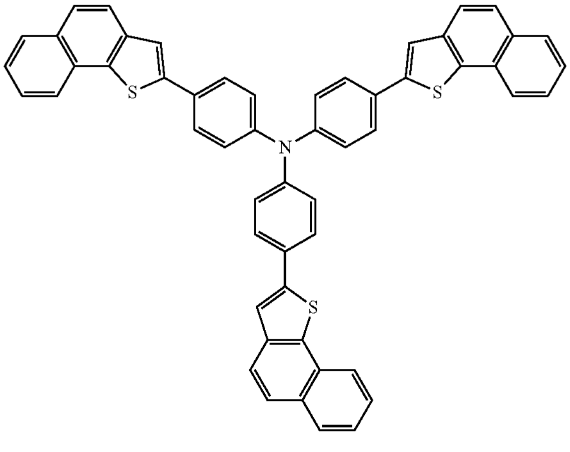

-continued
289
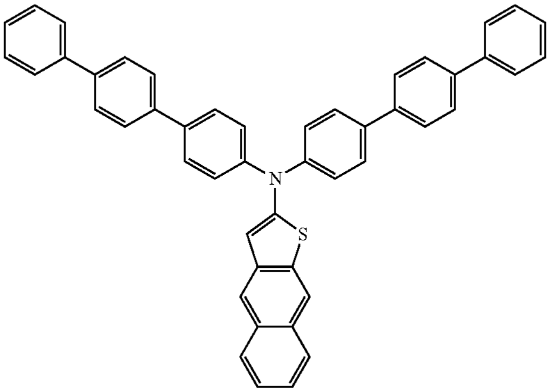
290
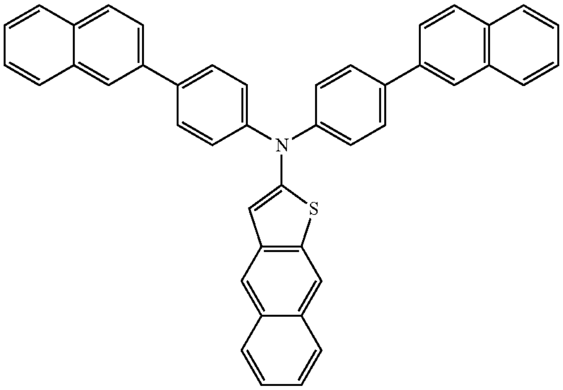
291
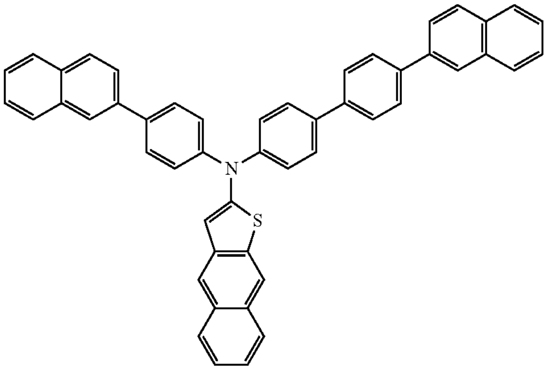
292
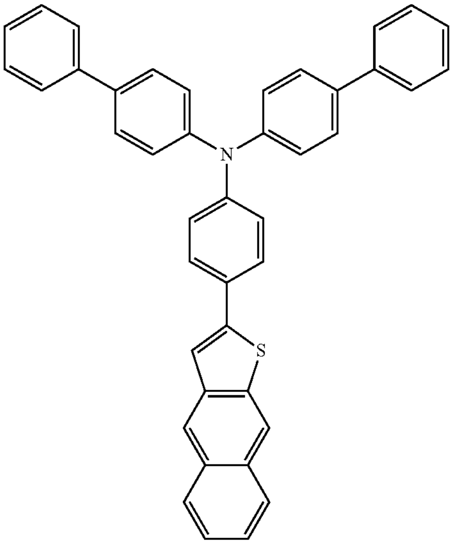
293
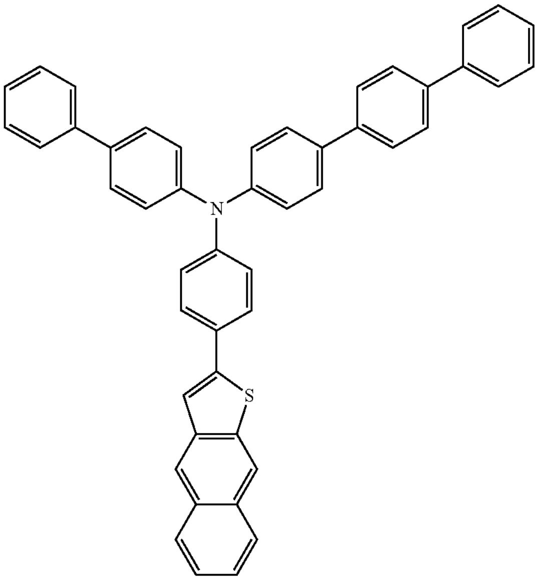
294
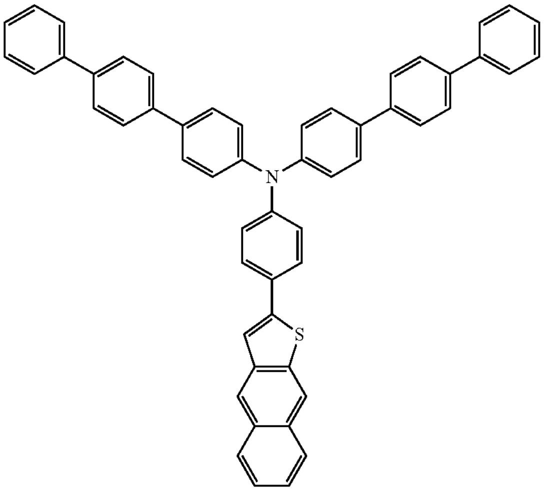

-continued
295
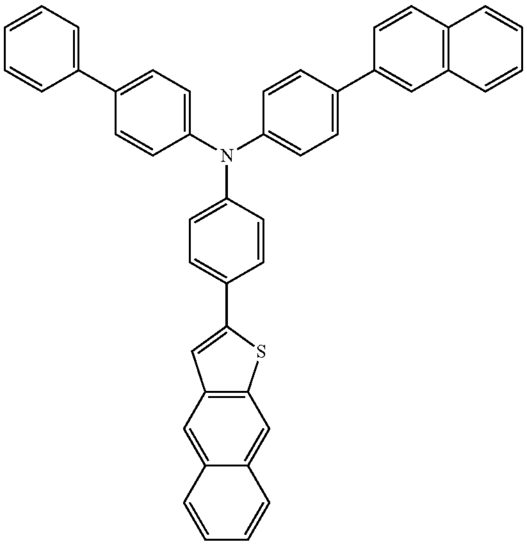
296
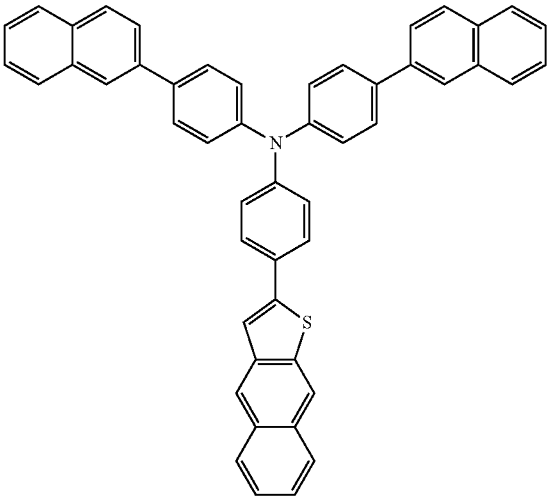
297
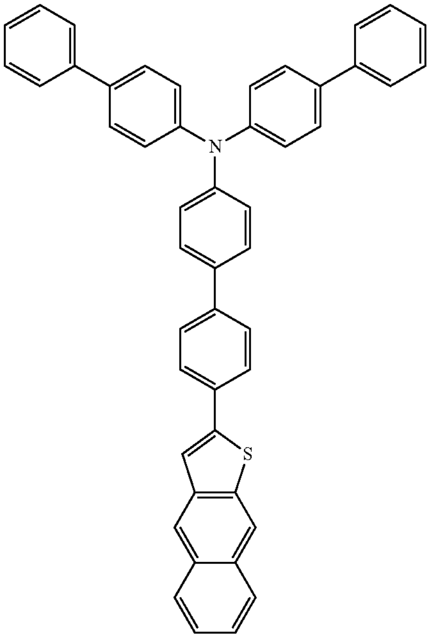
298
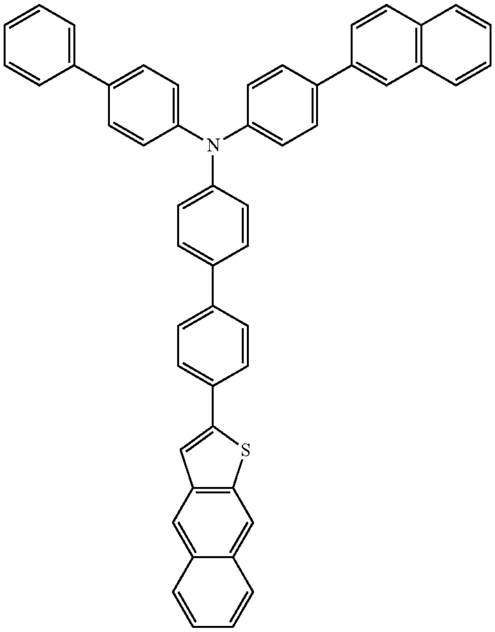

-continued
299
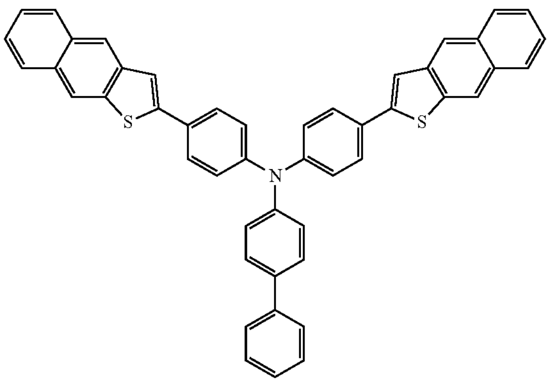
300
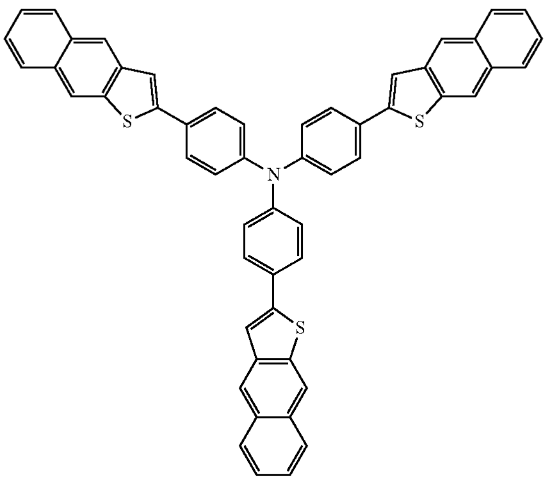
301
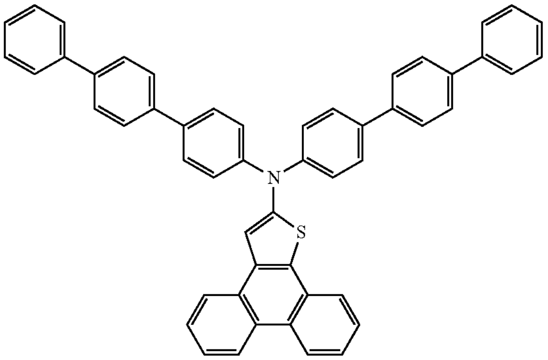
302
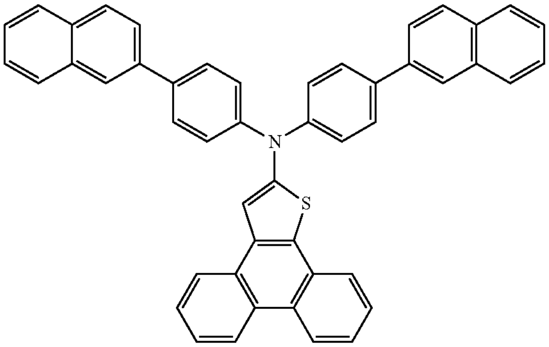
303
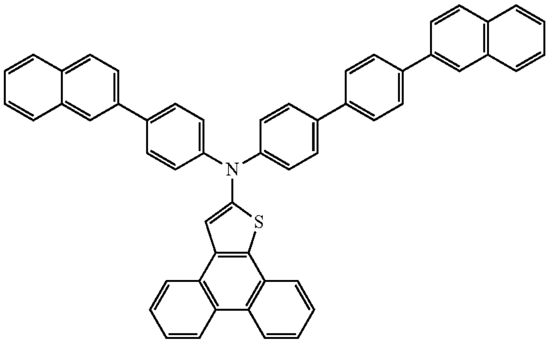
304
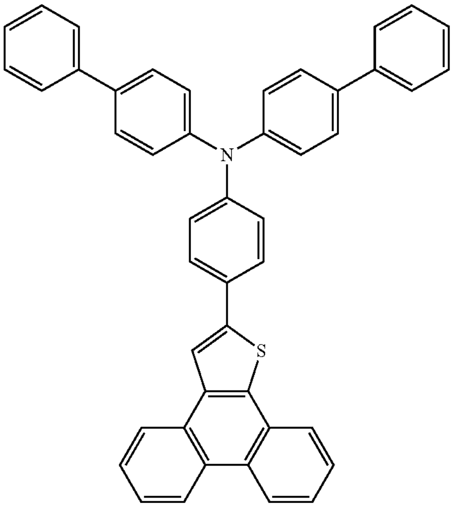

-continued
305
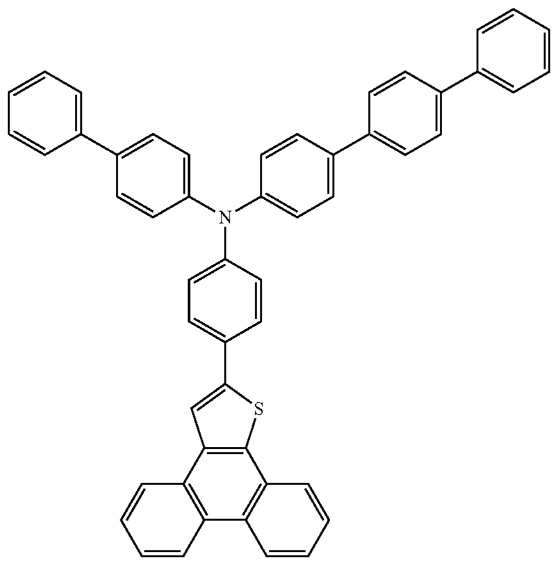
306
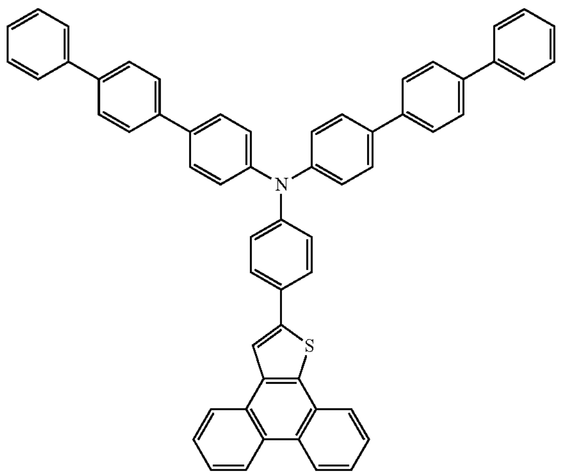
307
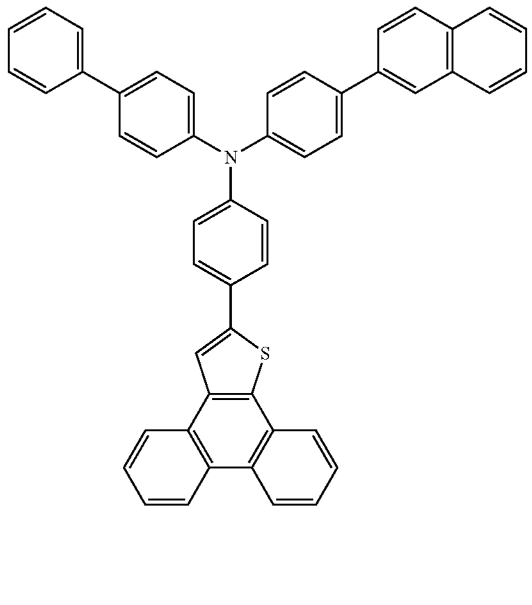
308
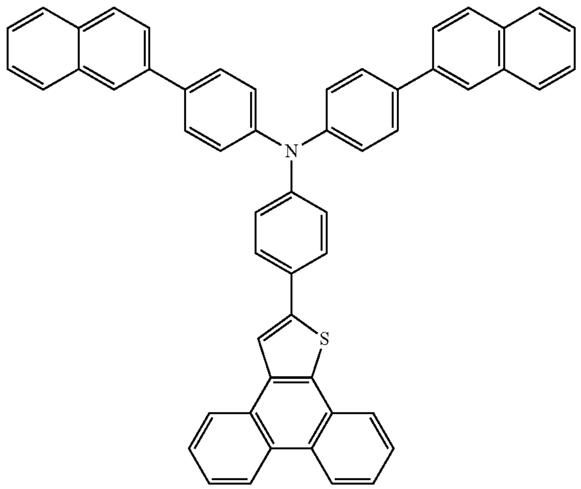

-continued
309
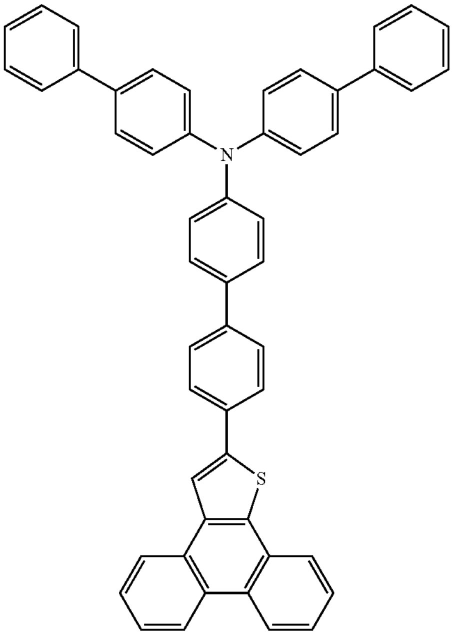
310
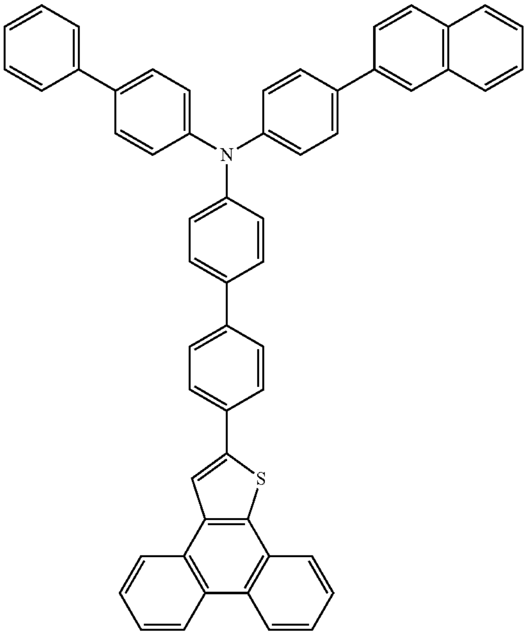
311
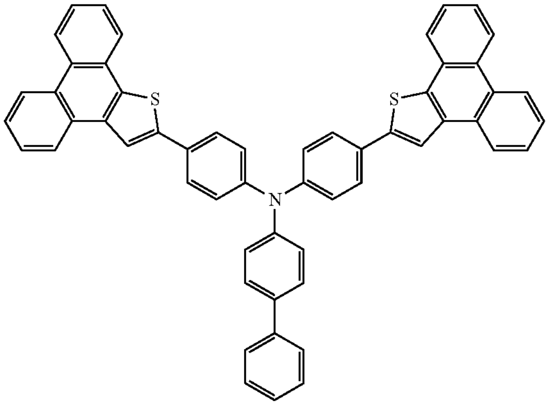
312
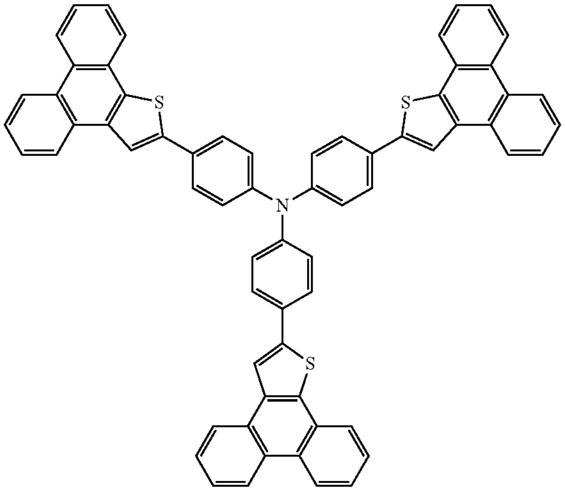
313
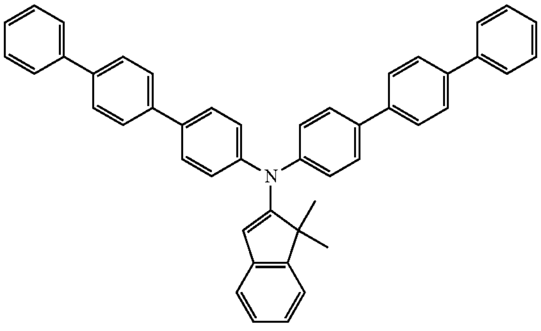
314
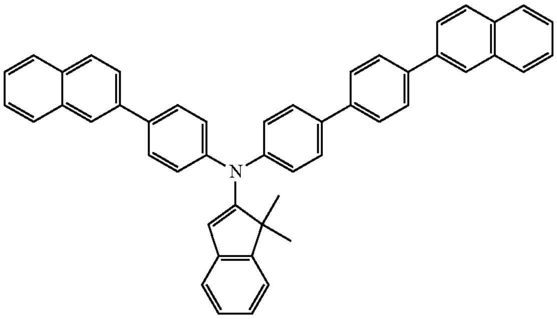

-continued
315
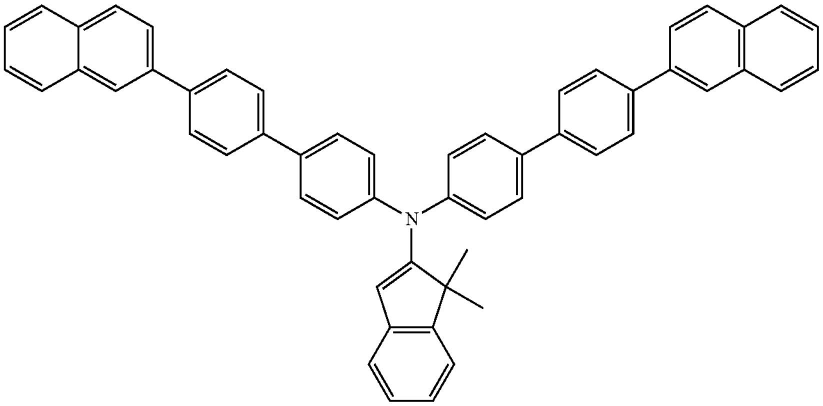
316
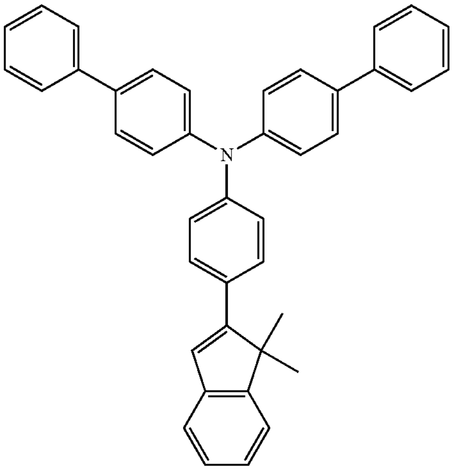
317
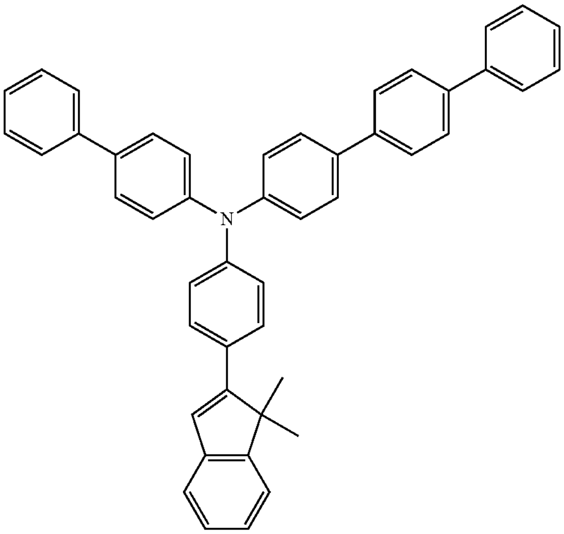
318
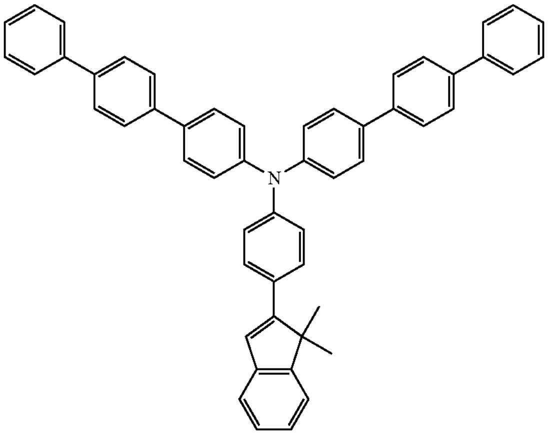
319
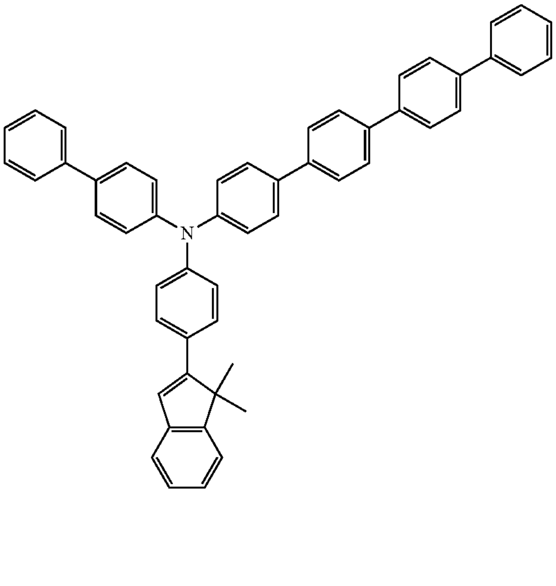

-continued
320
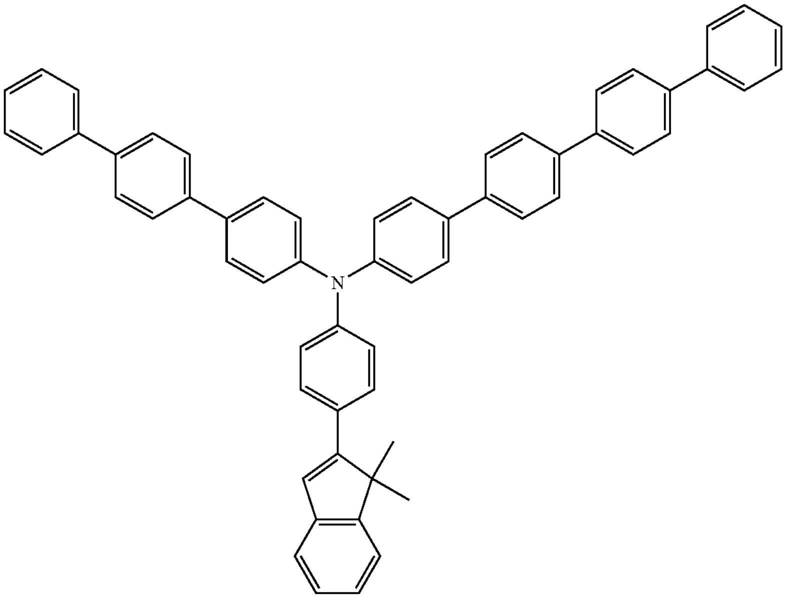
321
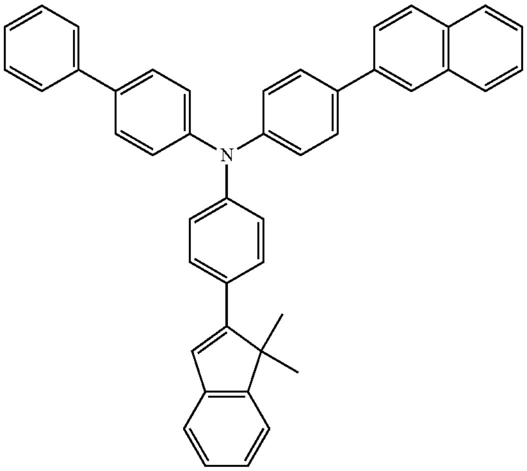
322
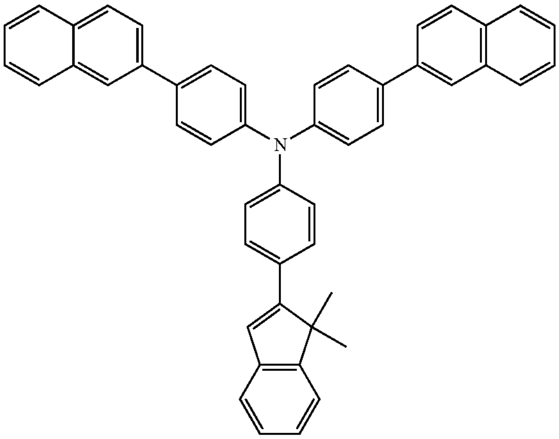
323
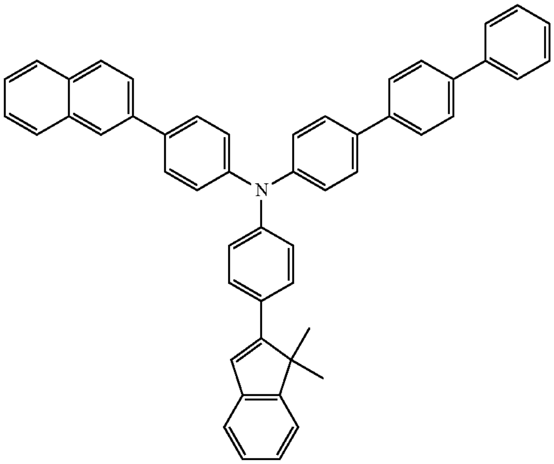
324
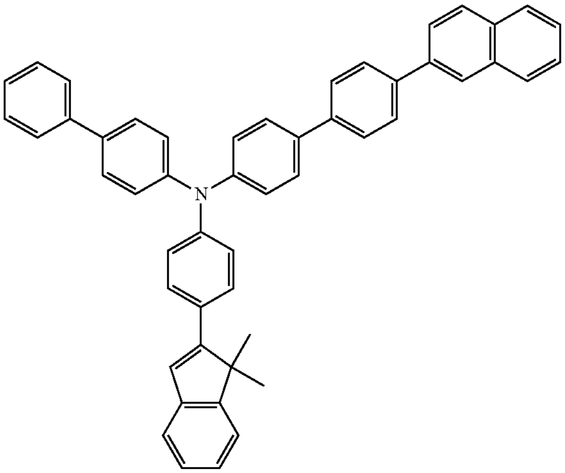

-continued
325
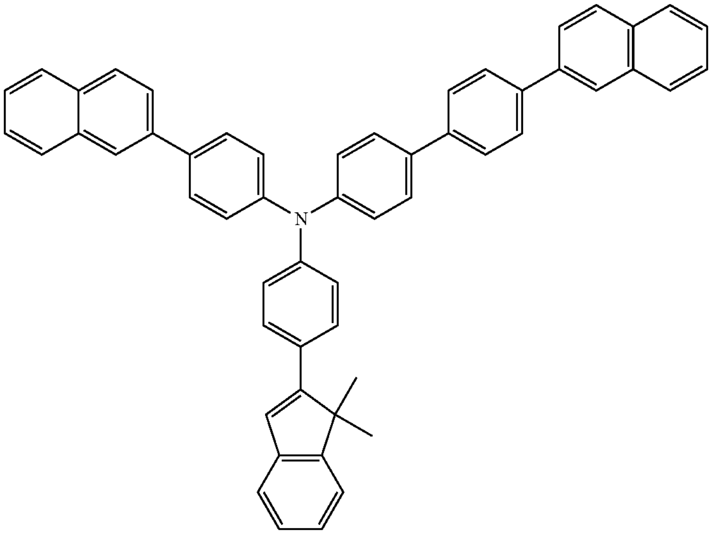
326
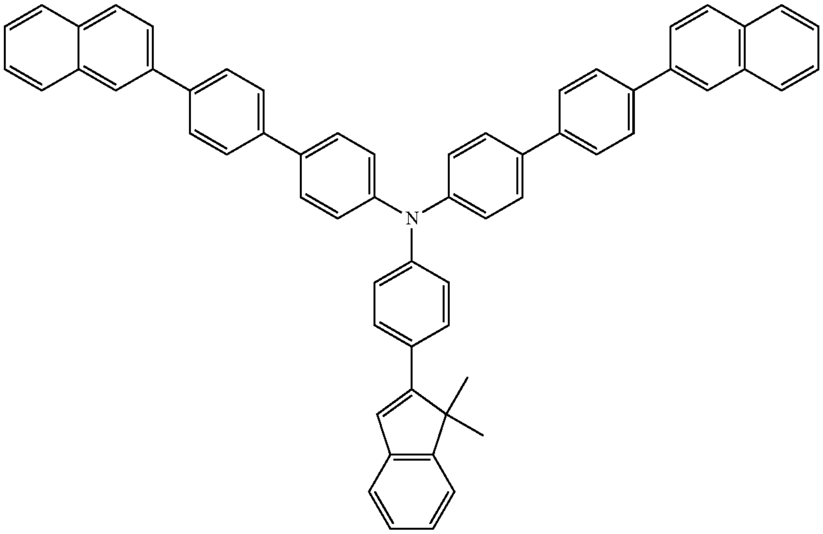
327
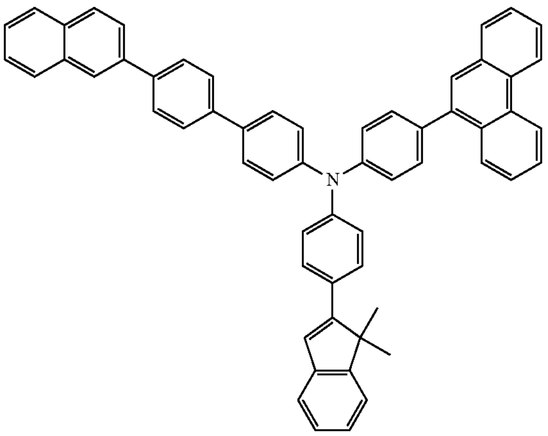
328
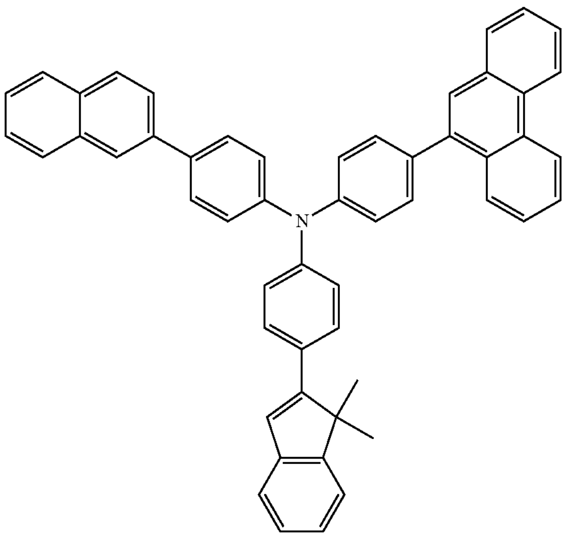

-continued
329
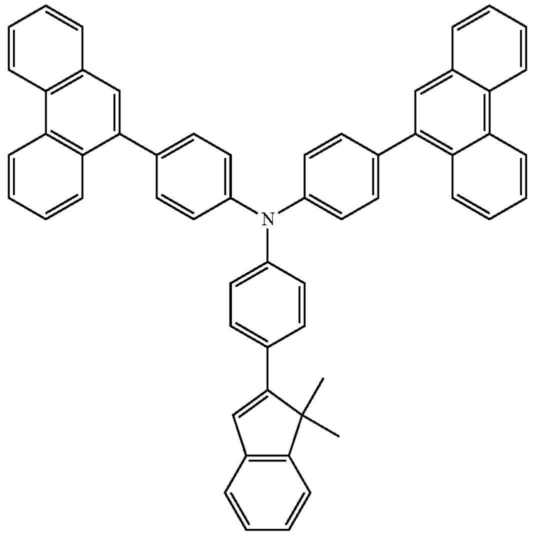
330
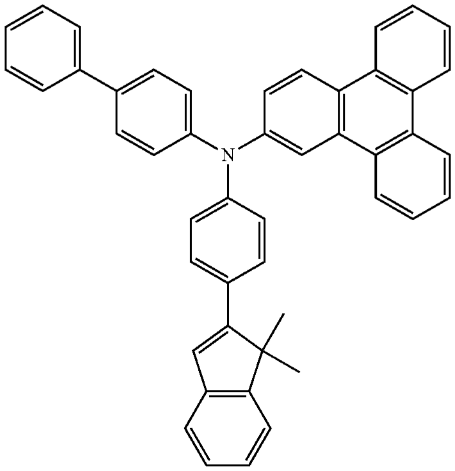
331
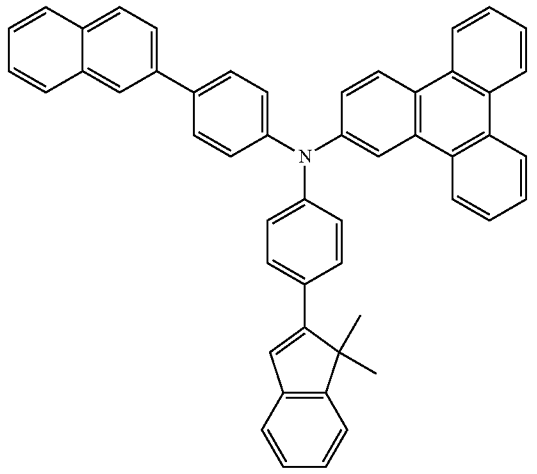
332
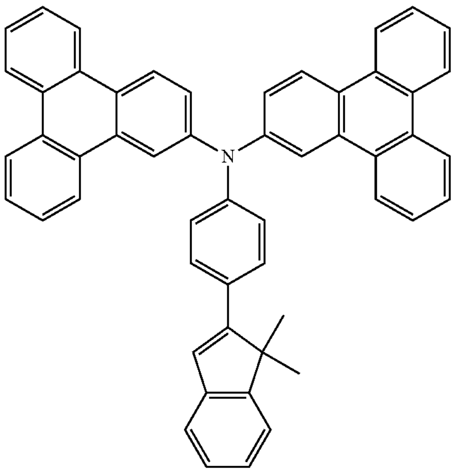
333
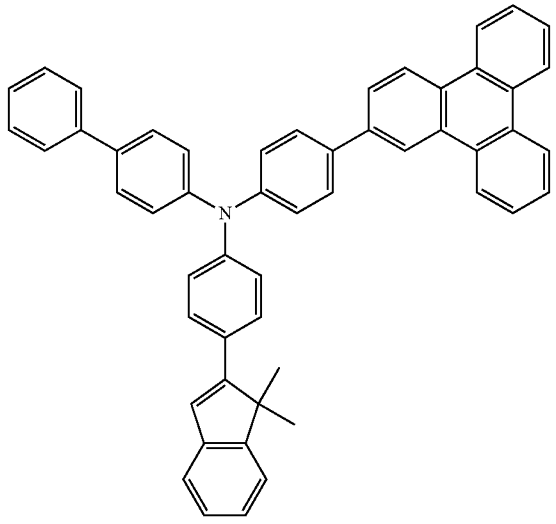
334
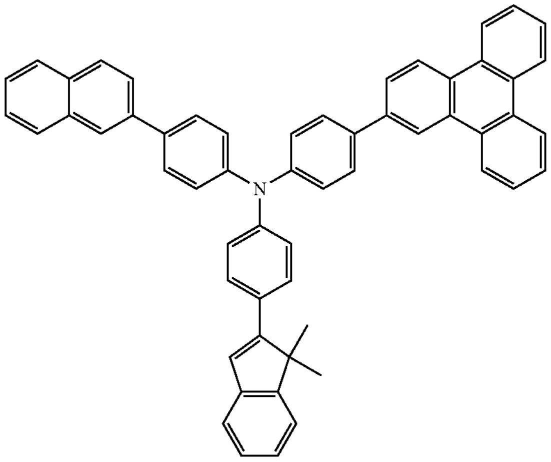

-continued
335
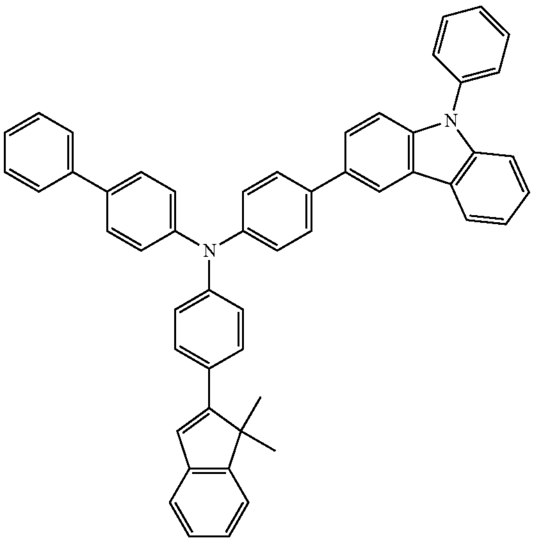
336
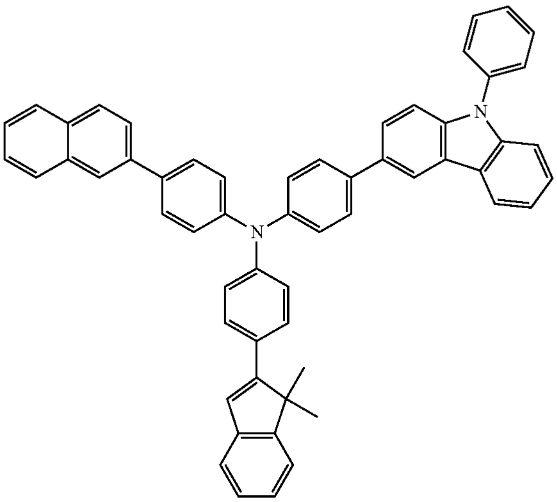
337
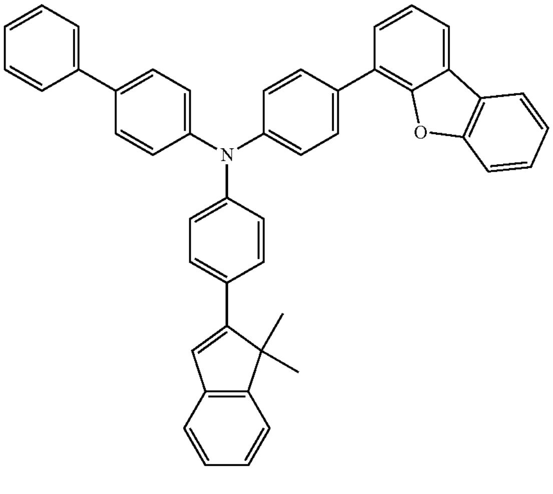
338
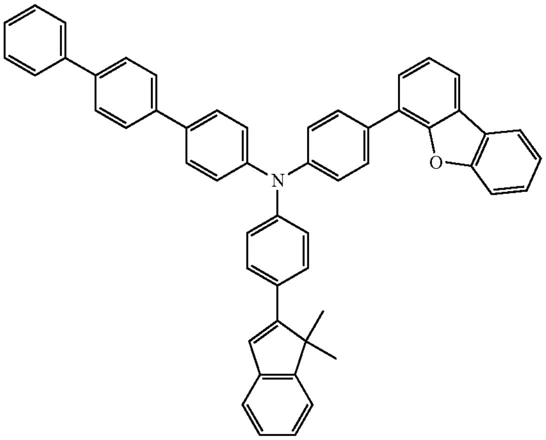
339
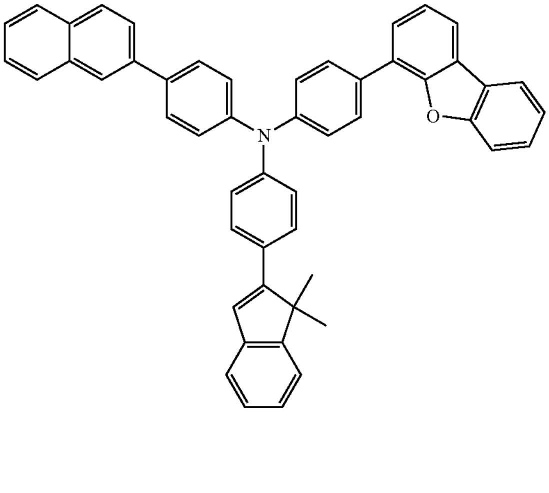
340
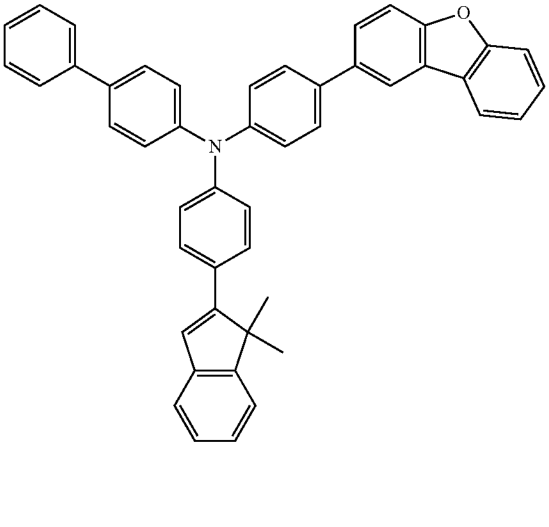

-continued
341
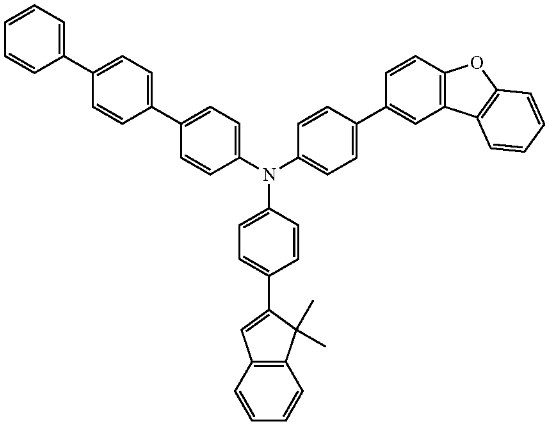
342
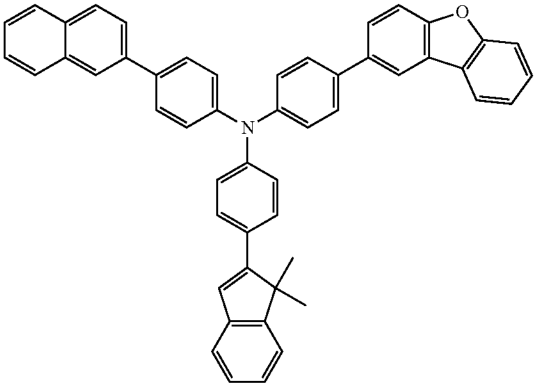
343
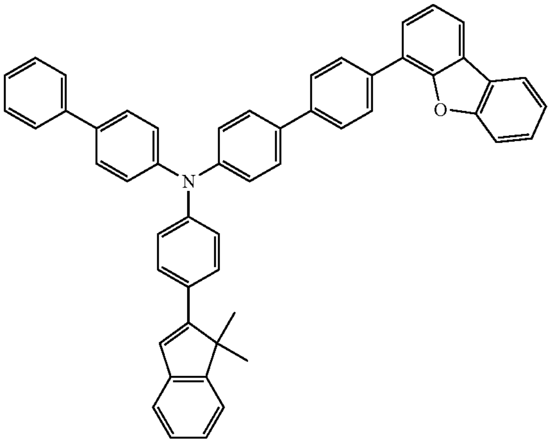
344
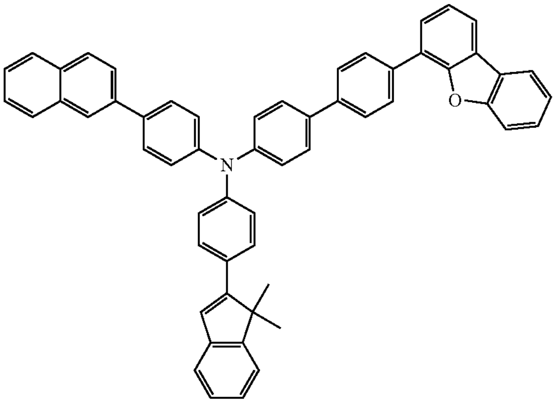
345
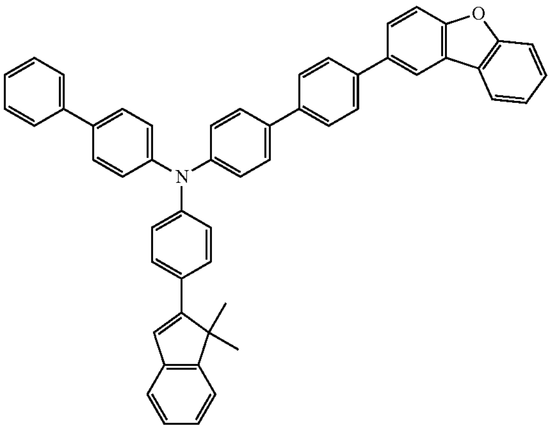
346
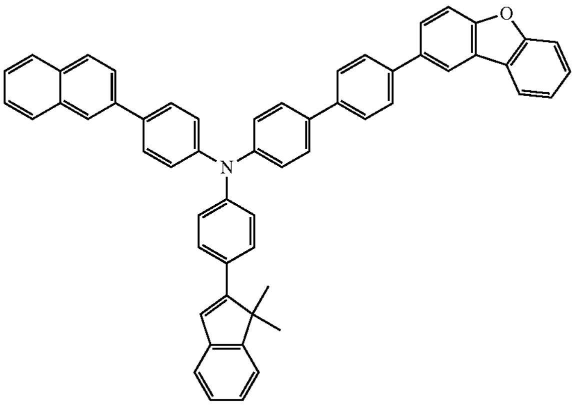

-continued
347
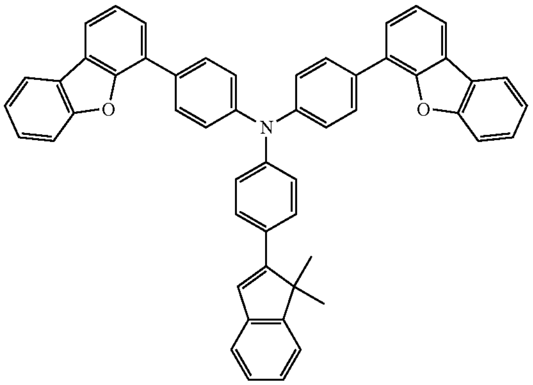
348
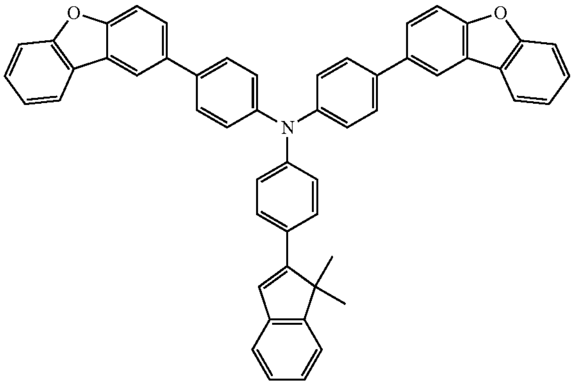
349
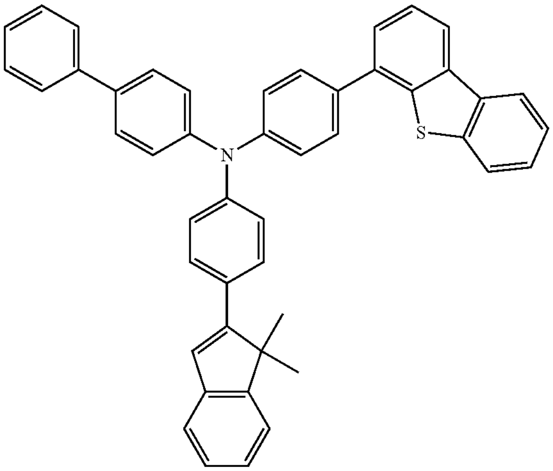
350
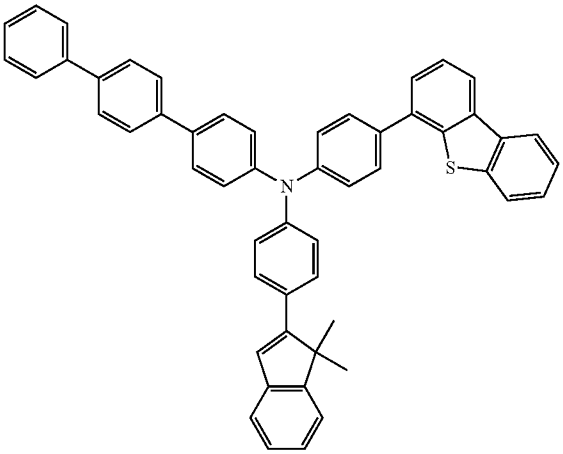
351
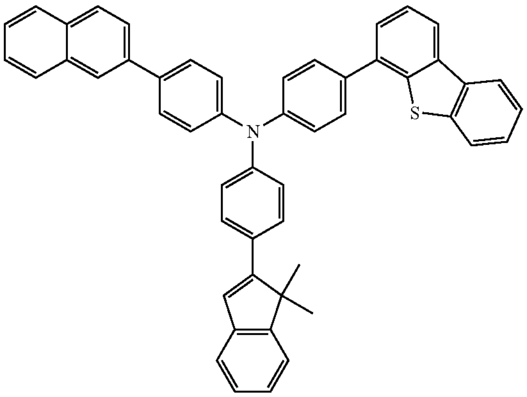
352
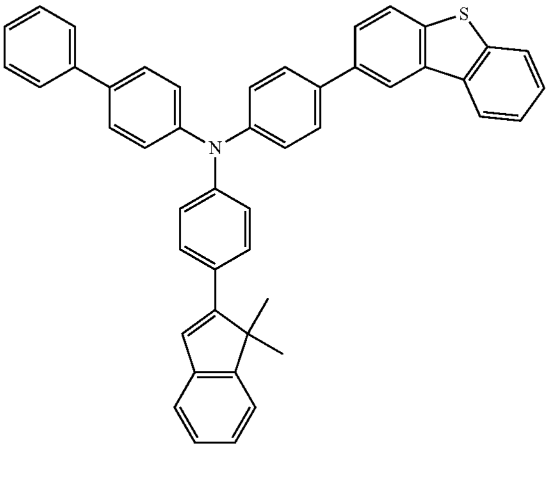

-continued
353
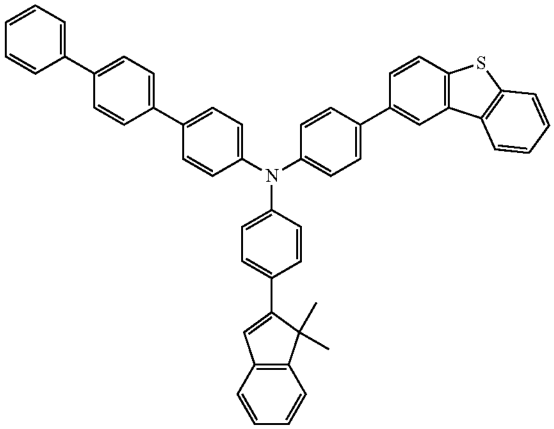
354
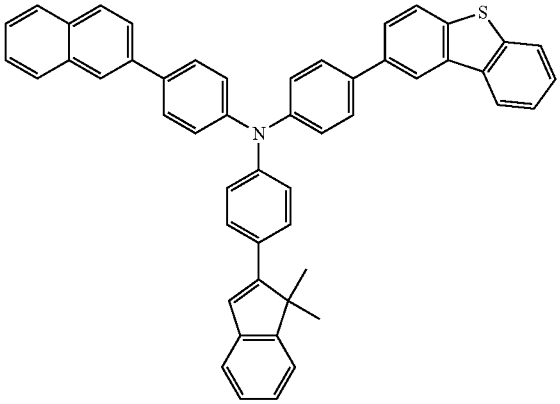
355
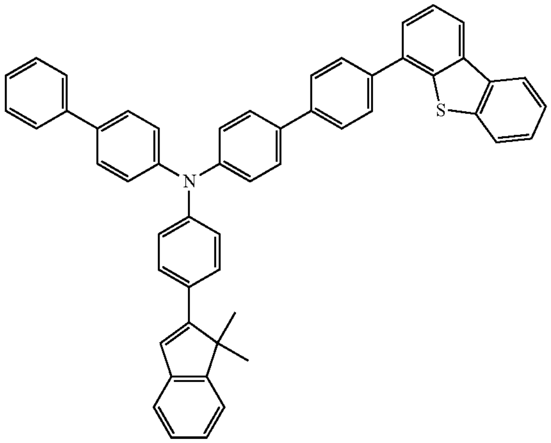
356
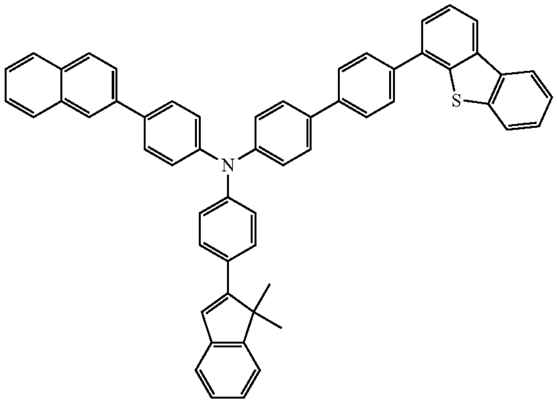
357
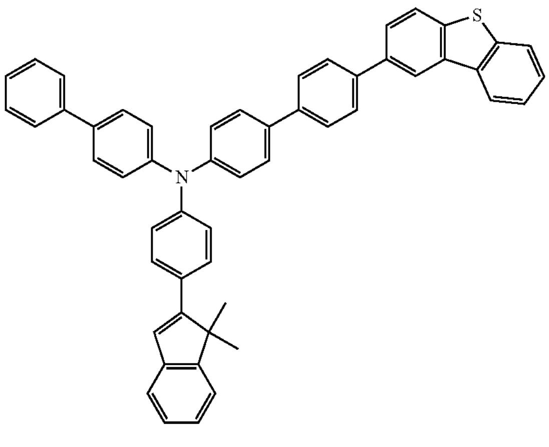
358
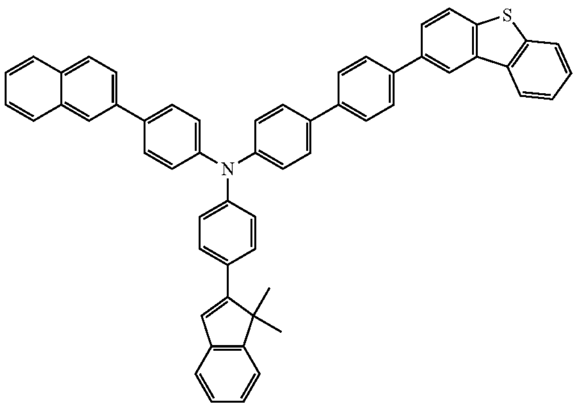

-continued
359
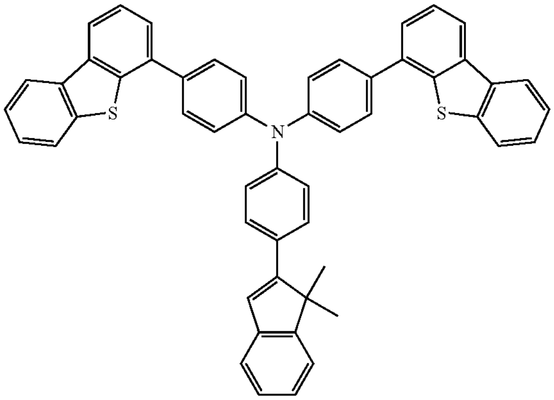
360
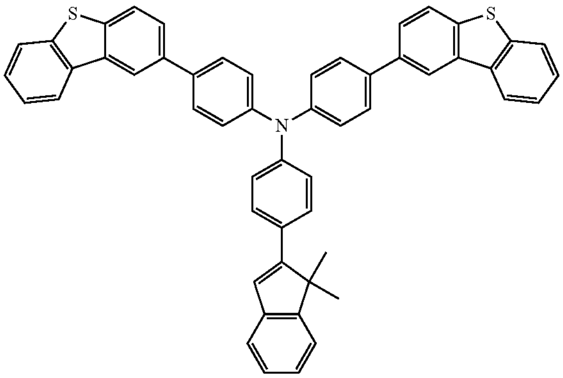
361
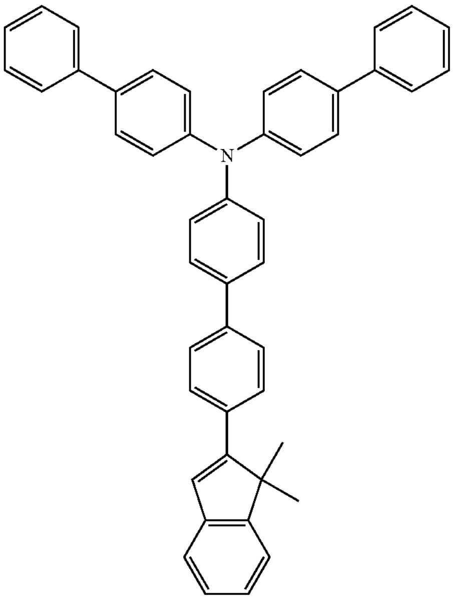
362
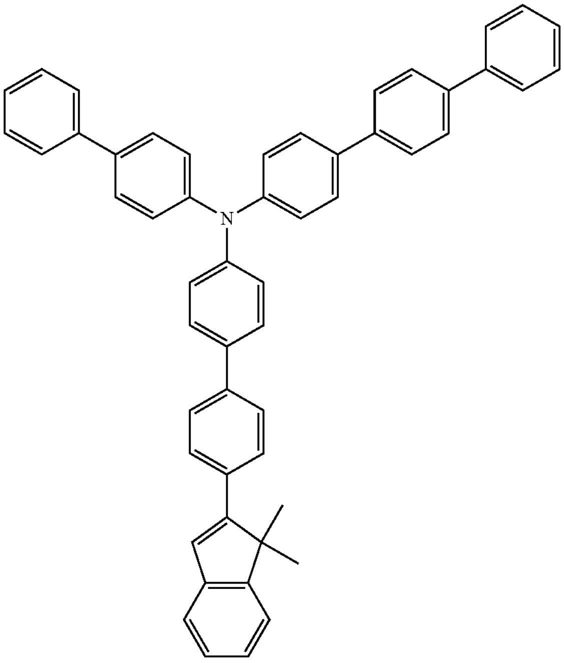

-continued
363
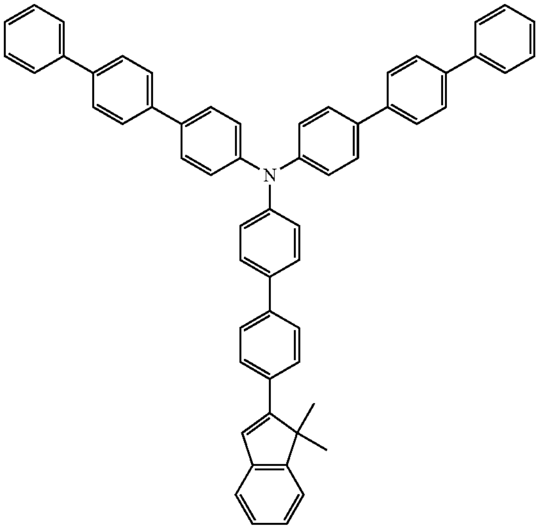
364
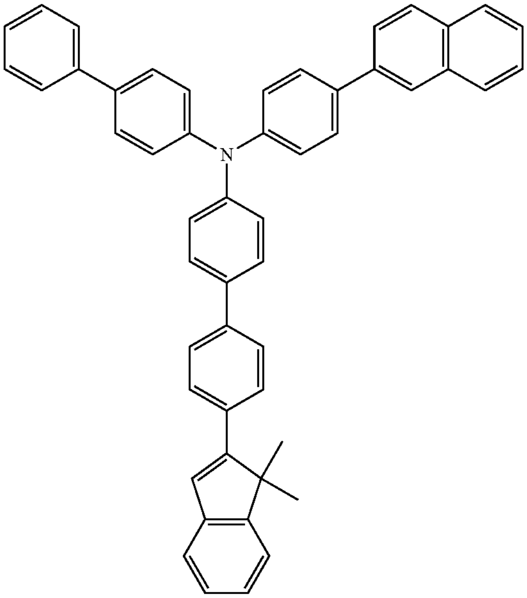
365
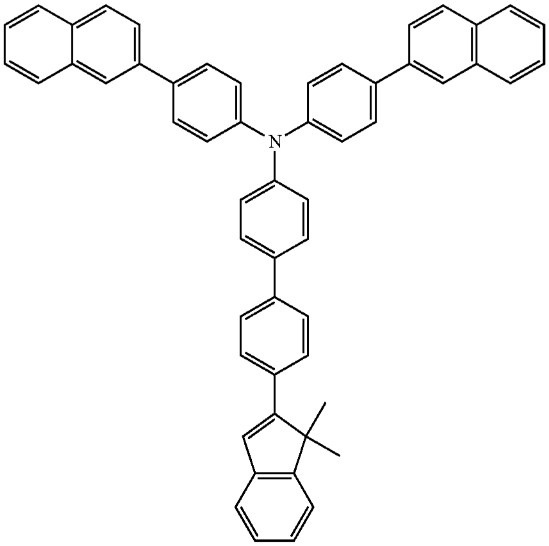
366
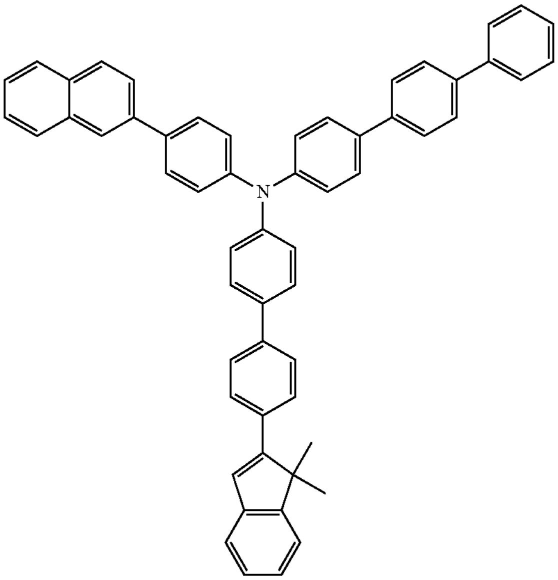

-continued
367
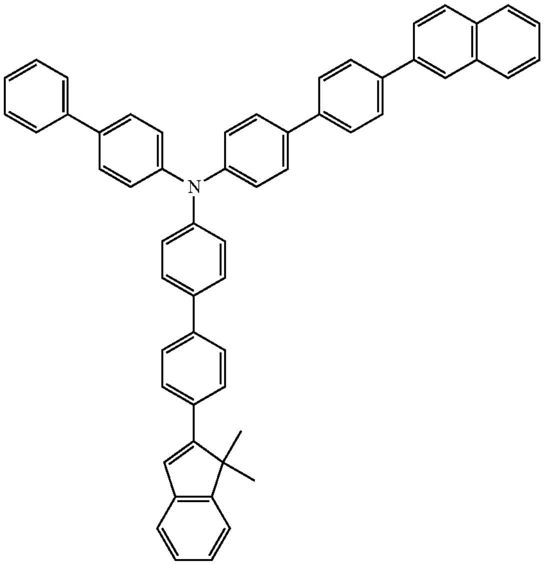
368
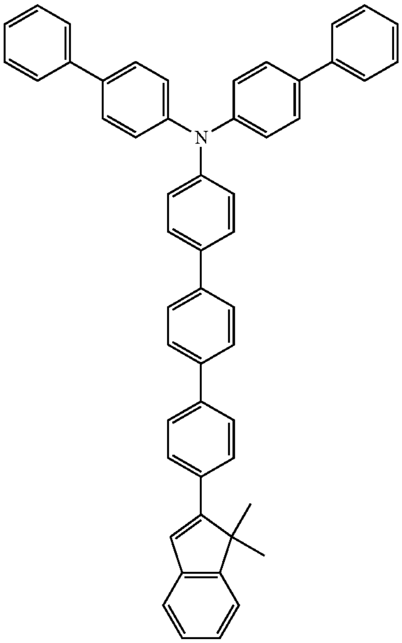
369
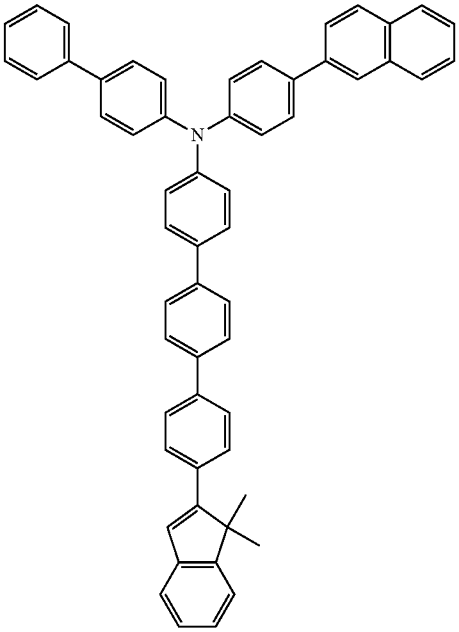
370
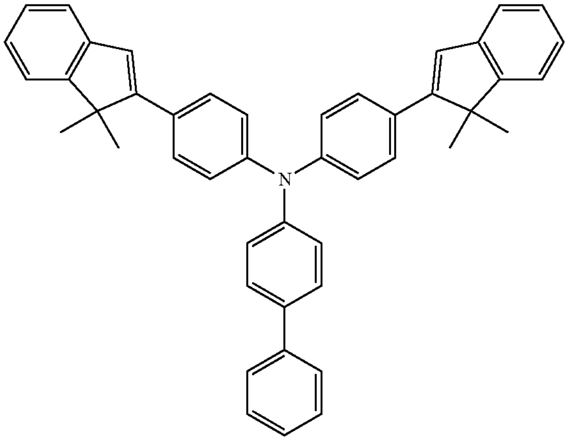

-continued
371
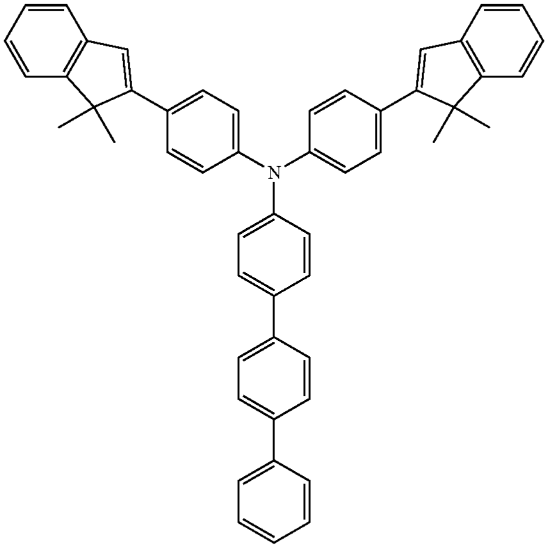
372
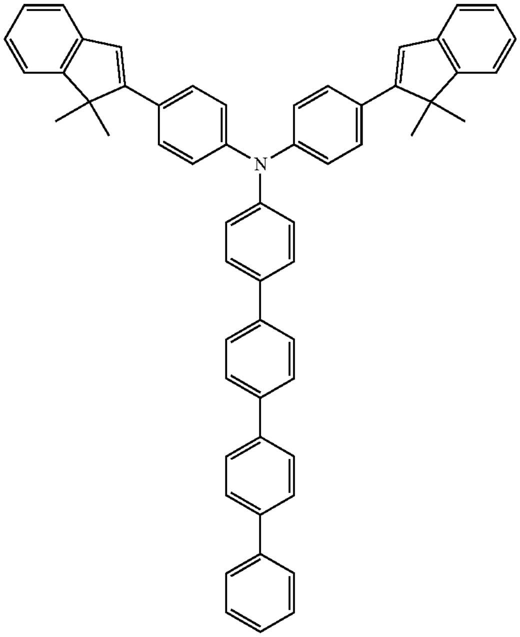
373
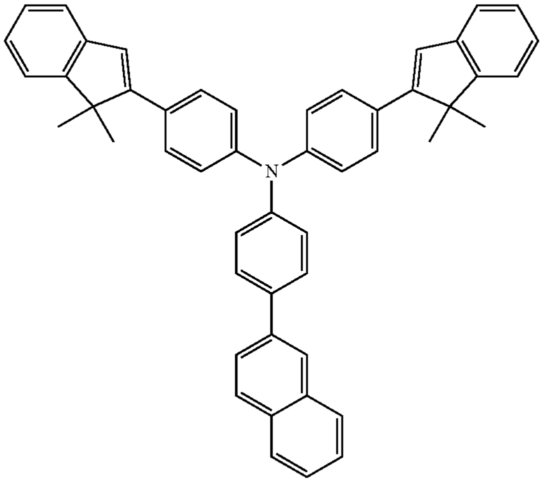
374
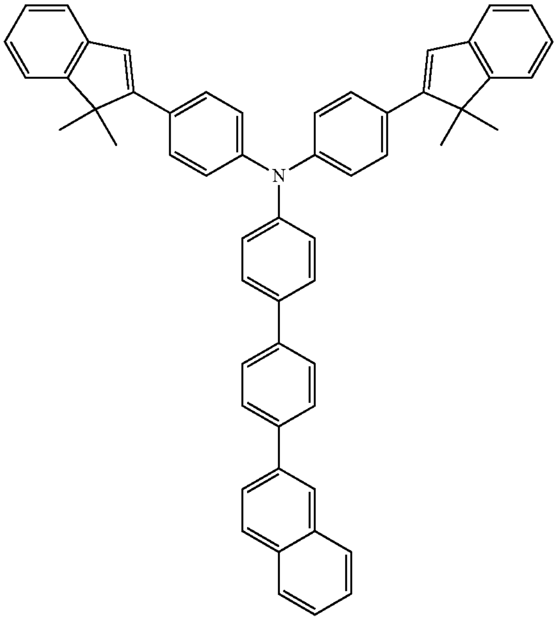

-continued
375
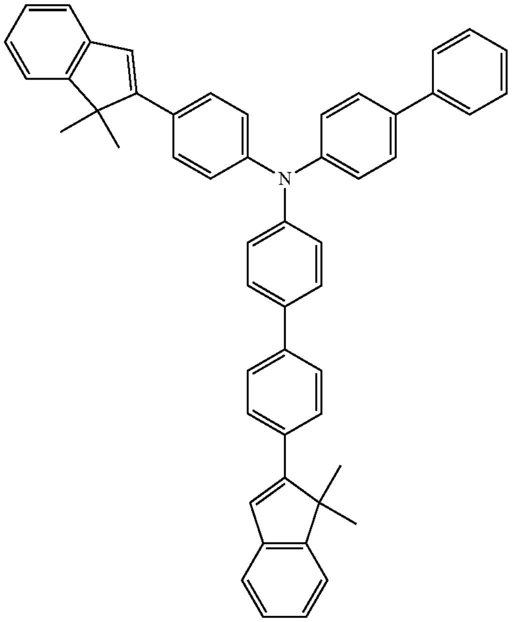
376
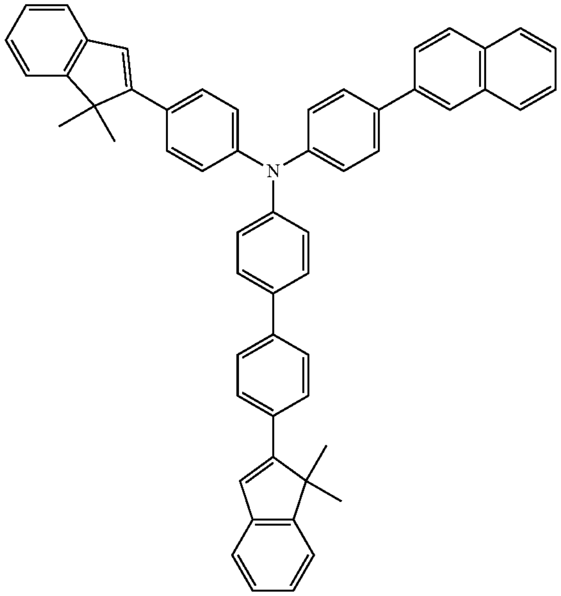
377
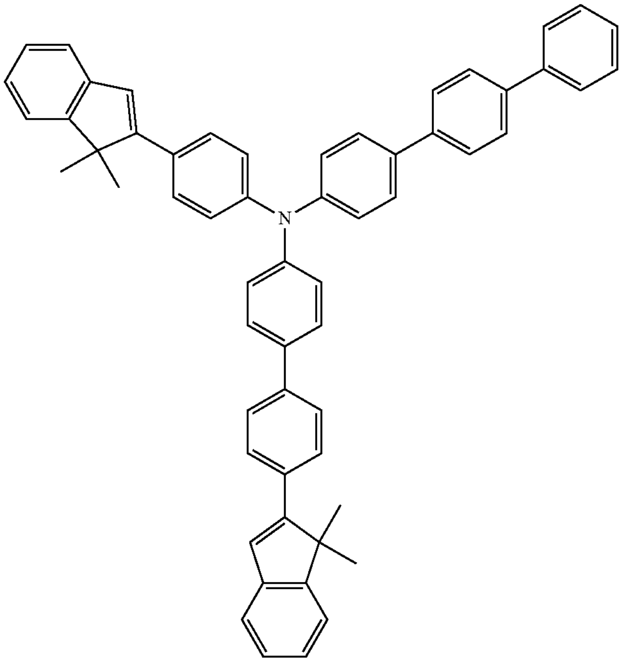

-continued
378
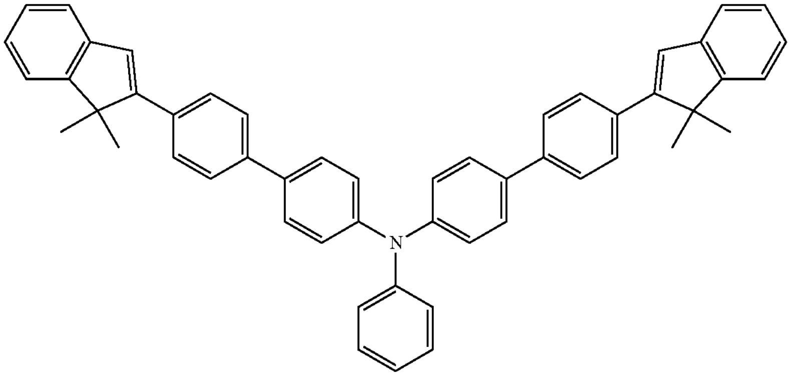
379
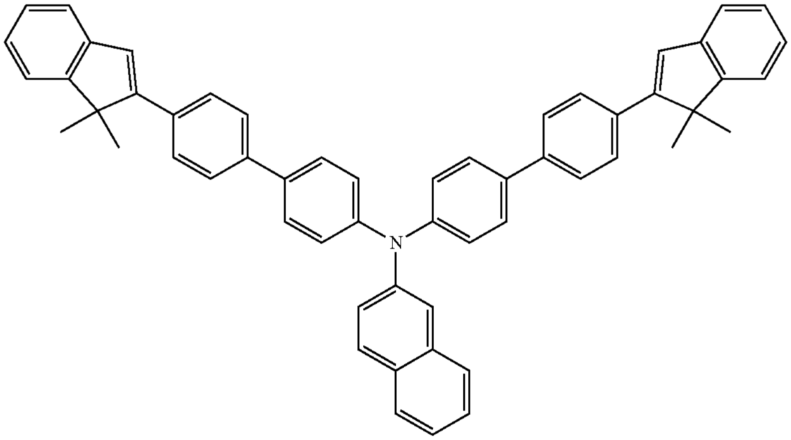
380
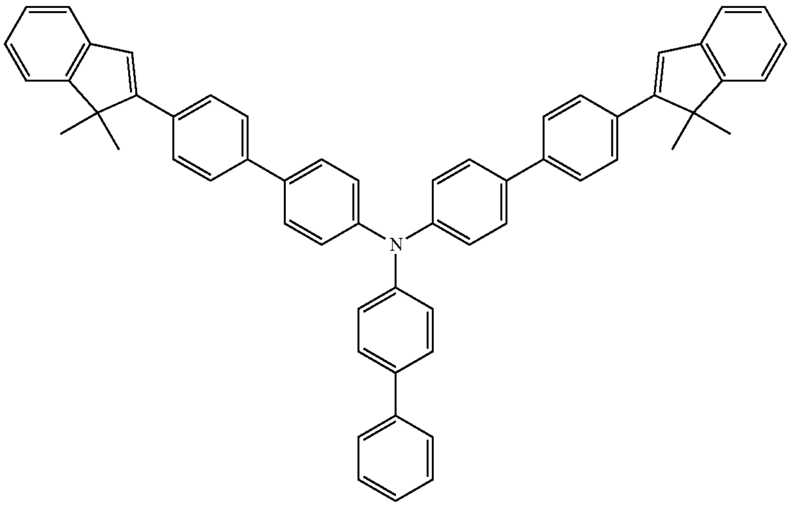

-continued
381
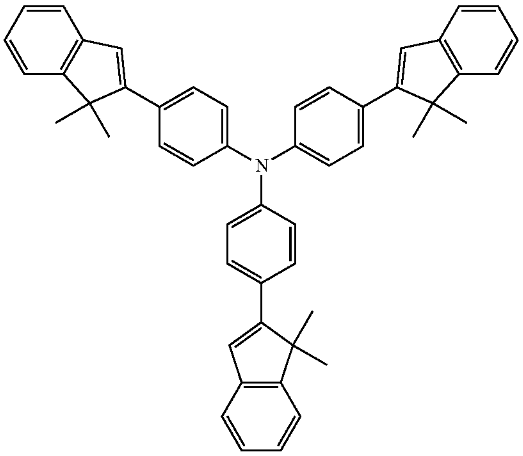
382
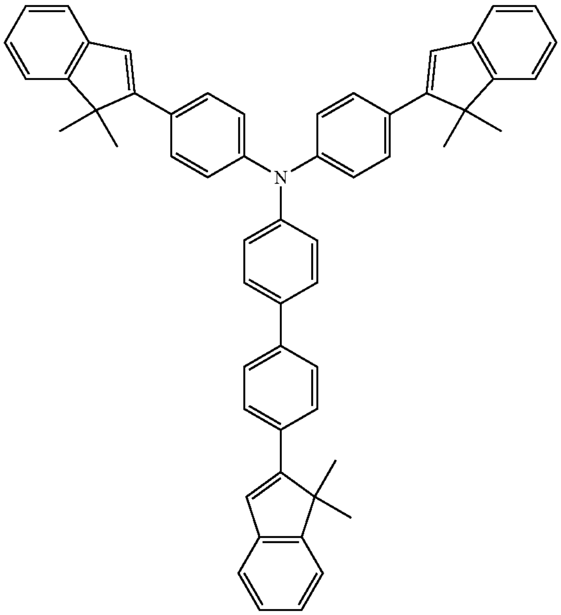
383
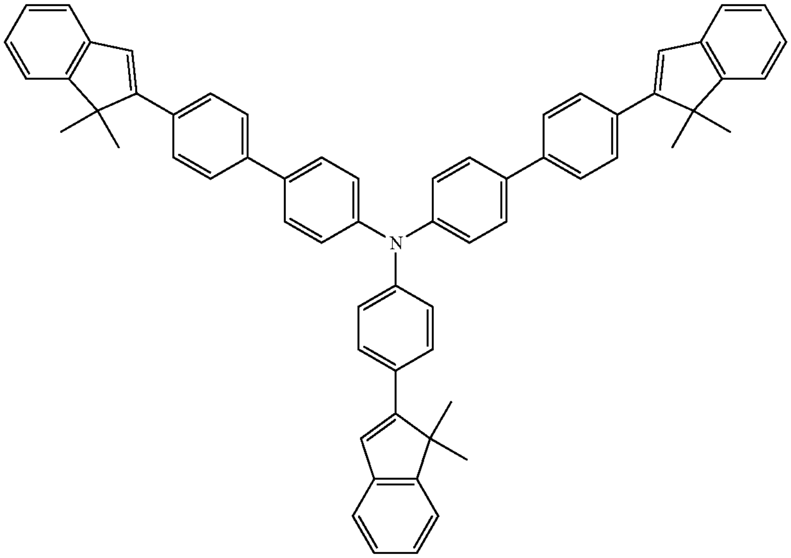

-continued
384
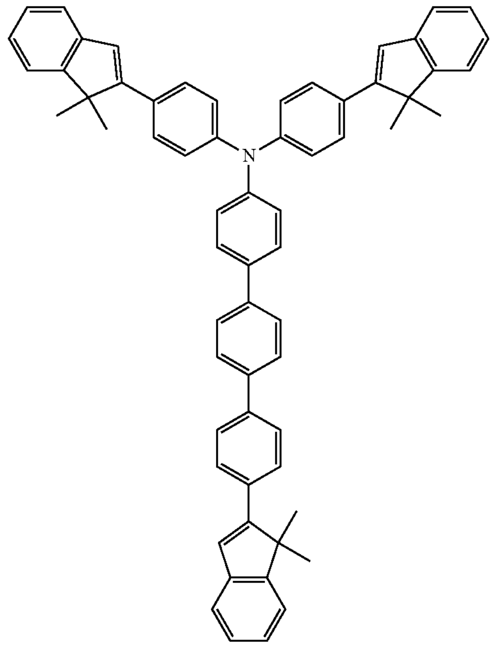
385
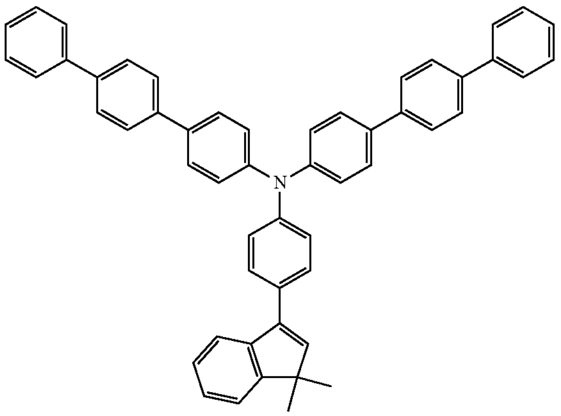
386
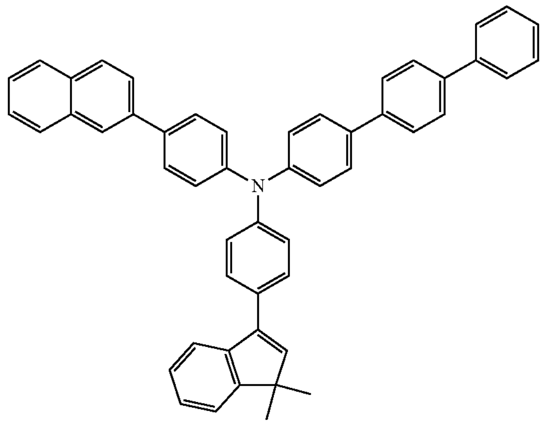
387
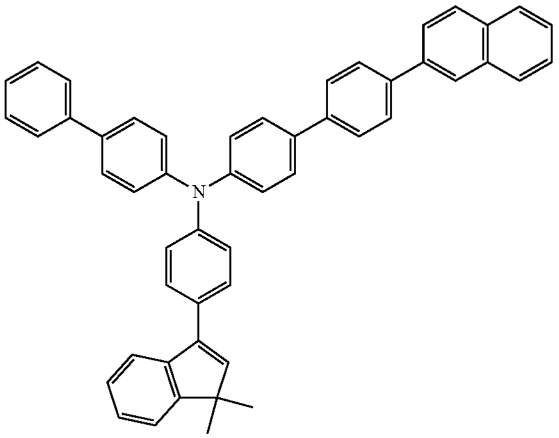
388
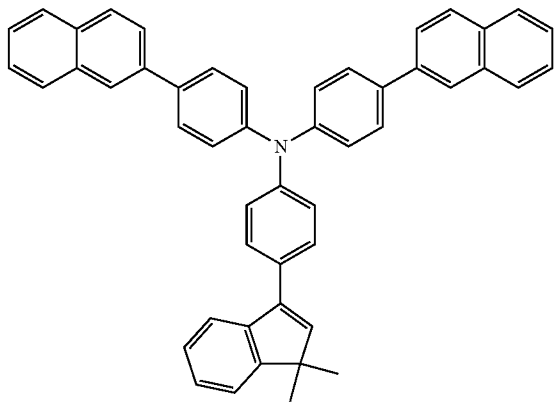
389
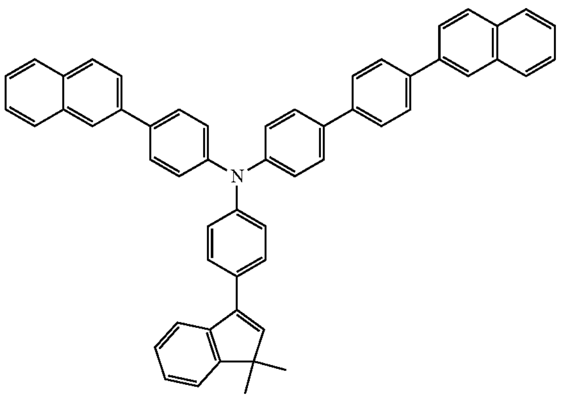

-continued
390
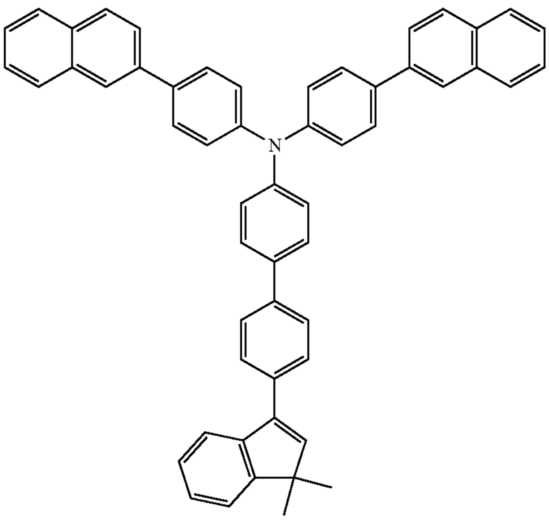
391
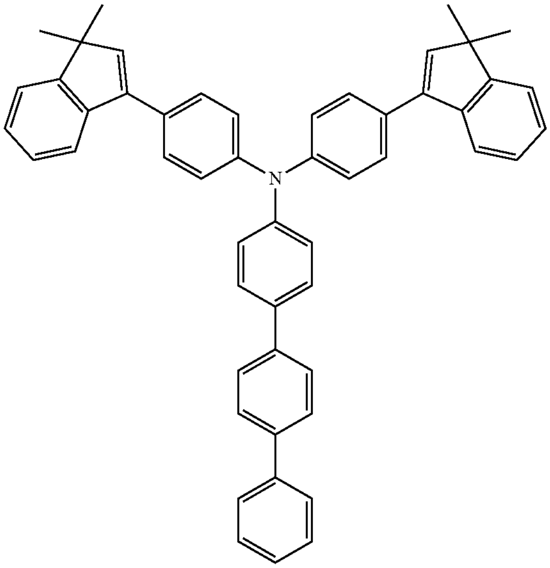
392
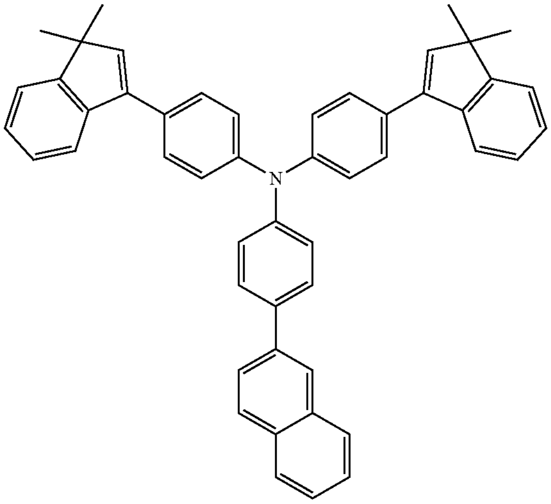
393
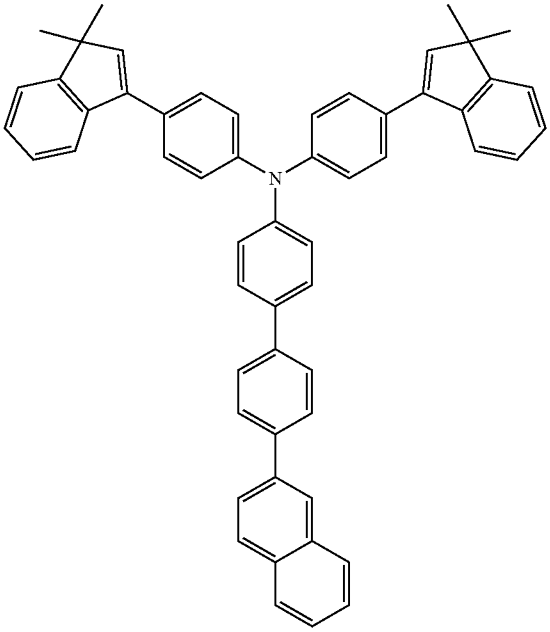

-continued
394
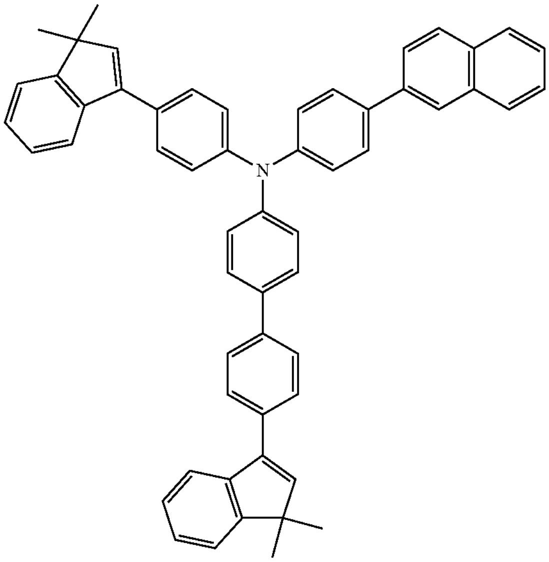
395
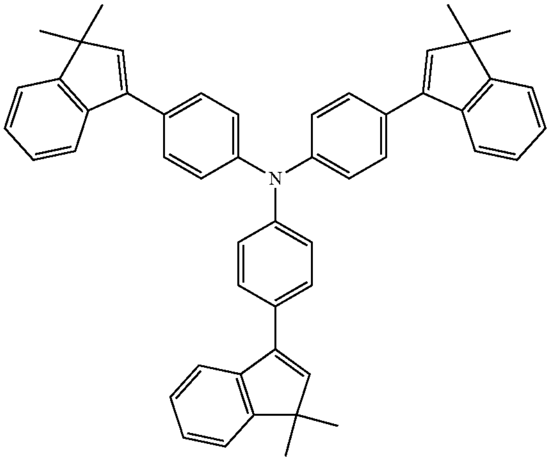
396
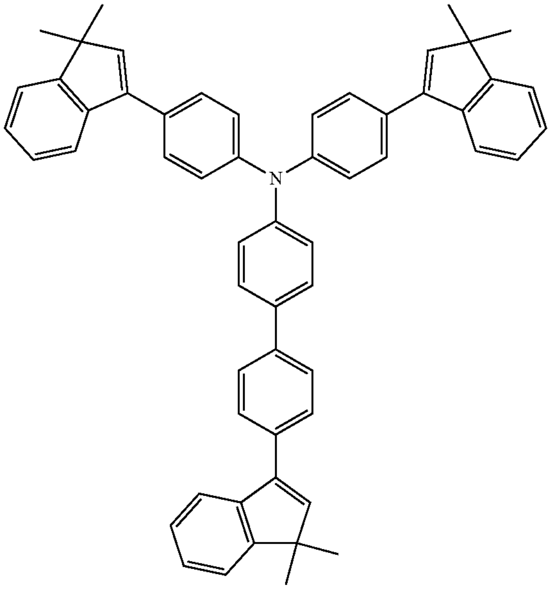
397
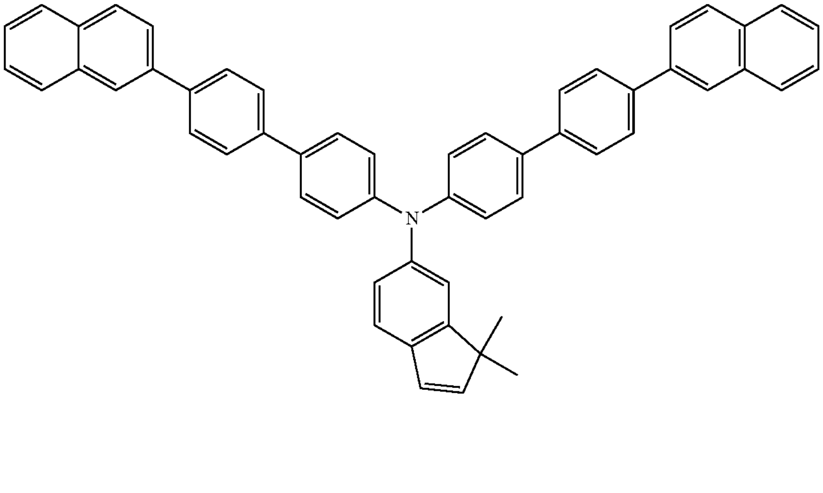

-continued
398
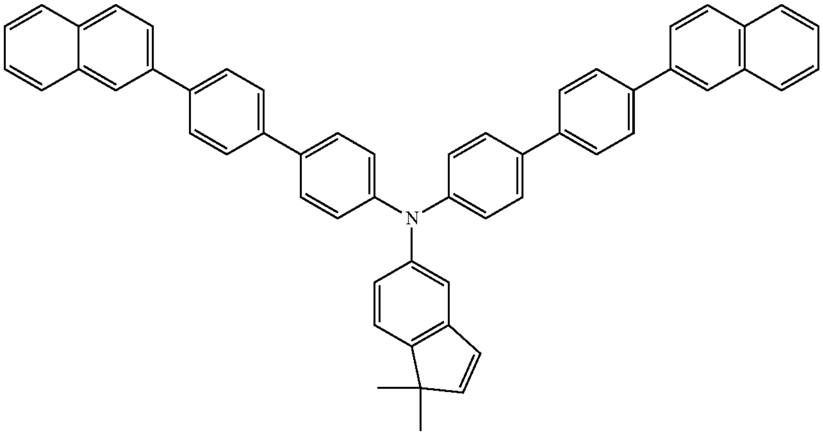
399
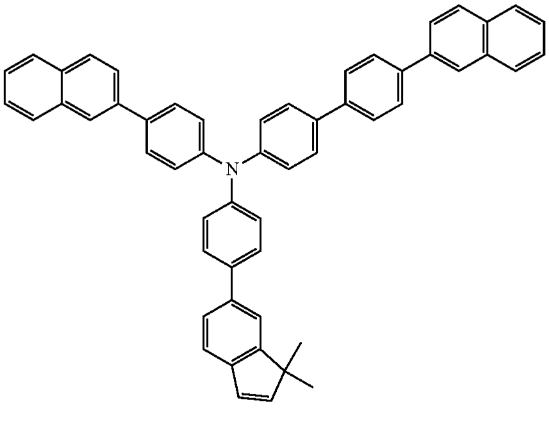
400
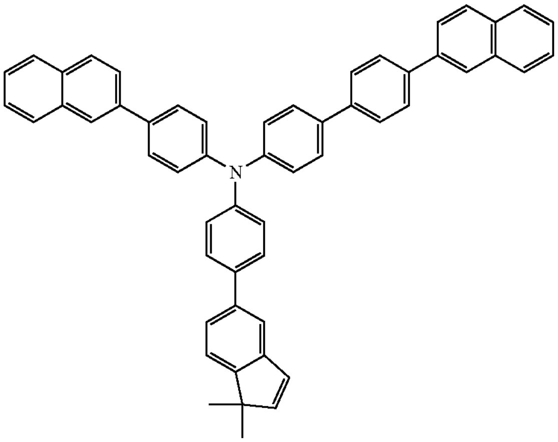
401
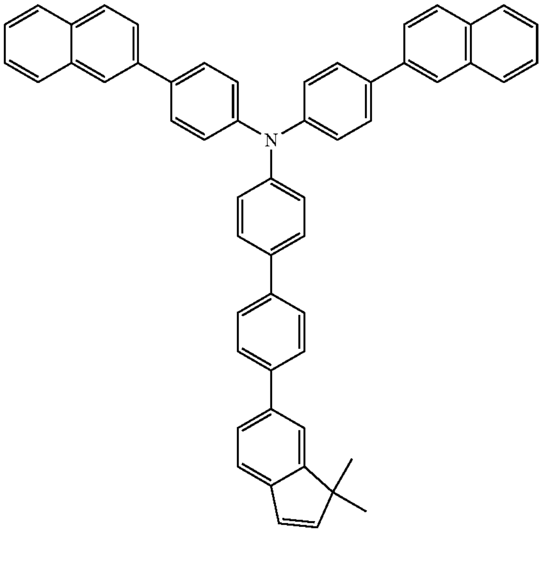
402
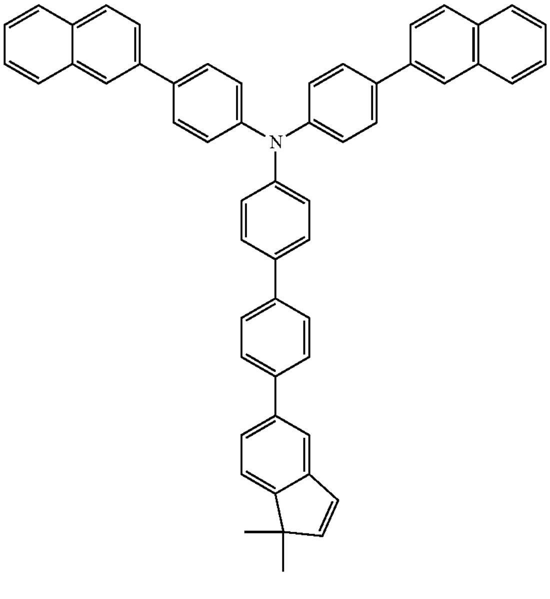

-continued
403
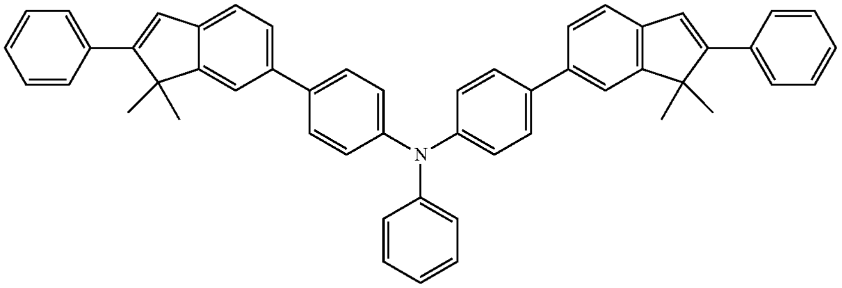
404
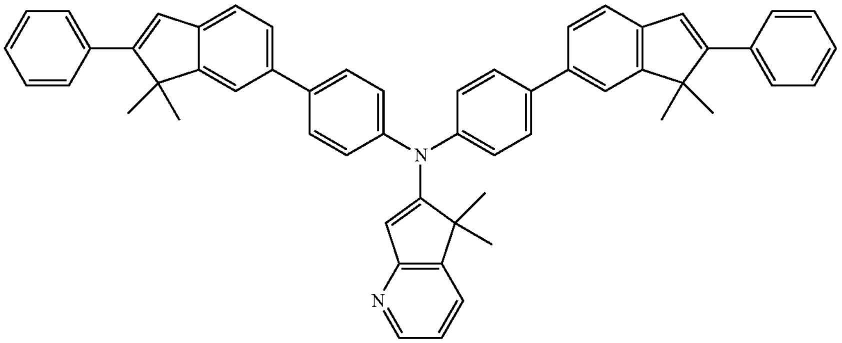
405
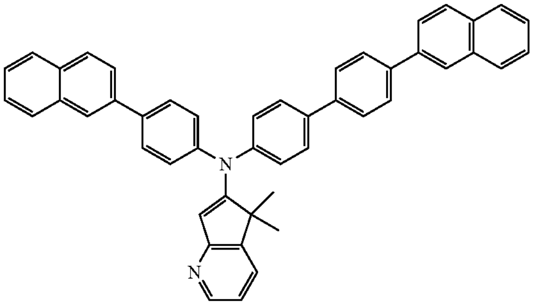
406
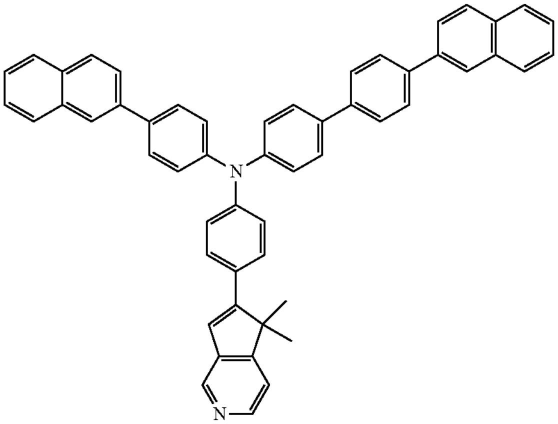
407
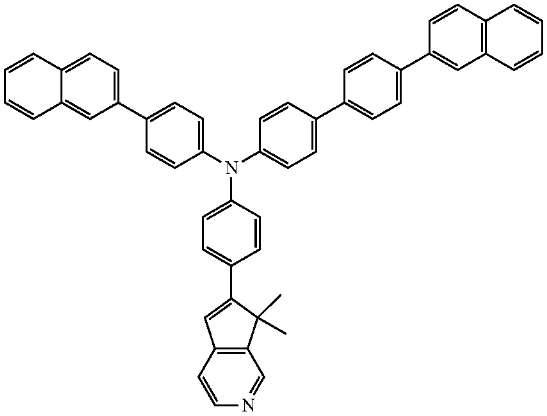
408
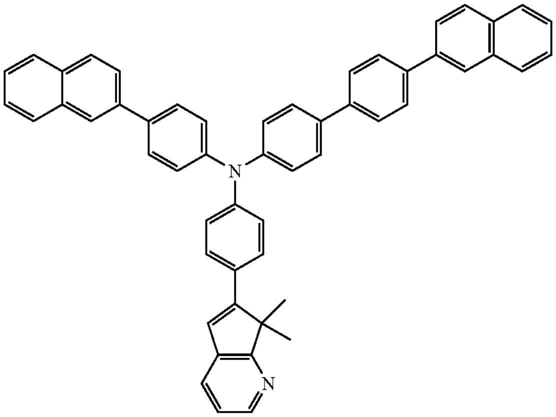

-continued
409
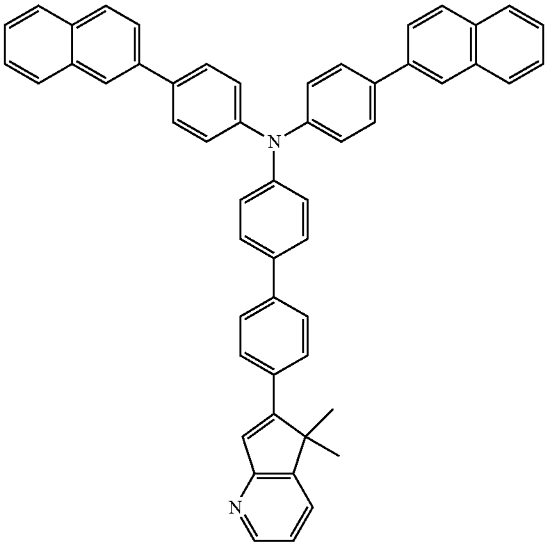
410
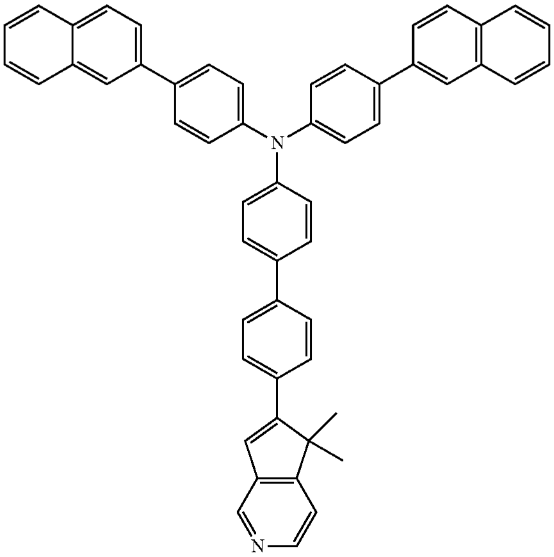
411
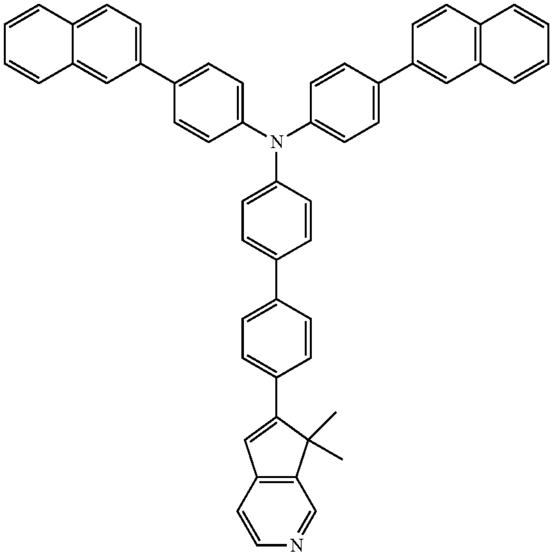
412
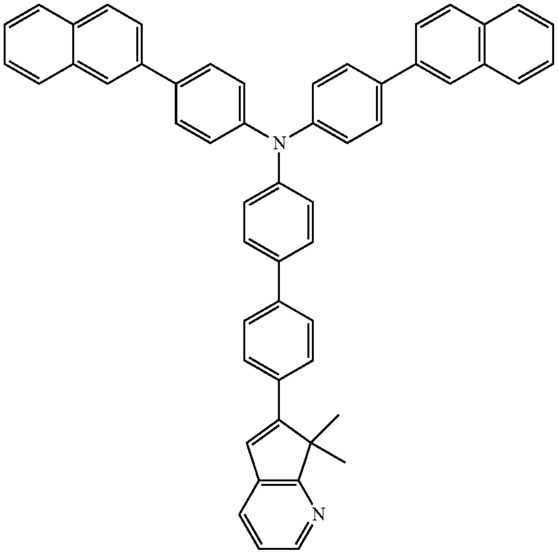
413
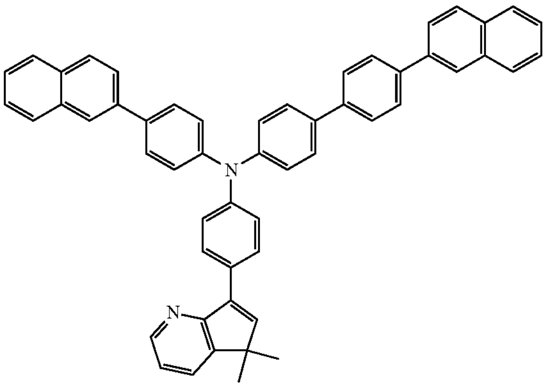
414
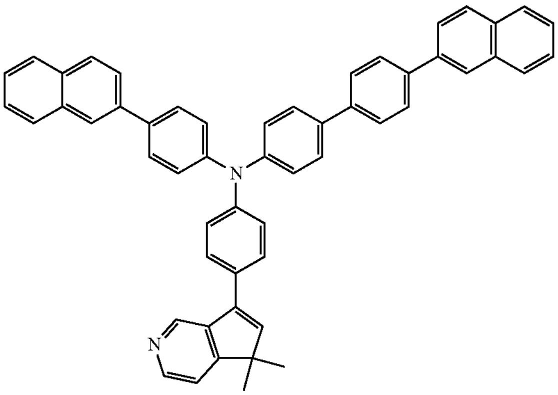

-continued
415
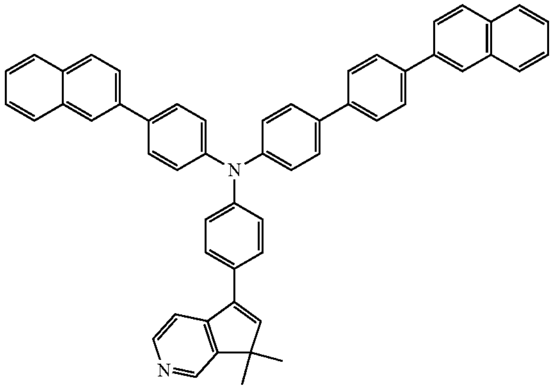
416
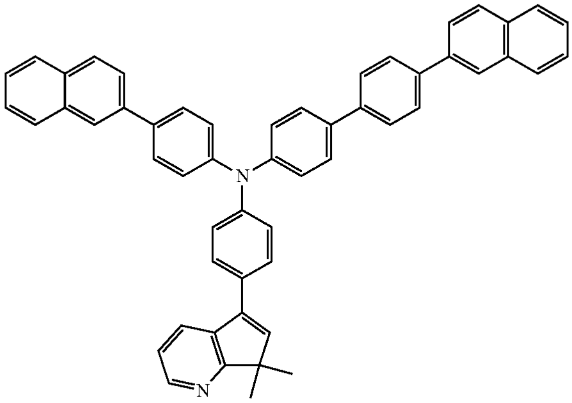
417
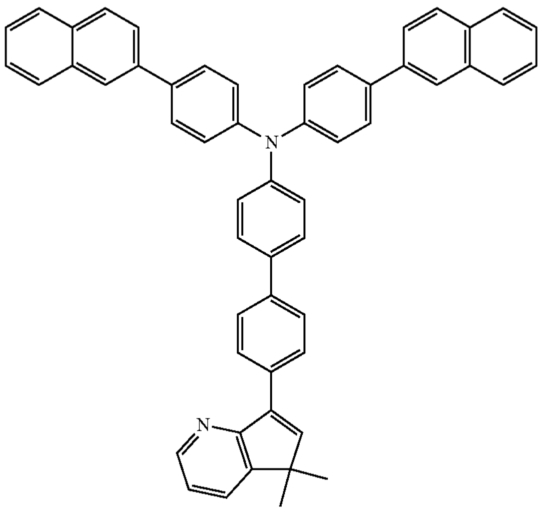
418
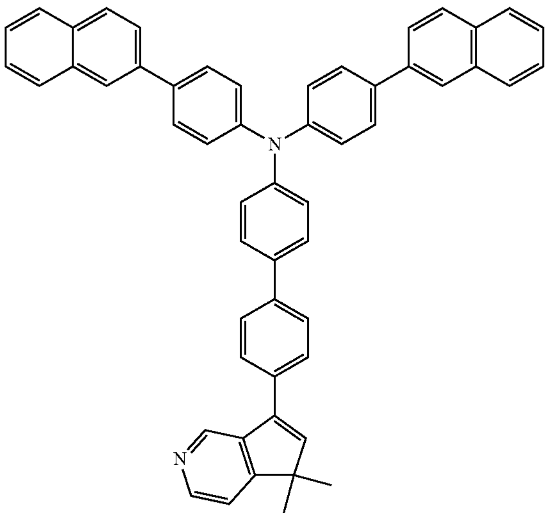
419
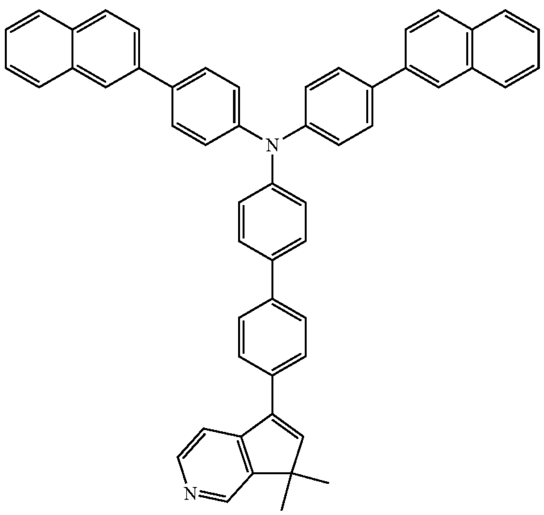
420
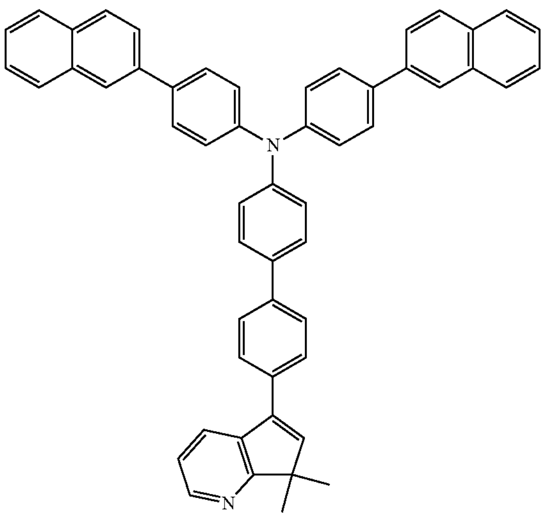

-continued
421
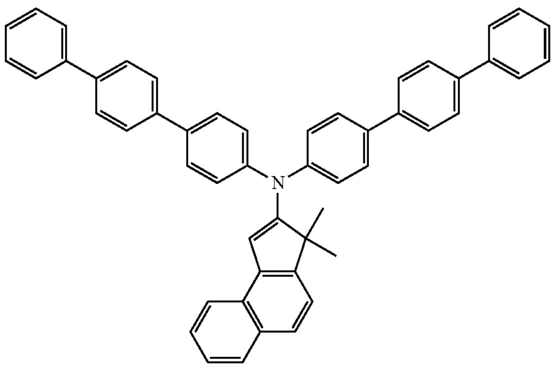
422
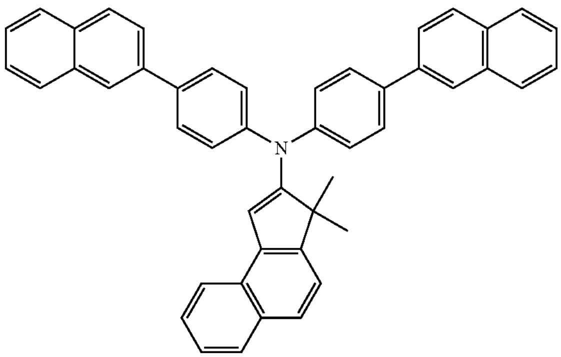
423
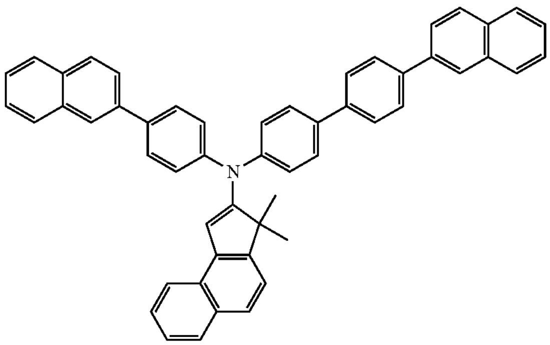
424
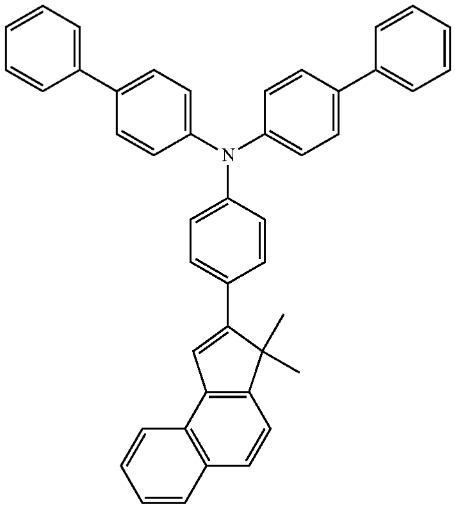
425
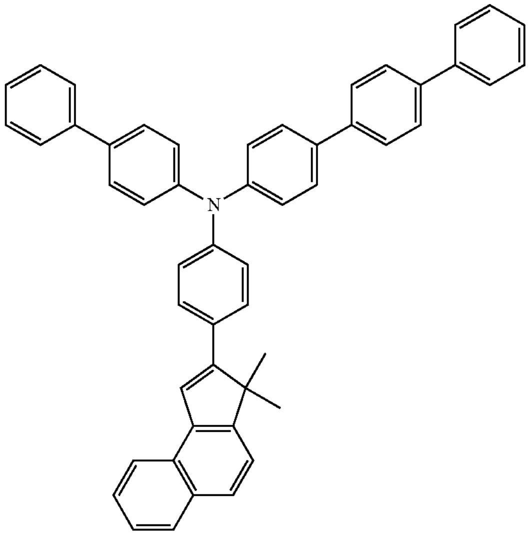
426
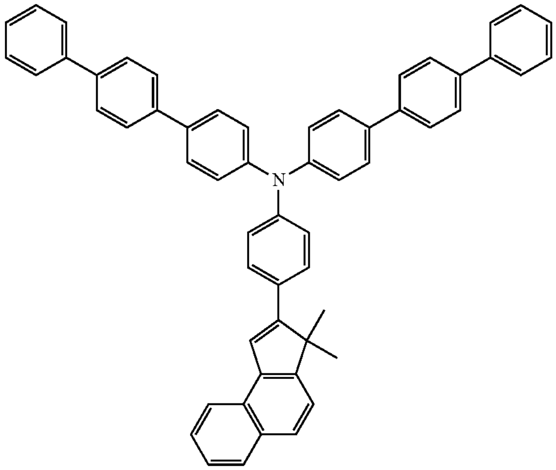

-continued
427
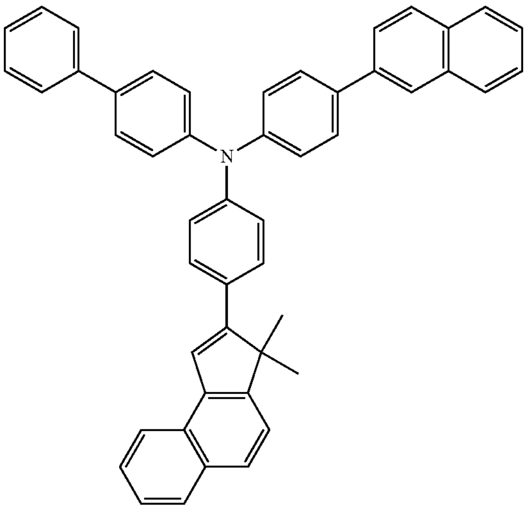
428
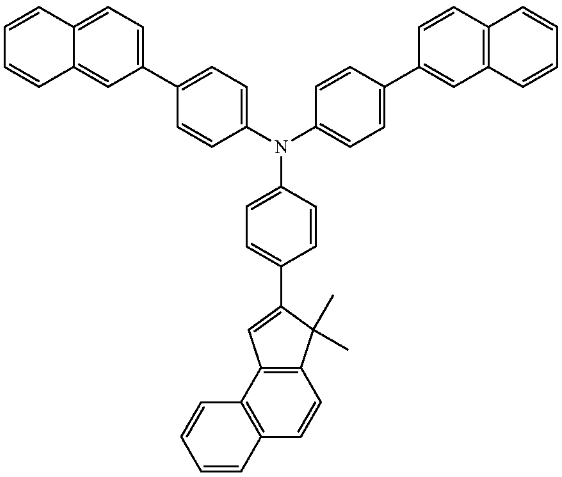
429
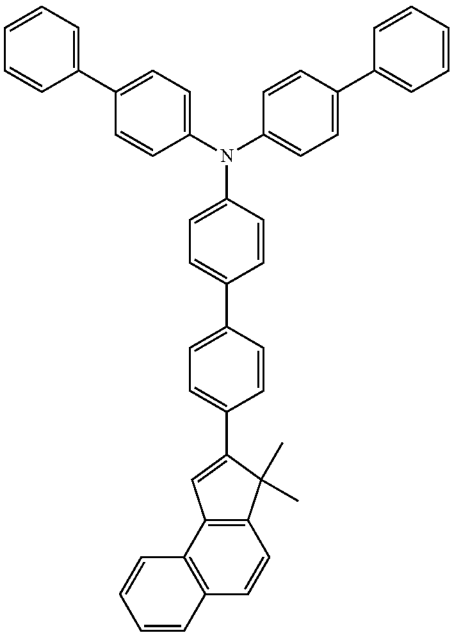
430
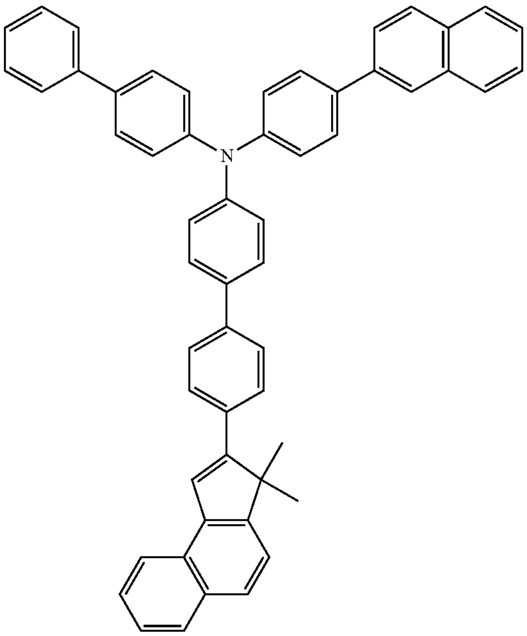
431
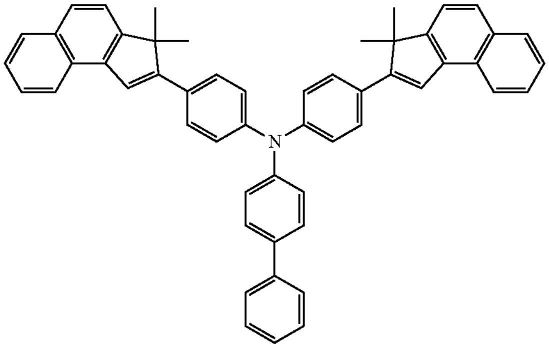
432
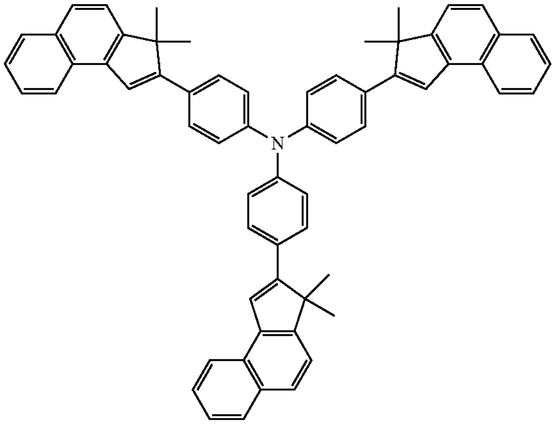

-continued
433
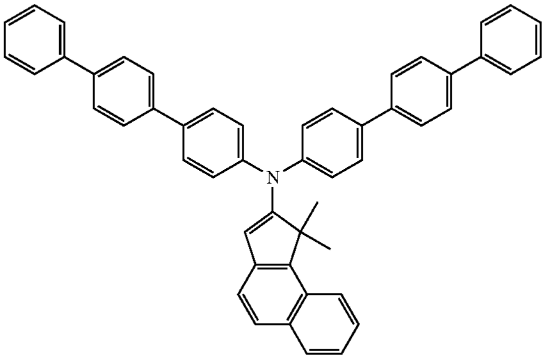
434
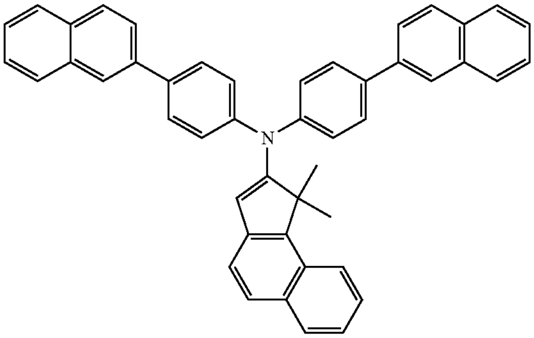
435
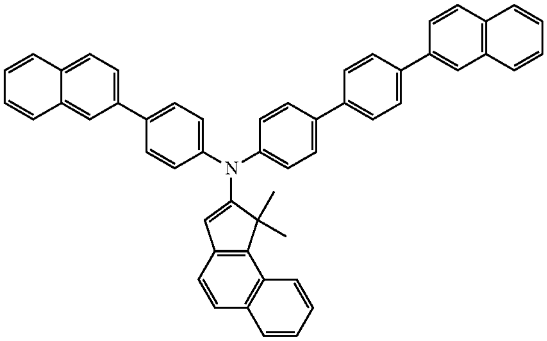
436
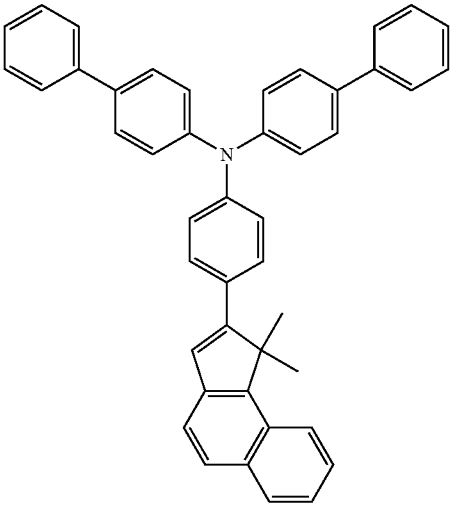
437
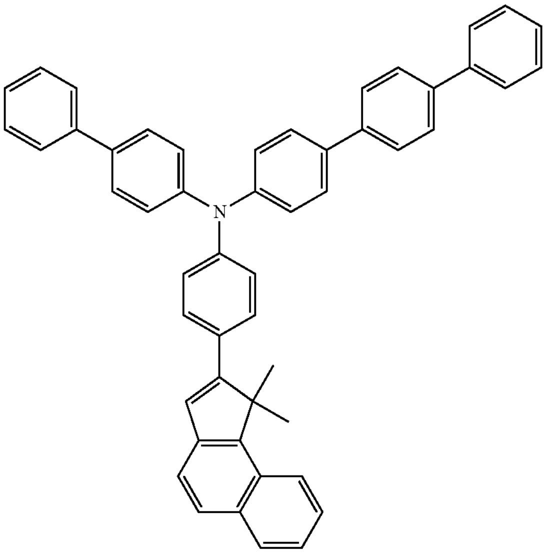
438
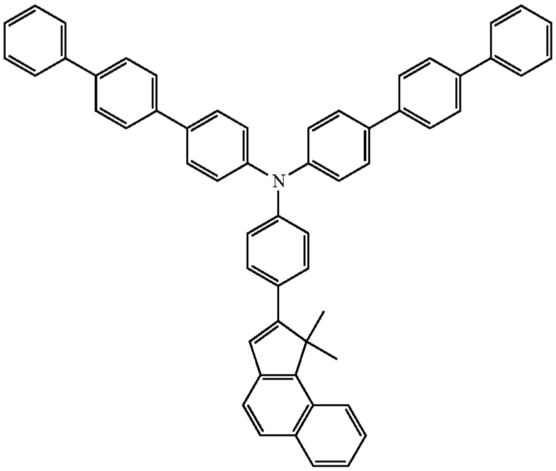

-continued
439
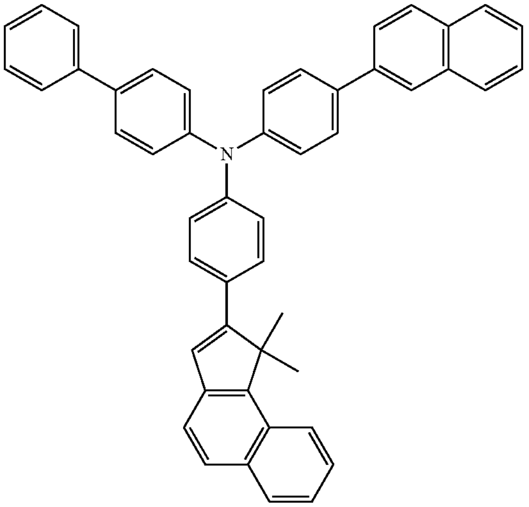
440
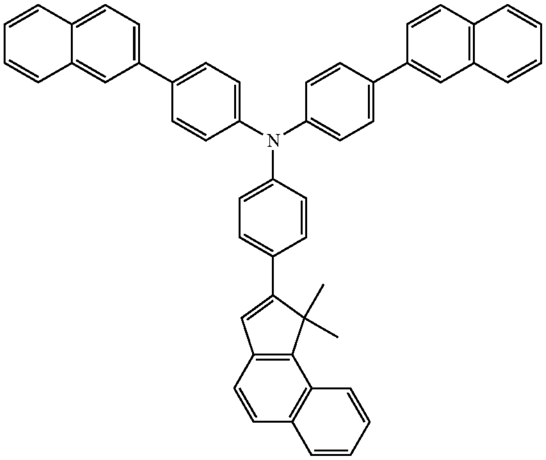
441
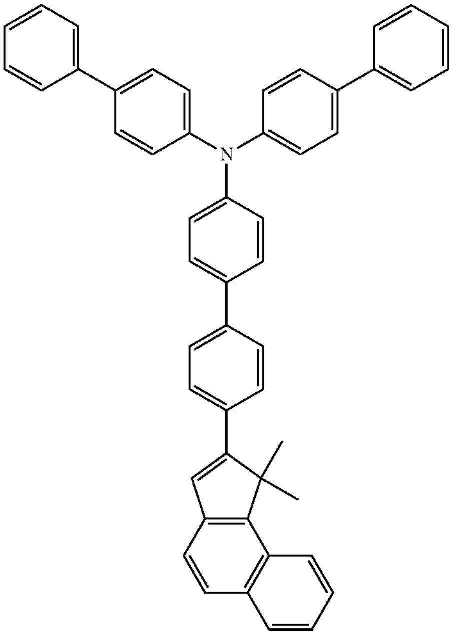
442
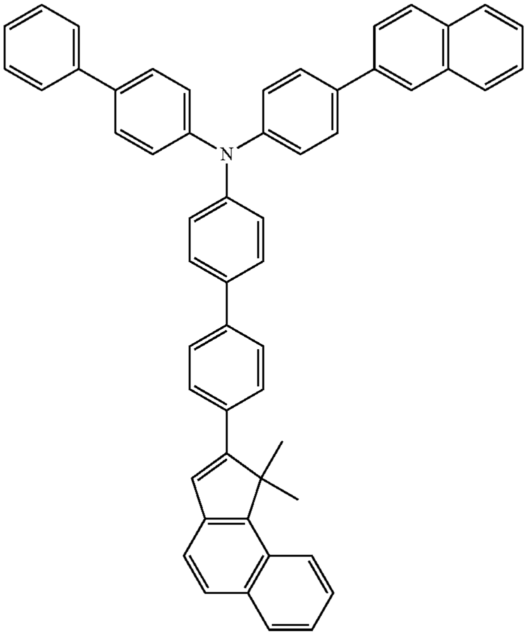
443
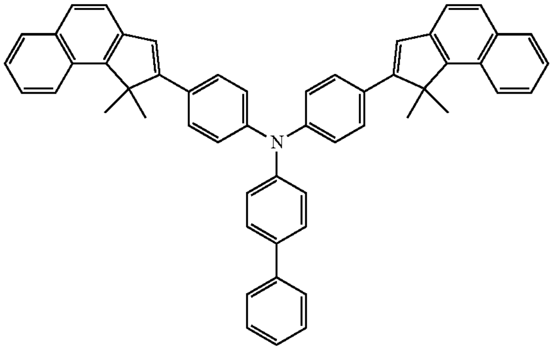
444
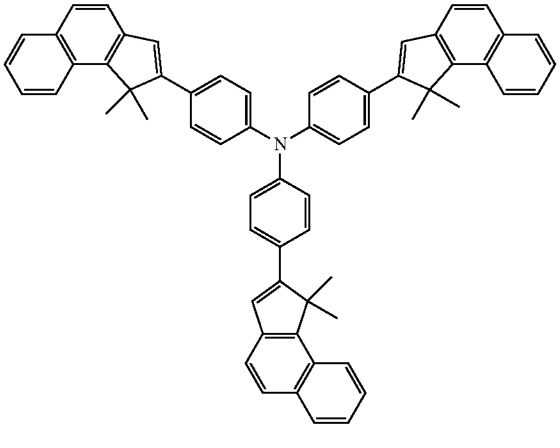

-continued
445
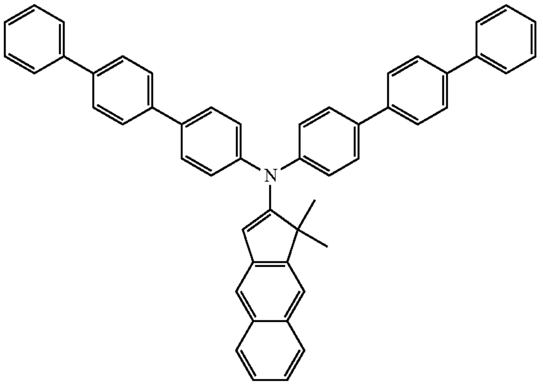
446
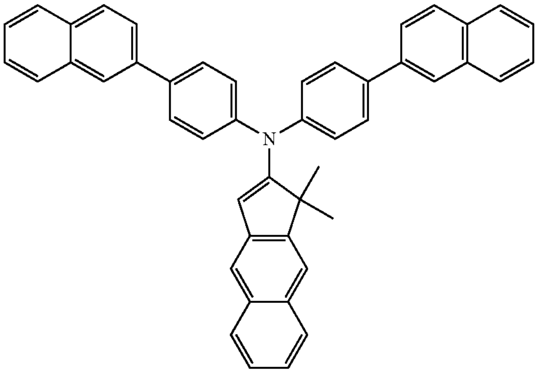
447
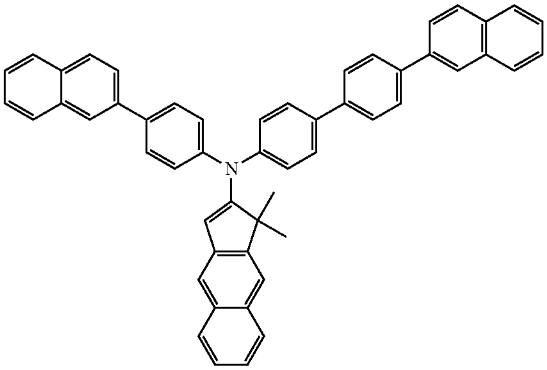
448
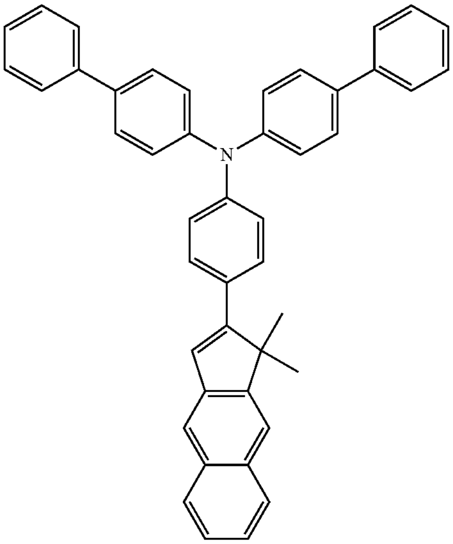
449
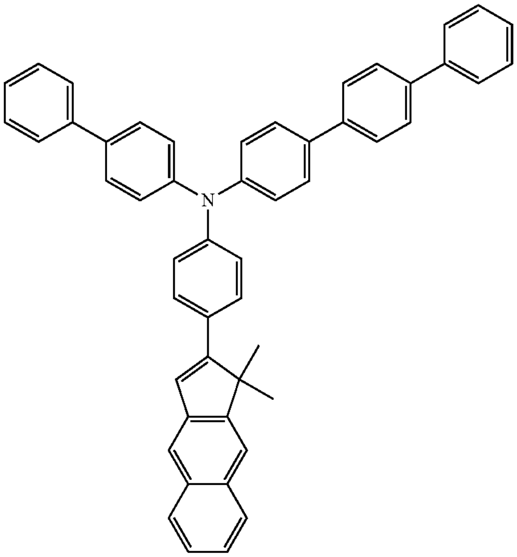
450
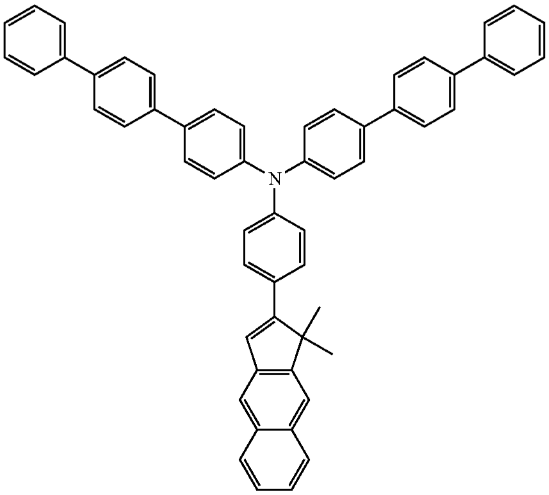

-continued
451
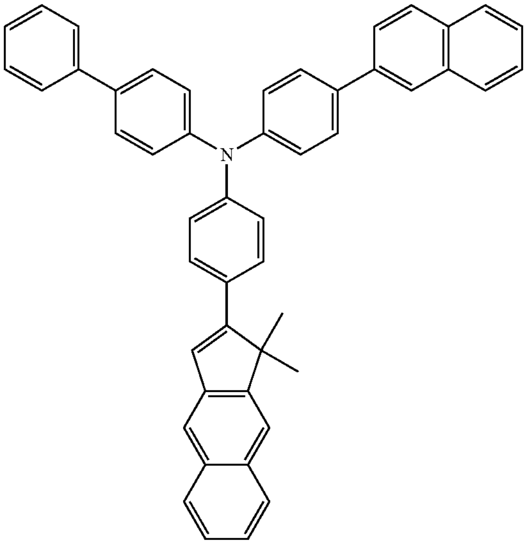
452
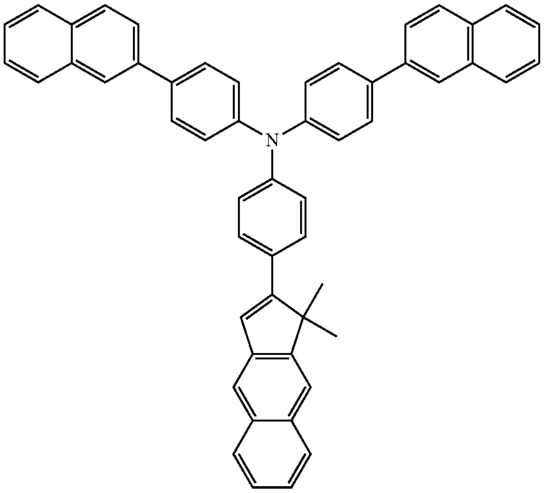
453
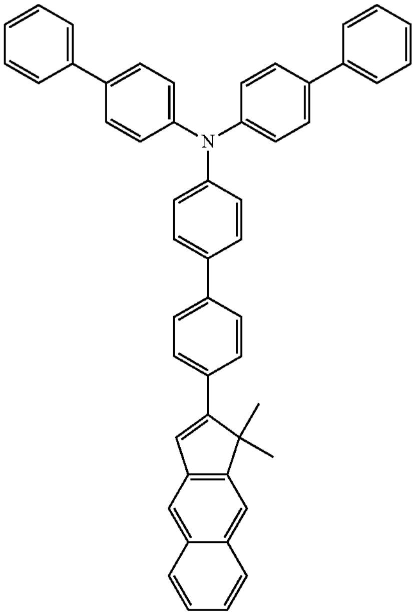
454
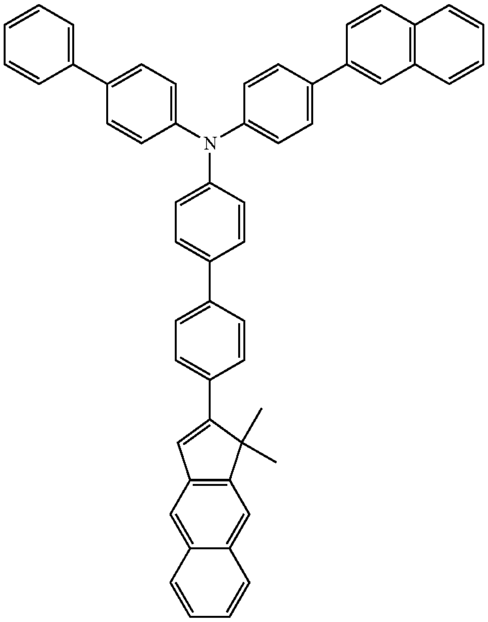
455
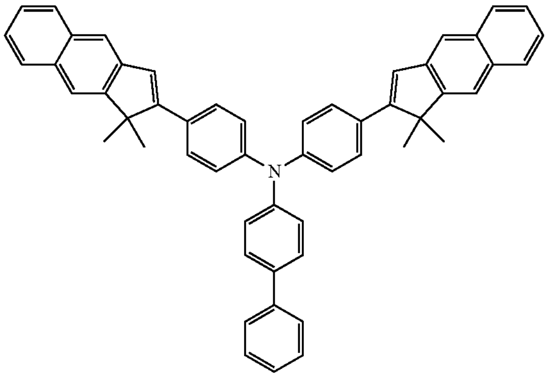
456
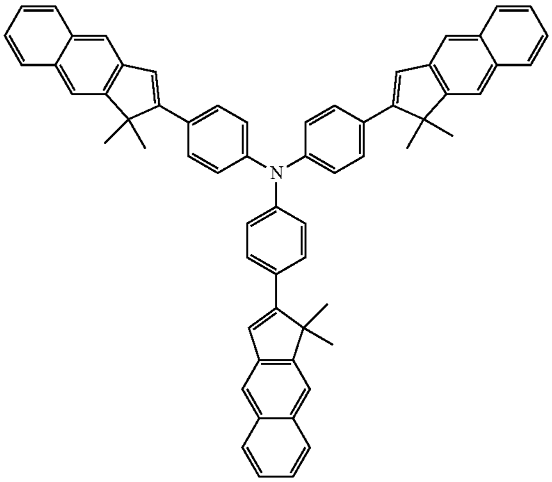

-continued
457
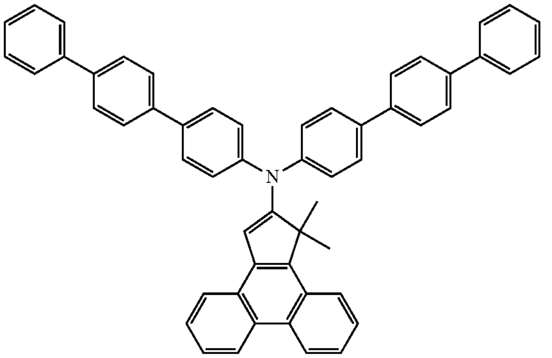
458
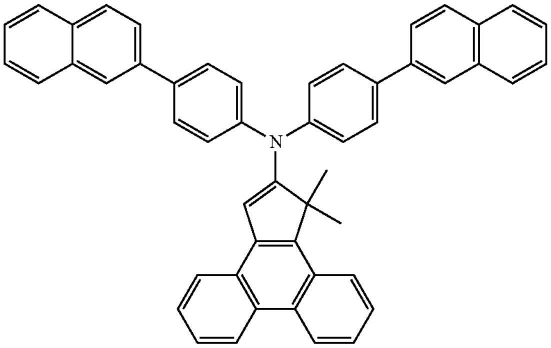
459
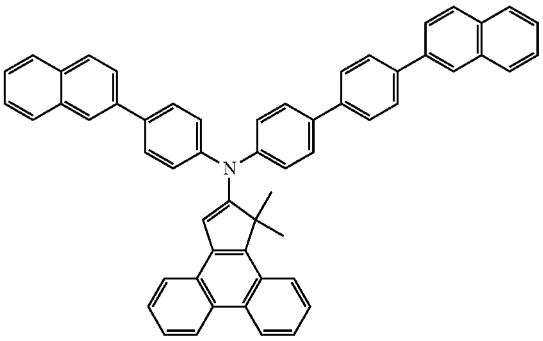
460
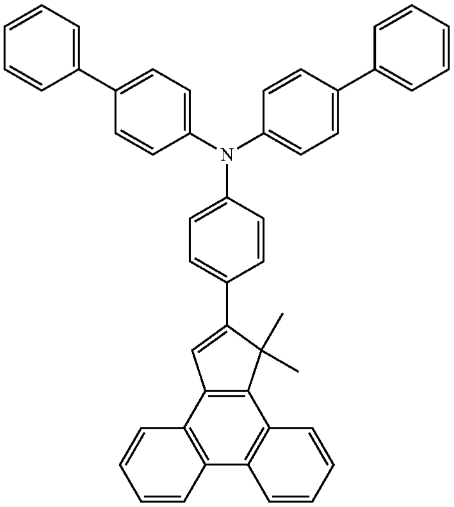
461
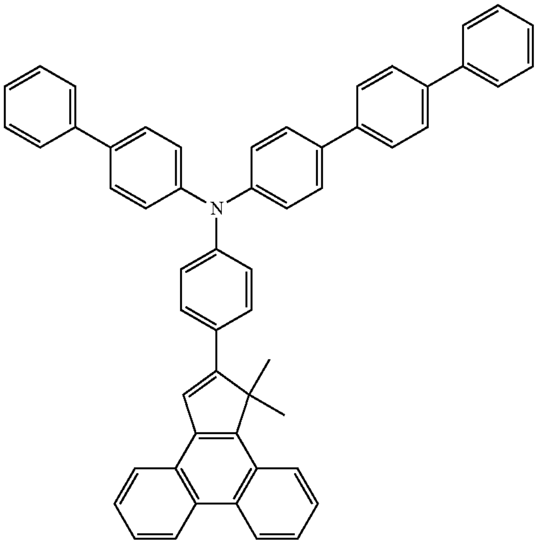
462
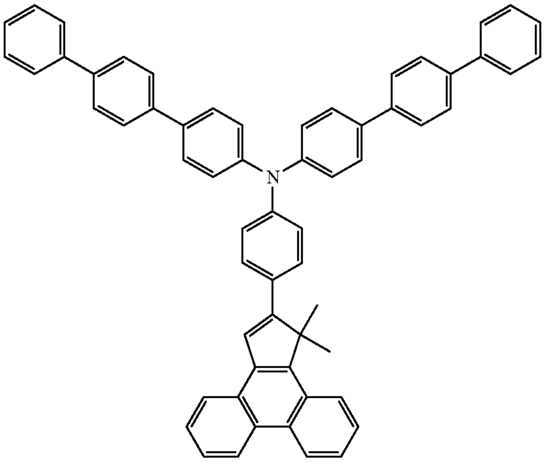

-continued
463
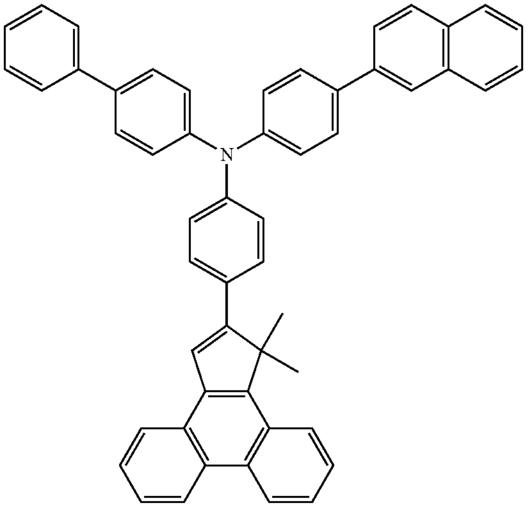
464
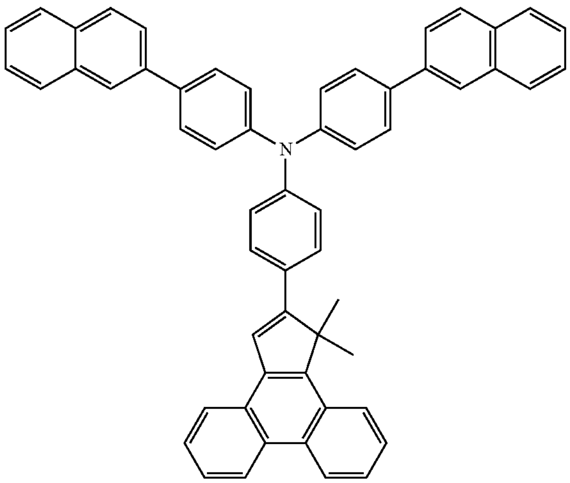
465
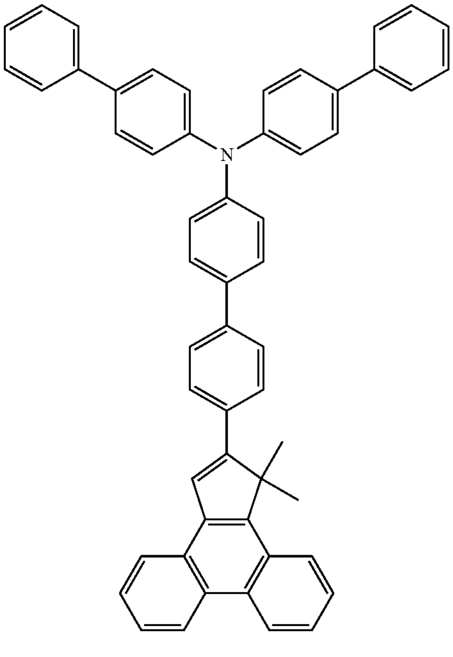
466
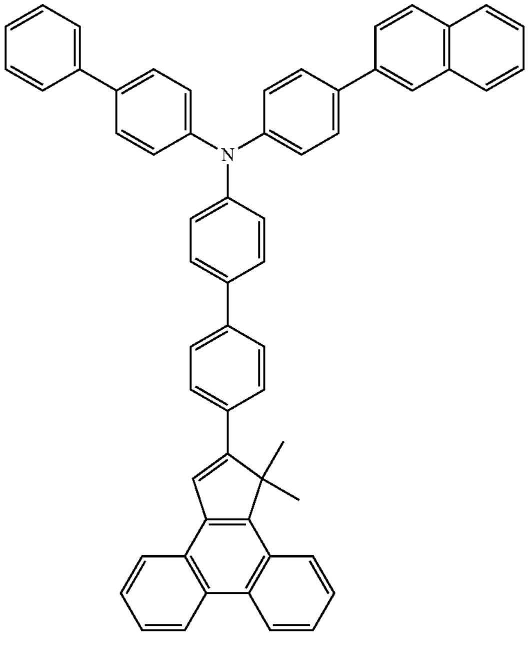

-continued
467
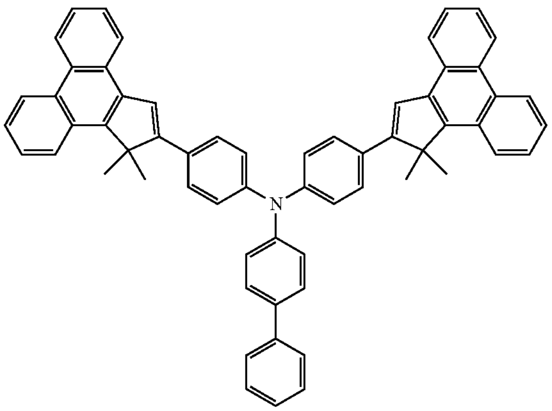
468
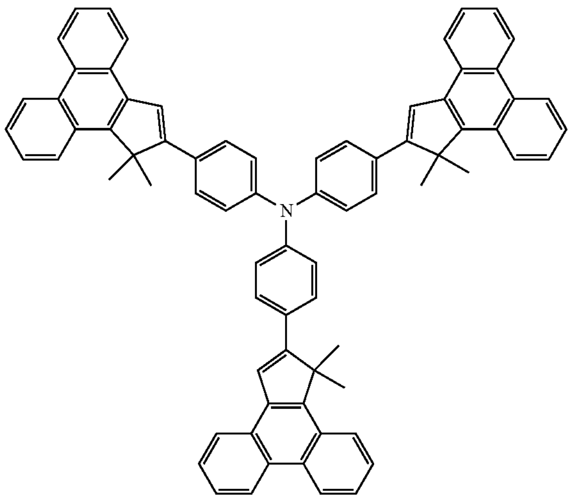
469
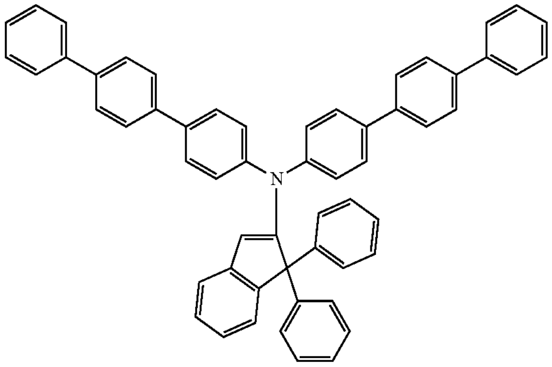
470
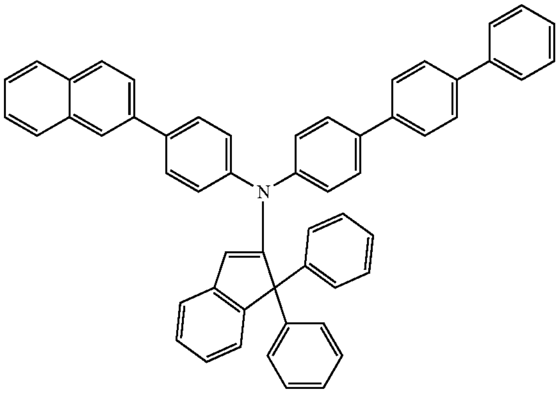
471
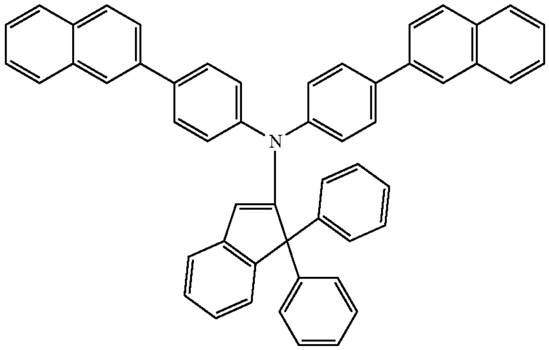
472
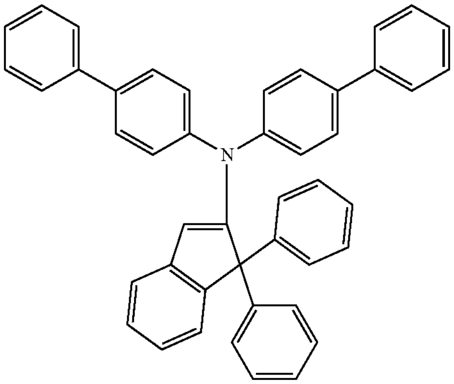

-continued
473
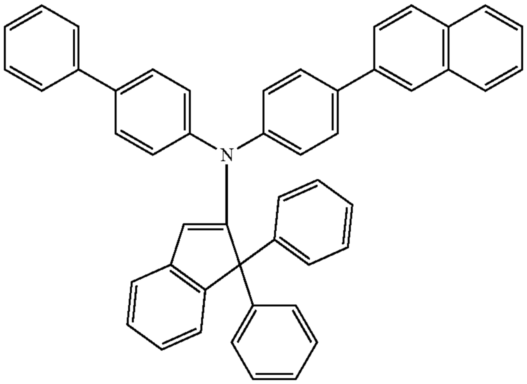
474
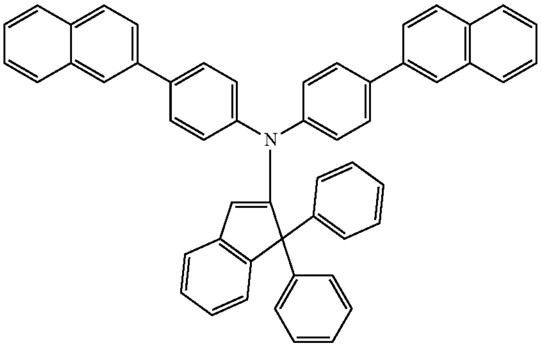
475
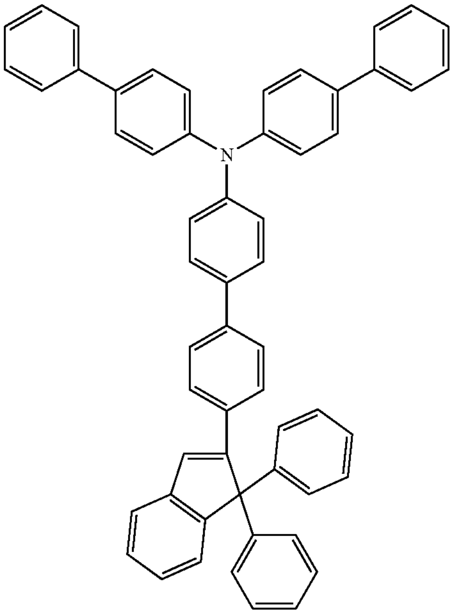
476
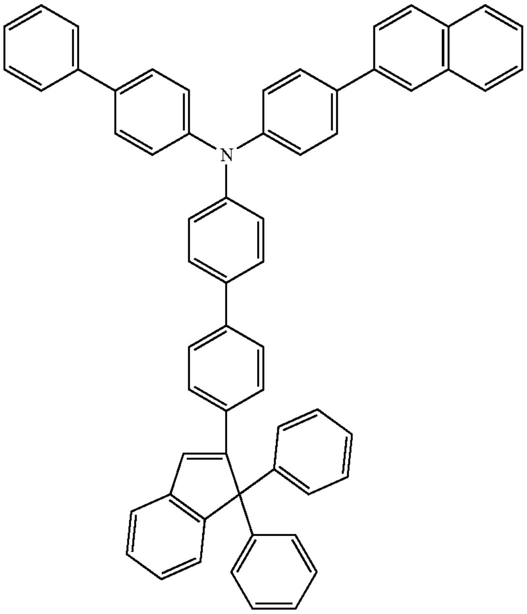
477
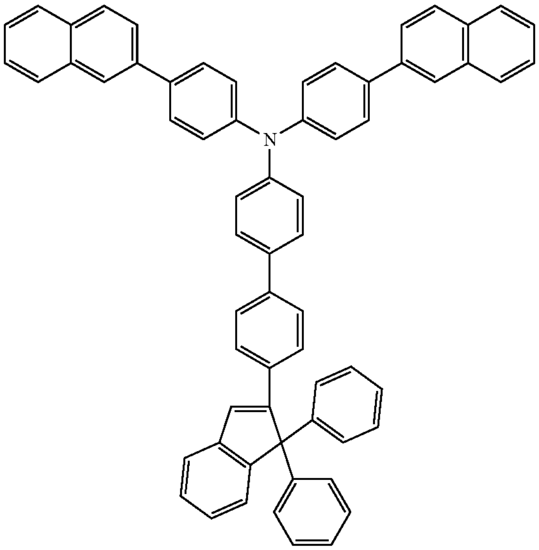
478
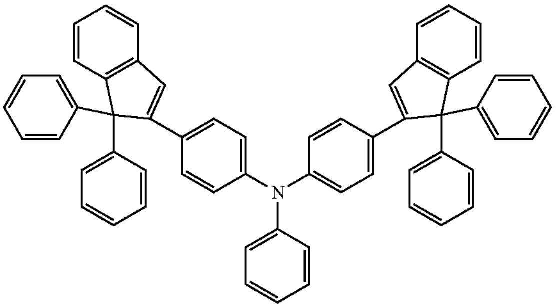

-continued
479
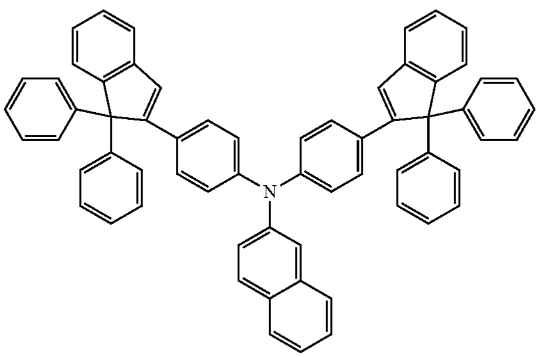
480
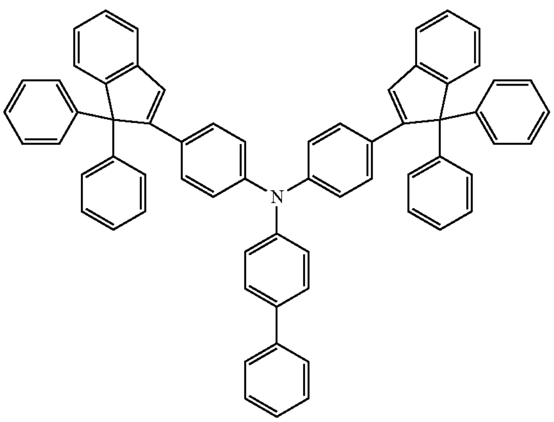
481
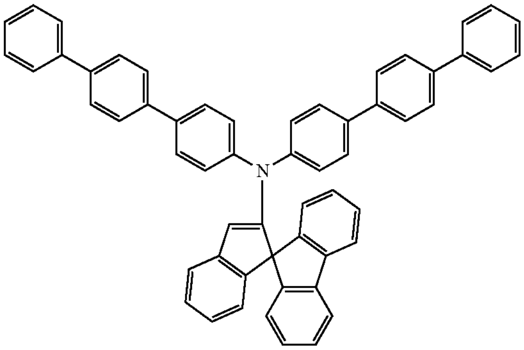
482
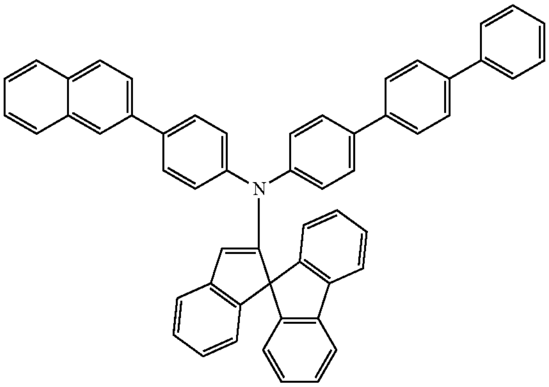
483
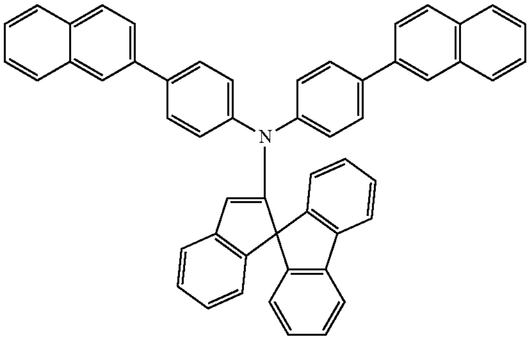
484
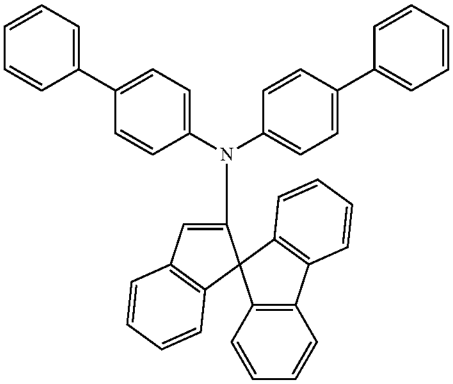
485
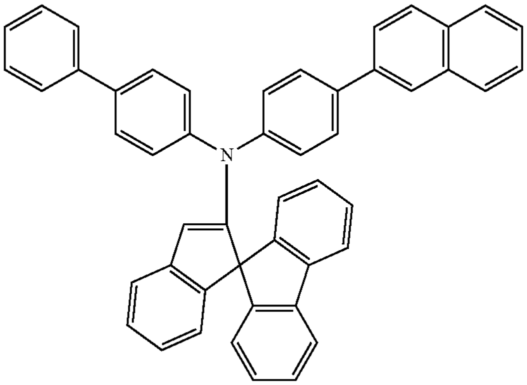
486
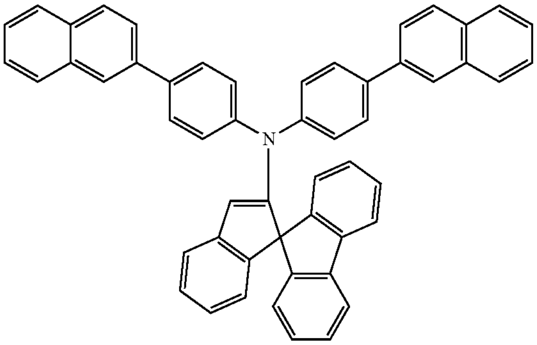

-continued
487
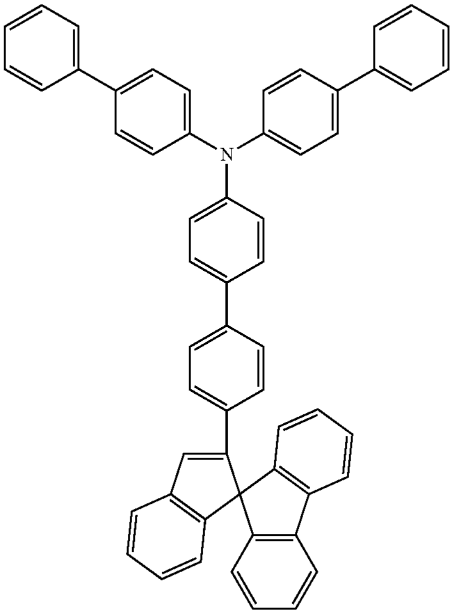
488
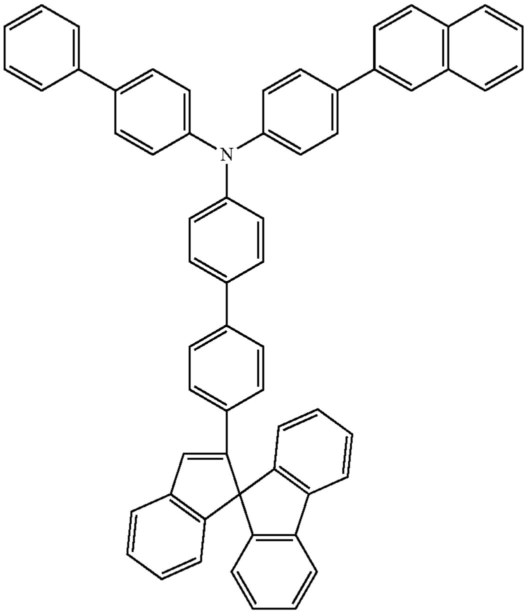
489
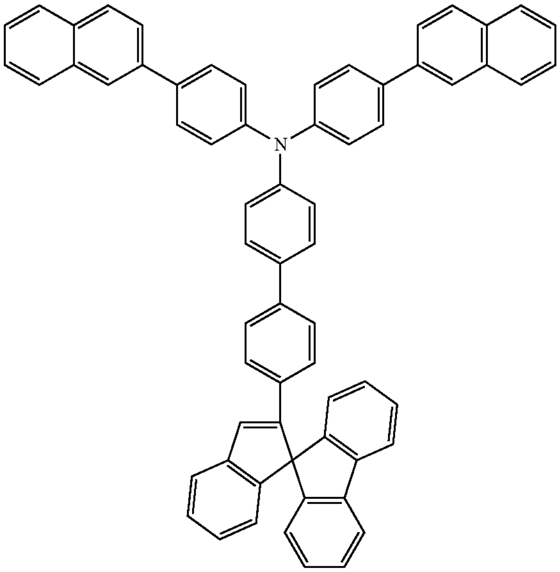
490
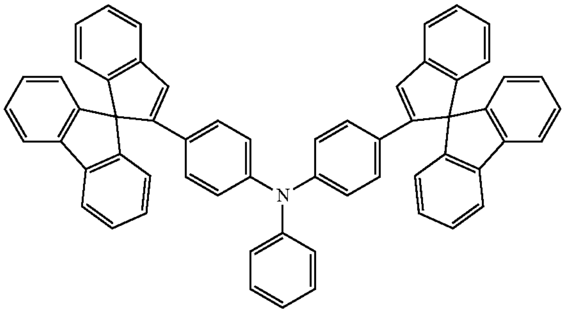
491
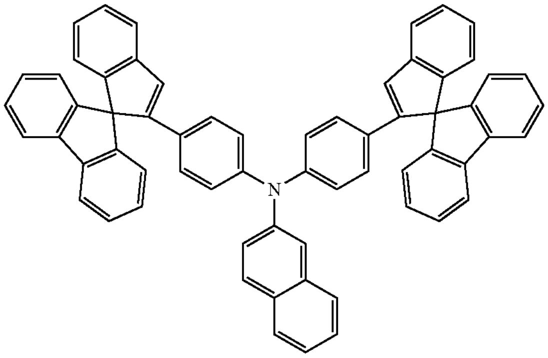
492
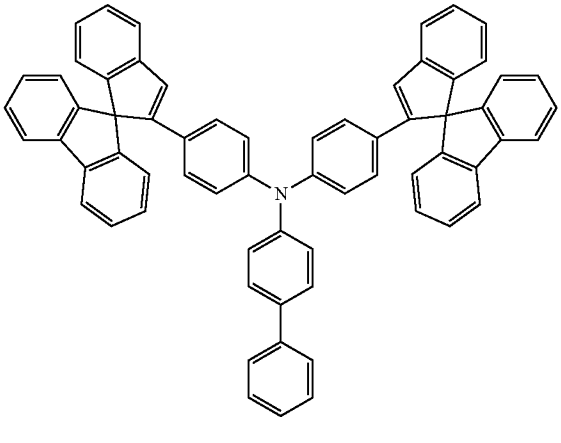

An embodiment of the capping layer compound of the present invention may be synthesized by an amination reaction, and a schematic synthesis reaction scheme is as follows. The following reaction scheme exemplifies the case of having two fused rings in which no N atoms are present, but the present invention is not limited thereto. In the fused rings, one or more N atoms may be present. In addition, in the case where three or more rings are present, the compound can be synthesized through the following reaction scheme.

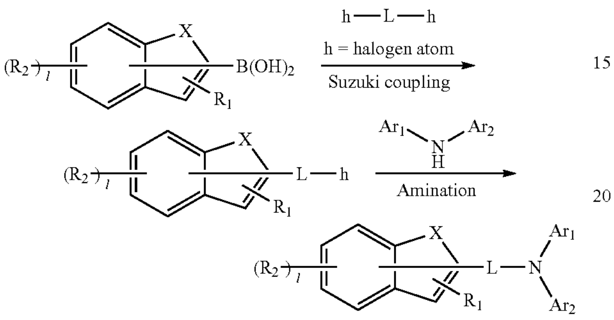

As another aspect of the present invention, there is provided an organic light emitting device including a capping layer, in which the capping layer contains the above-described capping layer compound.

According to one embodiment of the present invention, an organic light emitting device include a first electrode, a second electrode, an organic material layer interposed between the first electrode and the second electrode, and the capping layer disposed on an outer surface of either the first electrode or the second electrode.

Specifically, the capping layer may have a thickness of 300 to 1000 Å.

In addition, the capping layer may have a refractive index of 2.23 or more for a wavelength of 450 nm and preferably specifically 2.30 or more. The capping layer may have an ultraviolet absorption intensity of 0.8 or more for a wavelength of 380 nm and preferably 0.9 or more.

Here, of the both surfaces of each of the first and second electrodes, a surface adjacent to the organic material layer interposed between the first electrode and the second electrode is referred to as an inner surface, and a surface not adjacent to the organic material layer is referred to as an outer surface. That is, when the capping layer is disposed on the outer surface of the first electrode, the first electrode is interposed between the capping layer and the organic material layer while when the capping layer is disposed on the outer surface of the second electrode, the second electrode is interposed between the capping layer and the organic material layer.

According to one embodiment of the present invention, one or more organic material layers may be disposed between the first electrode and the second electrode. In this case, the capping layer may be formed on the outer surface of at least one of the first and second electrodes. That is, the capping layer may be formed on the outer surface of each of the first and second electrodes or may be formed on the outer surface of only either one of the first and second electrodes.

In addition, the capping layer may contain the capping layer compound according to the present invention. The capping layer may contain only one compound or contain two or more compounds, selected from among the capping layer compounds of the present invention. The capping layer compound(s) may be used in combination with a known compound.

The organic material layers generally include a hole transport layer, a light emitting layer, and an electron transport layer that constitute a light emitting unit but may not be limited thereto.

More specifically, the organic light emitting device according to one embodiment of the present invention includes one or more organic material layers such as a hole injection layer (HIL), a hole transport layer (HTL), and a light emitting layer (HTL), an electron transport layer (ETL), and an electron injection layer (EIL) that constitute a light emitting unit between the first electrode (i.e., anode) and the second electrode (i.e., cathode).

FIG. 1 is a cross-sectional view schematically illustrating an organic light emitting device according to one embodiment of the present invention. The organic light emitting device according to one exemplary embodiment of the present invention may be manufactured to have a structure illustrated in FIG. 1.

Referring to FIG. 1, the organic light emitting device includes a substrate 100, a first electrode 1000, a hole injection layer 200, a hole transport layer 300, a light emitting layer 400, an electron transport layer 500, an electron injection layer 600, a second electrode 2000, and a capping layer 3000 that are stacked in this order from the bottom.

As the substrate 100, a substrate that is commonly used in organic light emitting devices may be used. Specifically, a transparent glass substrate or a flexible plastic substrate excellent in mechanical strength, thermal stability, transparency, surface smoothness, ease of handling, and waterproofness may be used.

The first electrode 1000 is used as a hole injection electrode for injecting holes in the organic light emitting device. The first electrode 1000 is made of a material having a low work function to enable hole injection. Specifically, the first electrode 1000 is made of a transparent material such as indium tin oxide (ITO), indium zinc oxide (IZO), or graphene.

The hole injection layer 200 may be formed by depositing a hole injection material on the first electrode 1000 by a method such as a vacuum deposition method, a spin coating method, a casting method, a Langmuir-Blodgett (LB) method, or the like. In the case of forming the hole injection layer 200 by a vacuum deposition method, the deposition conditions vary depending on the compound used as the material of the hole injection layer 200, the structure and thermal characteristics of the desired hole injection layer 200, and the like. However, in general, the conditions are appropriately set to fall within a temperature range of 50° C. to 500° C., a vacuum degree range of $10^{-8}$ to $10^{-3}$ torr, a deposition rate range of 0.01 to 100 Å/sec, and a layer thickness range of 10 Å to 5 μm. In addition, a charge generating layer may be optionally deposited on the surface of the hole injection layer 200 if necessary. A conventional material may be used as the material for the charge generation layer. For example, HATCN may be used.

Next, the hole transport layer 300 may be formed by depositing a hole transport material on the hole injection layer 200 by a method such as a vacuum deposition method, a spin coating method, a casting method, a LB method, or the like. In the case of forming the hole transport layer 300 by the vacuum deposition method, the deposition conditions vary depending on the compound used. However, the conditions may be selected from the same ranges described in connection with the hole injection layer 200. The hole transport layer 300 may be formed using a known compound. The hole transport layer 300 may be composed of one or more layers. Although not illustrated in FIG. 1, an auxiliary light emitting layer may be additionally formed on the hole transport layer 300.

The light emitting layer 400 may be formed by depositing a light emitting material on the hole injection layer 300 by a method such as a vacuum deposition method, a spin coating method, a casting method, a LB method, or the like. In the case of forming the light emitting layer 400 by the vacuum deposition method, the deposition conditions vary depending on the compound used. However, the conditions may be selected from the same ranges described in connection with the hole injection layer 200. As the light emitting material, a known compound may be used as a host or a dopant.

On the other hand, when a phosphorescent dopant is used together for the light emitting material, a hole blocking material (HBL) may be deposited on the light emitting layer 400 by a vacuum deposition method or a spin coating method to prevent triplet excitons or holes from diffusing into the electron transport layer 500. The hole blocking material that can be used is not particularly limited, and an arbitrary existing material may be selected and used. Examples of the hole blocking material include oxadiazole derivatives, triazole derivatives, phenanthroline derivatives, and hole blocking materials described in Japanese Patent Application Publication No. H11-329734(A1). Representatively, Balq(bis(8-hyde) hydroxy-2-methylquinolinolnato)-aluminum biphenoxide), phenanthrolines-based compounds (for example, bathocuproine (BCP) available from UDC) may be used. The light emitting layer 400 of the present invention may include at least one blue light emitting layer.

The electron transport layer 500 is formed on the light emitting layer 400 by a vacuum deposition method, a spin coating method, a casting method, or the like. The deposition conditions for the electron transport layer 500 vary depending on the compound used. However, the conditions may be selected from the same ranges described in connection with the hole injection layer 200.

The electron injection layer 600 is formed on the electron transport 500 by depositing an electron injection material using a vacuum deposition method, a spin coating method, a casting method, or the like.

The organic material layers such as the hole injection layer 200, the hole transport layer 300, the light emitting layer 400, and the electron transport layer 500 of the organic light emitting device may be manufactured using a known material, but is not particularly limited.

The second electrode 2000 is used as an electron injection electrode and may be formed on the electron injection layer 600 by a method such as a vacuum deposition method or a sputtering method. Various metals may be used to form the second electrode 2000. Specific examples of the material include, but are not limited to, aluminum, gold, silver, and magnesium.

Aside from the organic light emitting device having the above-described structure including the capping layer 3000, the first electrode 1000, the hole injection layer 200, the hole transport layer 300, the light emitting layer 400, the electron transport layer 500, the electron injection layer 600, the second electrode 2000, and the capping layer 300, the compound of the present invention can be used for various other organic light emitting devices. The organic light emitting device may further include one or two intermediate layers if necessary.

On the other hand, the thickness of each organic material layer formed according to the present invention can be adjusted as desired. Specifically, the thickness may fall within a range of 10 to 1,000 nm and more specifically within a range of 20 to 150 nm.

The capping layer 3000 may be formed on the outer surface of the first electrode 1000. That is, the capping layer 3000 may be formed on the surface that is not provided with the hole injection layer 200, of the surfaces of the first electrode 1000. In addition, the capping layer 3000 may also be formed on the outer surface of both the surfaces of the second electrodes 2000. The outer surface is a surface that is not provided with the electron injection layer 600.

However, the surface on which the capping layer 3000 is formed is not limited thereto. The capping layer 3000 may be formed by a deposition process, and the capping layer 3000 may have a thickness of 100 to 2,000 Å and more specifically 300 to 1,000 Å. The thickness is adjusted to prevent a decrease in the transmittance of the capping layer 3000.

In addition, although not illustrated in FIG. 1, according to one embodiment of the present invention, an organic material layer having various functions may be additionally formed between the capping layer 3000 and the first electrode 1000 or between the capping layer 3000 and the second electrode 2000. Alternatively, an organic material layer having various functions may be additionally formed on the upper surface (outer surface) of the capping layer 3000 but the position of the organic material layer may not be limited thereto.

Hereinafter, an organic light emitting device including a capping layer according to an embodiment of the present invention will be described in detail with reference to preparation examples and embodiments of the present invention. The preparation examples and embodiments described below are presented only for illustrative purposes and the scope of the present invention is not limited to the preparation examples and embodiments.

<Preparation Example 1> Synthesis of Compound 13

13

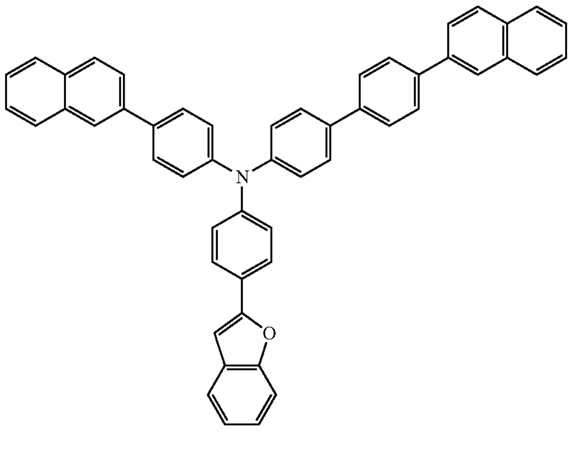

In a round bottom flask, 2.0 g of 2-(4-bromophenyl) benzofuran, 4.0 g of 4'-(naphthalen-2-yl)-N-(4-(naphthalen-2-yl)phenyl)-[1,1'-biphenyl]-4-amine, 1.0 g of t-BuONa, 0.3 g of Pd2(dba)3, and 0.3 ml of (t-Bu)3P were dissolved in 100 ml of toluene and stirred under reflux. The reaction was examined through thin layer chromatography (TLC), water was added, and the reaction was finished. An organic material layer was extracted with the use of methylene chloride (MC), filtered under reduced pressure, and recrystallized to obtain 3.2 g of Compound 13 (yield 64%).

m/z: 689.27 (100.0%), 690.28 (56.7%), 691.28 (16.0%), 692.28 (3.0%)

<Preparation Example 2> Synthesis of Compound 53

53

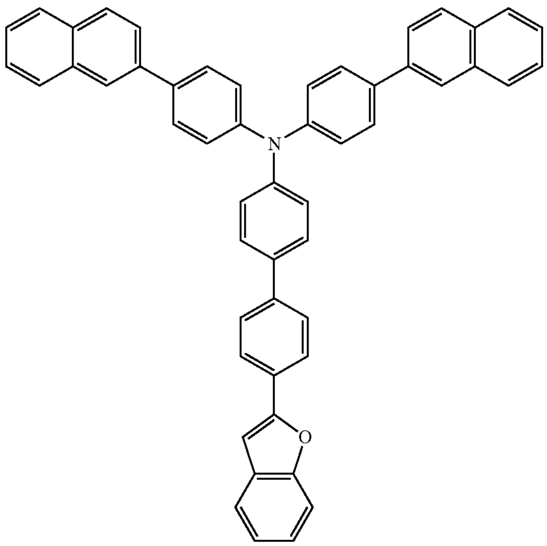

This compound was synthesized in the same manner as in Preparation Example 1 except that 2-(4'-bromo-[1,1'-biphenyl]-4-yl)benzofuran and bis(4-(naphthalen-2-yl)phenyl) amine were used instead of 2-(4-bromophenyl)benzofuran and 4'-(naphthalen-2-yl)-N-(4-(naphthalen-2-yl)phenyl)-[1,1'-biphenyl]-4-amine. (yield 68%) m/z: 689.27 (100.0%), 690.28 (56.7%), 691.28 (16.0%), 692.28 (3.0%)

<Preparation Example 3> Synthesis of Compound 209

209

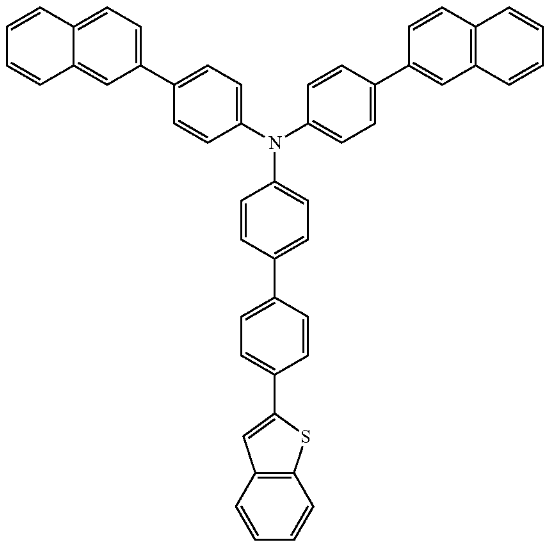

This compound was synthesized in the same manner as in Preparation Example 1 except that 2-(4'-bromo-[1,1'-biphenyl]-4-yl)benzo[b]thiophene and bis(4-(naphthalen-2-yl) phenyl)amine were used instead of 2-(4-bromophenyl)benzofuran and 4'-(naphthalen-2-yl)-N-(4-(naphthalen-2-yl) phenyl)-[1,1'-biphenyl]-4-amine. (yield 65%) m/z: 705.25 (100.0%), 706.25 (57.4%), 707.26 (15.7%), 707.24 (4.5%), 708.26 (3.0%), 708.25 (2.6%)

<Preparation Example 4> Synthesis of Compound 217

217

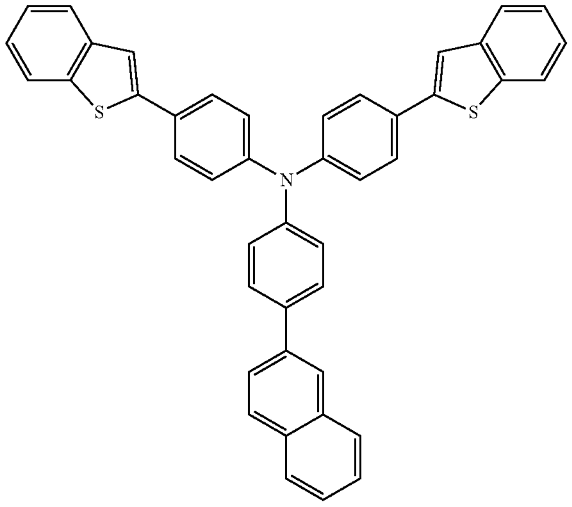

This compound was synthesized in the same manner as in Preparation Example 1 except that 2-(4-bromophenyl)benzo [b]thiophene and 4-(naphthalen-2-yl)aniline were used instead of 2-(4-bromophenyl)benzofuran and 4'-(naphthalen-2-yl)-N-(4-(naphthalen-2-yl)phenyl)-[1,1'-biphenyl]-4-amine. (yield 63%) m/z: 635.17 (100.0%), 636.18 (47.9%), 637.18 (12.0%), 637.17 (9.2%), 638.17 (4.4%), 636.17 (2.0%), 638.18 (1.9%), 639.18 (1.0%)

<Preparation Example 5> Synthesis of Compound 225

225

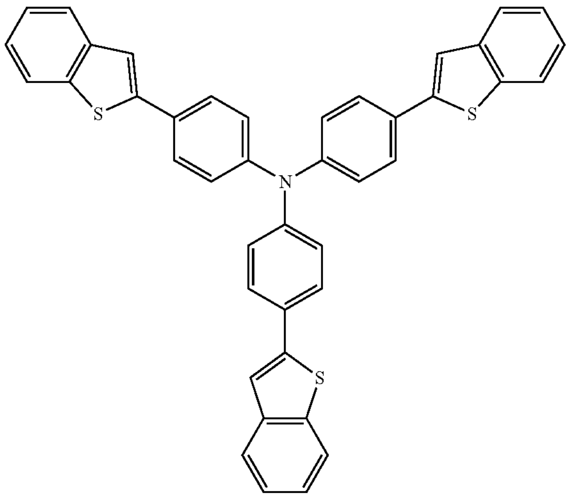

This compound was synthesized in the same manner as in Preparation Example 1 except that 2-(4-bromophenyl)benzo[b]thiophene and bis(4-(benzo[b]thiophen-2-yl)phenyl)amine were used instead of 2-(4-bromophenyl)benzofuran and 4'-(naphthalen-2-yl)-N-(4-(naphthalen-2-yl)phenyl)-[1,1'-biphenyl]-4-amine. (yield 65%)

m/z: 641.13 (100.0%), 642.13 (48.2%), 643.13 (14.8%), 643.14 (10.2%), 644.13 (6.5%), 644.14 (1.7%), 645.13 (1.6%)

Manufacture of Organic Light Emitting Device

An organic light emitting device having the structure of FIG. 1 was manufactured. The organic light emitting device includes a substrate 100, an anode (hole injection electrode 1000), a hole injection layer 200, a hole transport layer 300, a light emitting layer 400, an electron transport layer 500, an electron injection layer 600, a cathode (electron injection electrode 2000), and a capping layer 3000 that are stacked in this order from the bottom.

The compounds that can be used for the organic material layers interposed between the electrodes of the organic light emitting device of the present invention are shown in Table 1 below.

TABLE 1

| | |
|---|---|
| 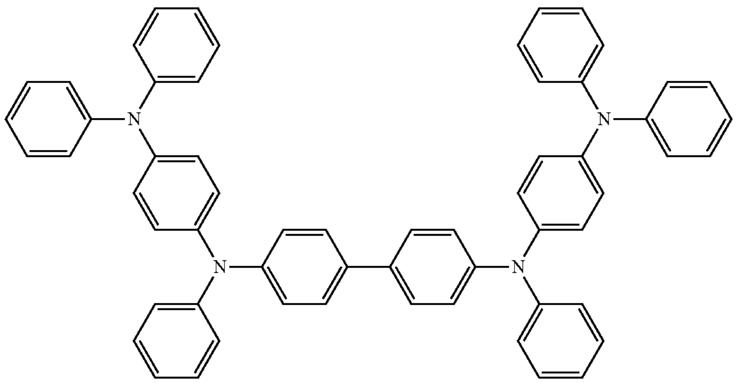 [SMILES: c1ccc(N(c2ccccc2)c2ccc(N(c3ccccc3)c3ccc(-c4ccc(N(c5ccccc5)c5ccc(N(c6ccccc6)c6ccccc6)cc5)cc4)cc3)cc2)cc1] | HI01 |
| 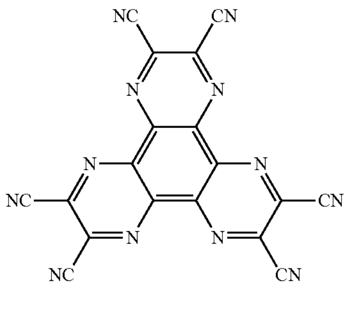 [SMILES: N#Cc1nc2c3nc(C#N)c(C#N)nc3c3nc(C#N)c(C#N)nc3c2nc1C#N] | HATCN |

TABLE 1-continued
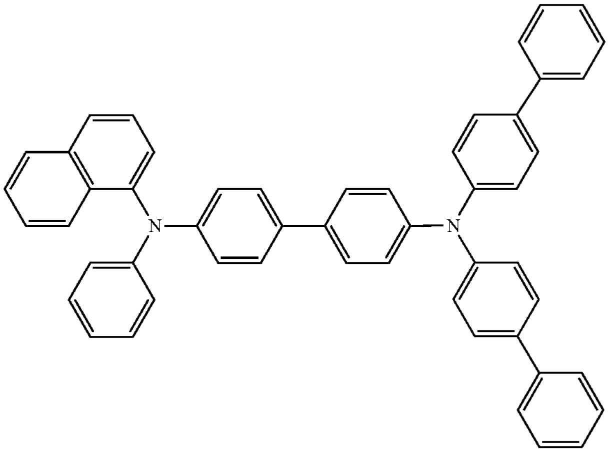 [SMILES: c1ccc(-c2ccc(N(c3ccc(-c4ccccc4)cc3)c3ccc(-c4ccc(N(c5ccccc5)c5cccc6ccccc56)cc4)cc3)cc2)cc1]
HT01
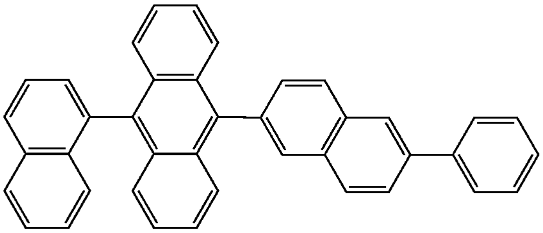 [SMILES: c1ccc(-c2ccc3cc(-c4c5ccccc5c(-c5cccc6ccccc56)c5ccccc45)ccc3c2)cc1]
BH01
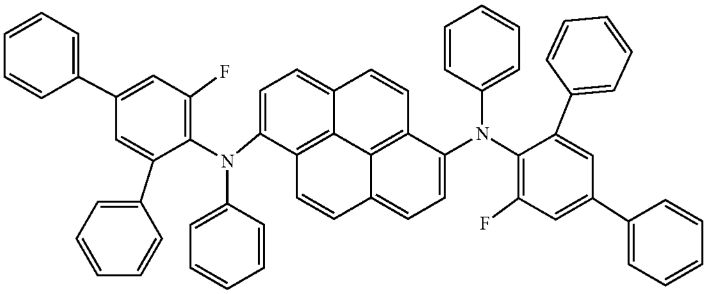 [SMILES: Fc1cc(-c2ccccc2)cc(-c2ccccc2)c1N(c1ccccc1)c1ccc2ccc3c(N(c4ccccc4)c4c(F)cc(-c5ccccc5)cc4-c4ccccc4)ccc4ccc1c2c43]
BD01
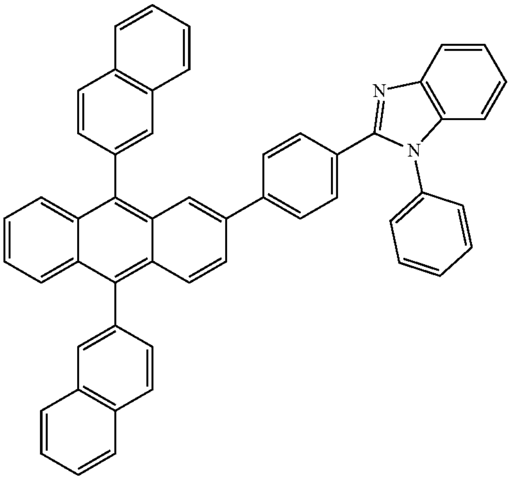 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
ET01

TABLE 1-continued

| | |
|---|---|
| 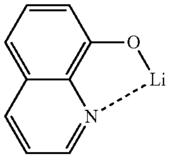 | Liq |

<Example 1> Manufacture of Organic Light Emitting Device

After forming HI01 600 Å and HATCN 50 Å as a hole injection layer on an ITO substrate coated with a anti-reflective layer containing Ag, HT01 500 Å was formed as a hole transport layer thereon. Next, a light emitting layer doped with BH01:BD01 3% was formed to have a thickness of 250 Å. Next, 300 Å of ET01:Liq(1:1) was formed as an electron transport layer, and then 10 Å of LiF was deposited to form an electron injection layer. Subsequently, MgAg was deposited to a thickness of 15 nm, and the compound prepared in Preparation Example 1 was deposited to a thickness of 600 Å as a capping layer on the cathode. The structure was encapsulated in a glove box so that the manufacturing of the organic light emitting device was completed.

<Examples 2 to 5> Manufacture of Organic Light Emitting Devices

Organic light emitting devices were manufactured in the same manner as in Example 1 except that the compounds prepared in Preparation Examples 2 to 5 were used in Examples 2 to 5, respectively, to form the capping layer.

<Comparative Examples 1 to 4> Manufacture of Organic Light Emitting Devices

Organic light emitting devices were manufactured in the same manner as in Example 1 except that the compounds of Ref. 1 to Ref. 4 listed in Table 2 were used in Comparative Examples 1 to 4, respectively, to form the capping layer.

TABLE 2

| | |
|---|---|
| 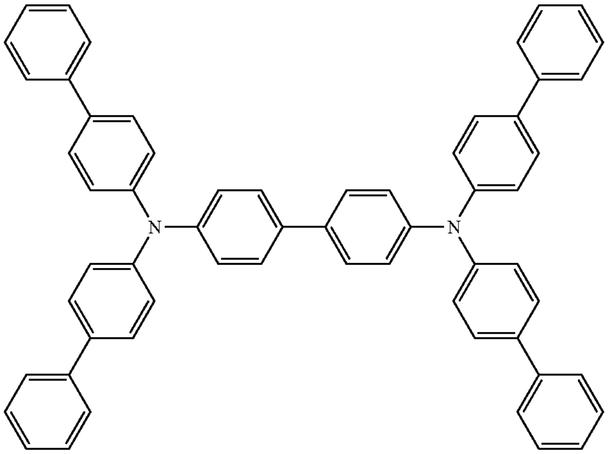 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | Ref. 1 |
| 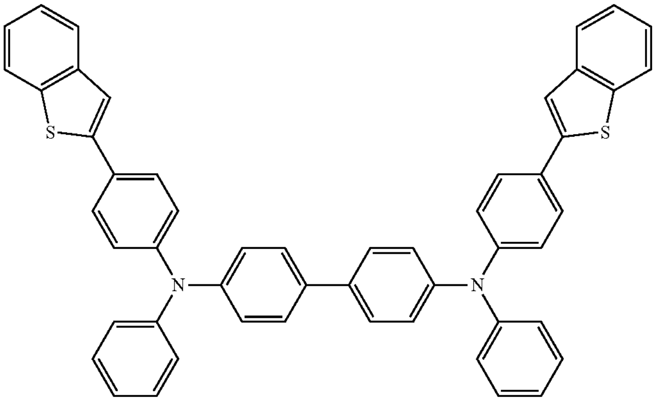 [SMILES: c1ccc(N(c2ccc(-c3ccc(N(c4ccccc4)c4ccc(-c5cc6ccccc6s5)cc4)cc3)cc2)c2ccc(-c3cc4ccccc4s3)cc2)cc1] | Ref. 2 |

TABLE 2-continued

Ref. 3

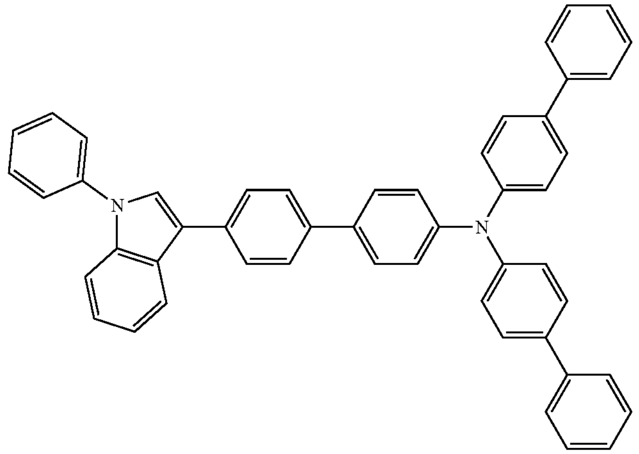 [SMILES: c1ccc(-c2ccc(N(c3ccc(-c4ccccc4)cc3)c3ccc(-c4ccc(-c5cn(-c6ccccc6)c6ccccc56)cc4)cc3)cc2)cc1]

Ref. 4

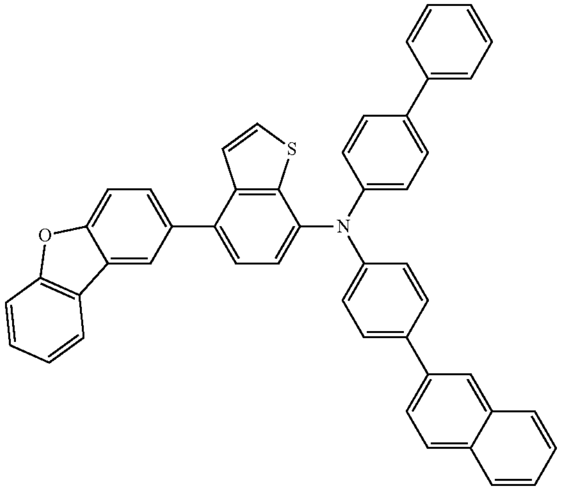 [SMILES: c1ccc(-c2ccc(N(c3ccc(-c4ccc5ccccc5c4)cc3)c3ccc(-c4ccc5oc6ccccc6c5c4)c4ccsc34)cc2)cc1]

<Experimental Example 1> Evaluation of Performance of Organic Light Emitting Device Electrons and holes were injected by applying a voltage using a Keithley 2400 source measurement unit, and the luminance was measured using a Konica Minolta spectroradiometer (CS-2000) when light is emitted. To evaluate the performance of each of the organic light emitting devices of Examples 1 to 5 and Comparative Examples 1 to 4, the current density and luminance with respect to the applied voltage under atmospheric pressure were measured, and the results are shown Table 3.

TABLE 3

| | Op.V | mA/cm$^2$ | cd/A | CIEx | CIEy | LT97 |
|---|---|---|---|---|---|---|
| Example 1 | 3.50 | 10 | 7.68 | 0.139 | 0.044 | 177 |
| Example 2 | 3.50 | 10 | 7.76 | 0.140 | 0.044 | 175 |
| Example 3 | 3.50 | 10 | 7.74 | 0.140 | 0.044 | 172 |
| Example 4 | 3.51 | 10 | 7.97 | 0.140 | 0.043 | 180 |
| Example 5 | 3.51 | 10 | 7.85 | 0.139 | 0.045 | 173 |
| Comparative Example 1 | 3.51 | 10 | 6.52 | 0.131 | 0.054 | 71 |
| Comparative Example 2 | 3.52 | 10 | 6.85 | 0.130 | 0.050 | 100 |
| Comparative Example 3 | 3.51 | 10 | 6.72 | 0.133 | 0.052 | 95 |

TABLE 3-continued

| | Op.V | mA/cm$^2$ | cd/A | CIEx | CIEy | LT97 |
|---|---|---|---|---|---|---|
| Comparative Example 4 | 3.51 | 10 | 6.20 | 0.133 | 0.054 | 68 |

Comparing the examples of the present invention with Comparative Examples 1 and 2, the present invention has a structure in which benzofuran or benzothiophene is bonded to the nitrogen of an arylamine and which specifically includes one arylamine rather than two arylamines. The structure of the compound of the present invention minimizes the bulky characteristic, thereby increasing a high refractive index, broadening a UV wavelength range that can be absorbed, and increasing a glass transition temperature Tg. Thus, the efficiency and lifespan of each of the organic light emitting devices as in the examples are improved.

In addition, in comparison with Comparative Example 3, the present invention is characterized in that the 5-membered cyclic ring of the fused ring contains 0 or S other than N, and nitrogen is bonded to the 5-membered cyclic ring other than the 6-membered cyclic ring, and O or S is bonded to the closest carbon. In comparison with Comparative Example 4, the present invention is characterized in that the bulky characteristic of the end of the fused ring is minimized to prevent a decrease in the refractive index and to form a stable thin film with an excellent thin film arrangement. Since the refractive index can be improved with a small molecular weight, it is possible to realize an organic light emitting element with high color purity, high efficiency, and long lifespan.

<Experimental Example 2> Evaluation of Refractive Index

Each of various compounds including Compound 13 (Preparation Example 1), Compound 209 (Preparation Example 3), and the compounds of Ref. 1, Ref. 2, Ref. 3, and Ref. 4 of the comparative examples was used to form a 30 nm-thick deposition film on a silicon substrate using a vacuum deposition apparatus, and the refractive index of each deposition was measured for a wavelength of 450 nm, using an ellipsometer (M-2000X available from JAWoollam Co. Inc). The measurement results are shown in Table 4.

TABLE 4

| At 450 nm | Ref. 1 | Ref. 2 | Ref. 3 | Ref. 4 | Compound 13 | Compound 209 |
|---|---|---|---|---|---|---|
| Refractive index, n | 2.10 | 2.22 | 2.15 | 2.10 | 2.35 | 2.37 |

Referring to Table 4 above, it can be confirmed that the compounds of Preparation Examples 1 and 3 of the present invention exhibit a high refractive index of 2.23 or more, specifically 2.30 or more, and more specifically 2.35 or more.

Figure 2:
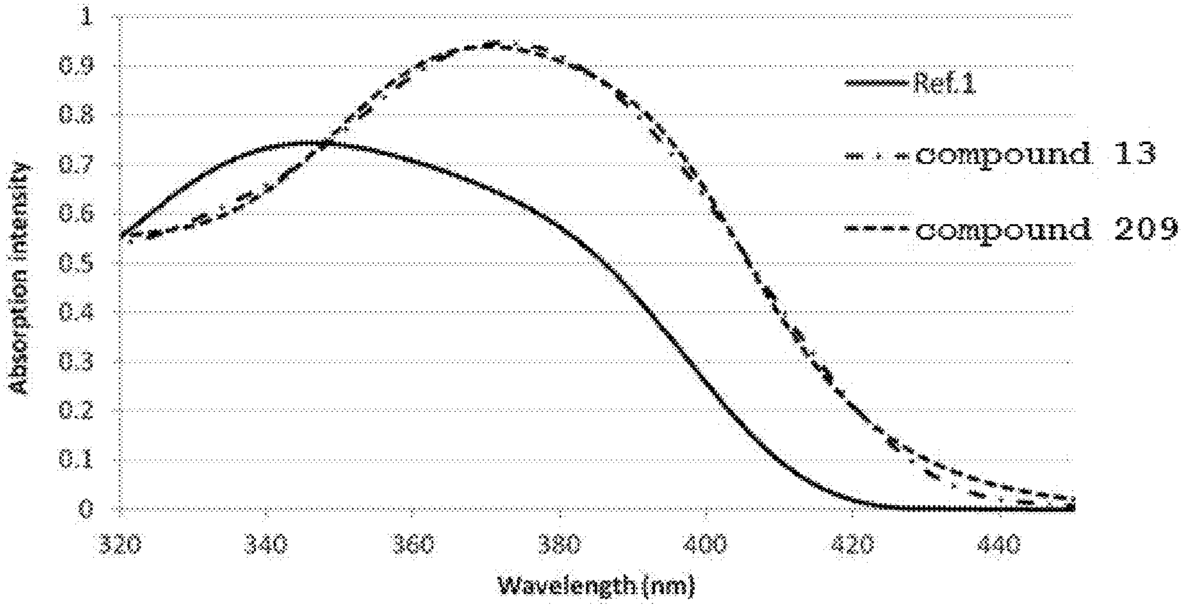
FIG. 2 is a graph illustrating measurements of absorption intensity for a wavelength range of 320 nm to 450 nm.

<Experimental Example 3> Evaluation of Absorption Intensity for Ultraviolet Region Each of various compounds including Compound 13 (Preparation Example 1), Compound 209 (Preparation Example 3), and the compound of Ref. 1 was used to form a 30 nm-thick deposition film on a silicon substrate using a vacuum deposition apparatus, and the absorption intensity of each deposition film was measured for a wavelength range of from 320 nm to 450 nm, using an ellipsometer (M-2000X available from JAWoollam Co. Inc). The results are shown in FIG. 2.

The absorption intensity of each of Compound 13 and Compound 209 of the present invention for a wavelength of 380 nm in a ultraviolet absorption region is 0.8 or more and more specifically 0.9 or more. That is, it is confirmed that the absorption intensity of each compound of the present invention is 30% or more and more specifically 50% or more than the compound of Ref. 1.

What is claimed is:

1. A capping layer that is disposed on an outer surface of a first electrode or a second electrode of an organic light emitting device, wherein the capping layer comprises a compound represented by Formula 3 below:

<Formula 3>

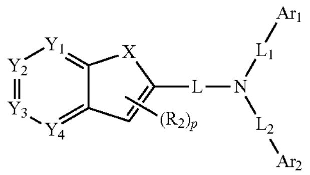

wherein X is O, S, Se, Te, or CRR',

R and R' are each independently hydrogen, deuterium, halogen, a nitro group, a nitrile group, a substituted or unsubstituted C1-C30 alkyl group, a substituted or unsubstituted C2-C30 alkenyl group, a substituted or unsubstituted C1-C30 alkoxy group, a substituted or unsubstituted C1-C30 sulfide, a substituted or unsubstituted C6-C50 aryl group, or a substituted or unsubstituted C2-C50 heteroaryl group, wherein R and R' that are adjacent to each other form or do not form a ring by combining with each other, $Y_1$ to $Y_4$ are each independently C, $CR_1$, or N, $R_1$s are each independently hydrogen, deuterium, halogen, a nitro group, a nitrile group, a substituted or unsubstituted C1-C30 alkyl group, a substituted or unsubstituted C2-C30 alkenyl group, a substituted or unsubstituted C1-C30 alkoxy group, a substituted or unsubstituted C1-C30 sulfide group, or a substituted or unsubstituted C6-C50 aryl group, wherein the $R_1$s adjacent to each other form or do not form a ring by combining with each other, $Ar_1$ and $Ar_2$ are each independently selected from the group consisting of an unsubstituted C6-C50 aryl group, a C6-C50 aryl group that is substituted with either an unsubstituted C6-C50 aryl group or an unsubstituted C2-C50 heteroaryl group, and an unsubstituted C2-C50 heteroaryl group, $R_2$s are each independently hydrogen, deuterium, halogen, a nitro group, a nitrile group, a substituted or unsubstituted C1-C30 alkyl group, a substituted or unsubstituted C2-C30 alkenyl group, a substituted or unsubstituted C1-C30 alkoxy group, a substituted or unsubstituted C1-C30 sulfide group, a substituted or unsubstituted C6-C50 aryl group, or a substituted or unsubstituted heteroaryl group, L is a substituted or unsubstituted phenylene, a substituted or unsubstituted biphenylene, or a substituted or unsubstituted terphenylene, $L_1$, and $L_2$ are each independently a directly-linked, substituted or unsubstituted C6-C50 arylene group, or a substituted or unsubstituted C2-C50 heteroarylene group, and p is 0 or 1.

2. The capping layer of claim 1, wherein Formula 3 is a compound represented by Formula 2-1 below:

<Formula 2-1>

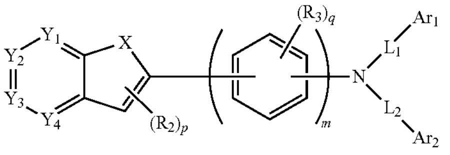

wherein $R_3$ is defined in the same way as $R_2$ in Formula 3, provided that the number of carbon atoms in $R_3$ satisfies the carbon number range defined for L, q is an integer in a range of from 0 to 4, and m is an integer in a range of from 2 to 3.

3. The capping layer of claim 1, wherein Formula 3 is a compound represented by Formula 4-1 below:

<Formula 4-1>

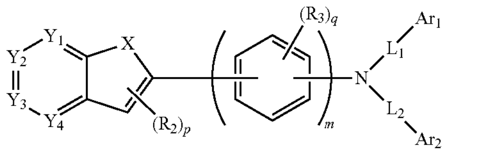

wherein $R_3$ is defined in the same way as $R_2$ in Formula 3, provided that the number of carbon atoms in $R_3$ satisfies the carbon number range defined for L, q is an integer in a range of from 0 to 4, and m is an integer in a range of from 2 to 3.

4. The capping layer of claim 1, wherein Formula 3 is a compound represented by Formula 5-1 below:

<Formula 5-1>

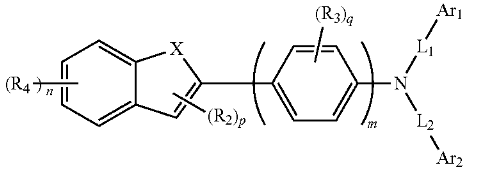

wherein $R_3$s are each independently defined in the same way as $R_2$ in Formula 3, provided that the number of carbon atoms in $R_3$ satisfies the carbon number range defined for L, $R_4$s are each independently defined in the same way as $R_1$ in Formula 3, p is 0 or 1, q is an integer in a range of from 0 to 4, m is an integer in a range of from 2 to 3, and n is an integer in a range of from 0 to 4.

5. The capping layer of claim 1, wherein Formula 3 is a compound represented by Formula 6-1 below:

<Formula 6-1>

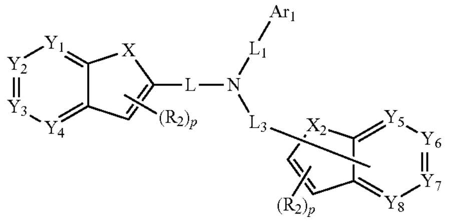

wherein $L_3$ is defined in the same way as $L_2$ in Formula 3, $X_2$ is defined in the same way as X in Formula 3, and $Y_5$ to $Y_8$ are each independently defined in the same way as $Y_1$ to $Y_4$ in Formula 3, provided that the number of carbon atoms in $Y_5$ to $Y_8$ satisfies the carbon number range defined for $Ar_2$.

6. The capping layer of claim 1, wherein Formula 3 is a compound represented by Formula 7-1 below:

<Formula 7-1>

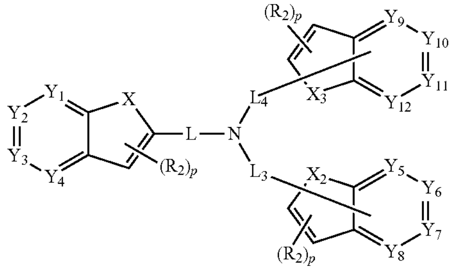

wherein $L_3$ and $L_4$ are each independently defined in the same way as $L_1$ and $L_2$ in Formula 3, $X_2$ and $X_3$ are each independently defined in the same way as X in Formula 3, and $Y_5$ to $Y_{12}$ are each independently defined in the same way as $Y_1$ to $Y_4$ in Formula 3, provided that the number of carbon atoms in $Y_5$ to $Y_{12}$ satisfies the carbon number range defined for $Ar_1$ or $Ar_2$.

7. The capping layer of claim 1, wherein the X is O or S.

8. The capping layer of claim 1, wherein the $R_1$ and $R_2$ are each independently selected from the group consisting of hydrogen, deuterium, a methyl group, a methoxy group, a phenyl group, and combinations thereof.

9. The capping layer of claim 8, wherein the $R_1$ and $R_2$ are each independently selected from the group consisting of hydrogen, a phenyl group, a biphenyl group, and combinations thereof.

10. The capping layer of claim 1, wherein the $L_1$, and $L_2$ of the compound are not directly-linked.

11. The capping layer of claim 1, wherein the $Ar_1$ and $Ar_2$ are each independently selected from the group consisting of a phenyl group, a biphenyl group, a terphenyl group, a naphthyl group, a phenanthrenyl group, a triphenylenyl group, a benzofuran group, a benzothiophene group, and combinations thereof.

12. The capping layer of claim 1, wherein the compound is any one selected from the following compounds:

4
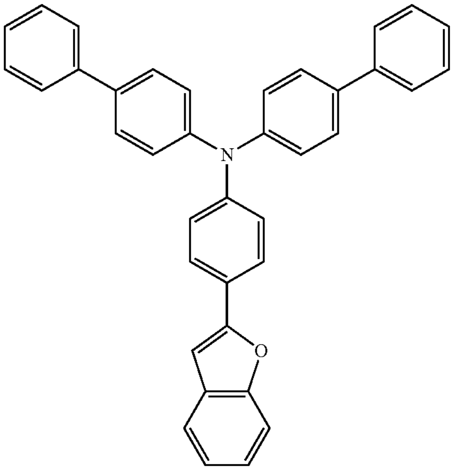
5
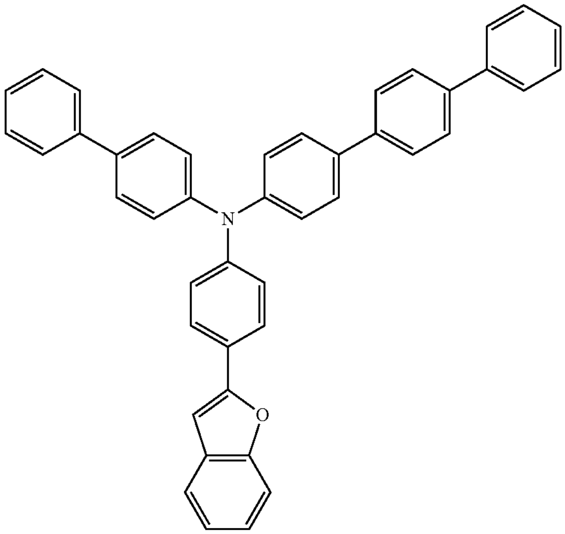
6
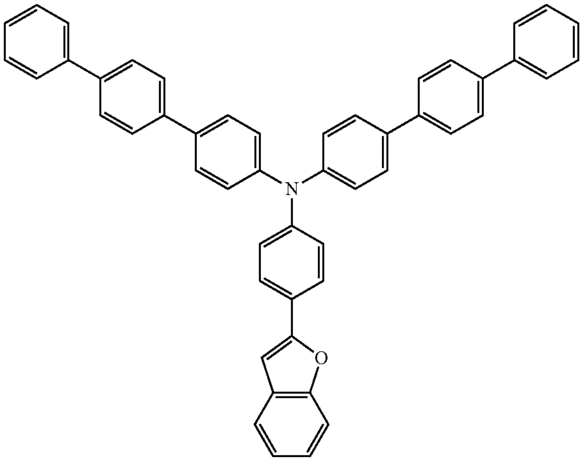
7
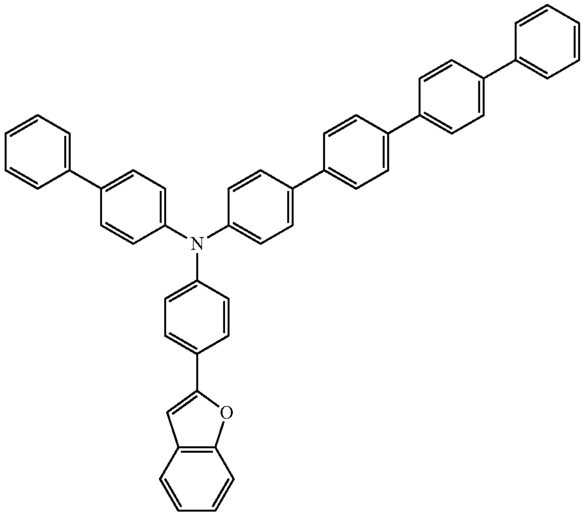
8
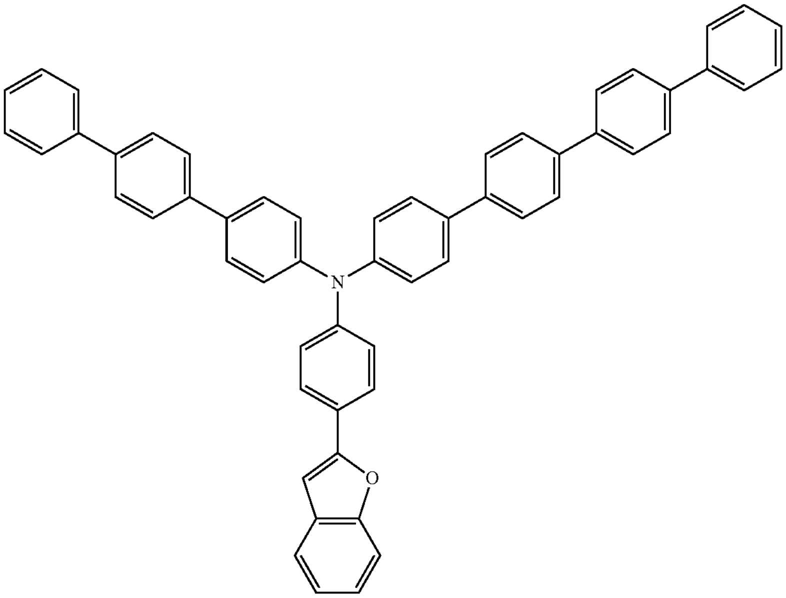

-continued
9
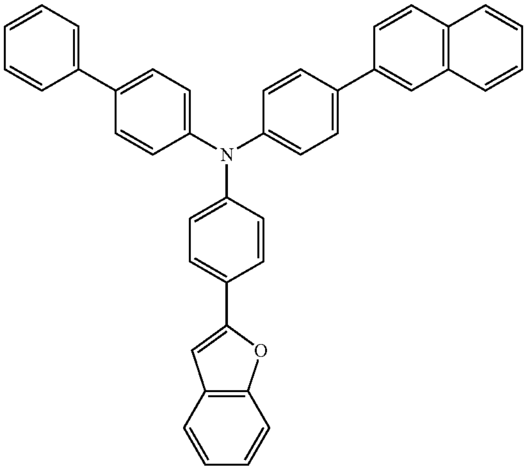
10
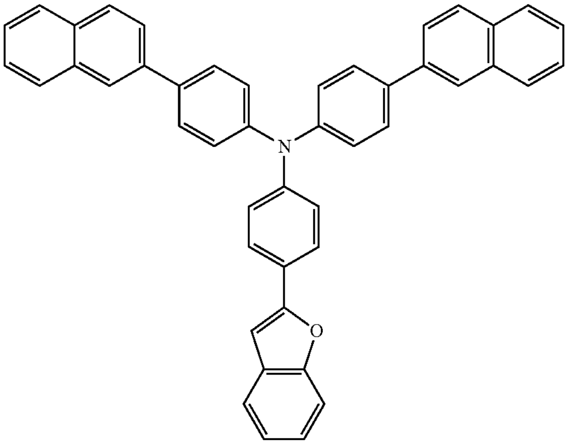
11
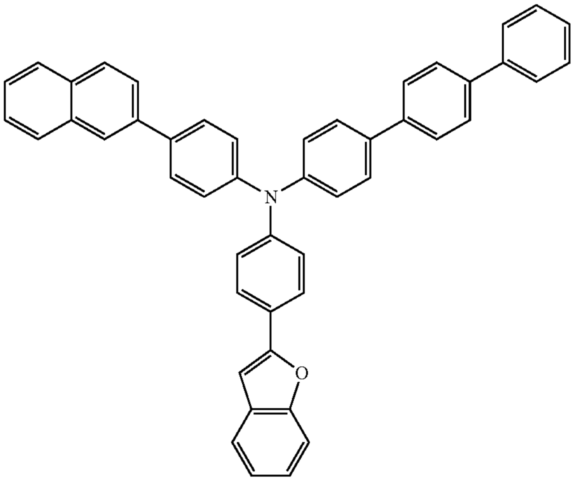
12
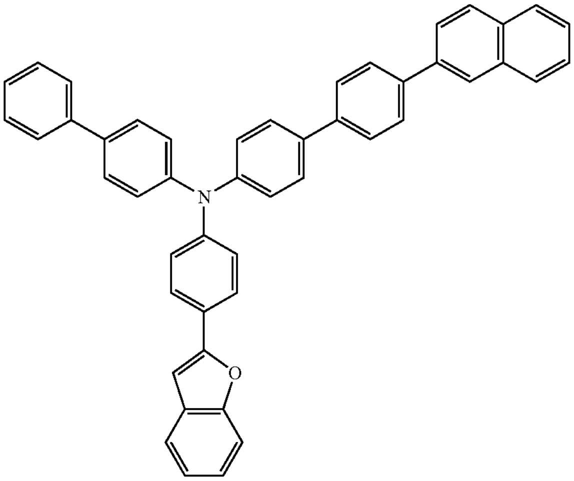
13
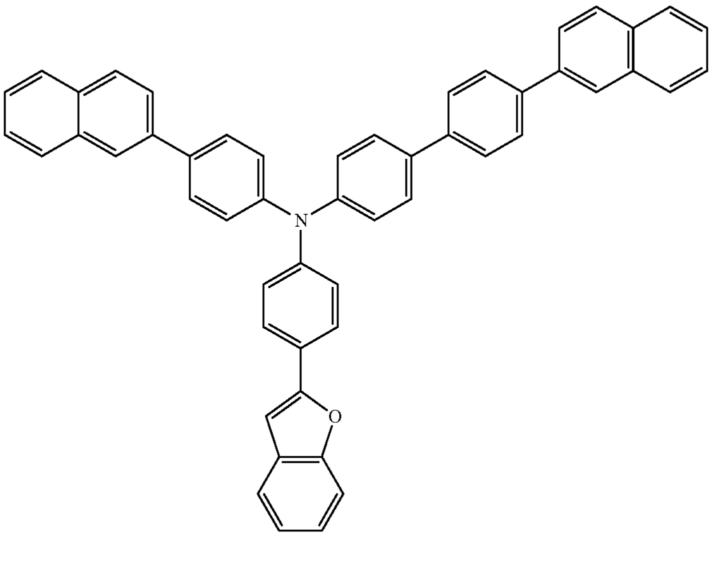

-continued
14
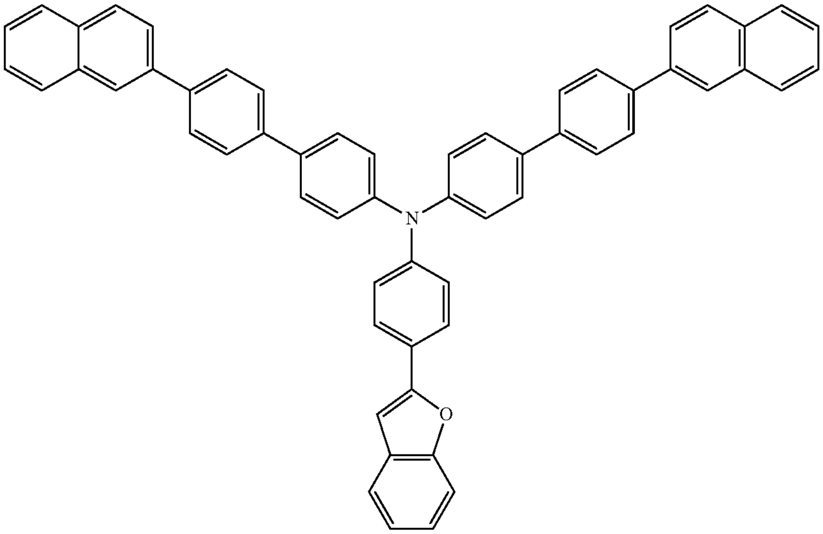
15
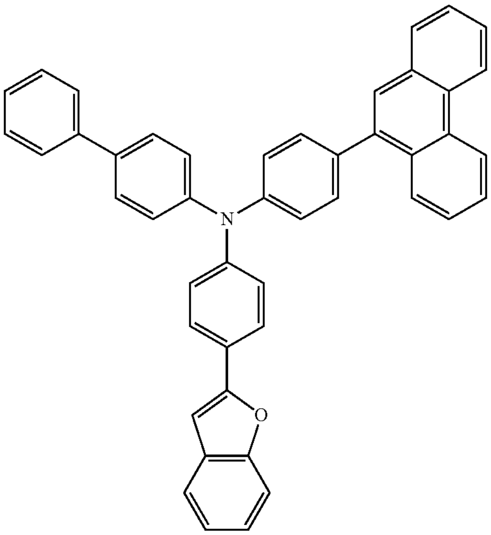
16
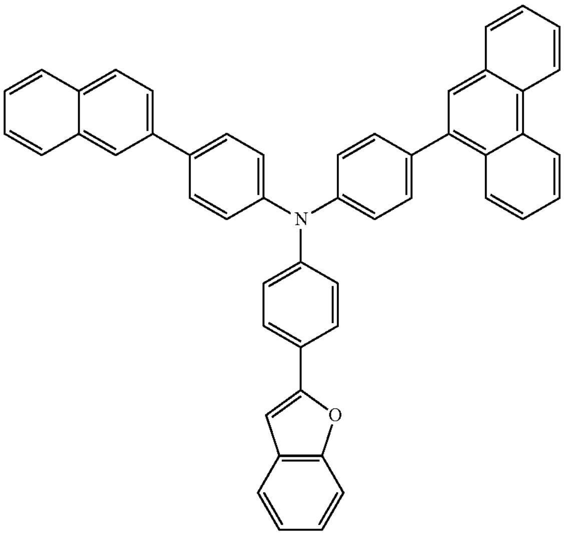
17
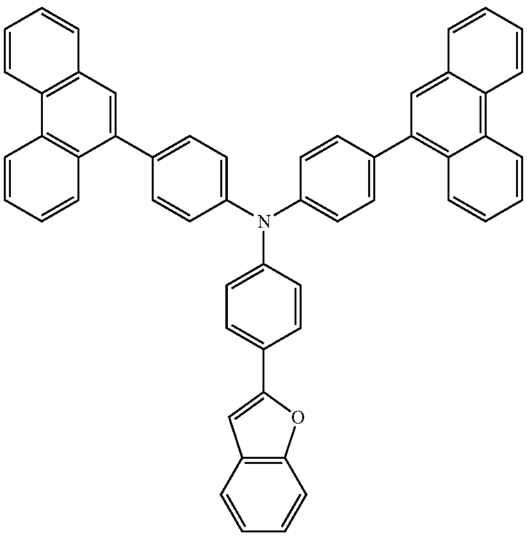
18
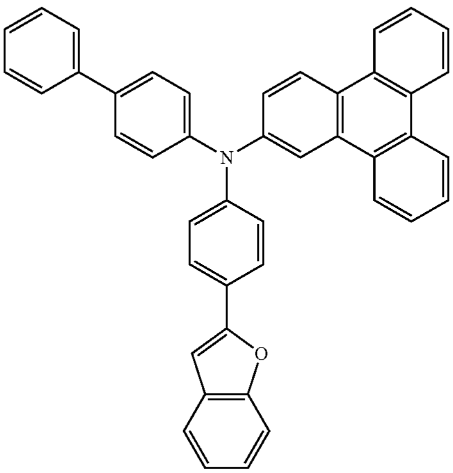

-continued
19
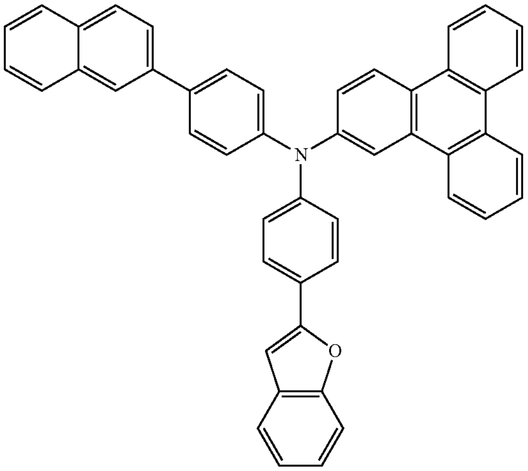
20
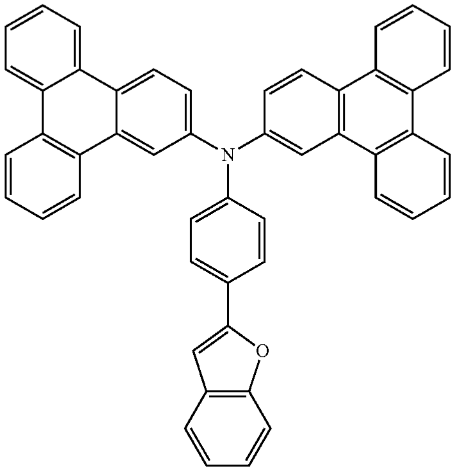
21
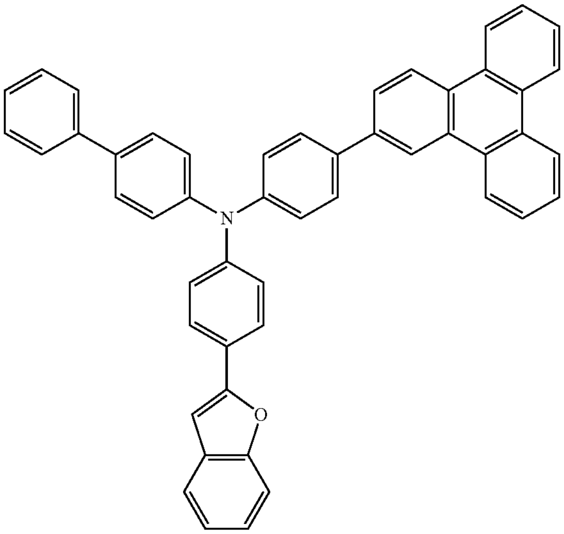
22
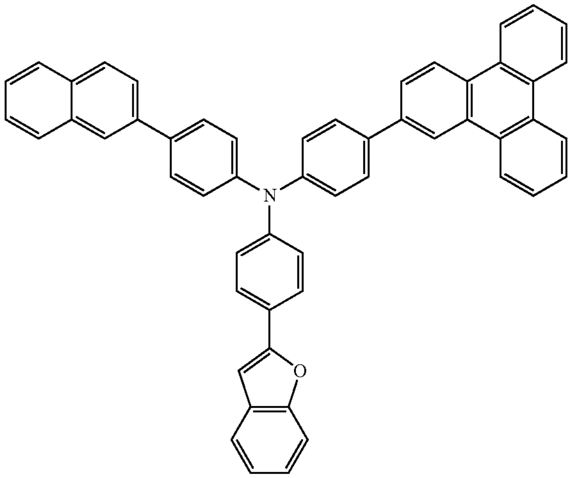
23
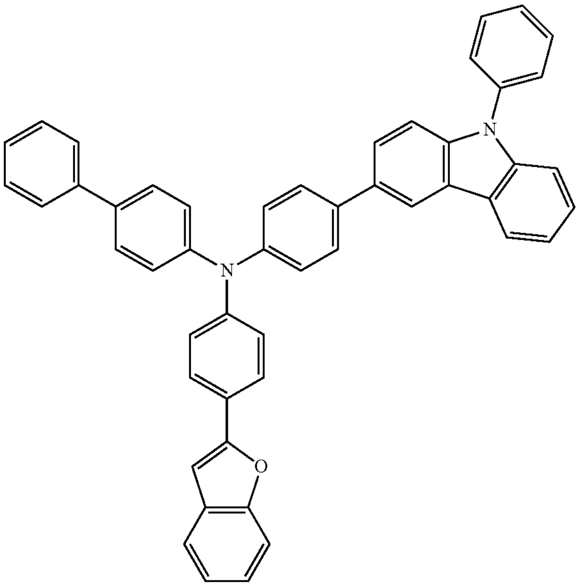
24
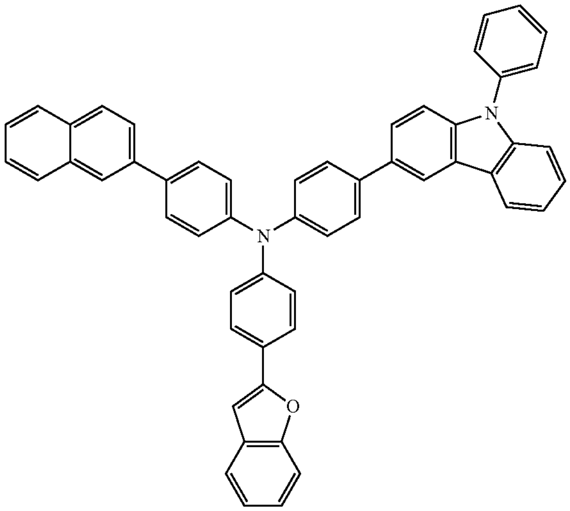

-continued
25
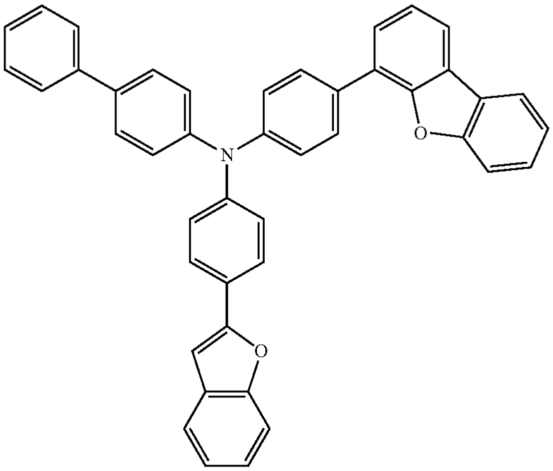
26
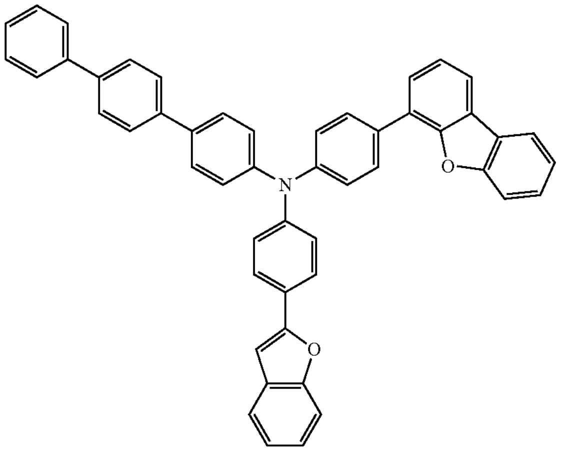
27
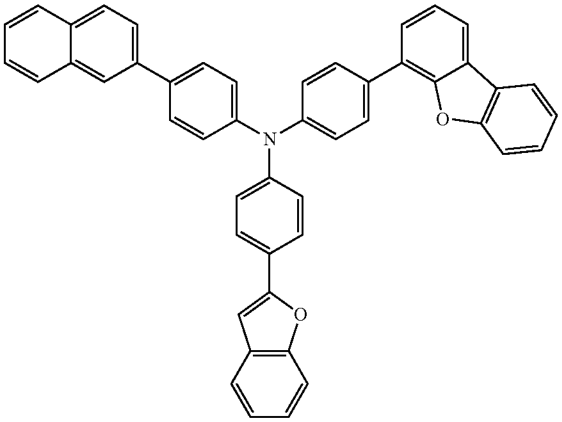
28
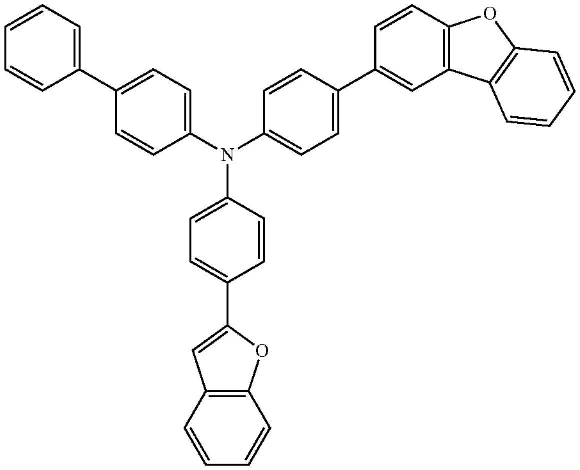
29
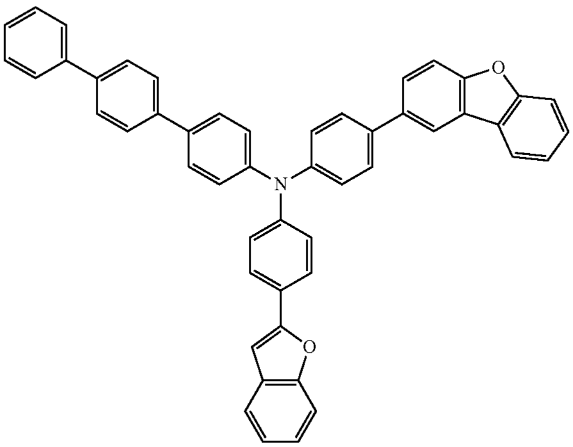
30
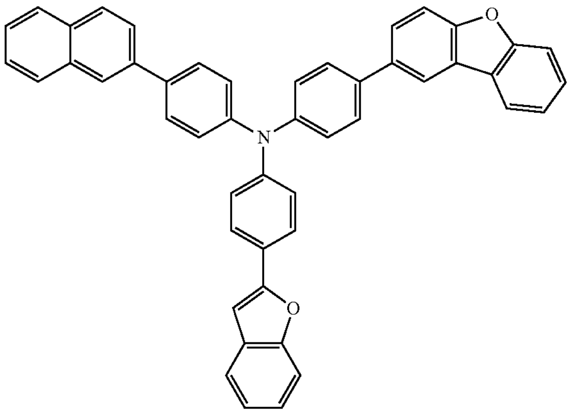

-continued
31
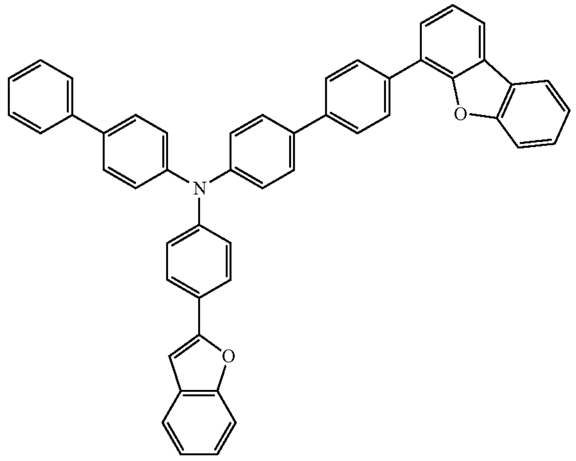
32
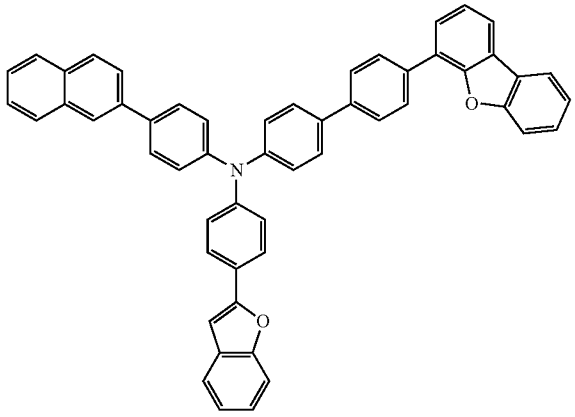
33
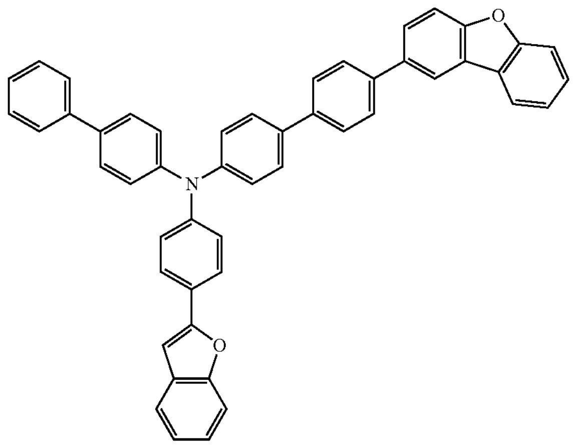
34
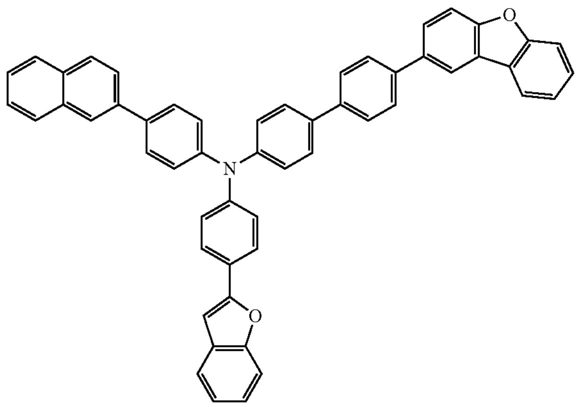
35
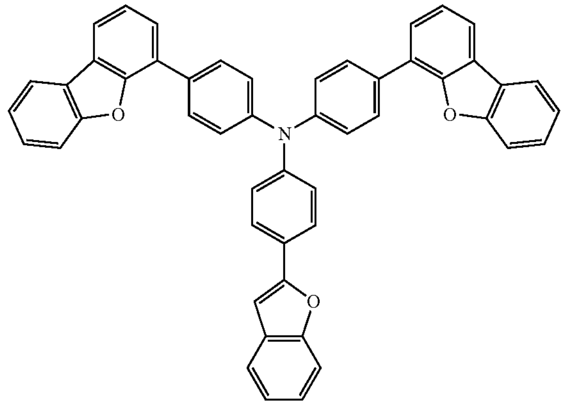
36
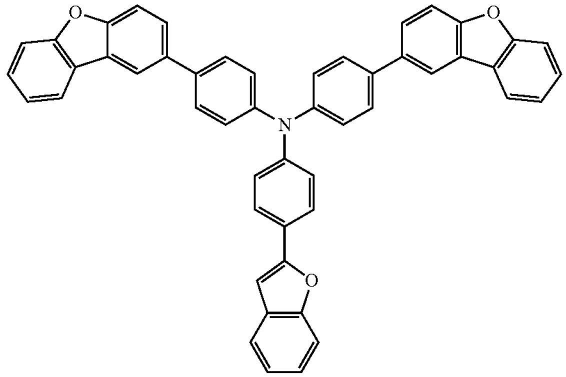

-continued
37
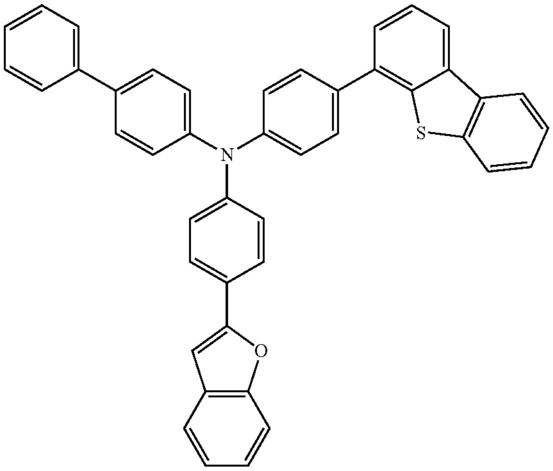
38
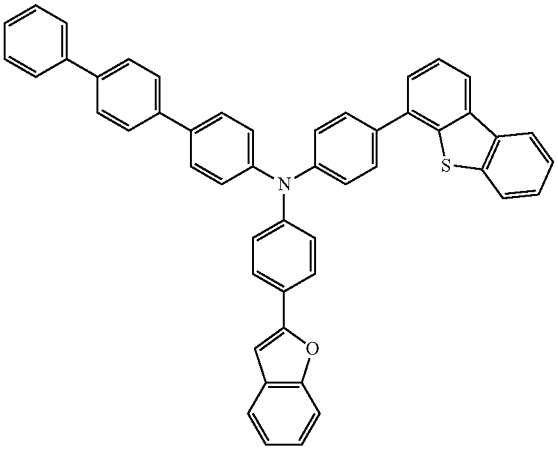
39
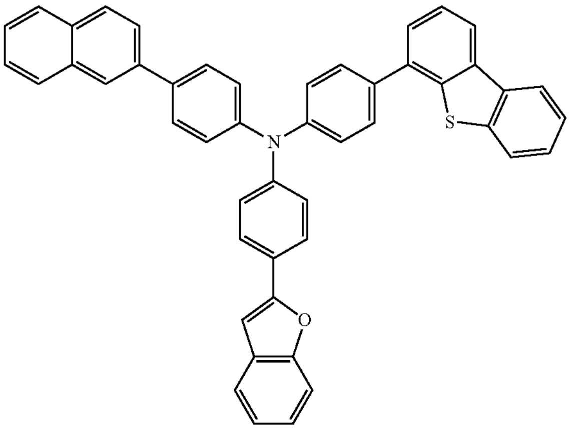
40
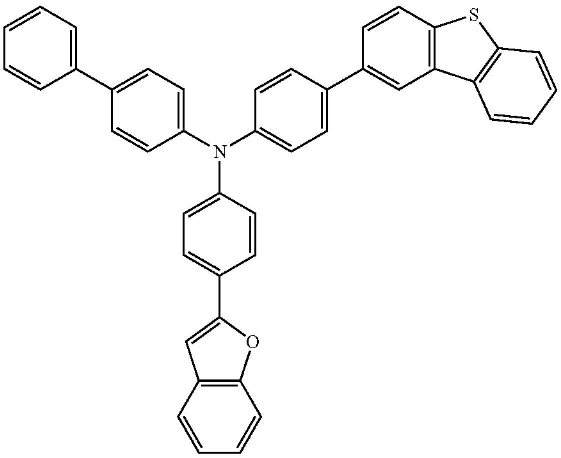
41
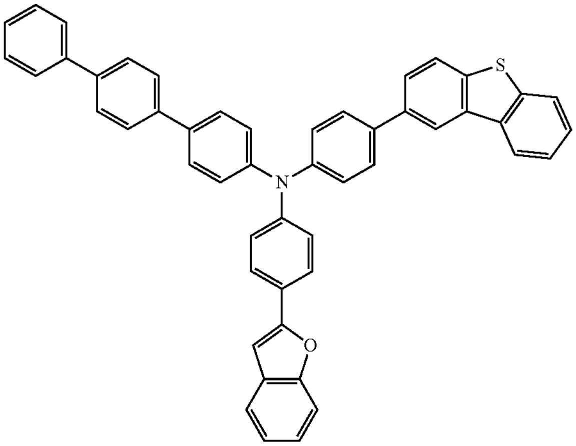
42
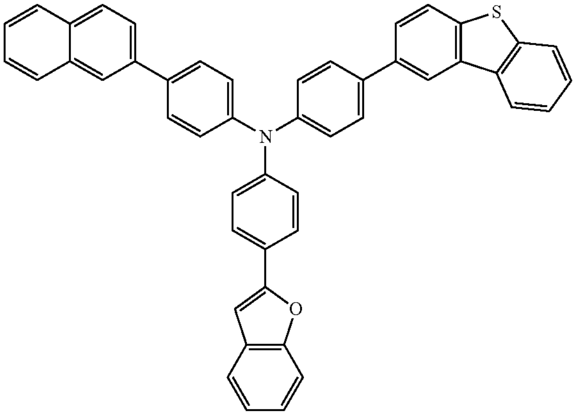

-continued
43
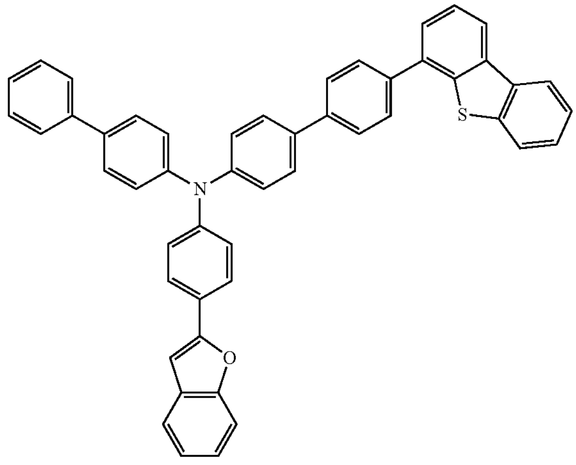
44
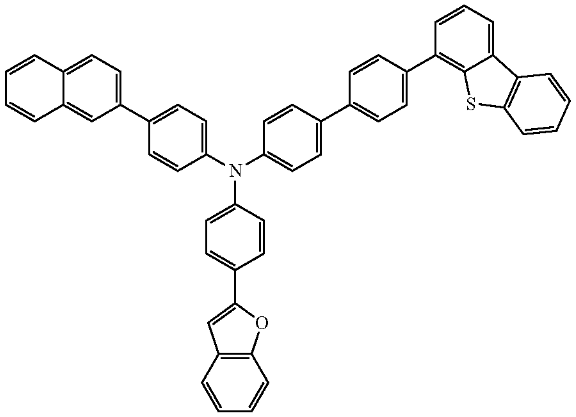
45
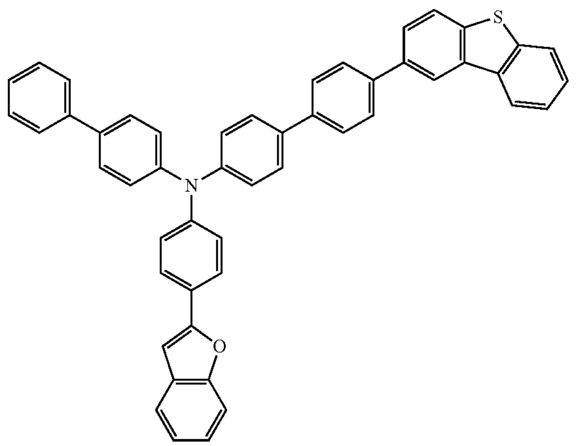
46
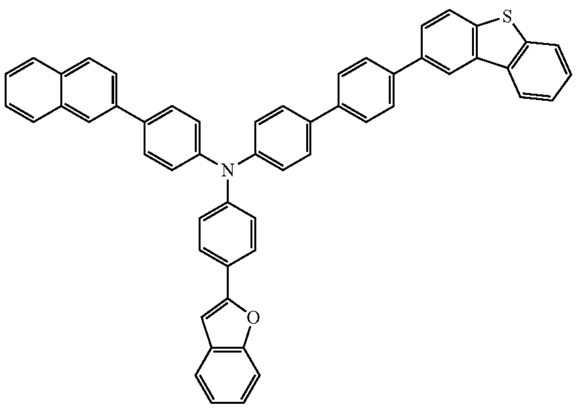
47
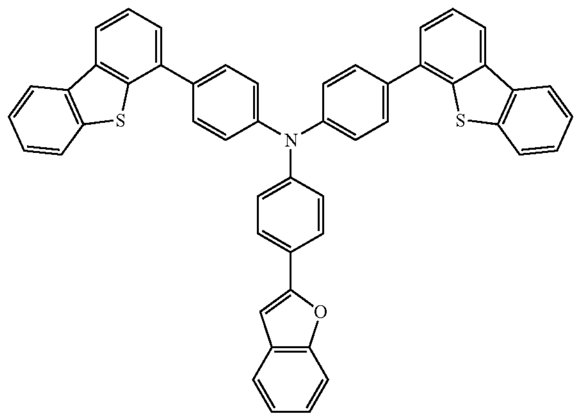
48
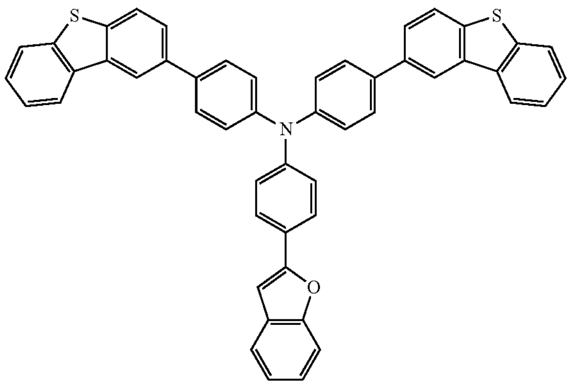

-continued
49
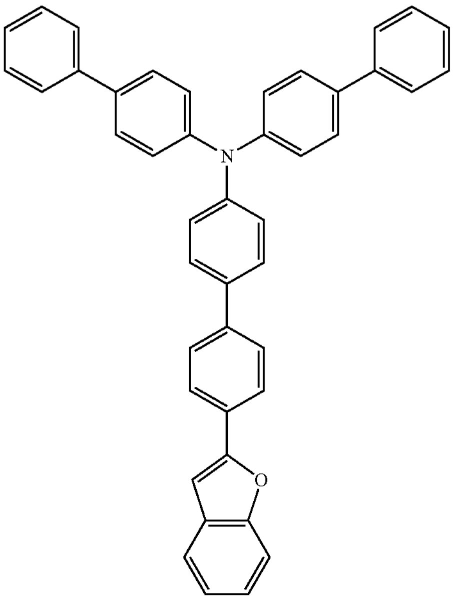
50
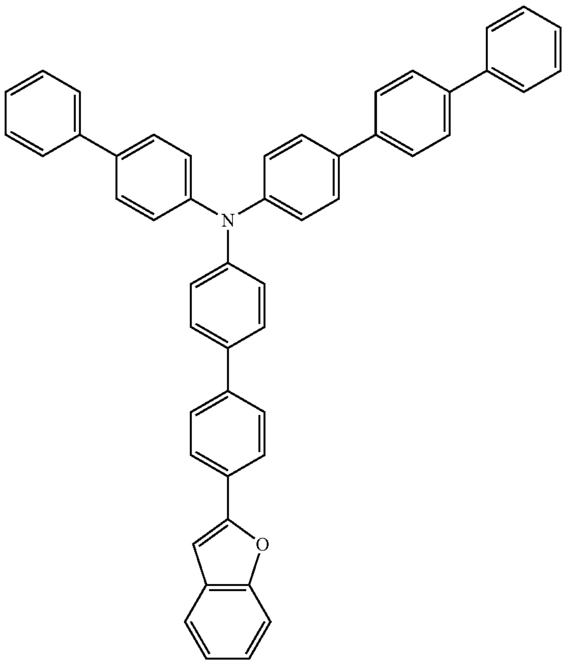
51
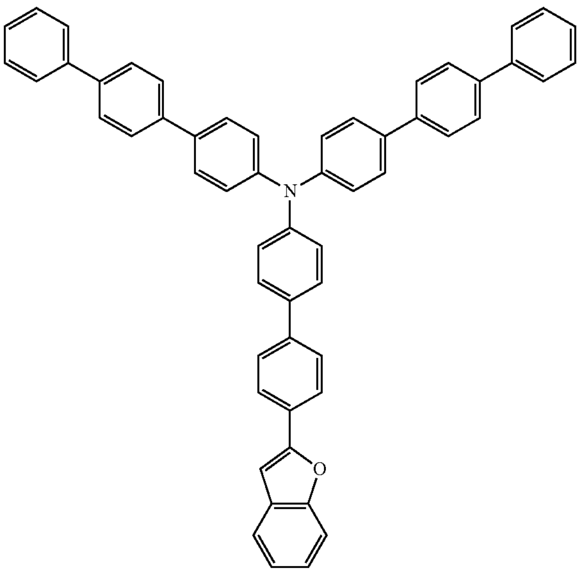
52
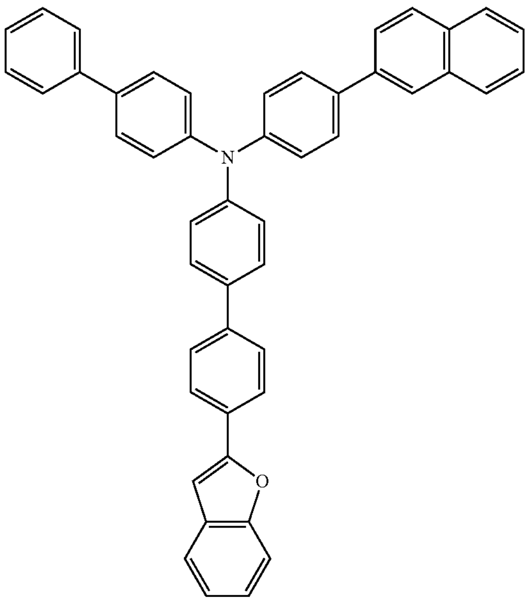

-continued
53
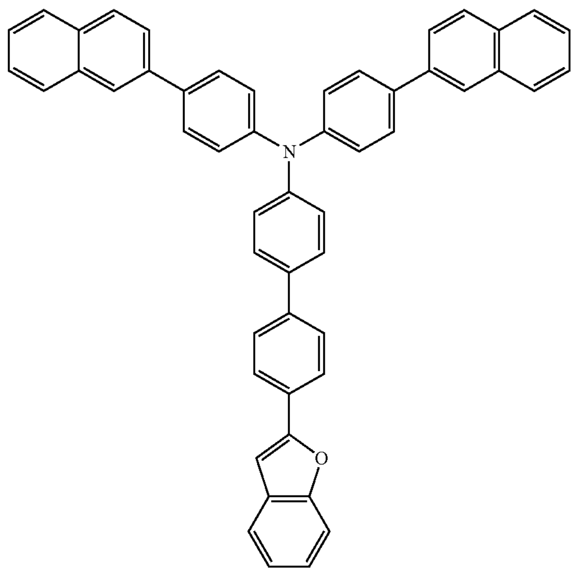
54
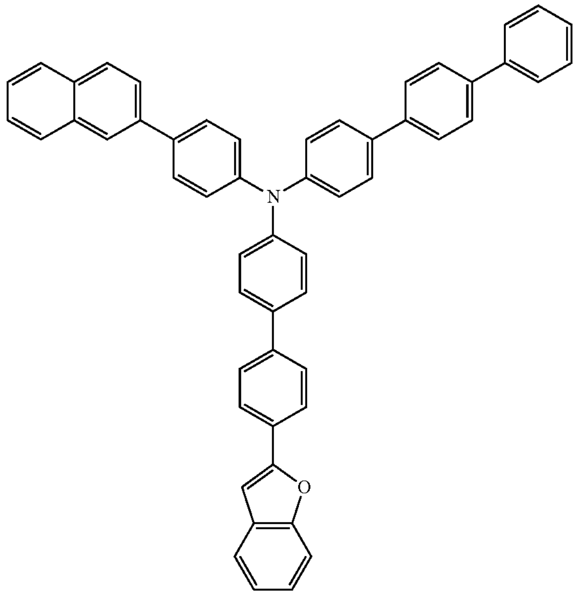
55
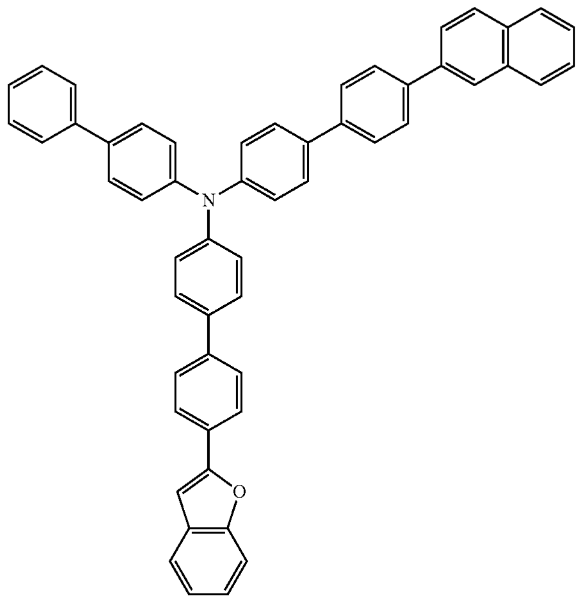
56
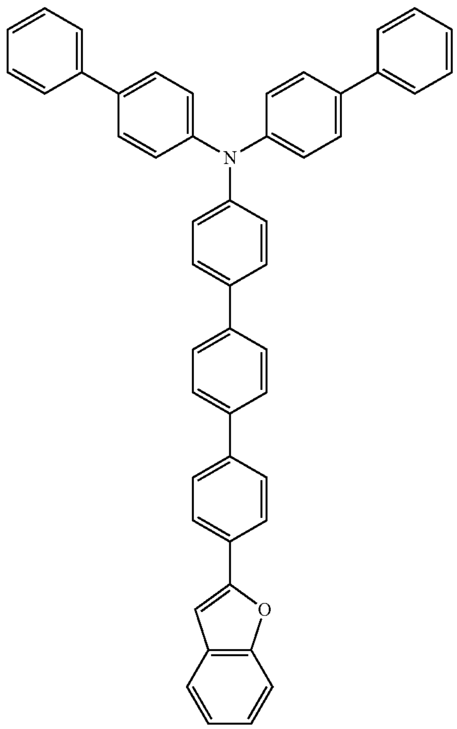

-continued
57
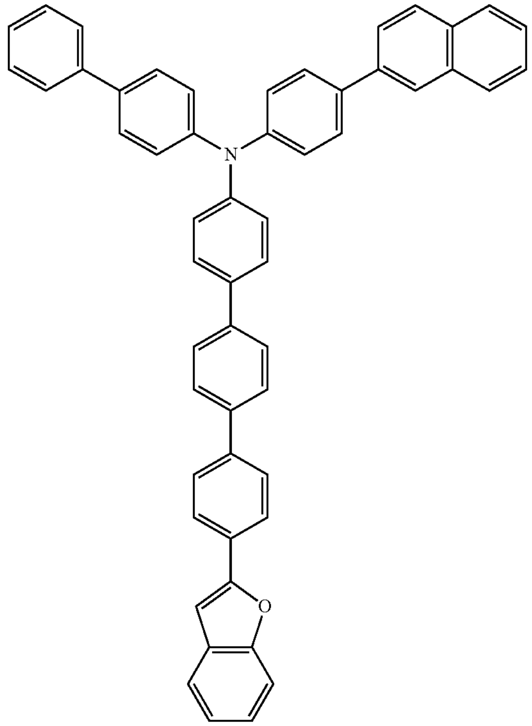
58
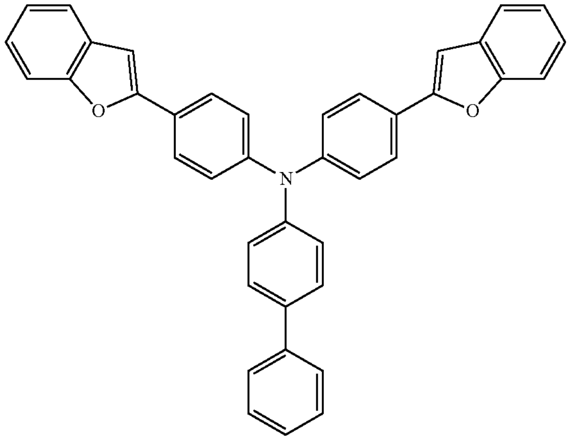
59
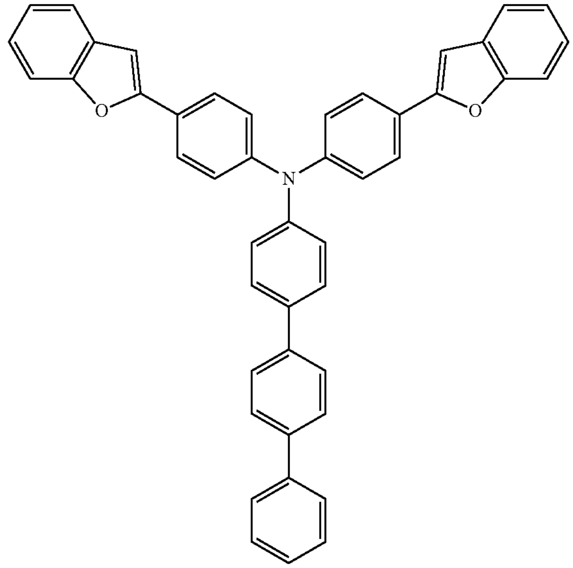
60
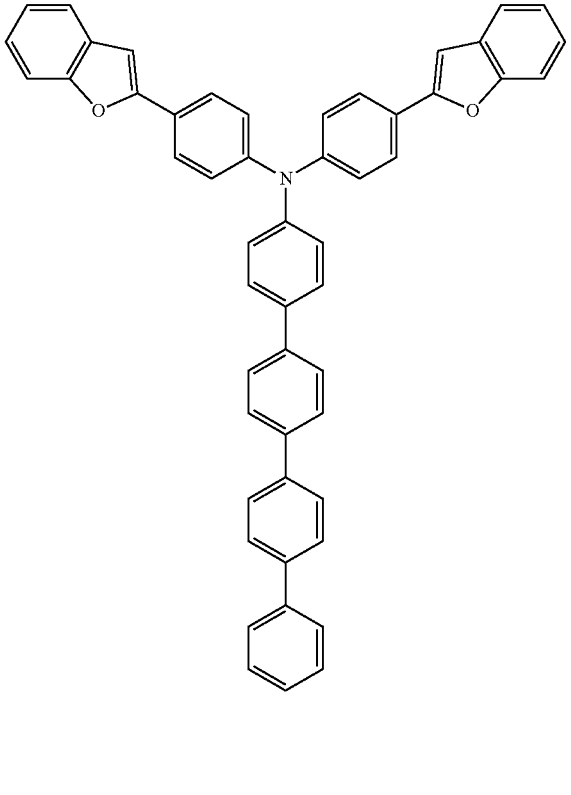

-continued
61
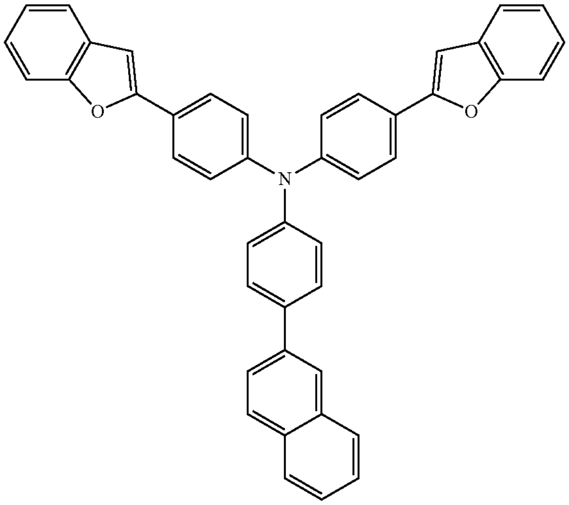
62
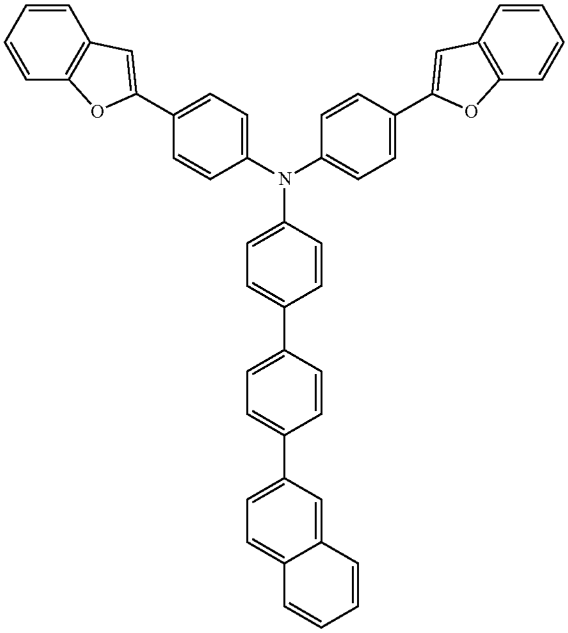
63
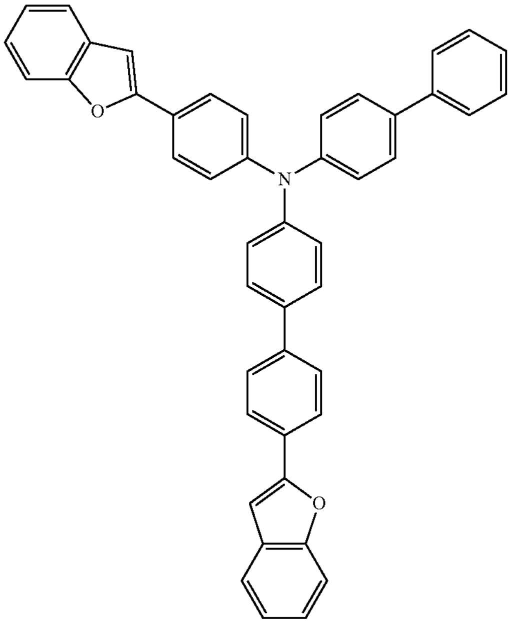
64
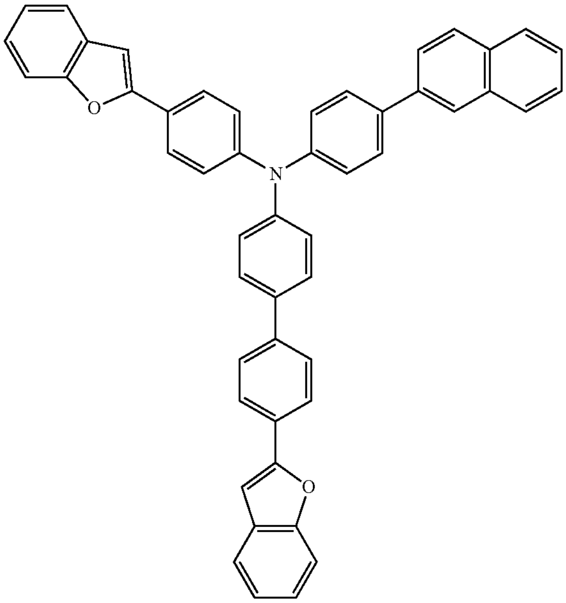

-continued
65
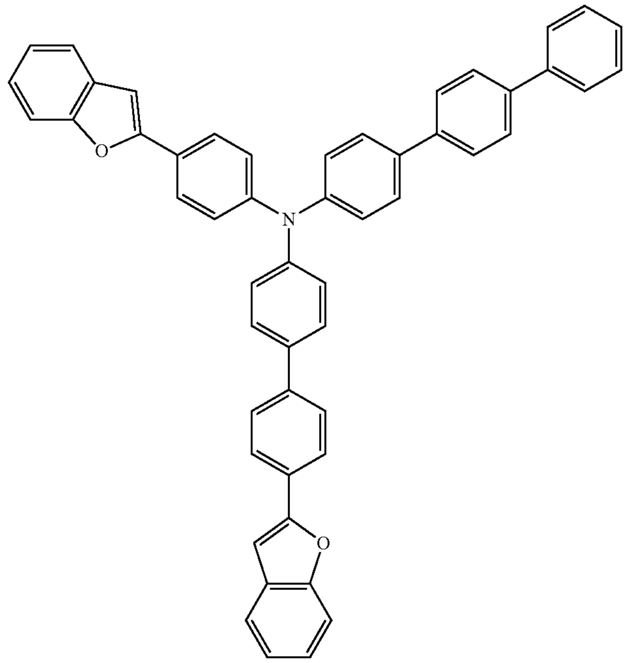
66
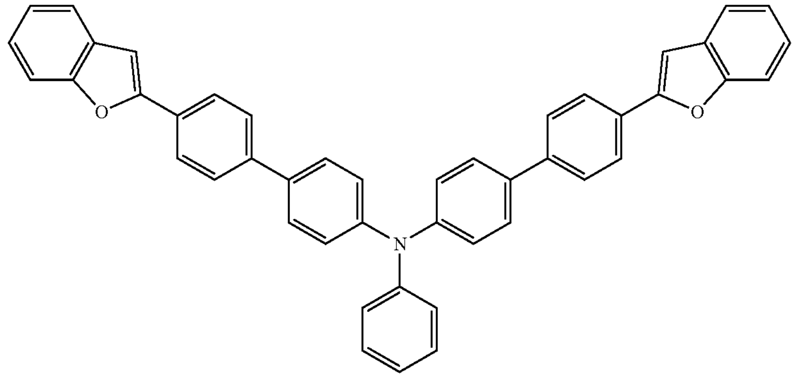
67
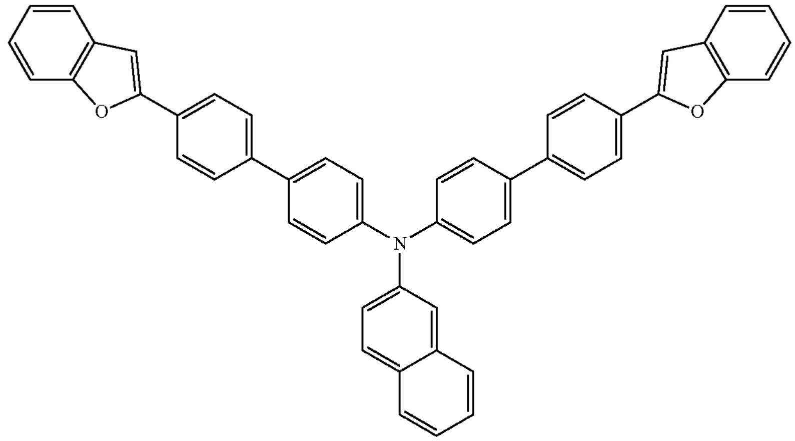

-continued
68
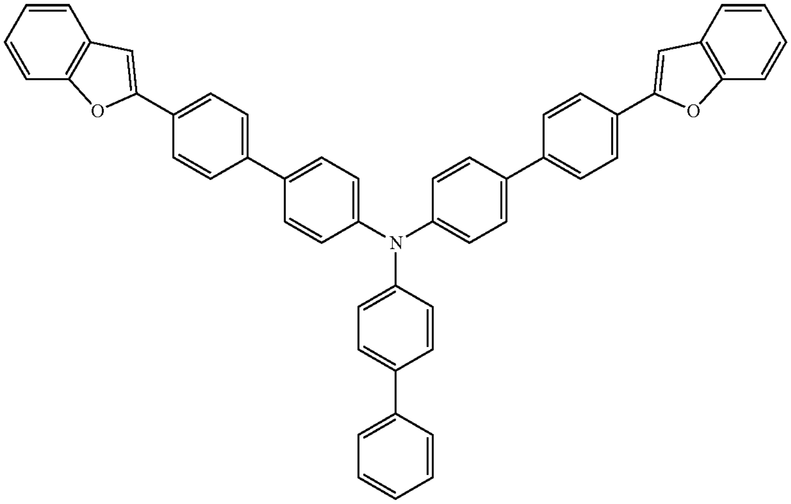
69
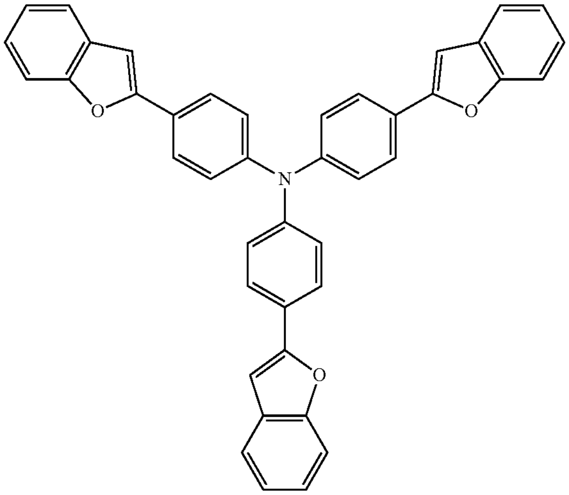
70
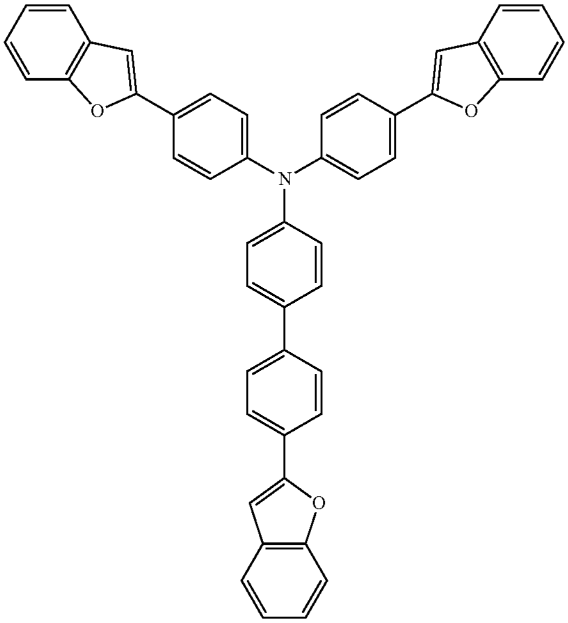

-continued
71
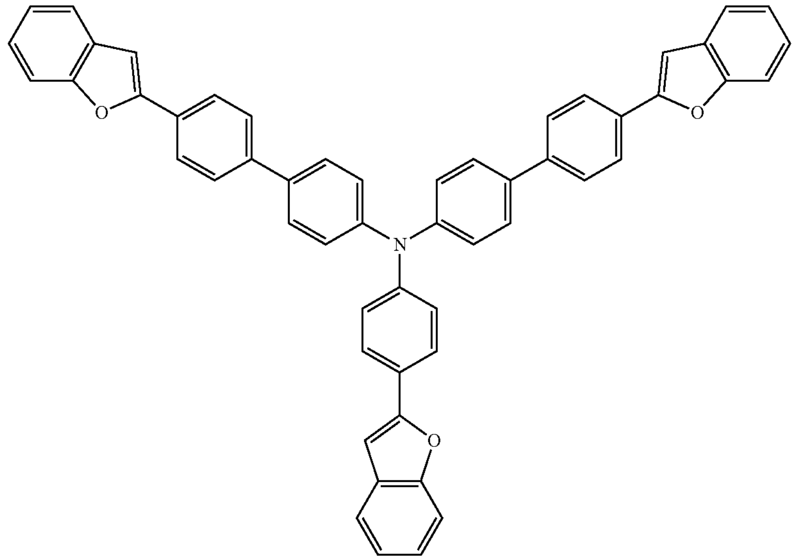
72
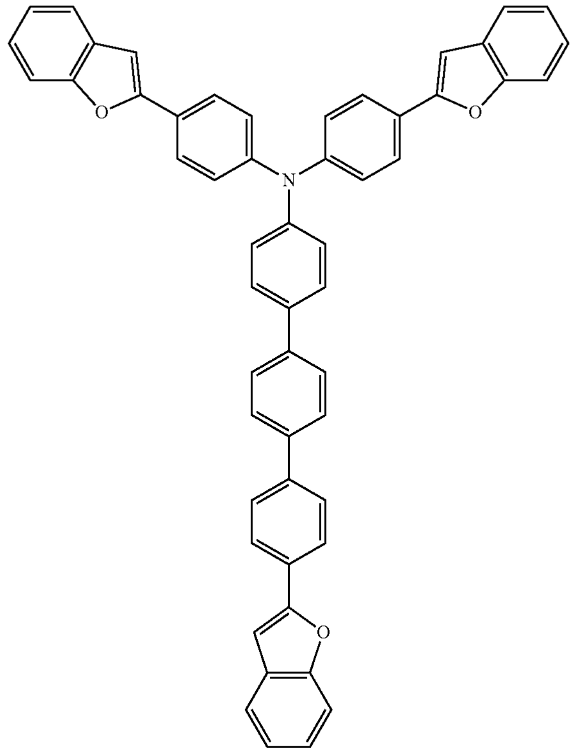

93
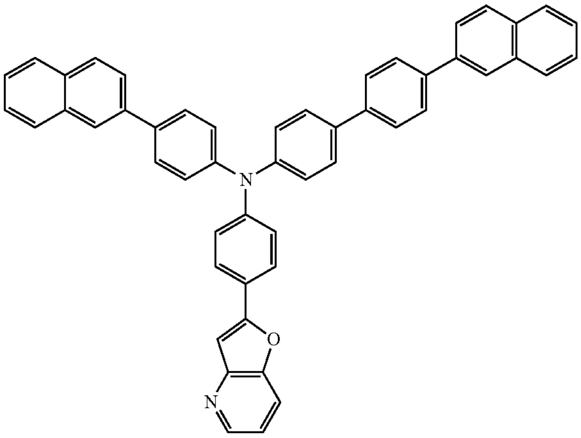
94
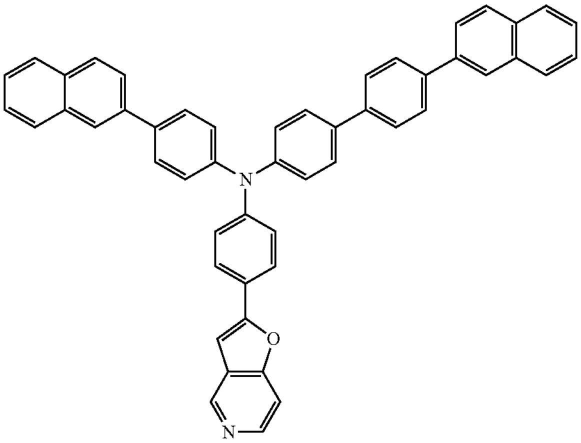
95
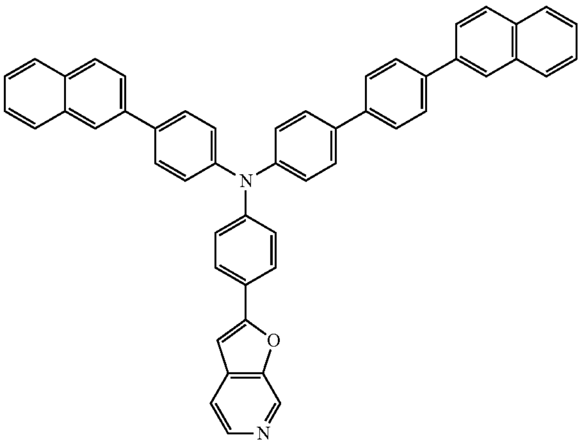
96
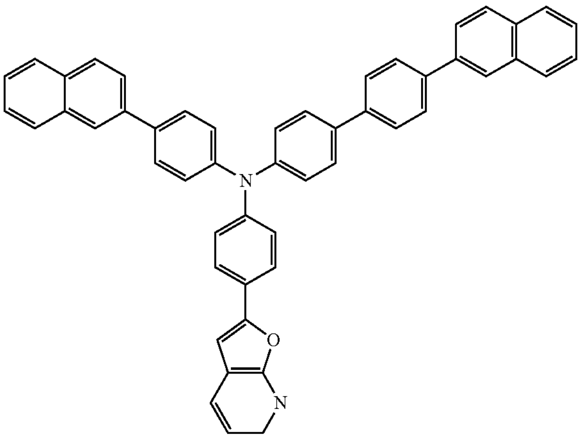
97
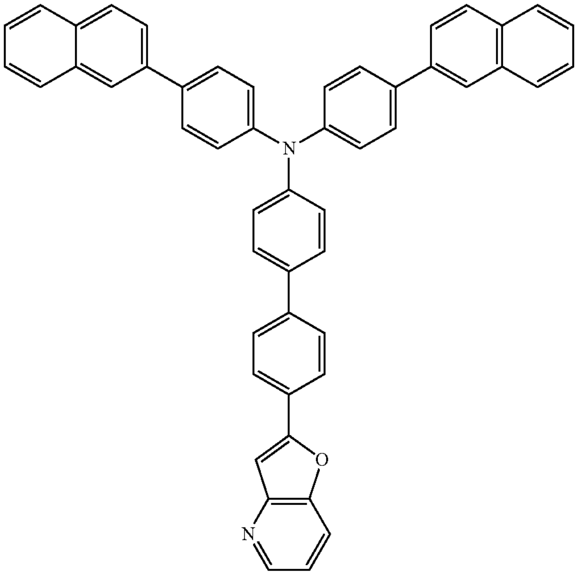
98
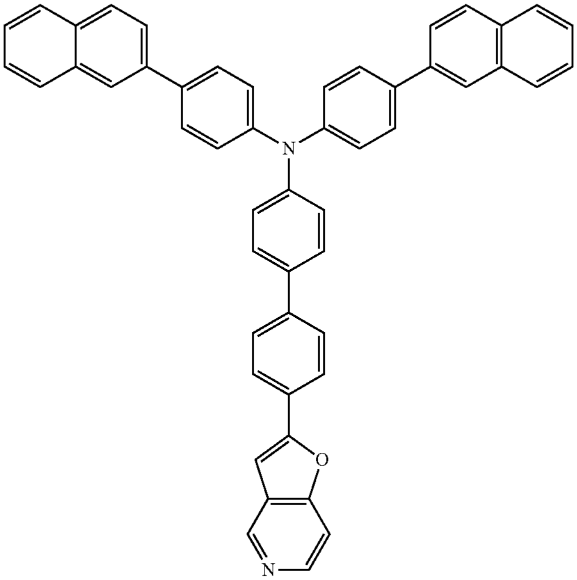

-continued
99
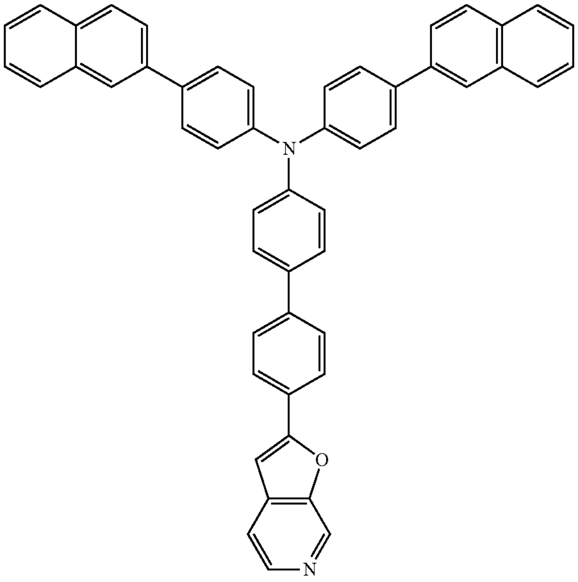
100
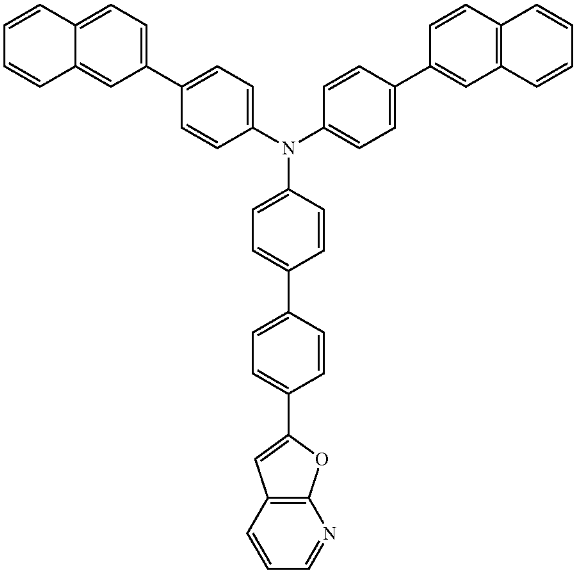
112
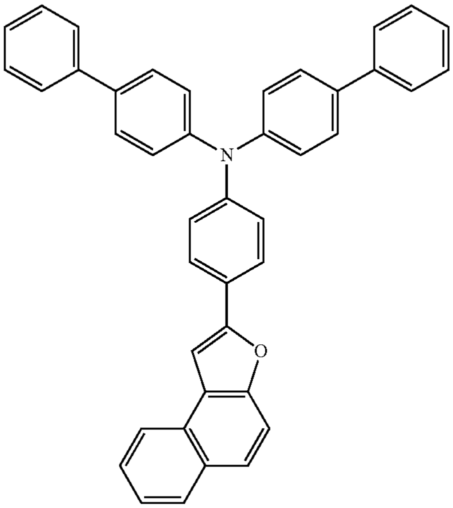
113
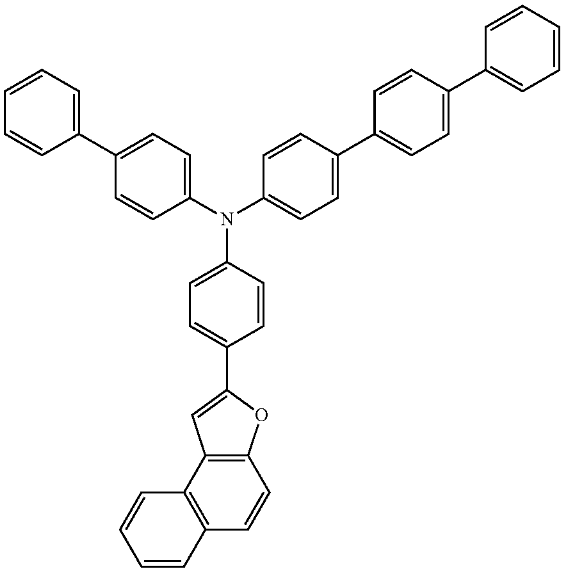

-continued
114
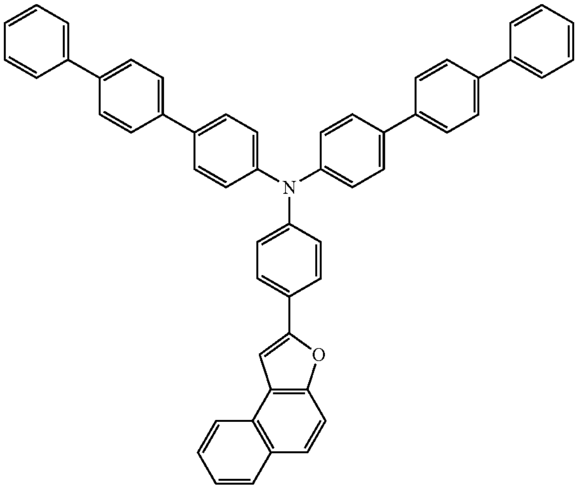
115
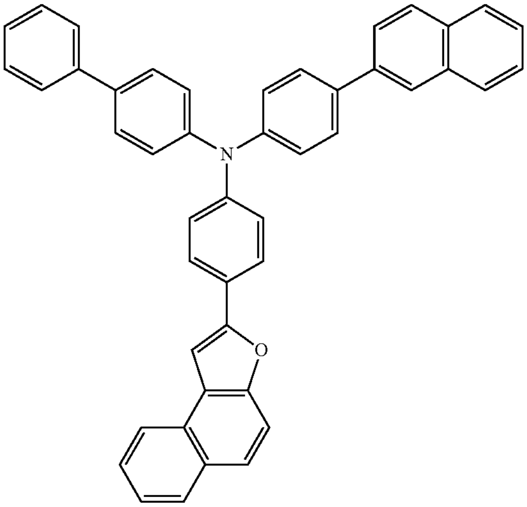
116
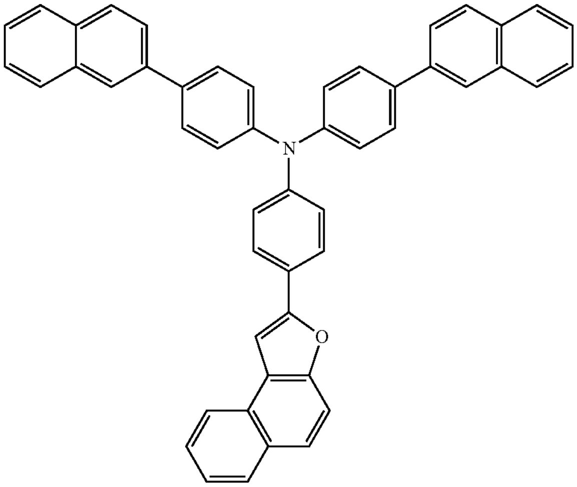
117
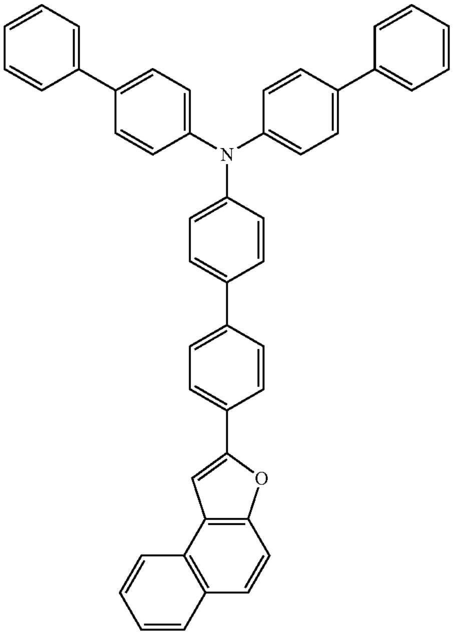

-continued
118
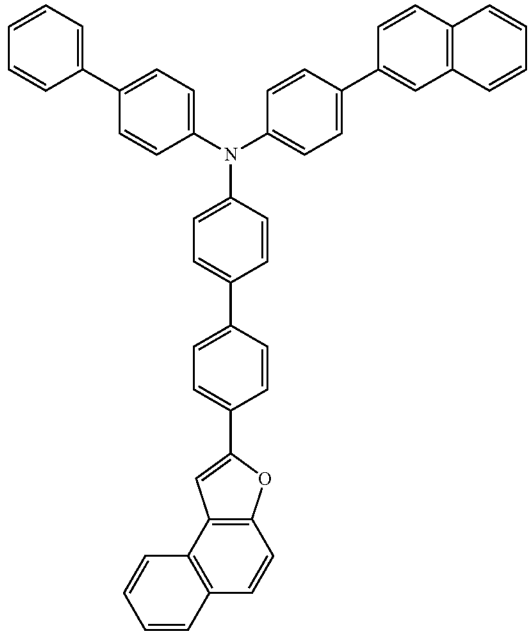
119
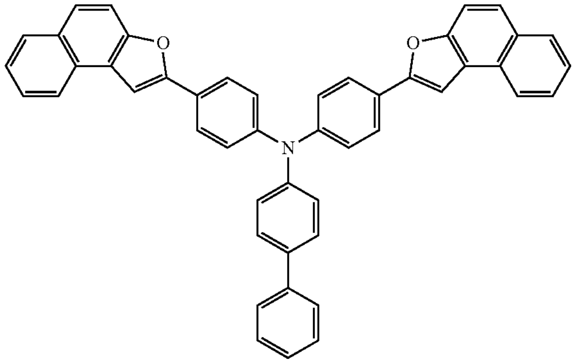
120
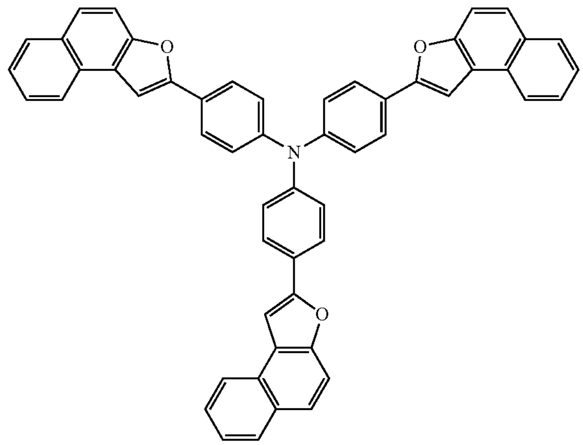
124
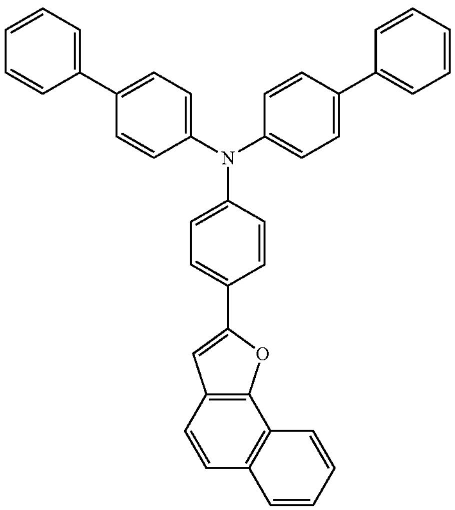

-continued
125
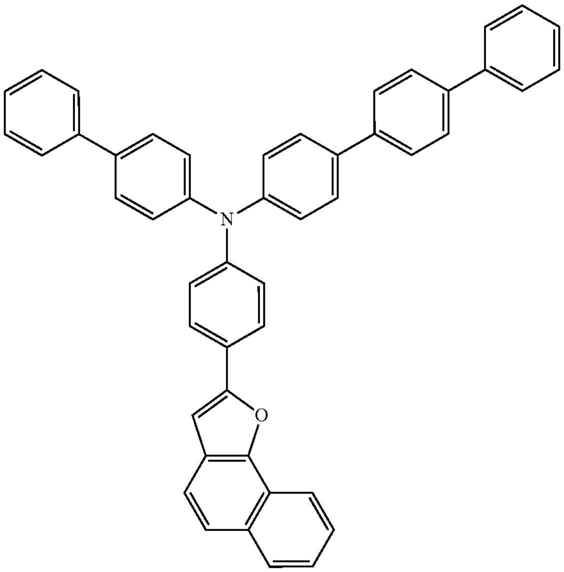
126
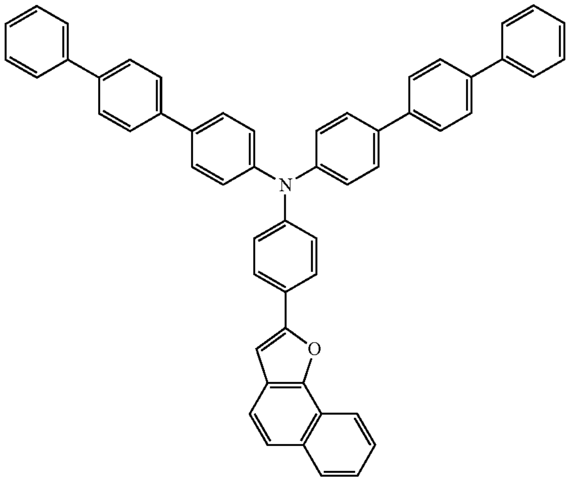
127
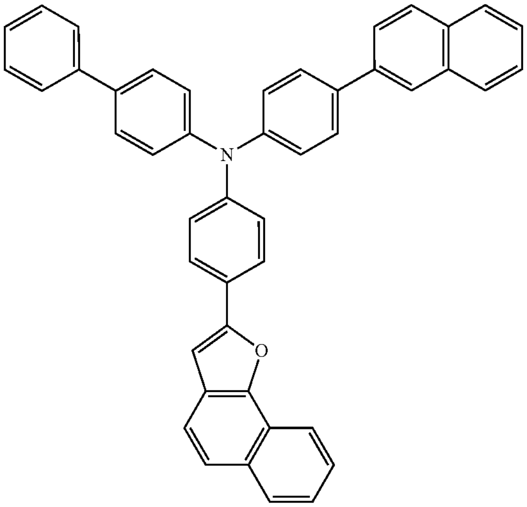
128
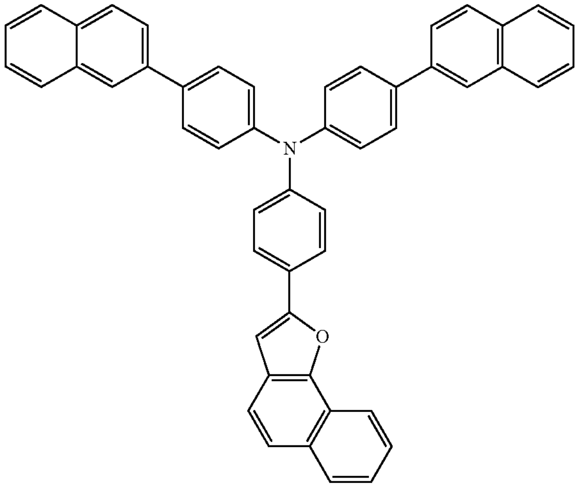

-continued
129
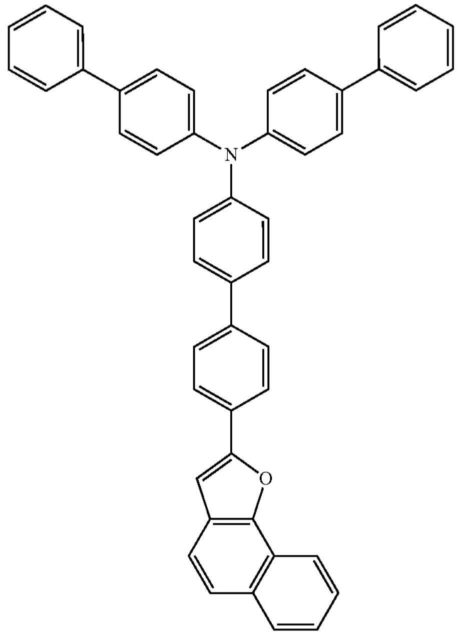
130
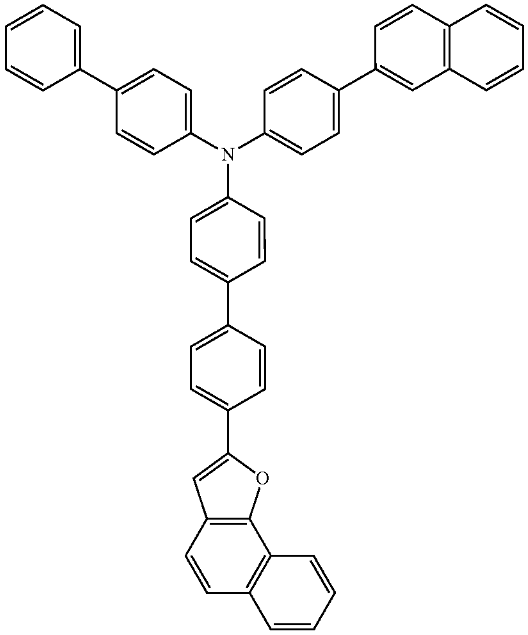
131
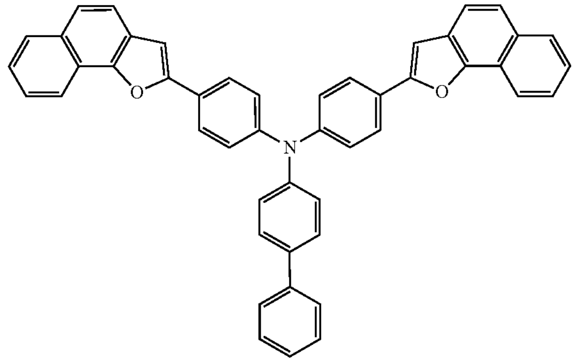
132
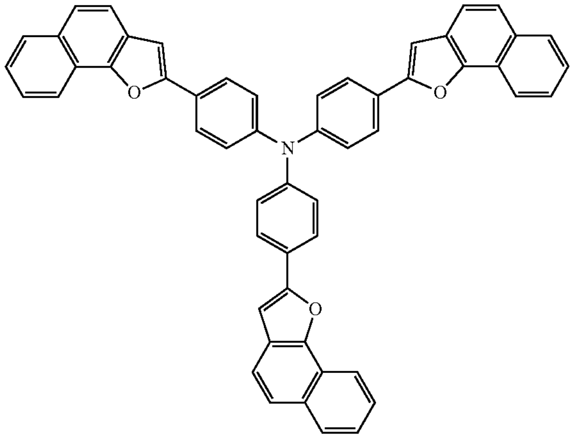

-continued
136
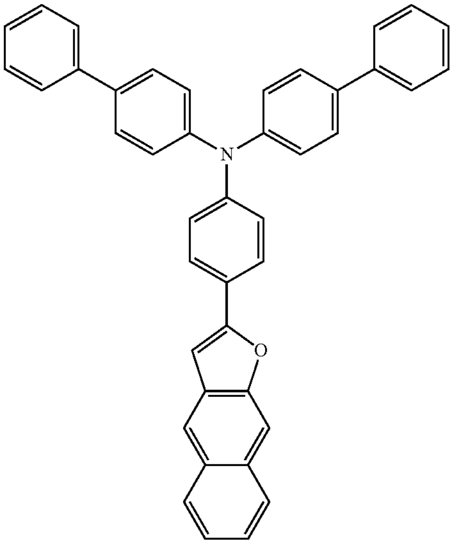
137
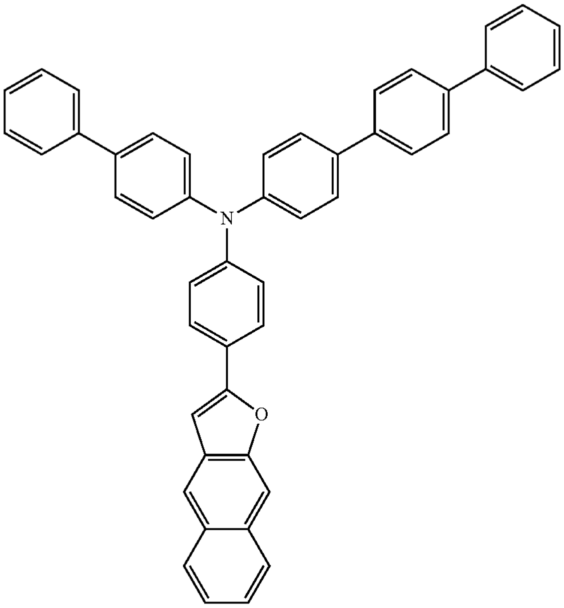
138
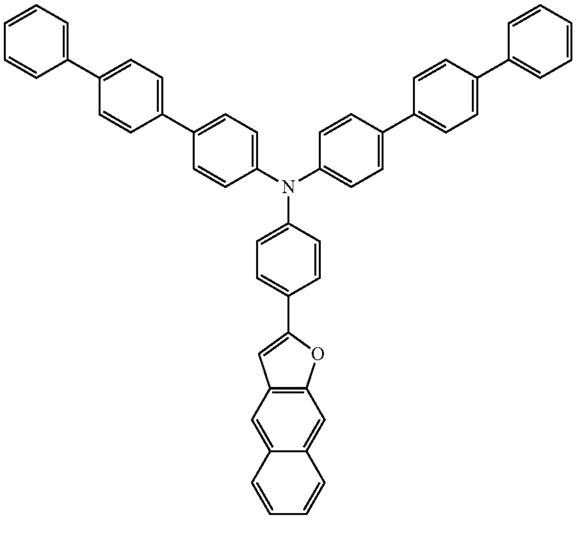
139
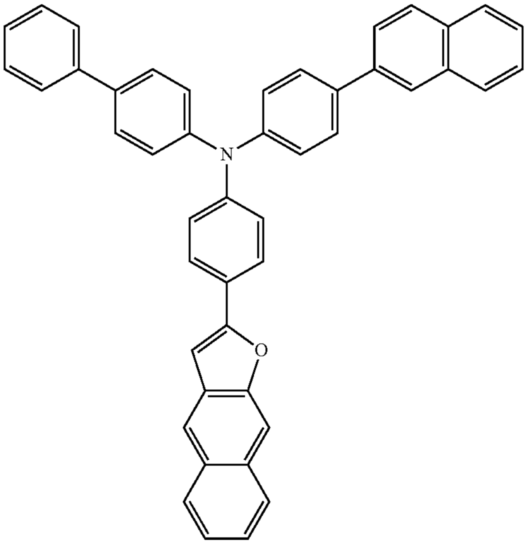

-continued
140
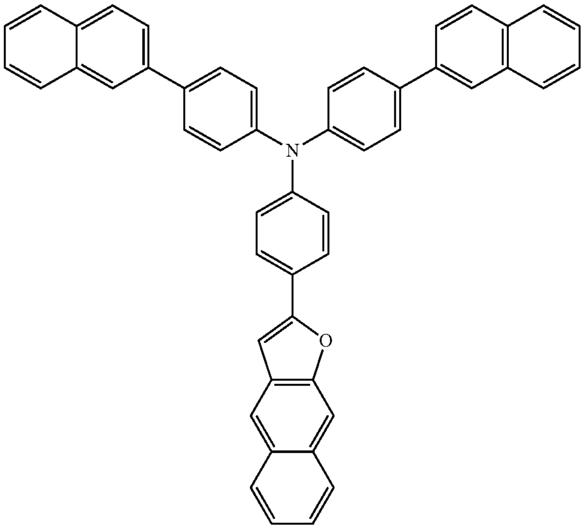
141
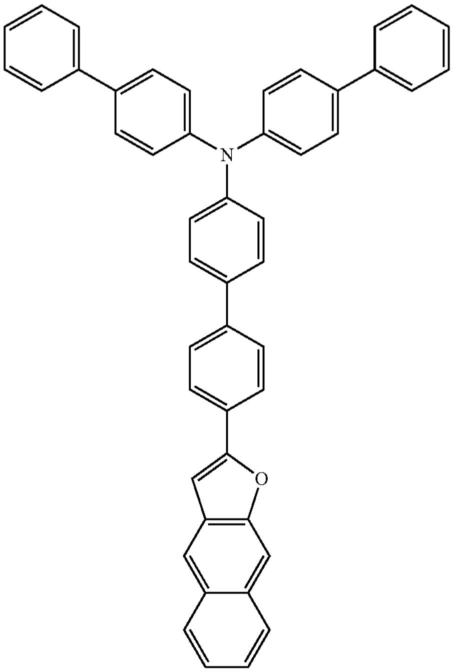
142
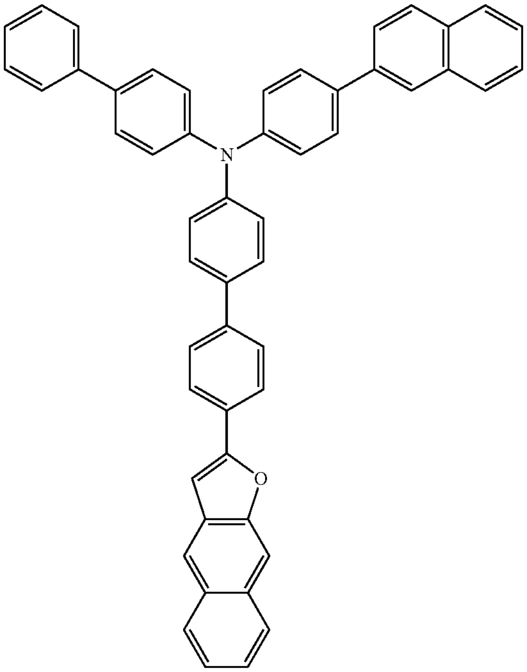
143
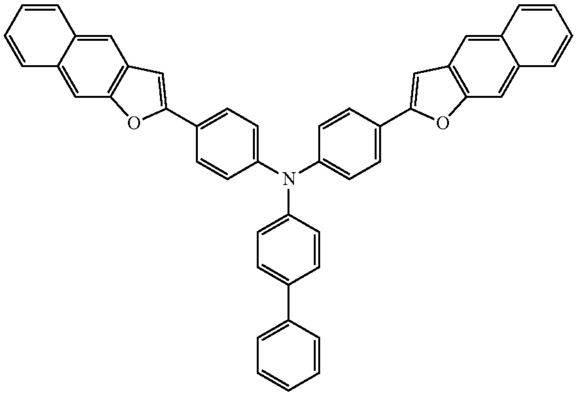

-continued
144
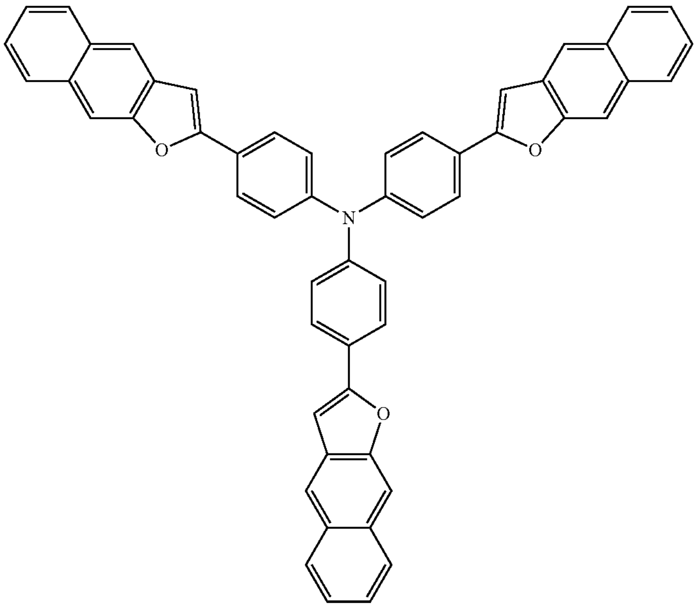
160
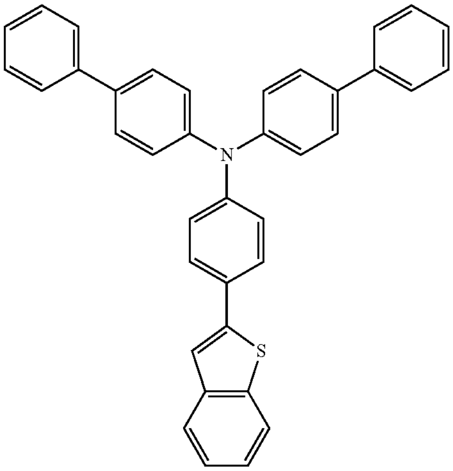
161
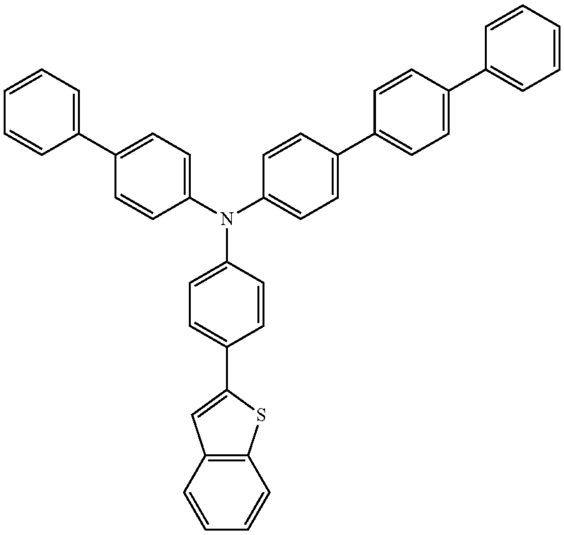

-continued
162
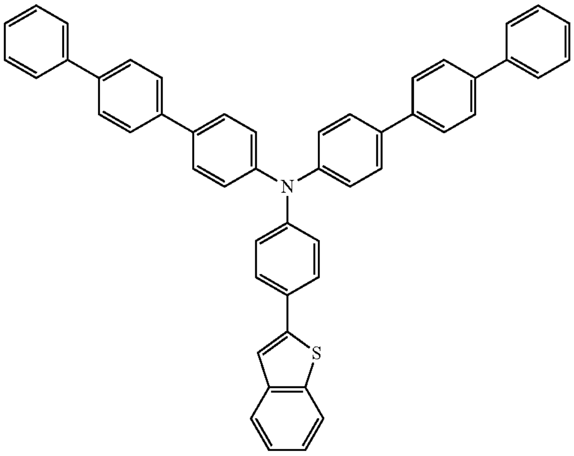
163
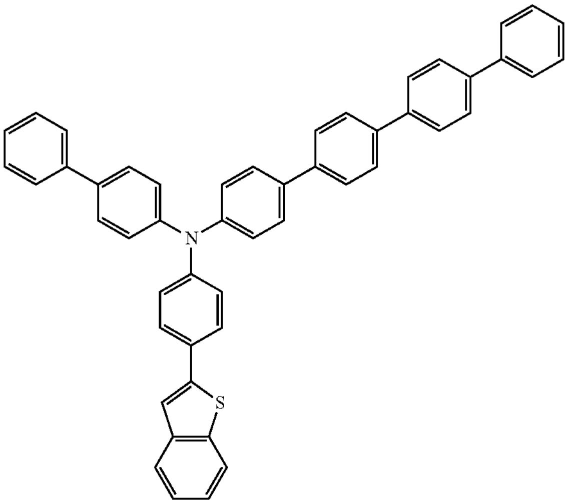
164
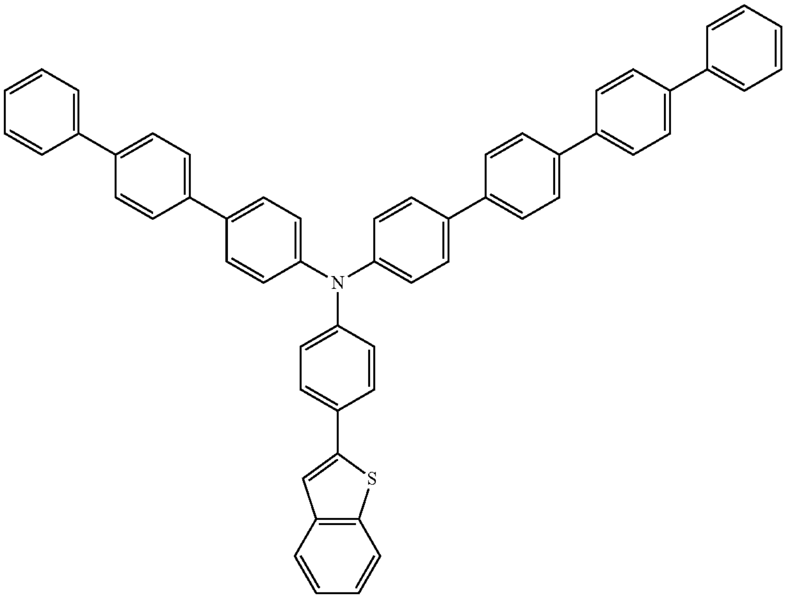
165
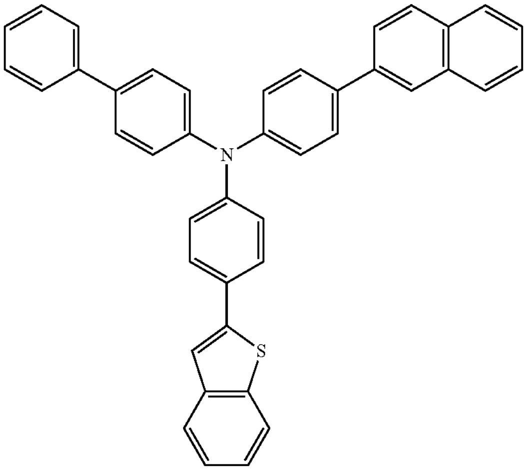
166
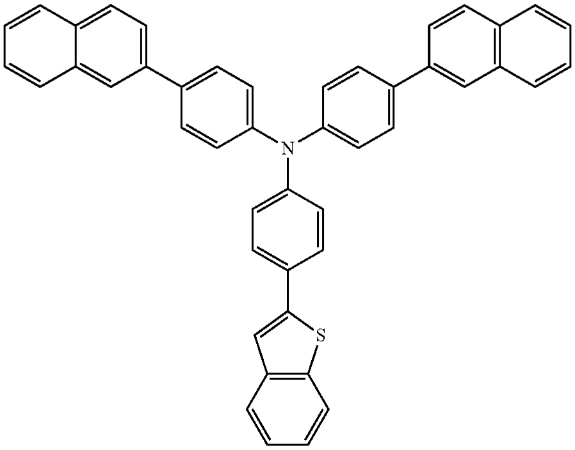

-continued
167
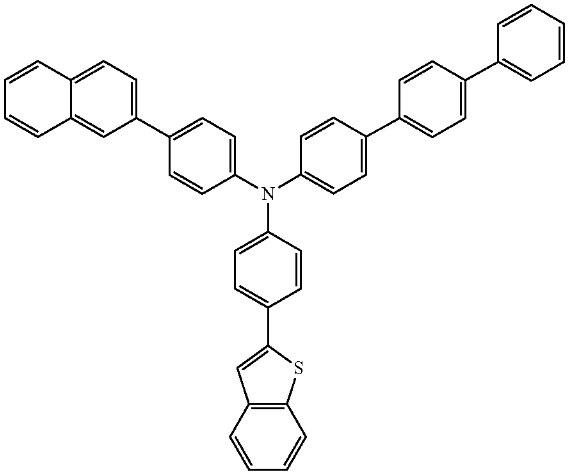
168
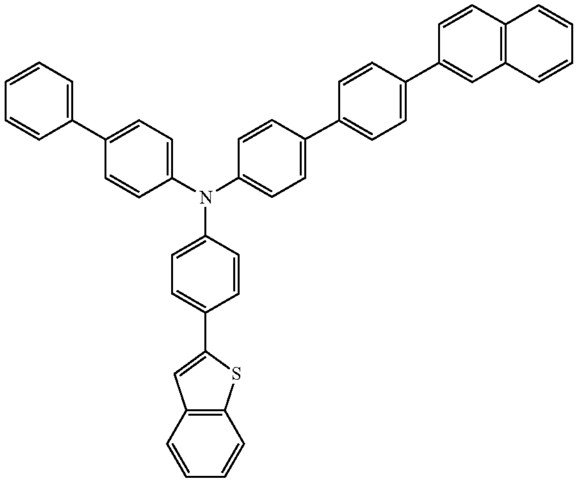
169
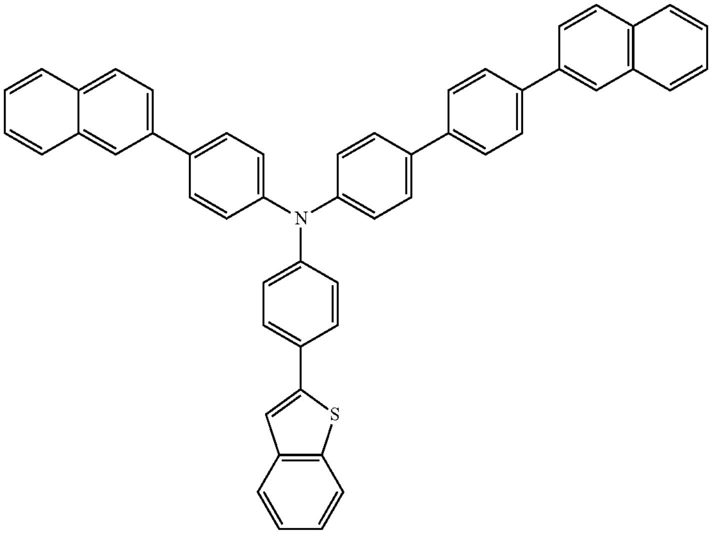
170
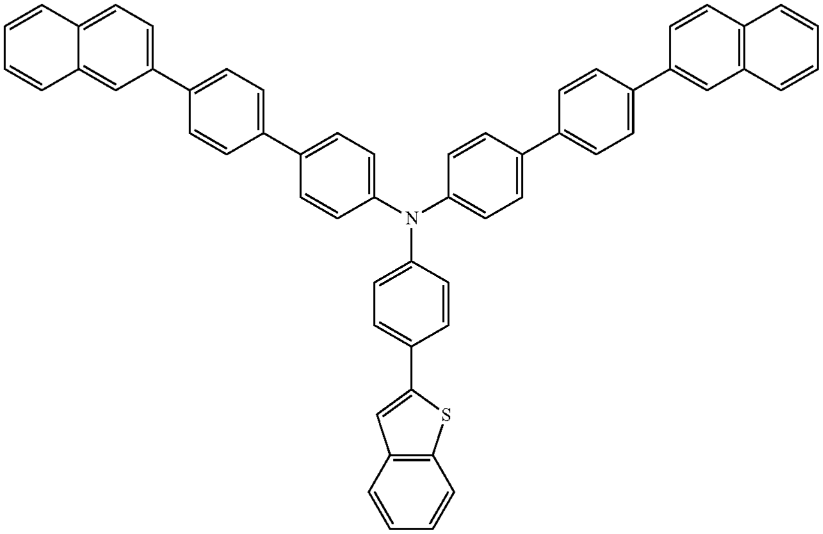

-continued
171
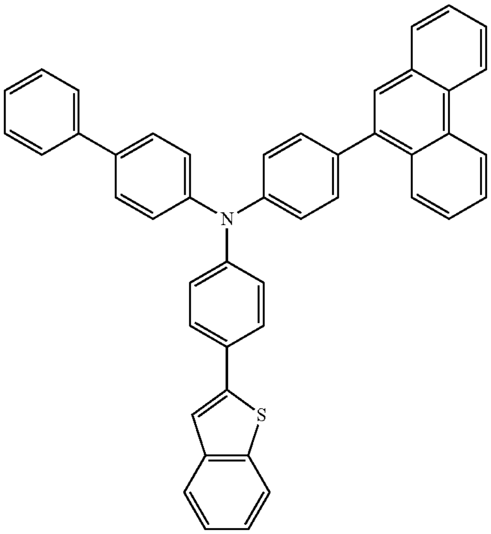
172
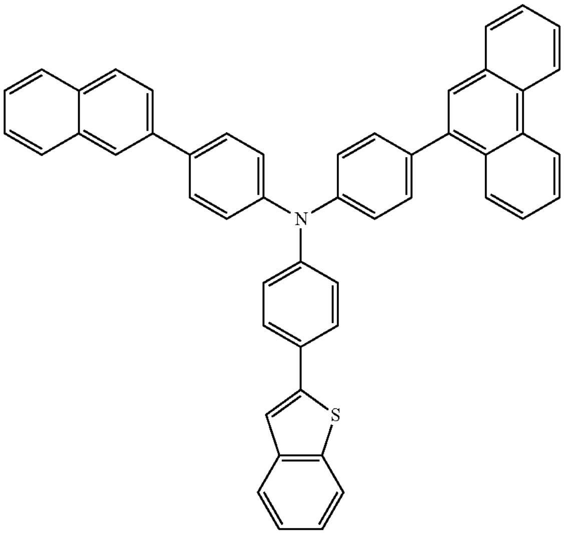
173
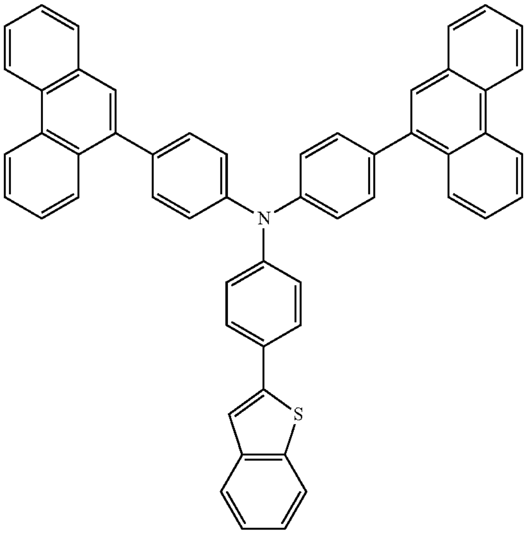
174
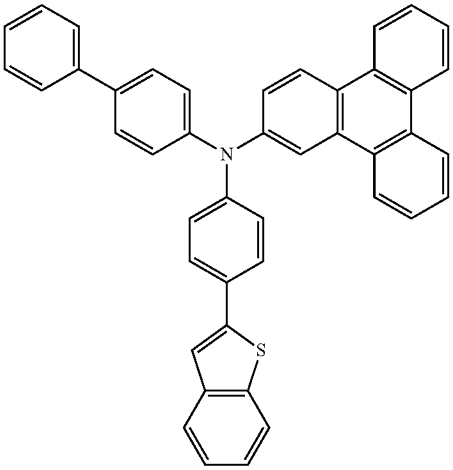
175
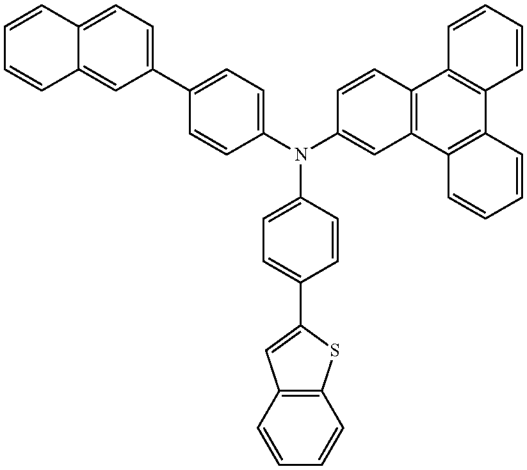
176
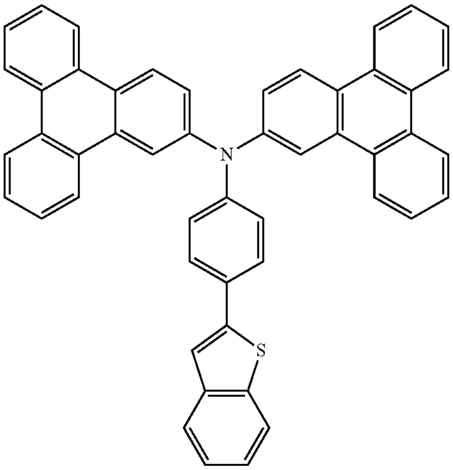

-continued
177
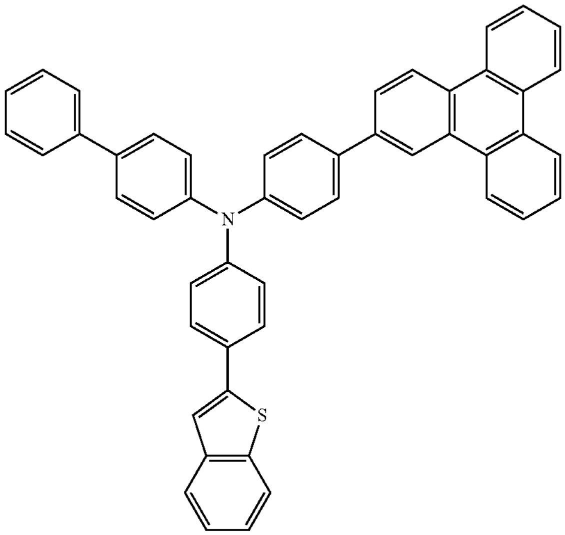
178
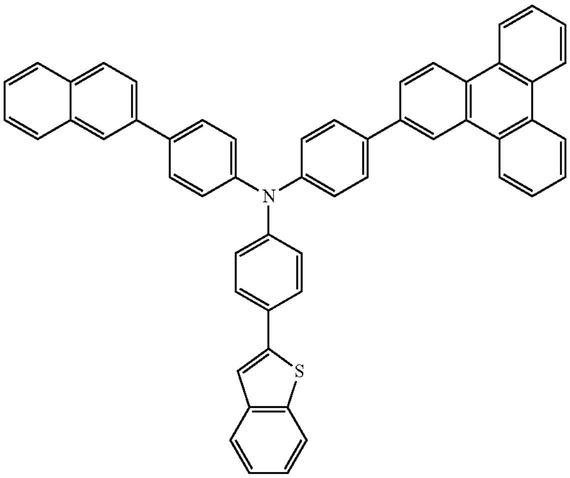
179
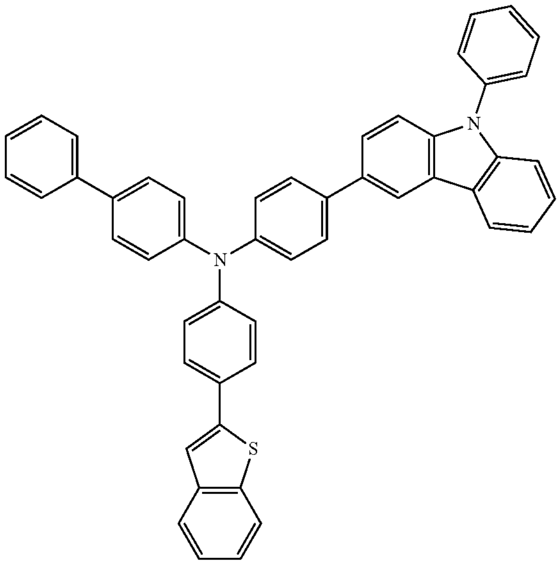
180
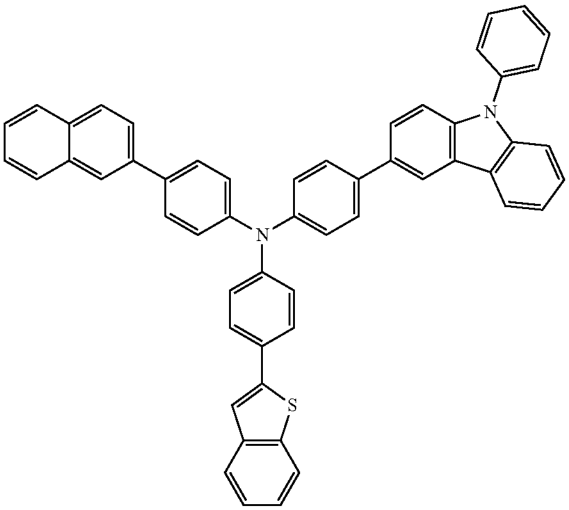
181
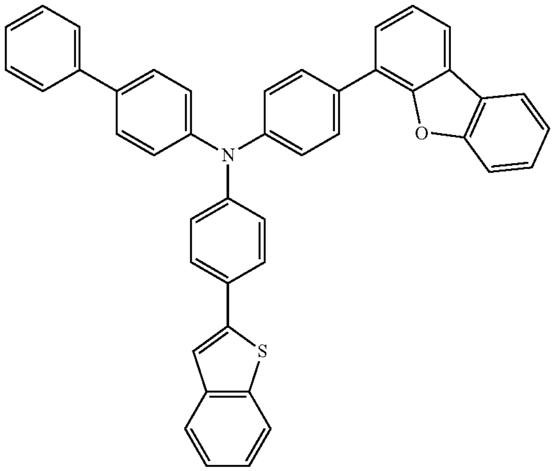
182
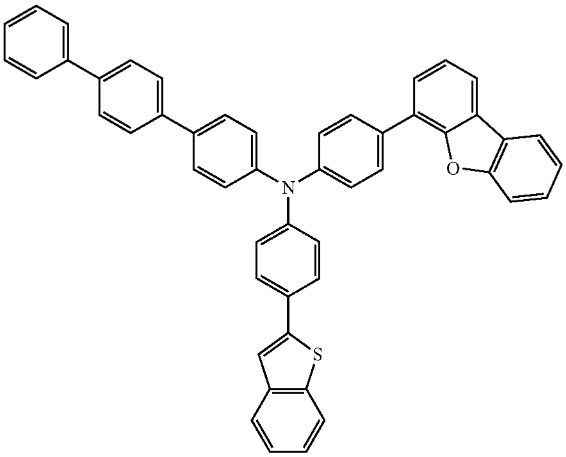

-continued
183
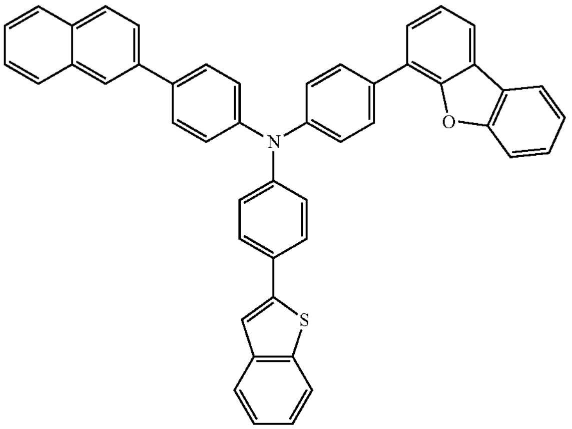
184
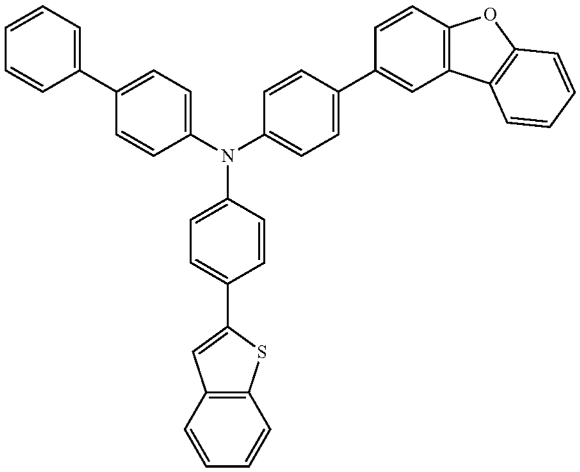
185
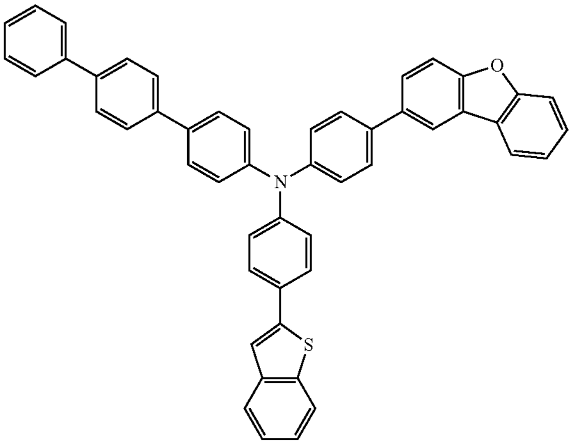
186
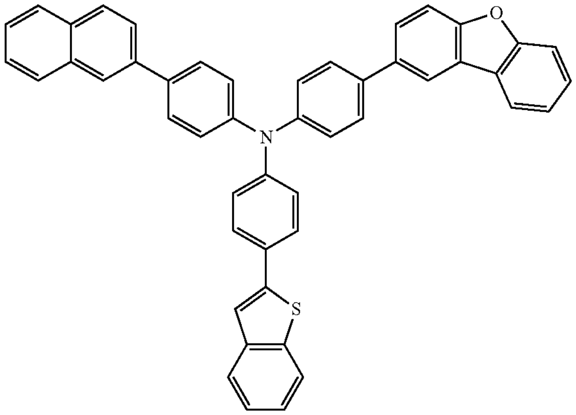
187
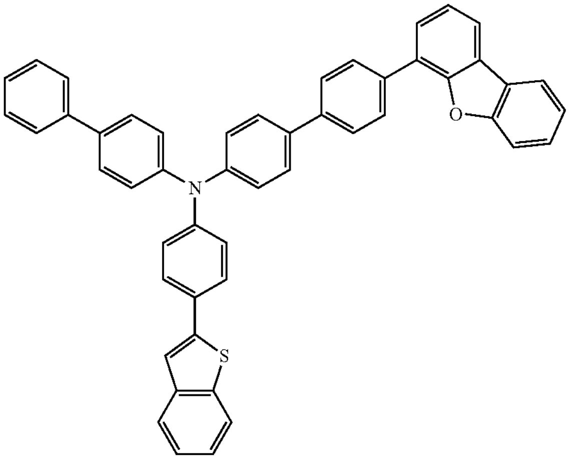
188
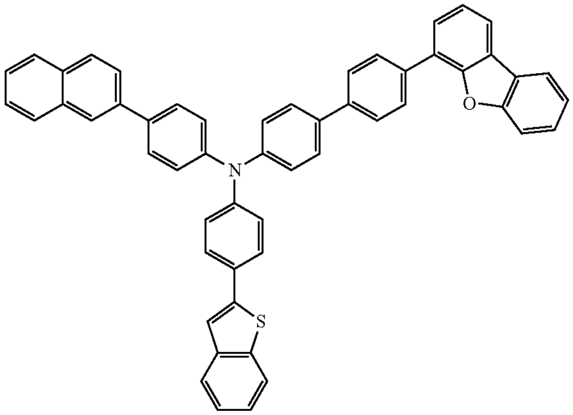

-continued
189
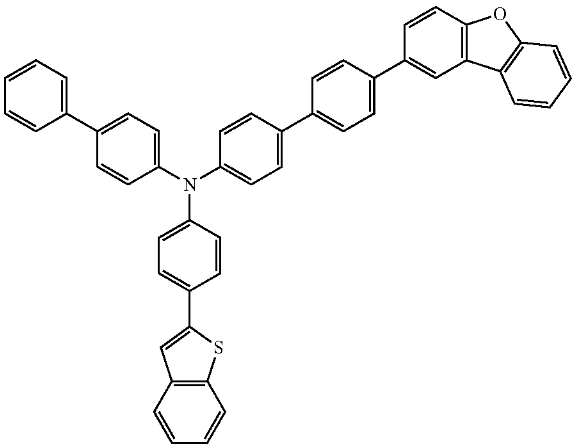
190
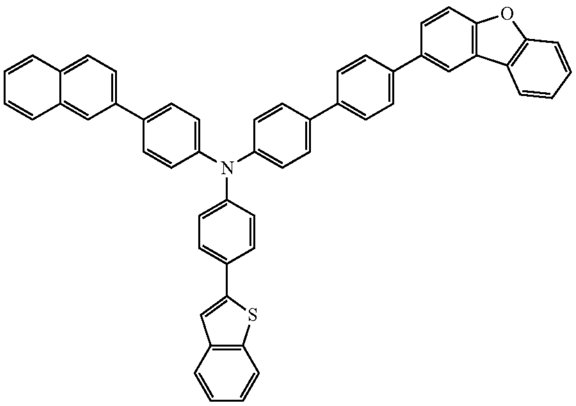
191
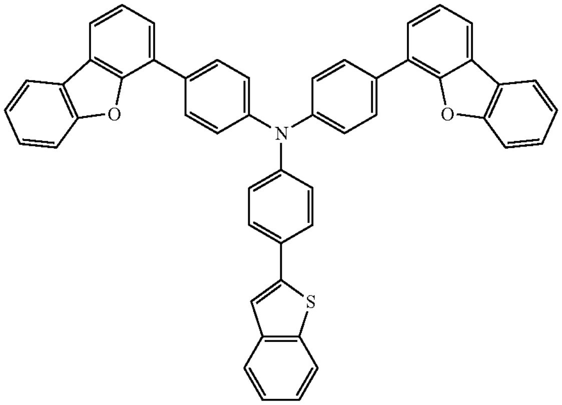
192
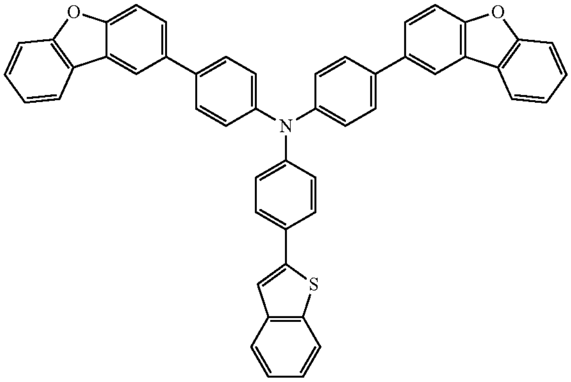
193
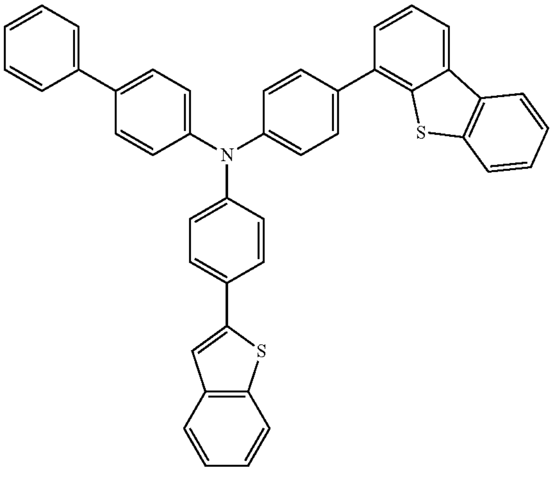
194
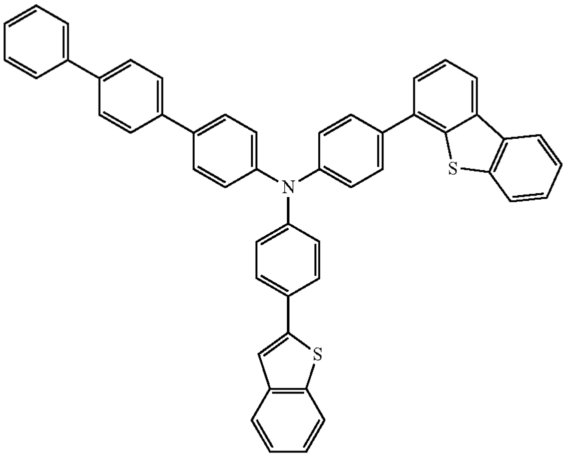

-continued
195
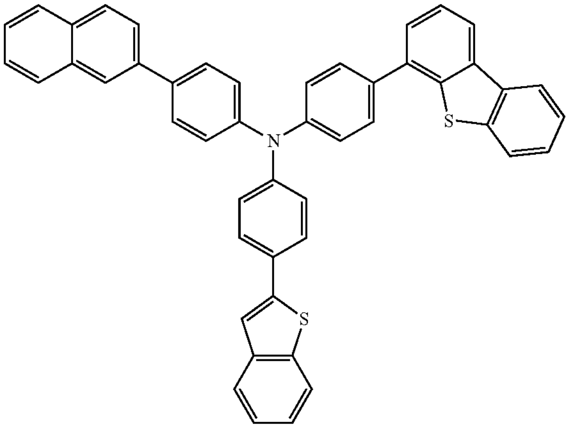
196
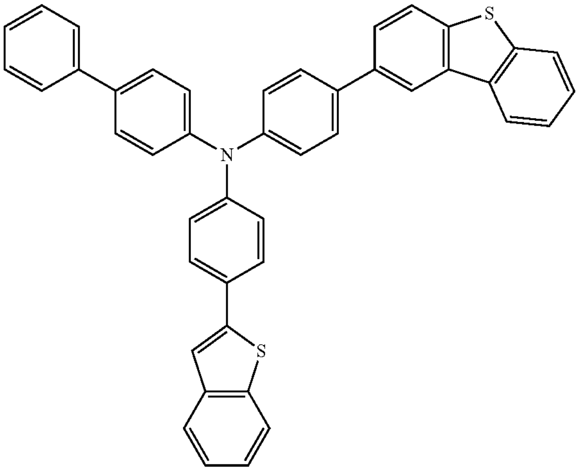
197
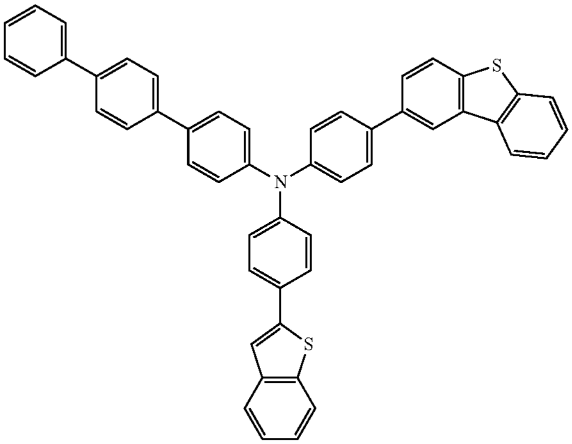
198
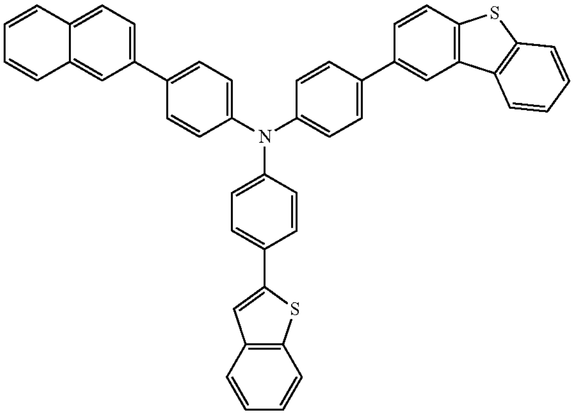
199
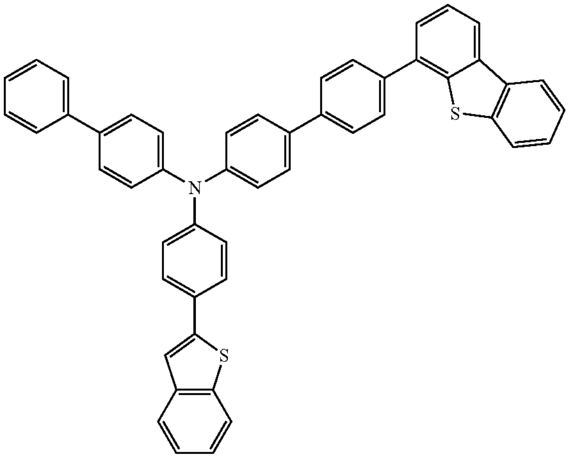
200
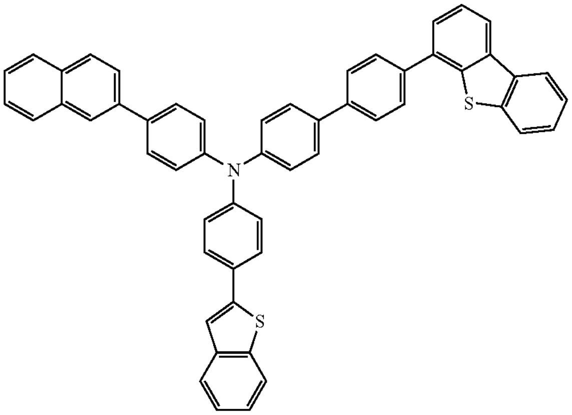

-continued
201
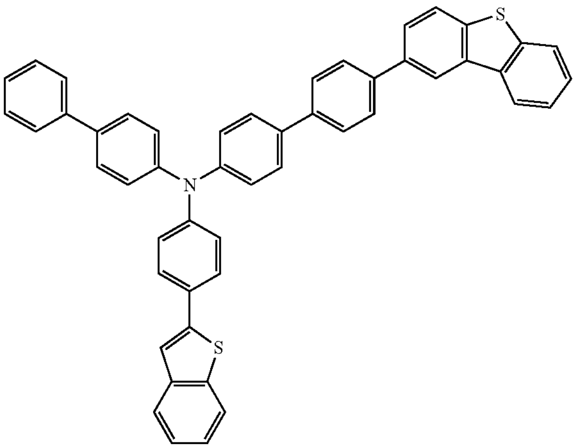
202
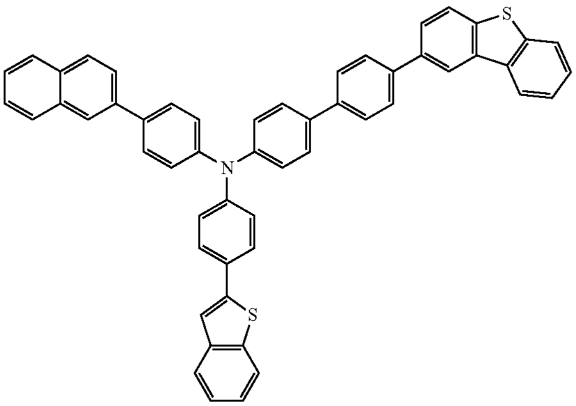
203
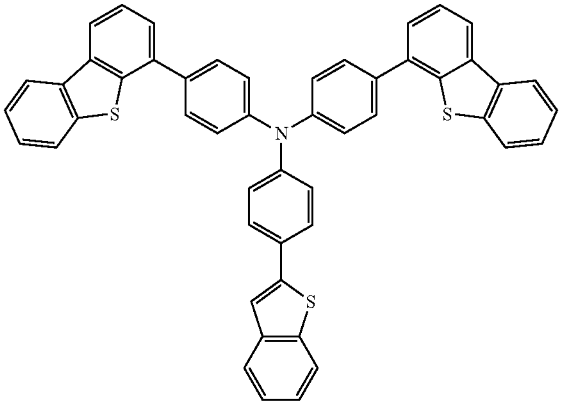
204
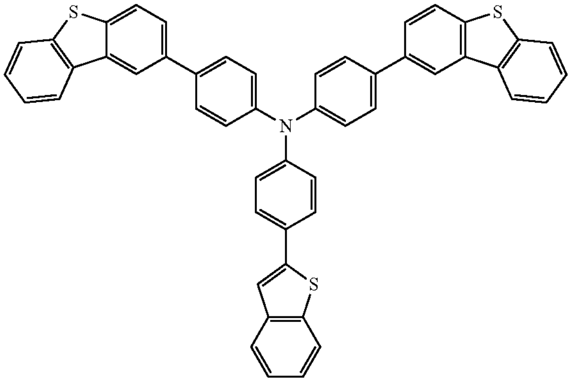
205
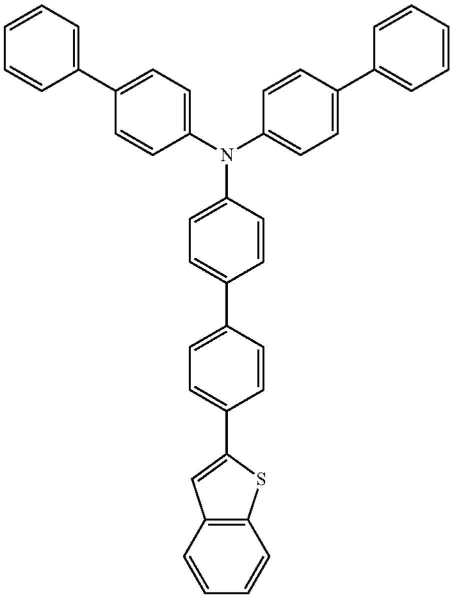
206
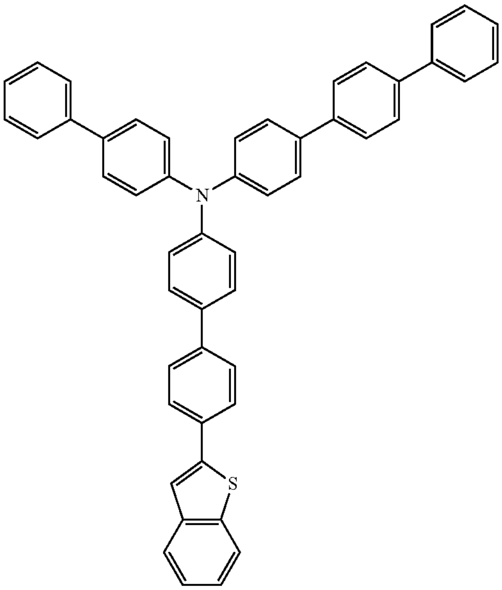

-continued
207
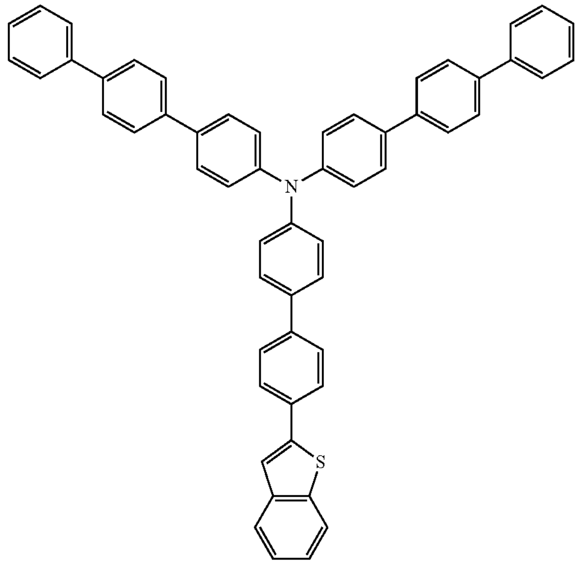
208
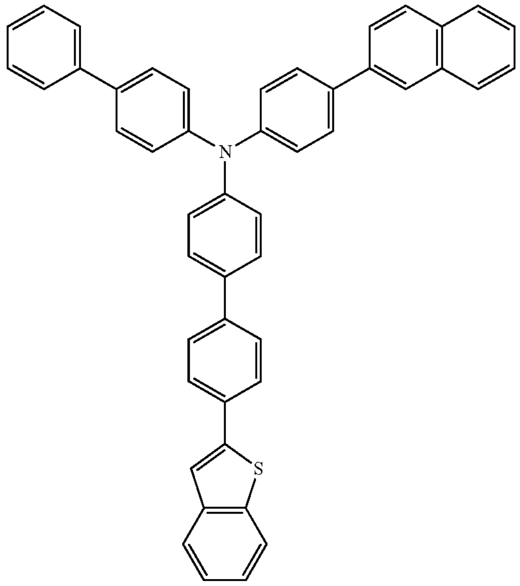
209
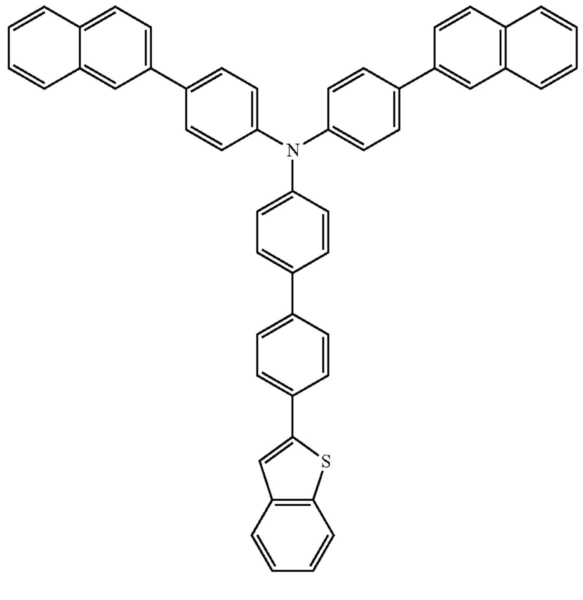
210
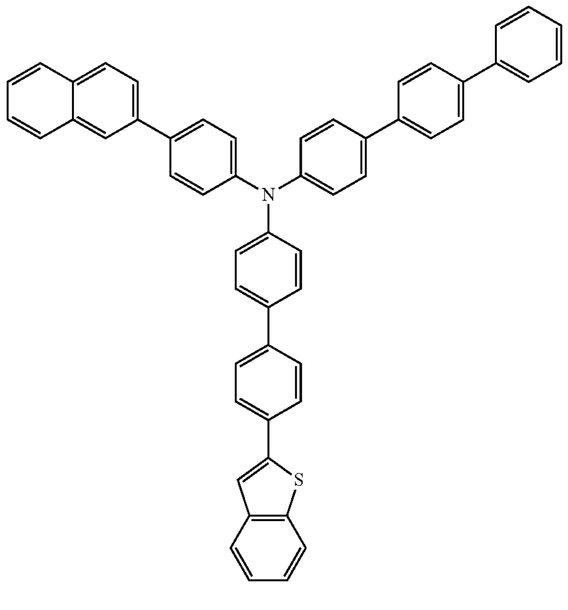

-continued
211
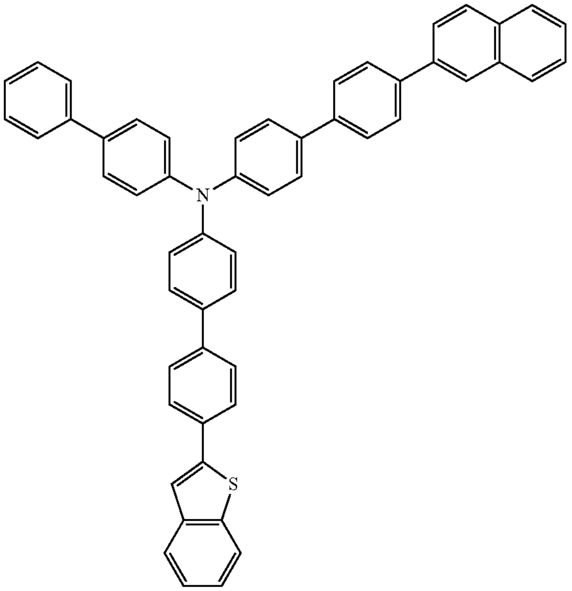
212
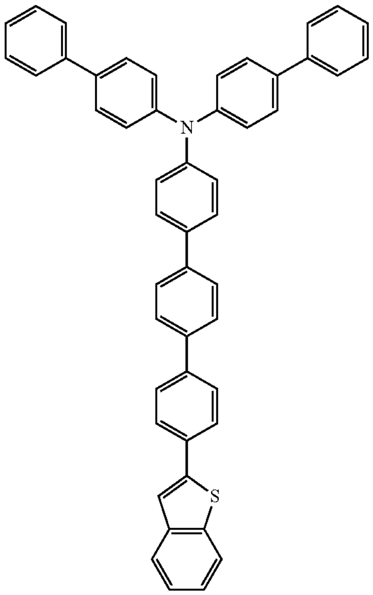
213
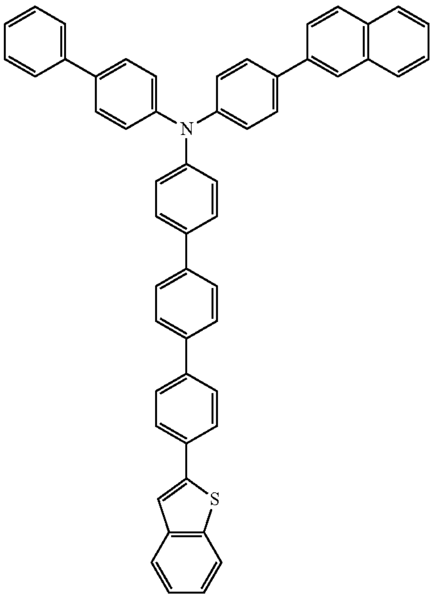
214
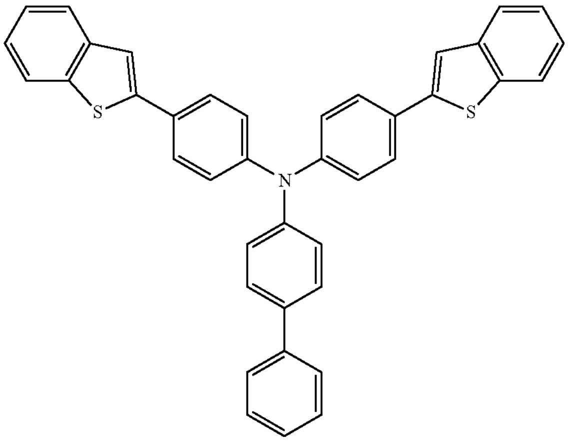

-continued
215
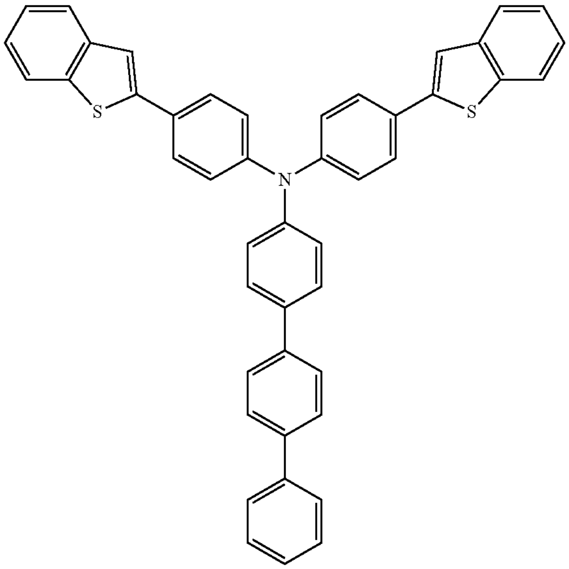
216
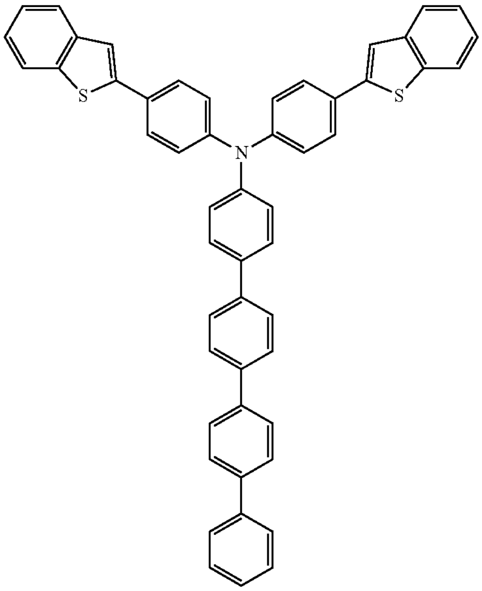
217
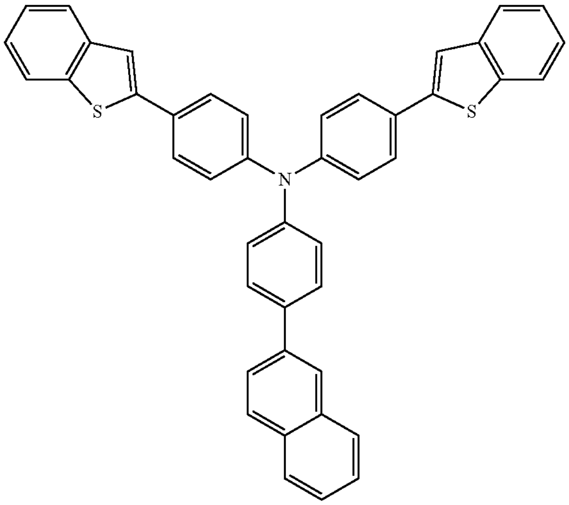
218
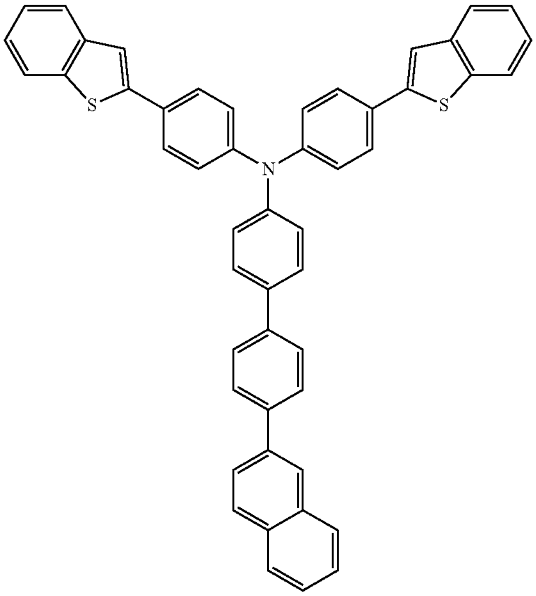

-continued
219
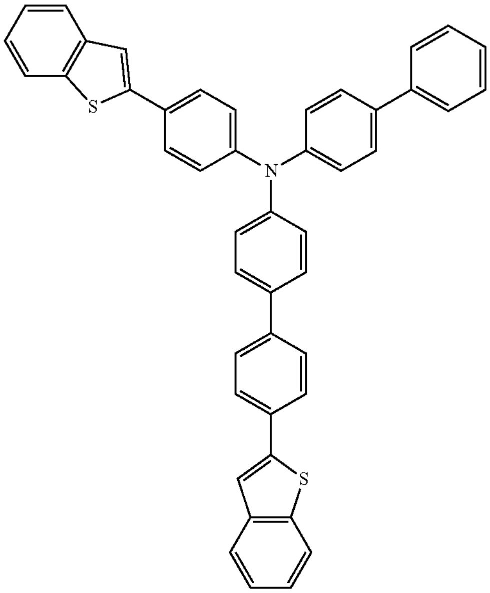
220
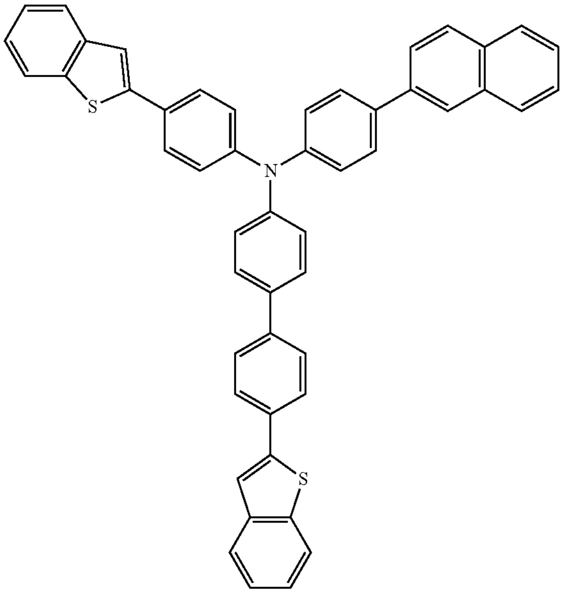
221
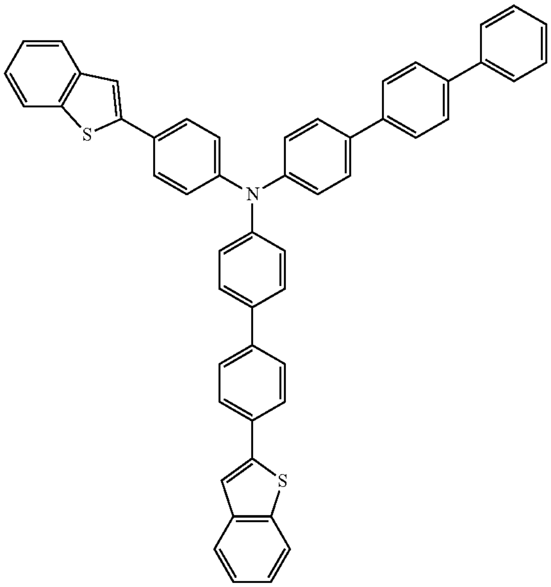
222
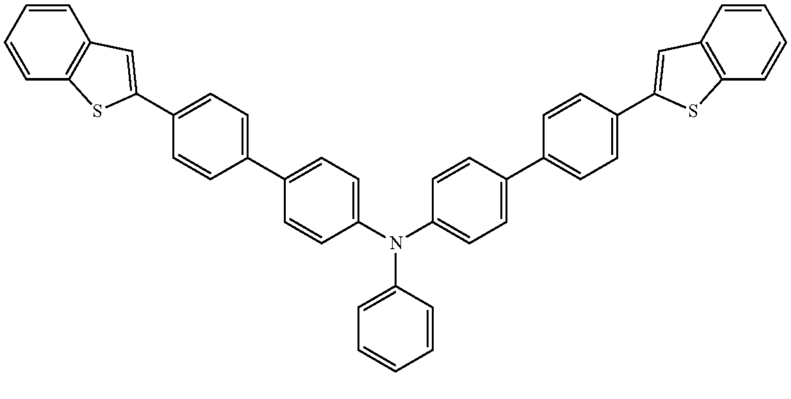

-continued
223
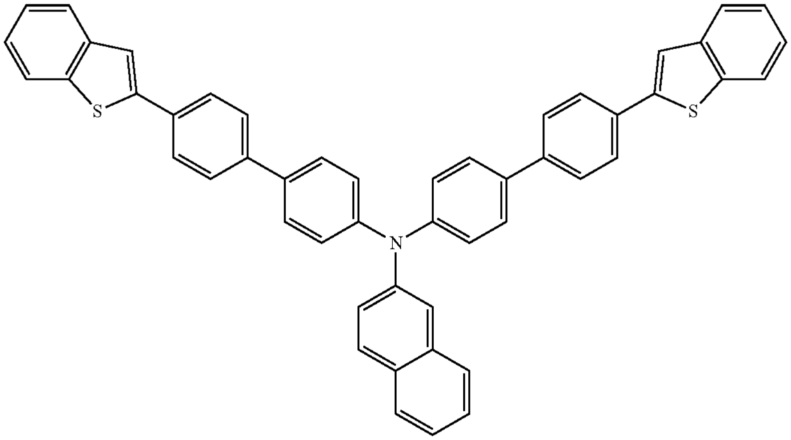
224
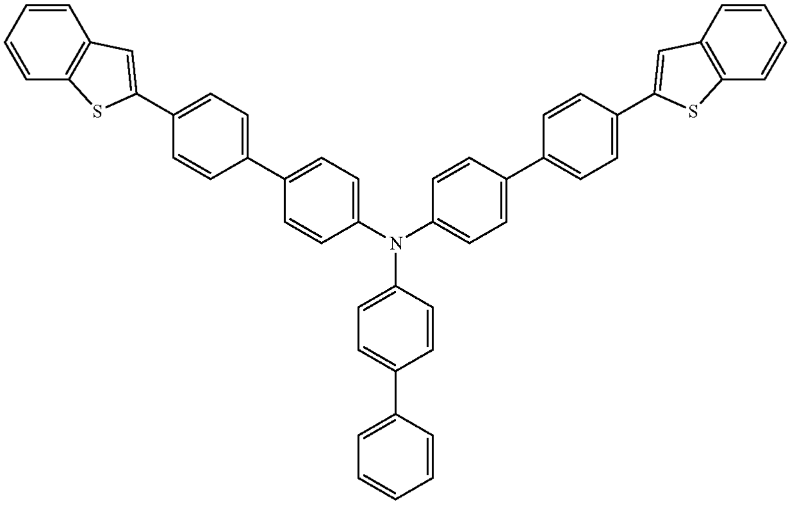
225
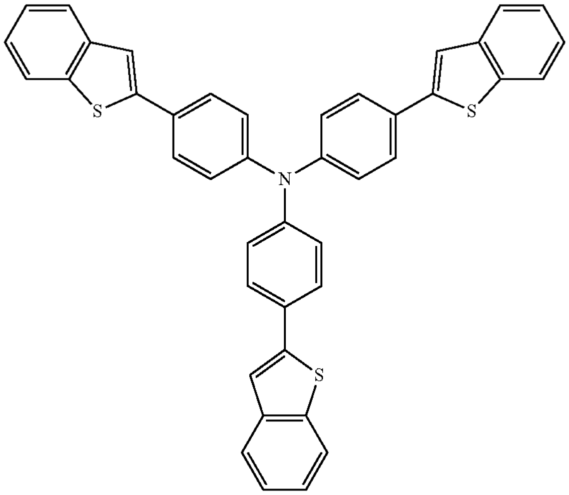
226
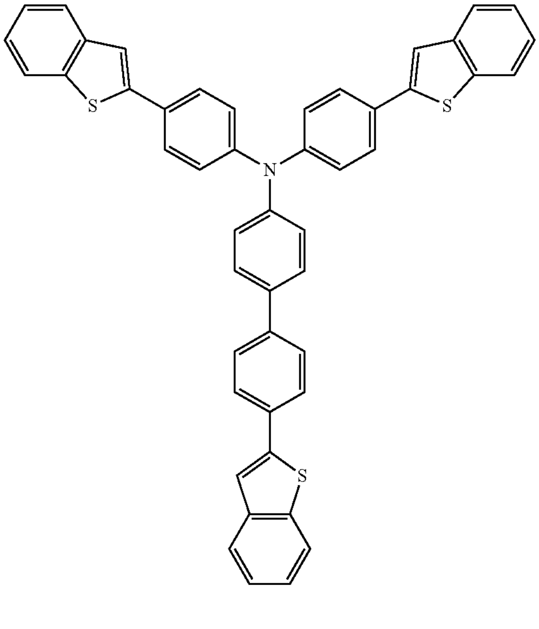

-continued
227
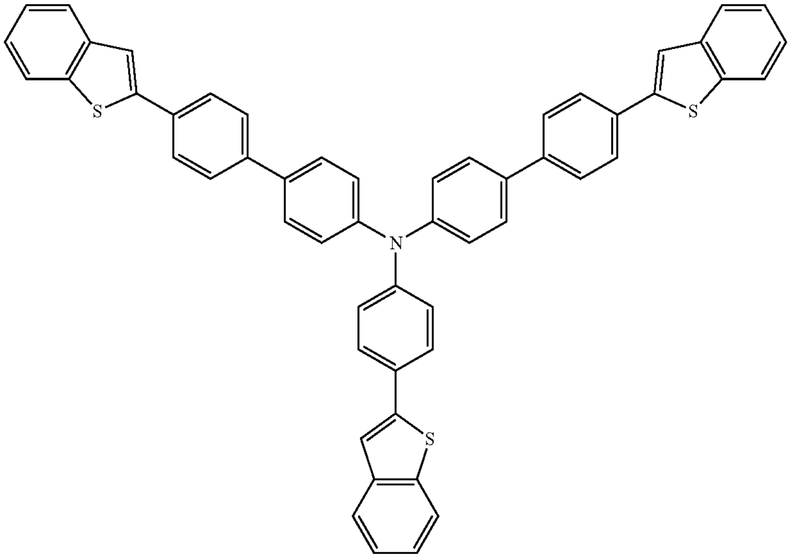
228
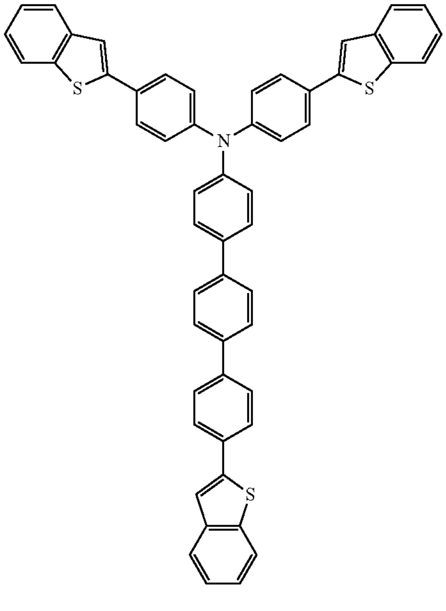

-continued
249
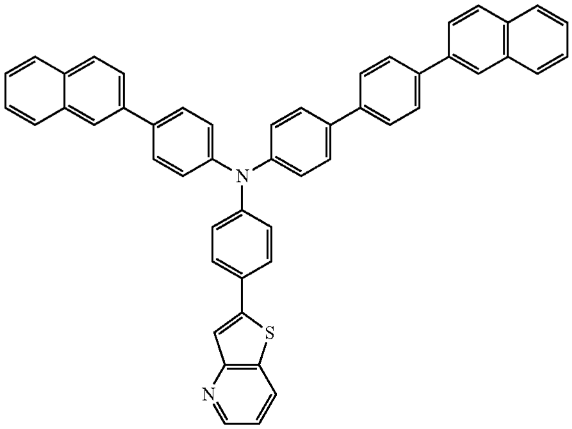
250
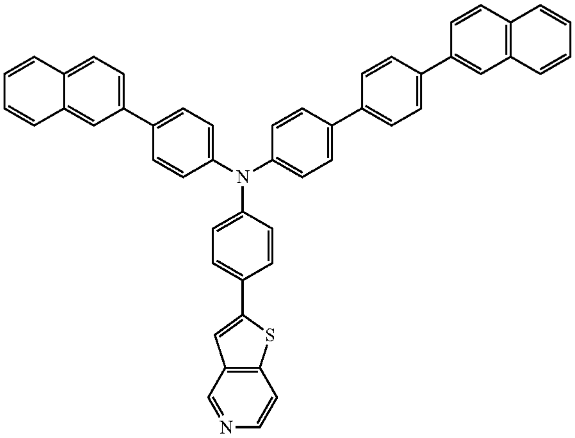
251
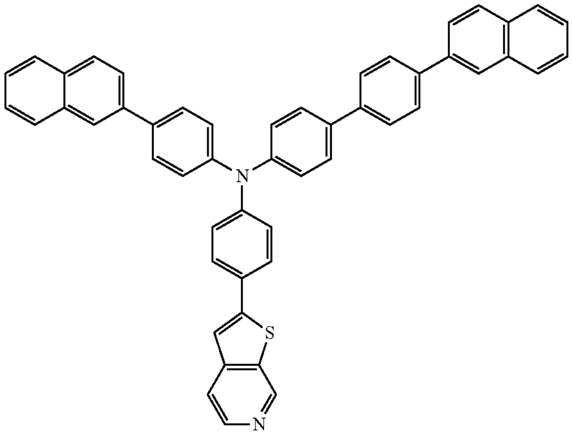
252
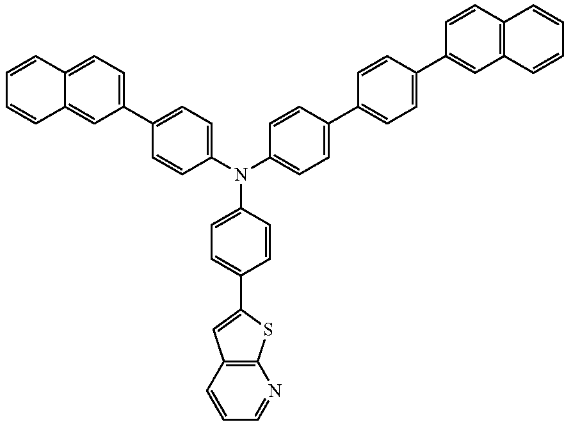
253
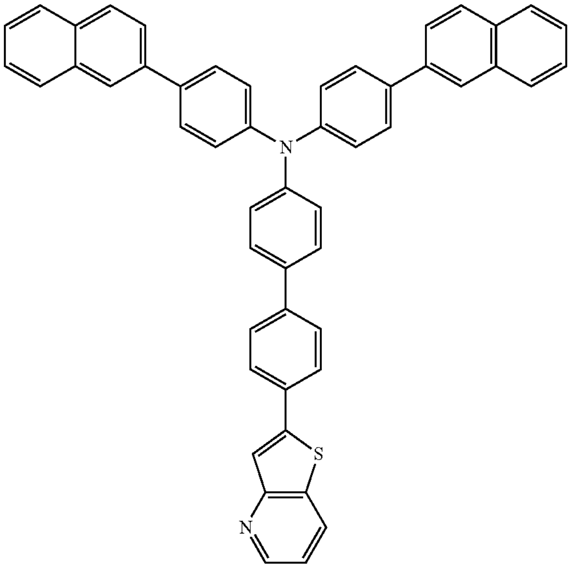
254
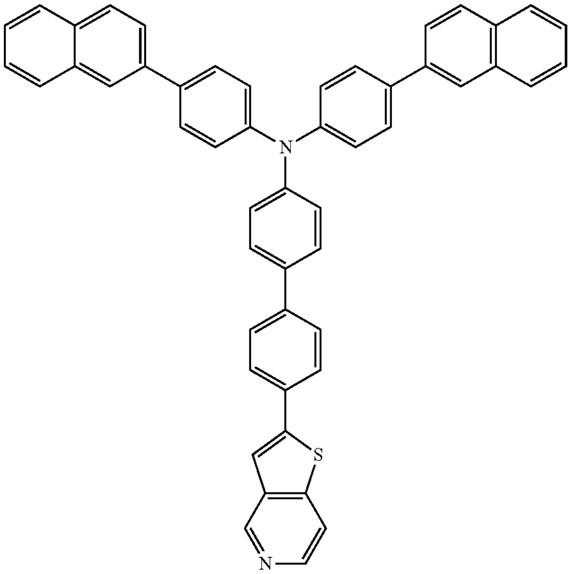

-continued
255
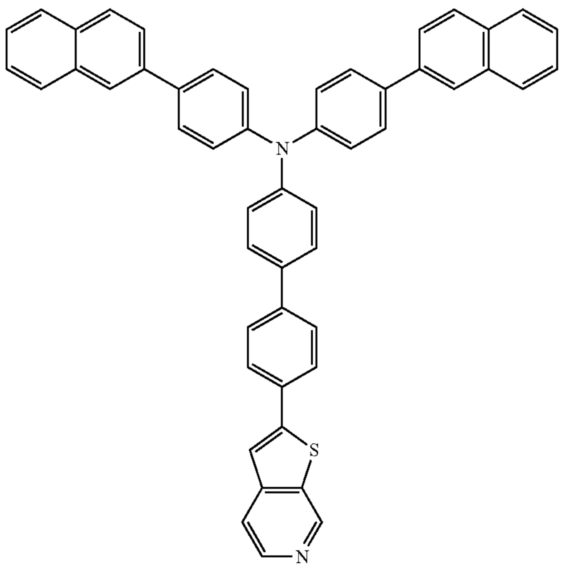
256
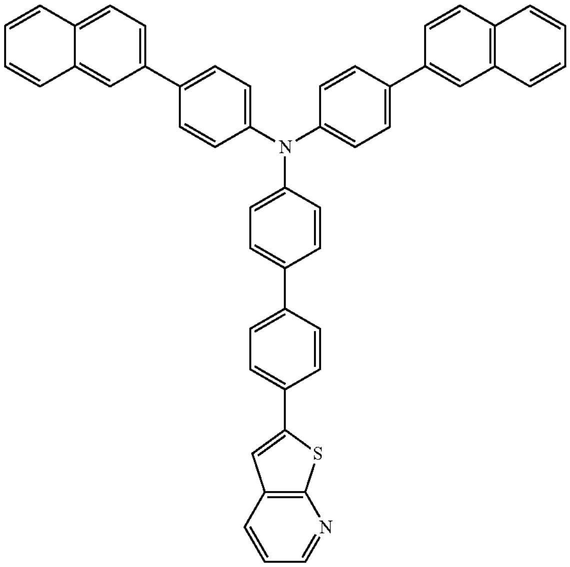
-continued
268
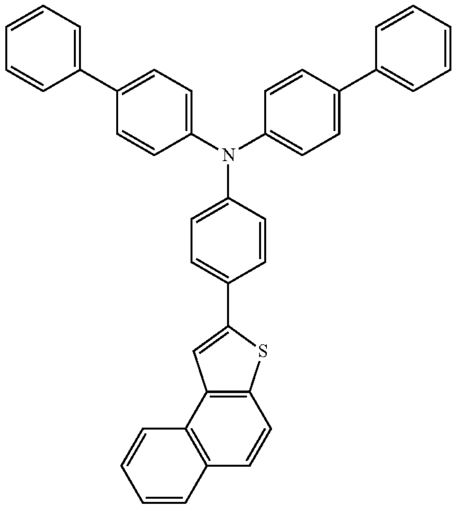
269
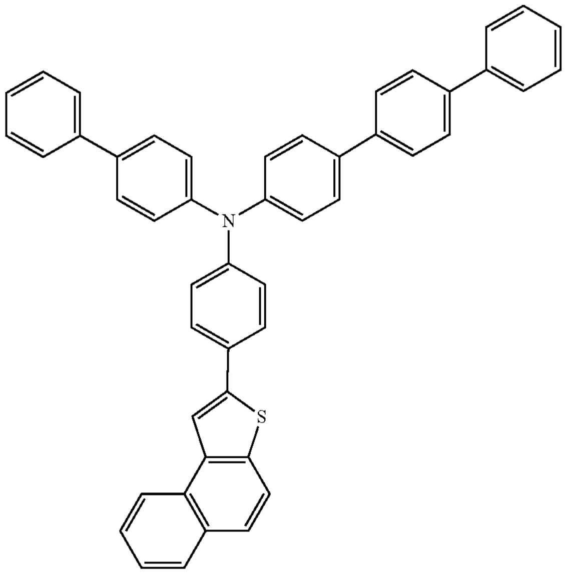
270
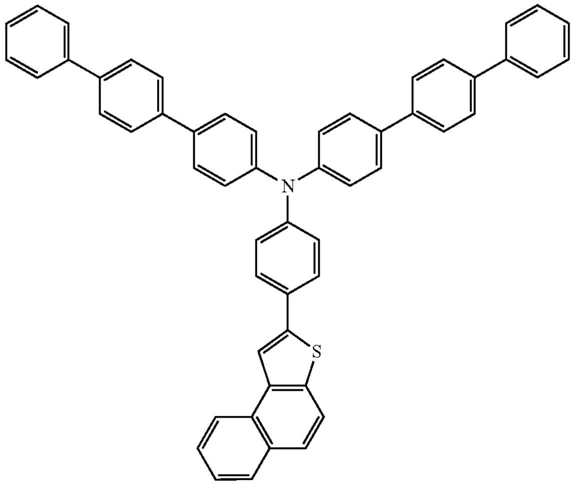

-continued
271
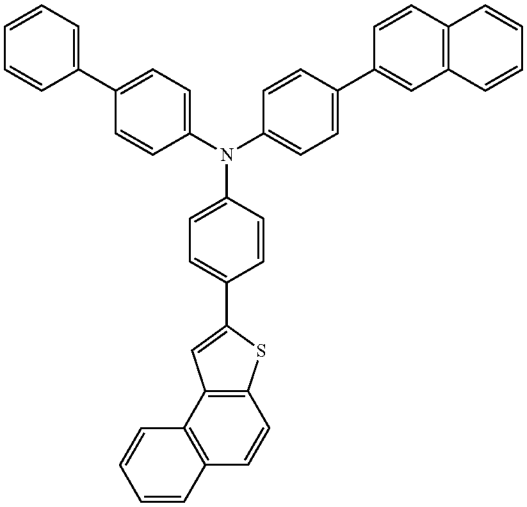
272
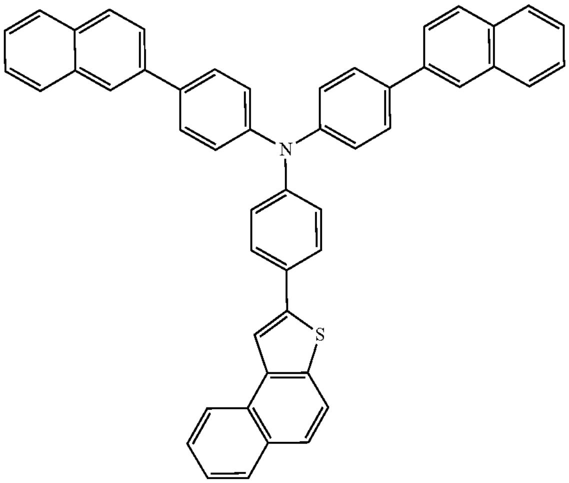
273
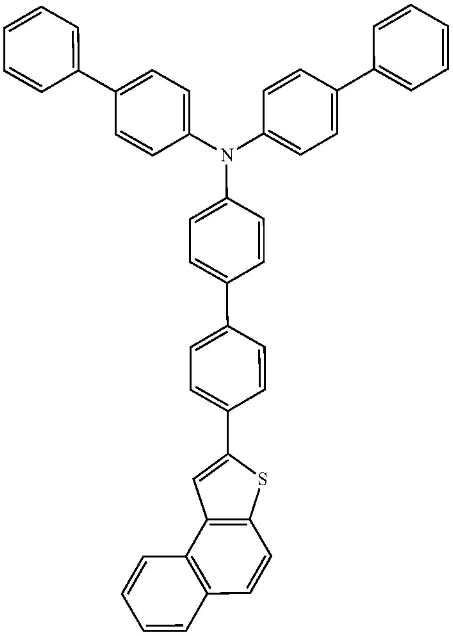
-continued
274
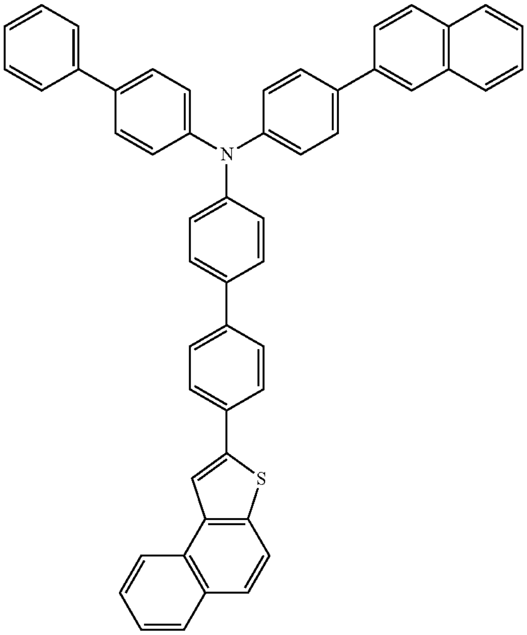
275
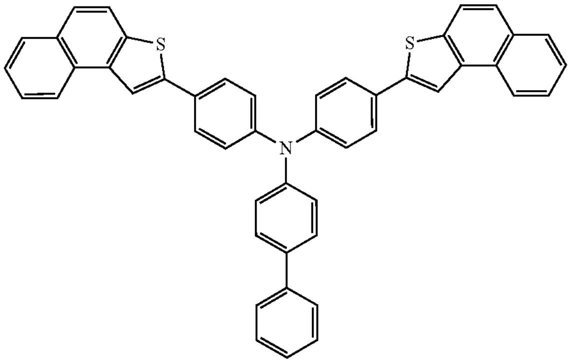
276
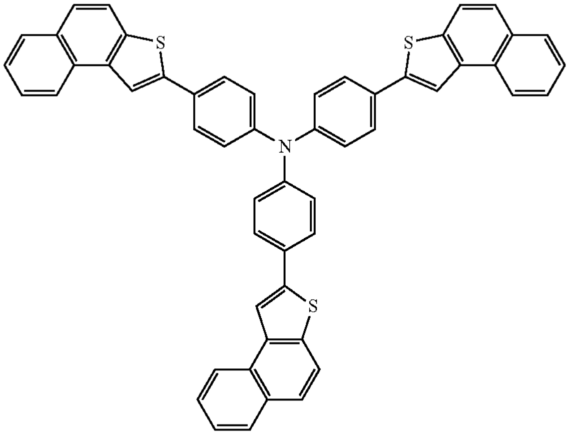

280
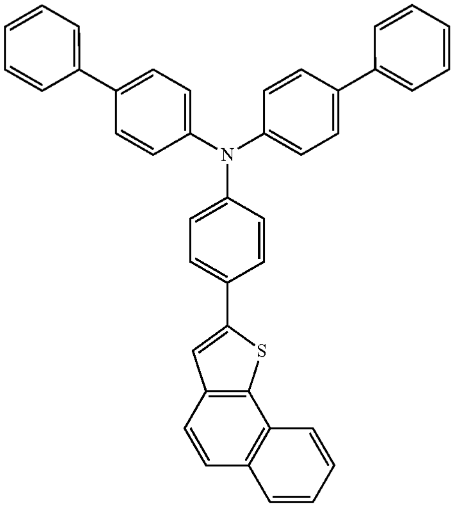
281
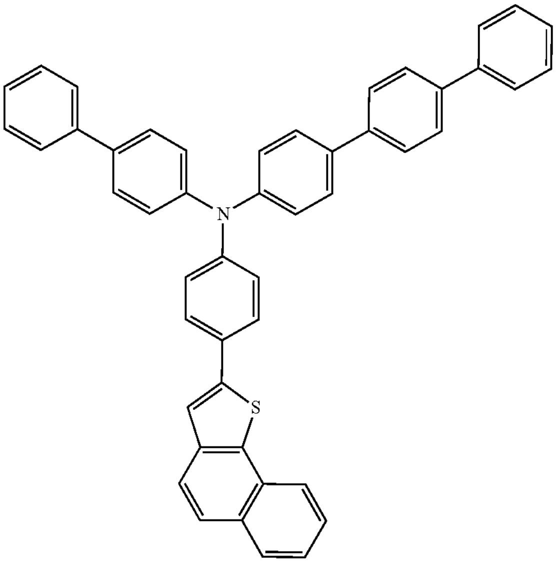
282
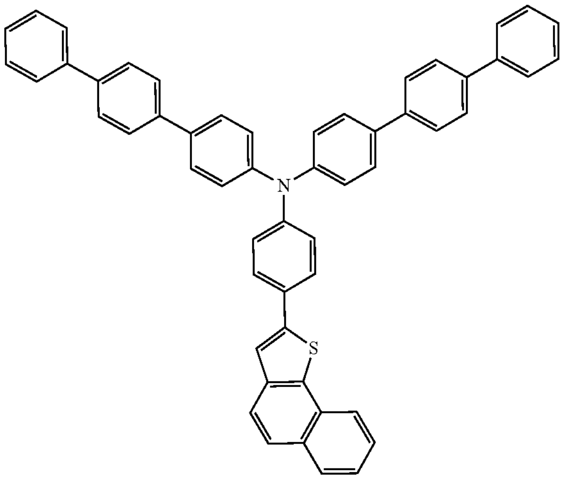
283
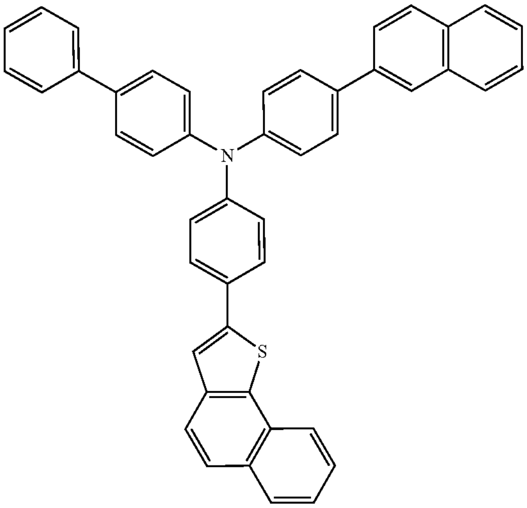
284
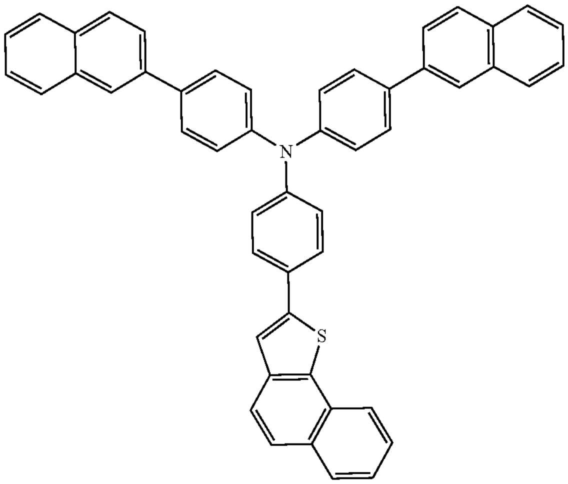
285
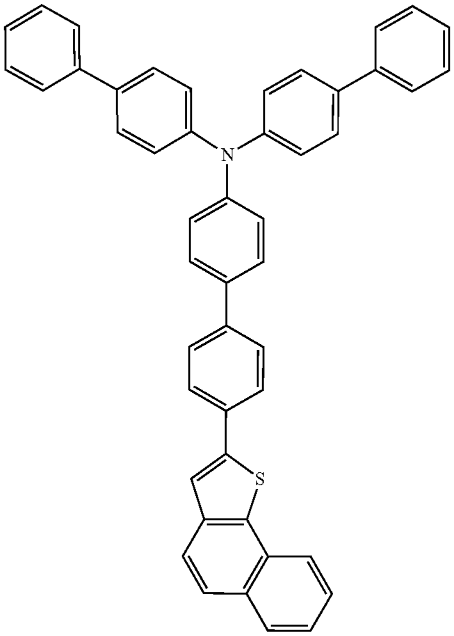

-continued
286
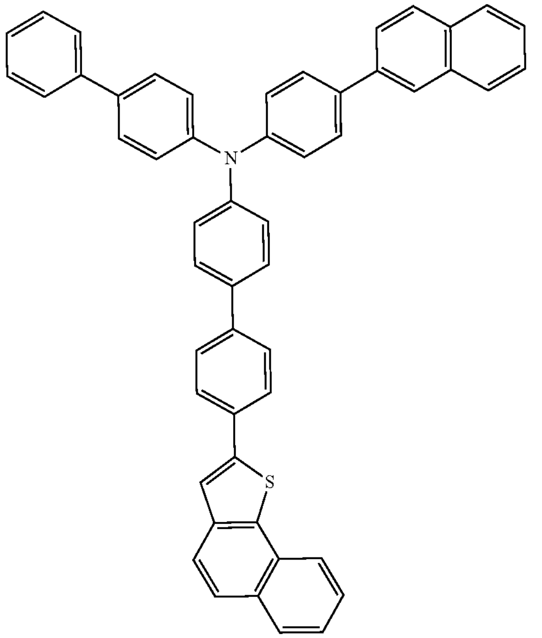
287
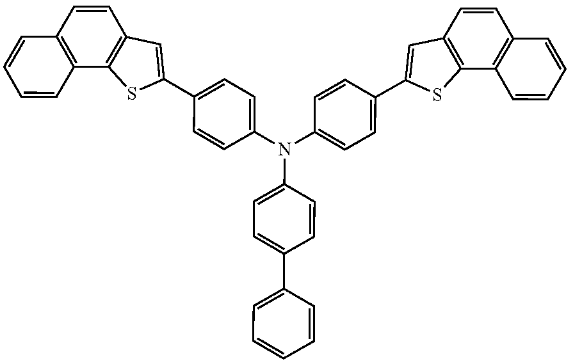
288
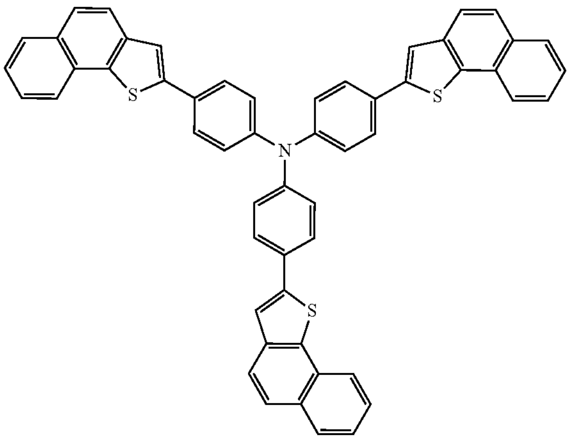
-continued
292
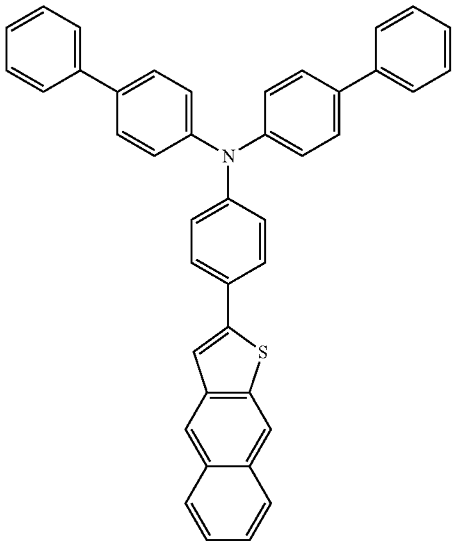
293
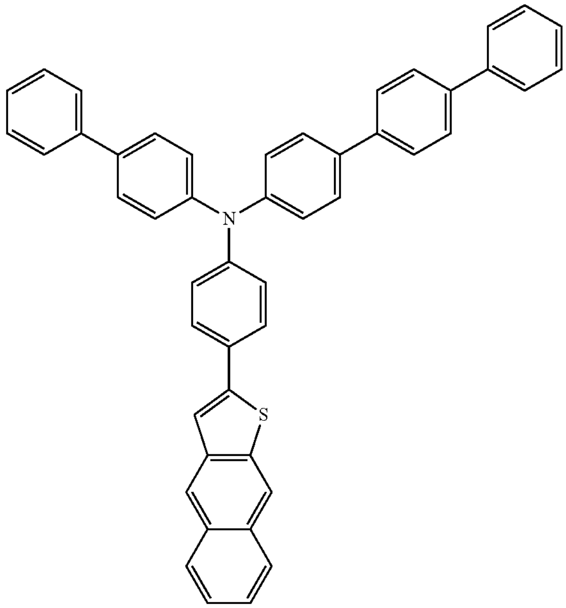

-continued
294
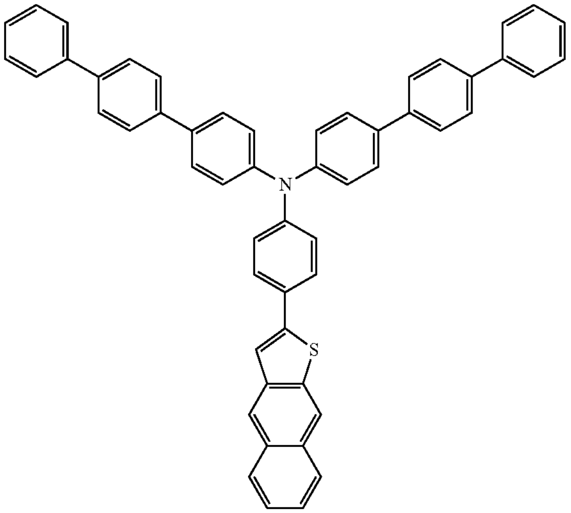
295
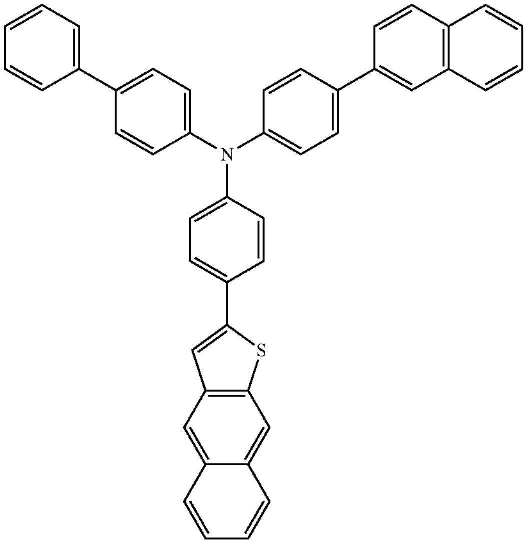
296
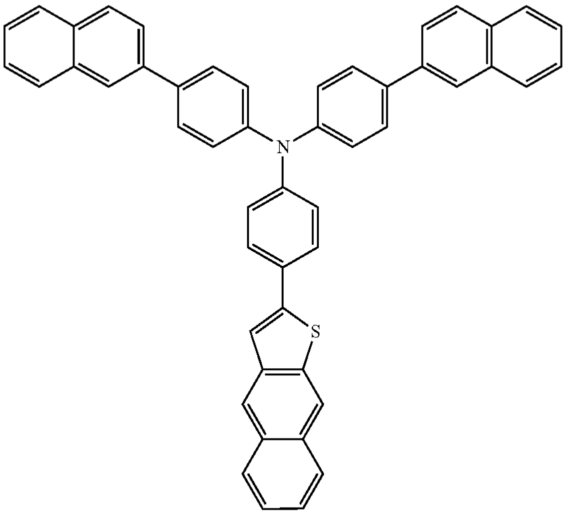
-continued
297
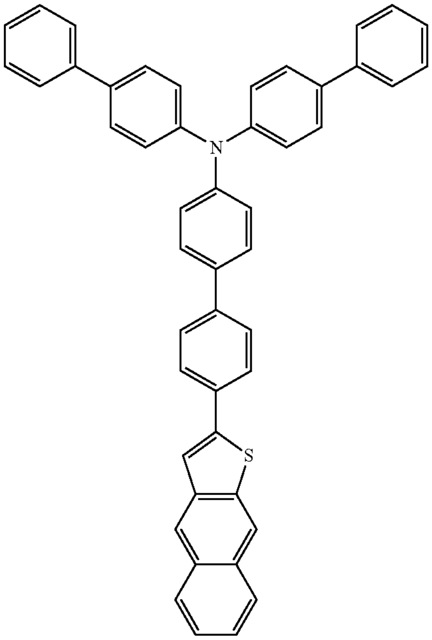
298
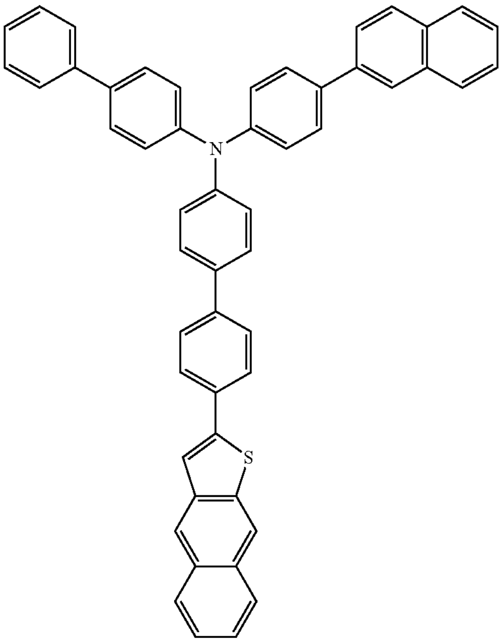

-continued
299
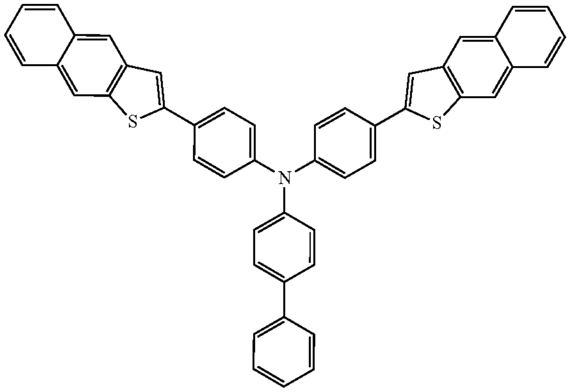
300
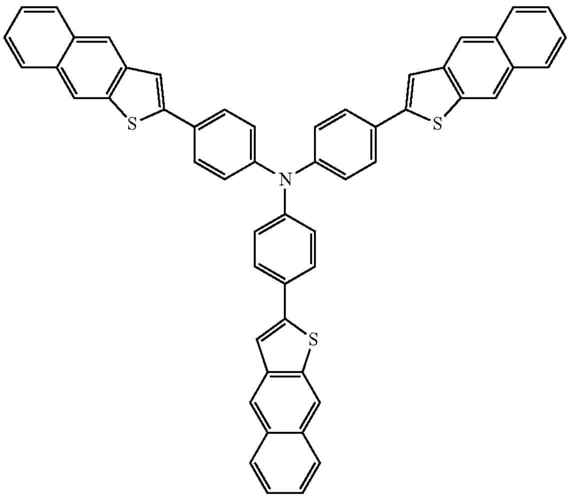
304
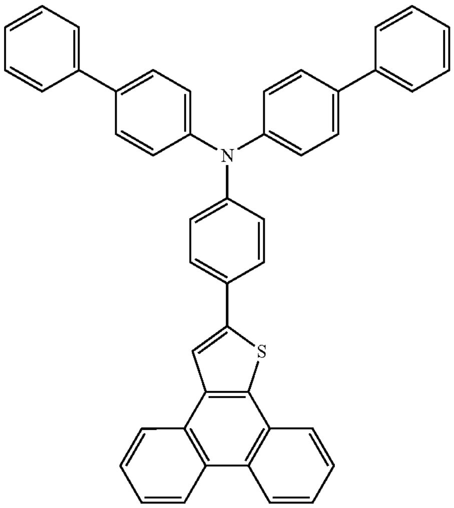
-continued
305
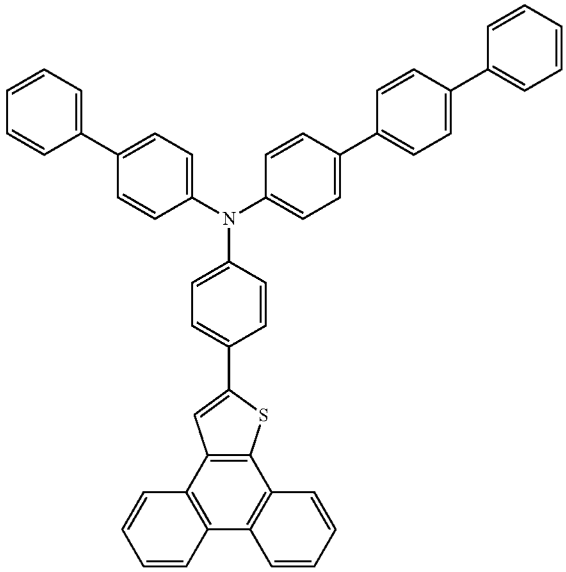
306
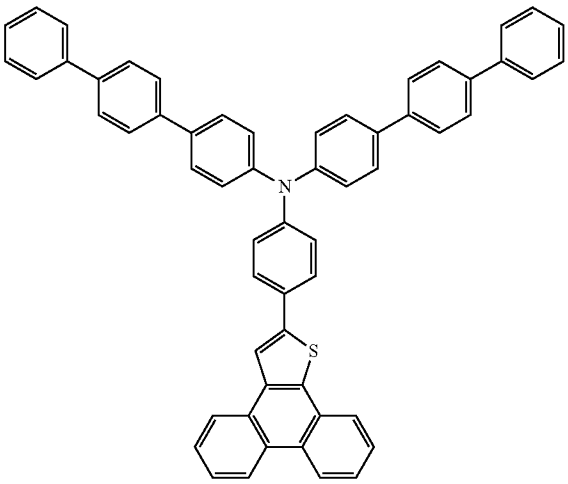
307
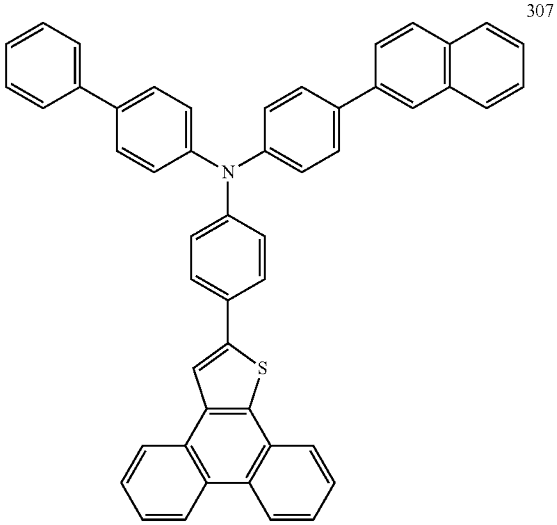

-continued
308
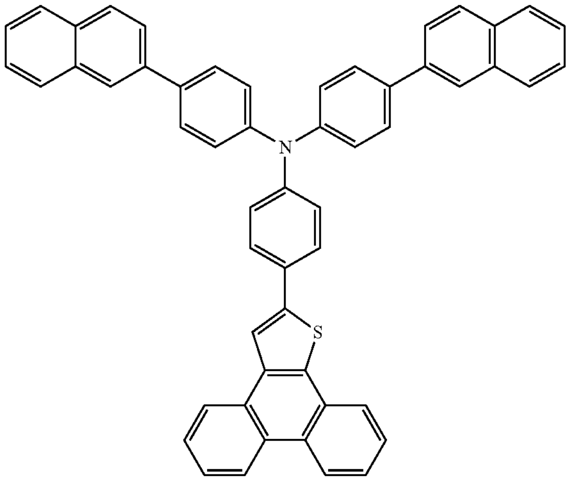
309
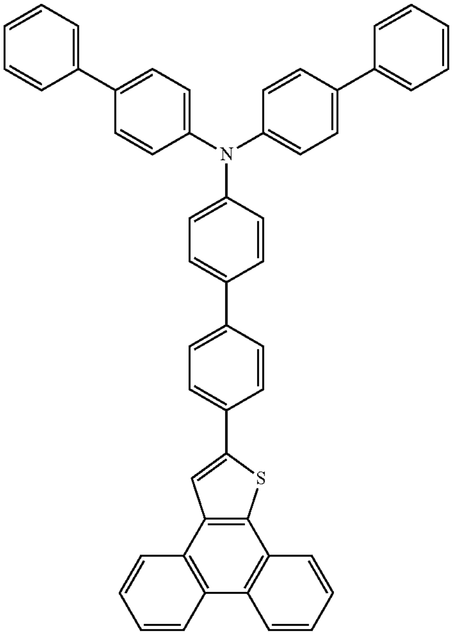
-continued
310
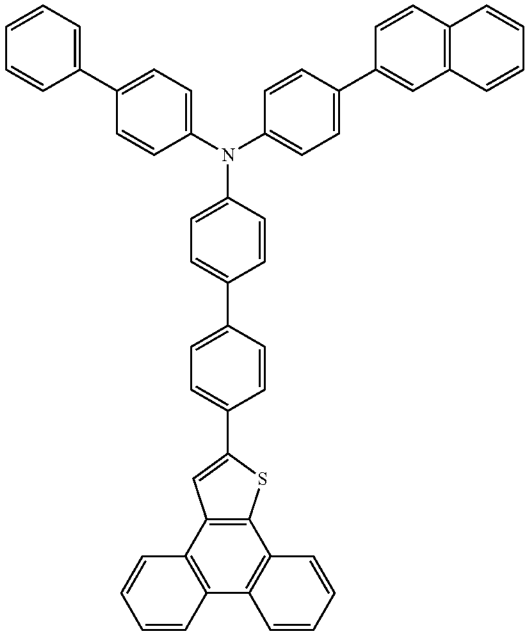
311
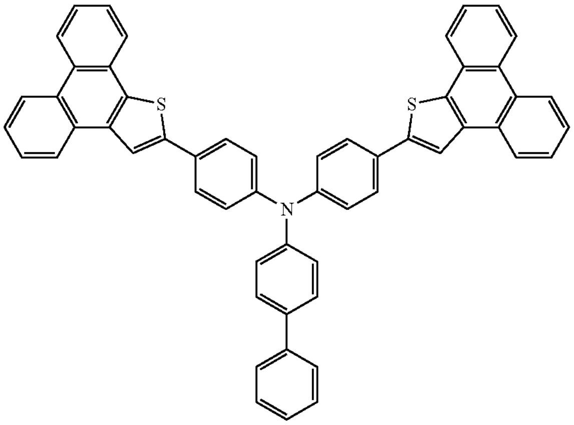
312
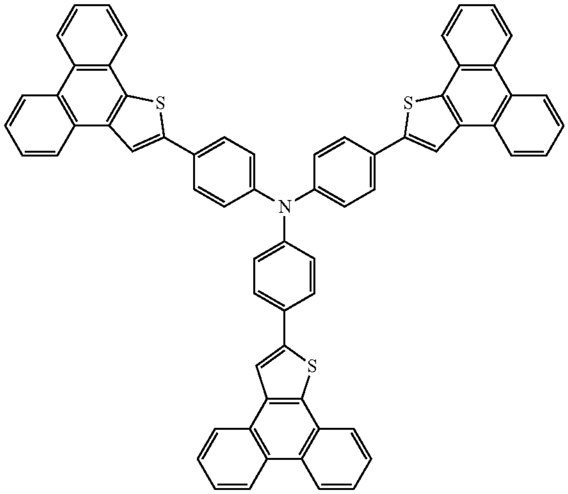

316
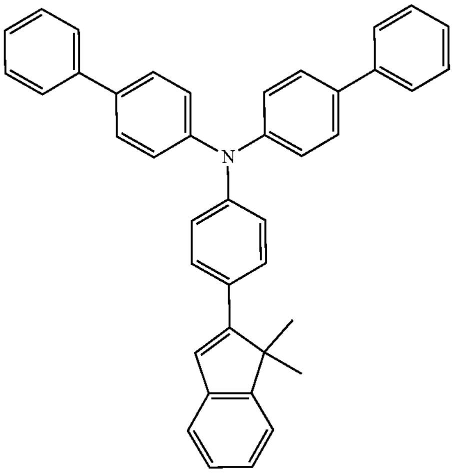
317
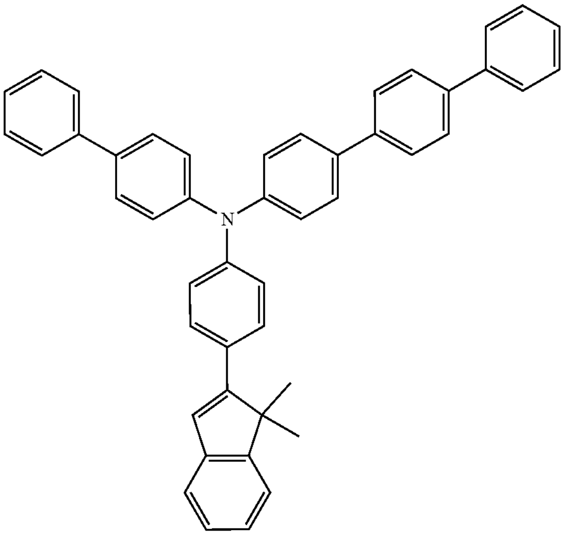
318
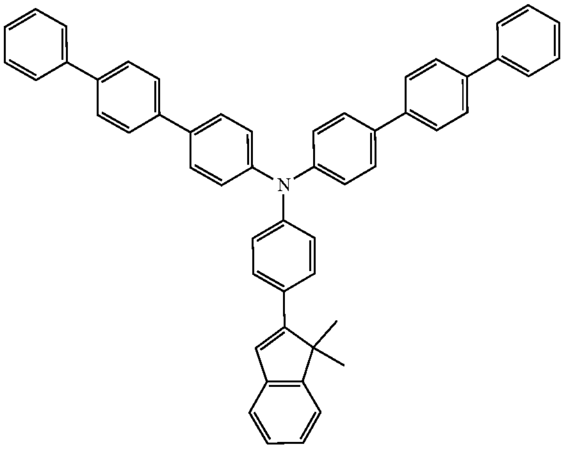
319
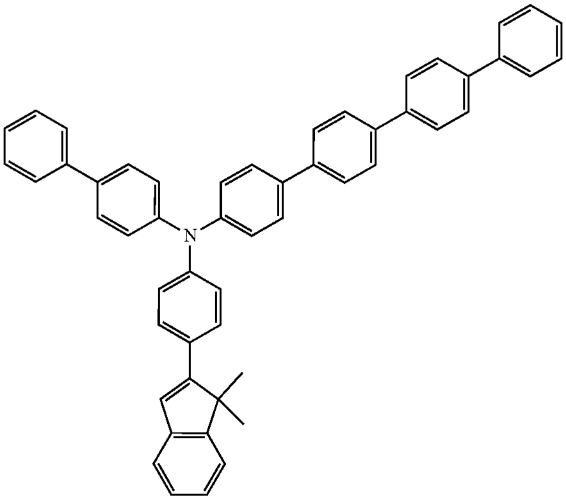

-continued
320
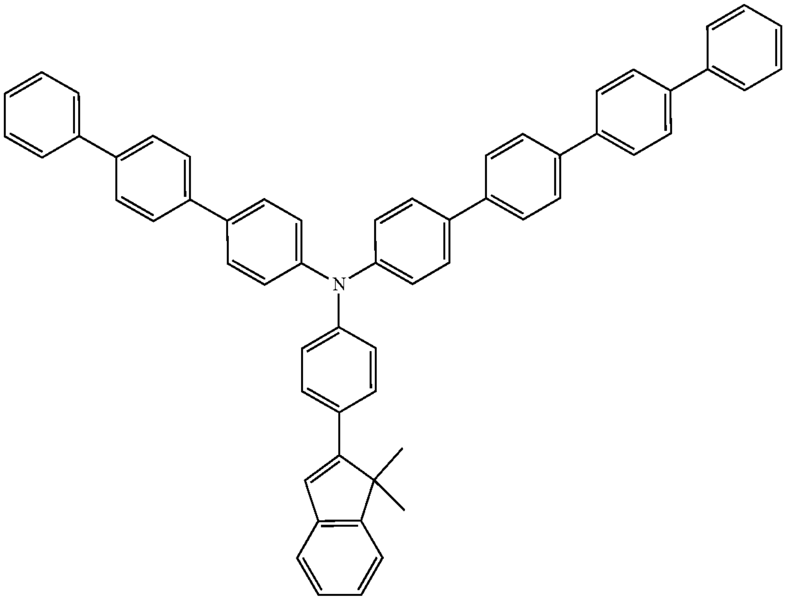
321
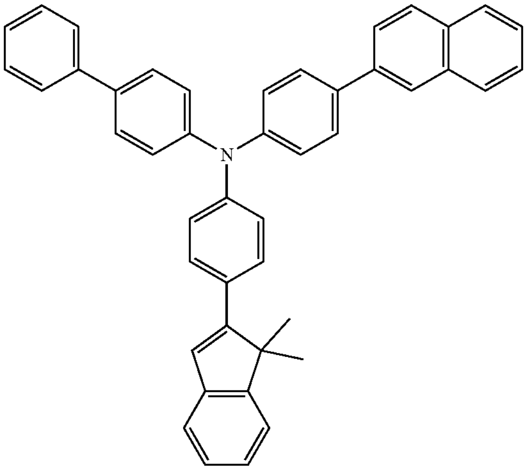
322
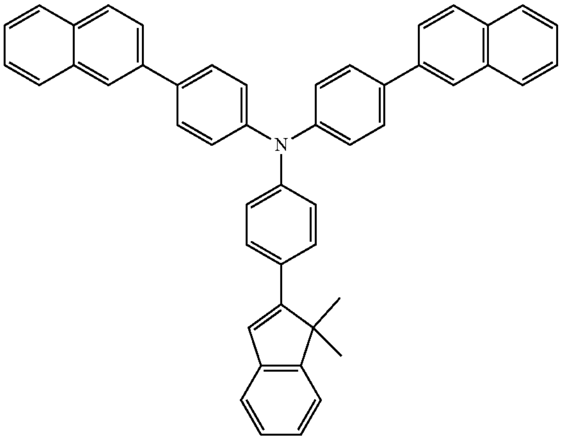
323
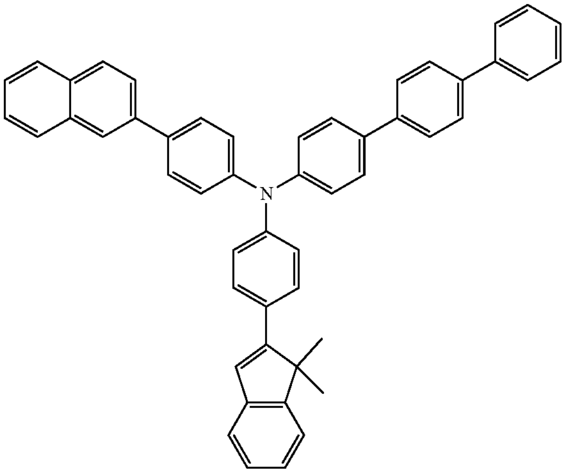
324
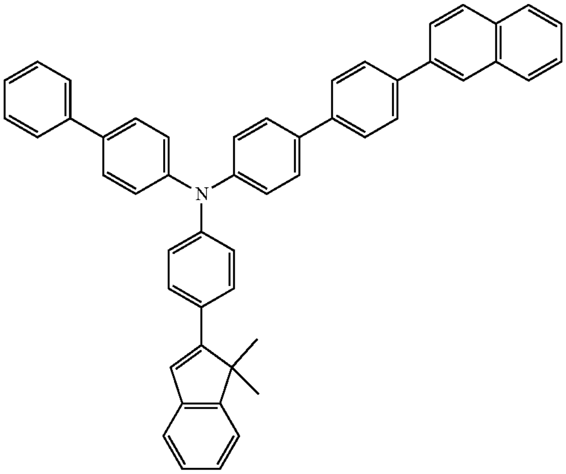

-continued
325
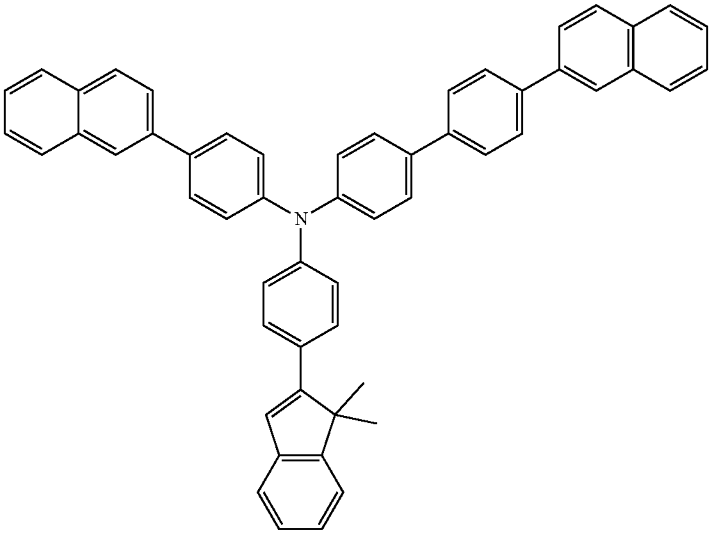
326
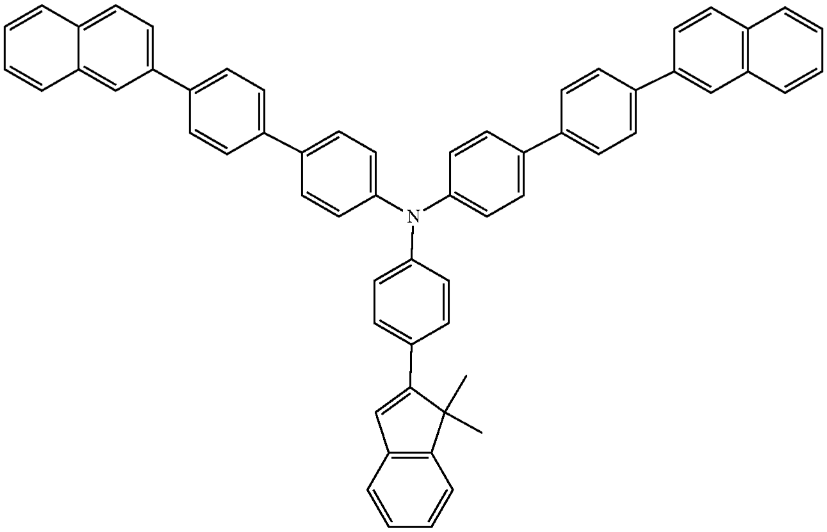
327
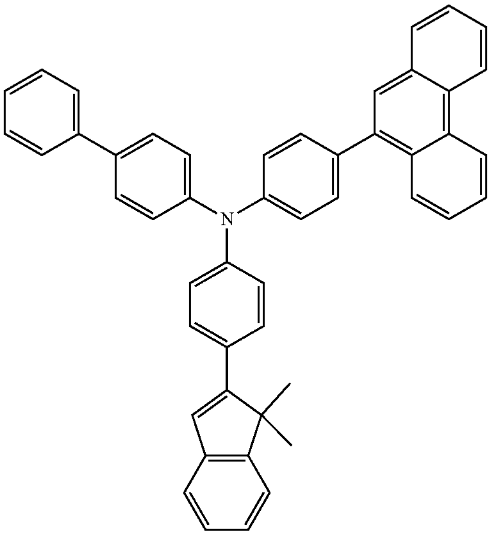
328
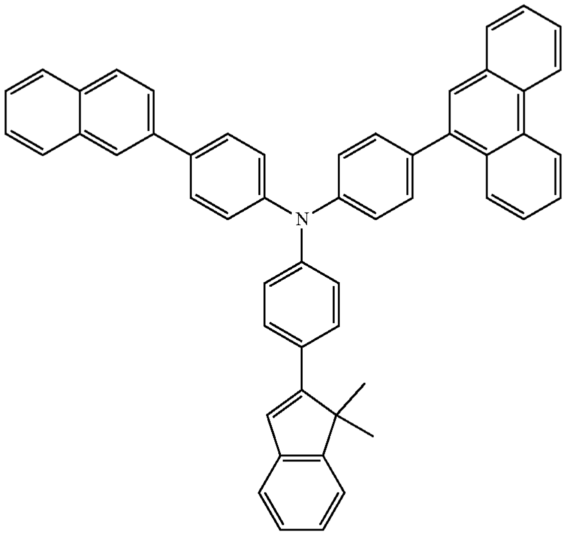

-continued
329
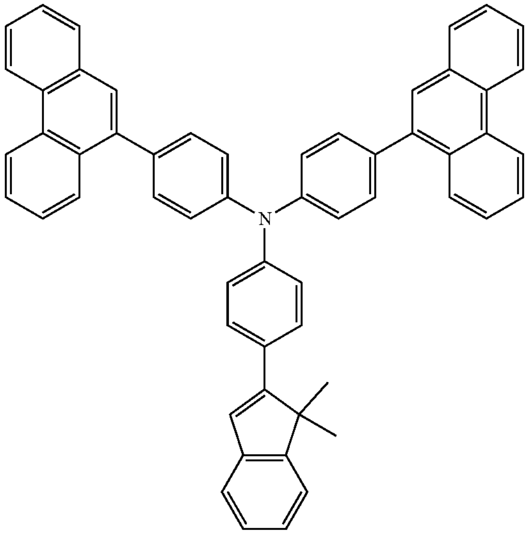
330
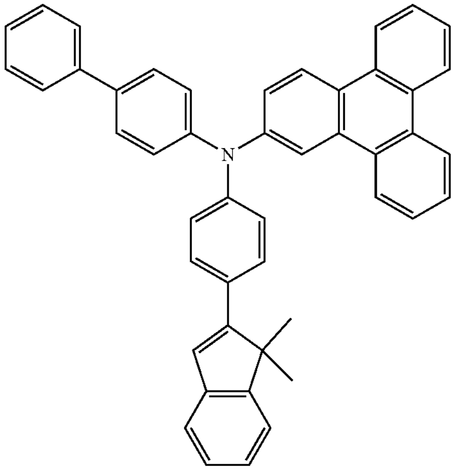
331
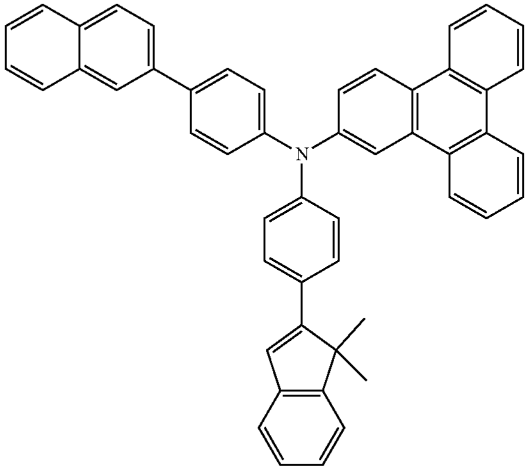
332
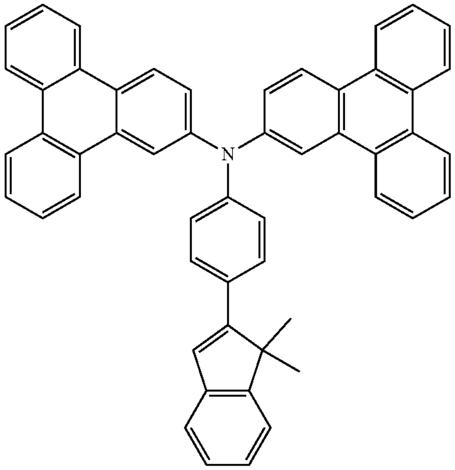
333
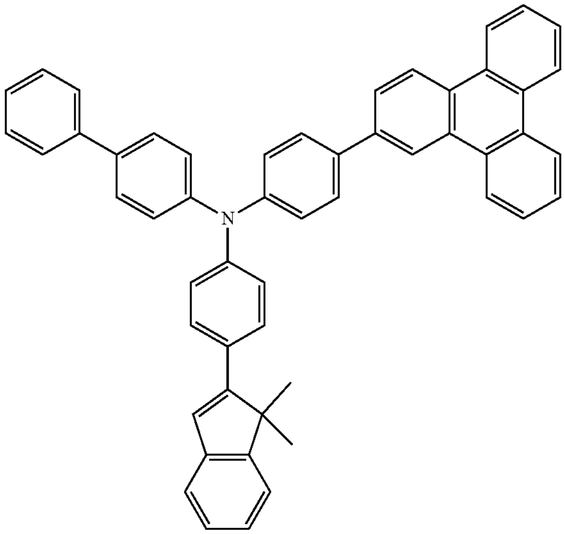
334
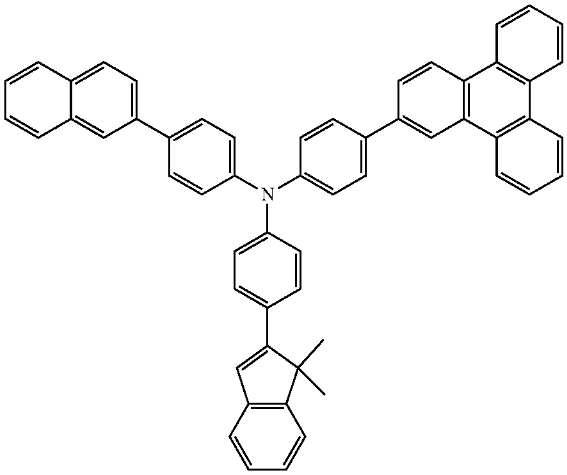

-continued
335
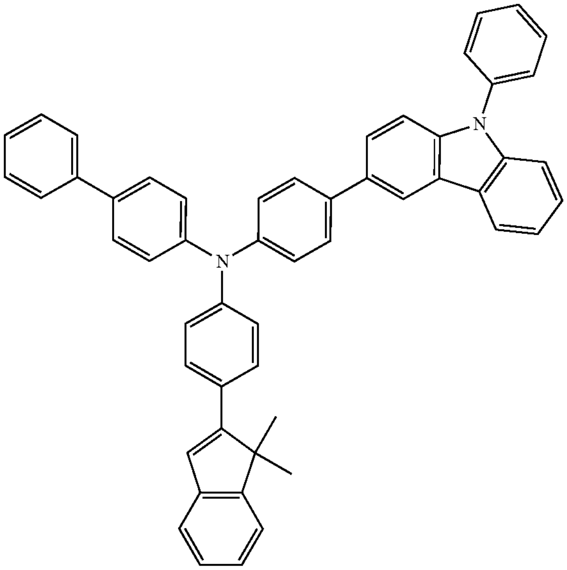
336
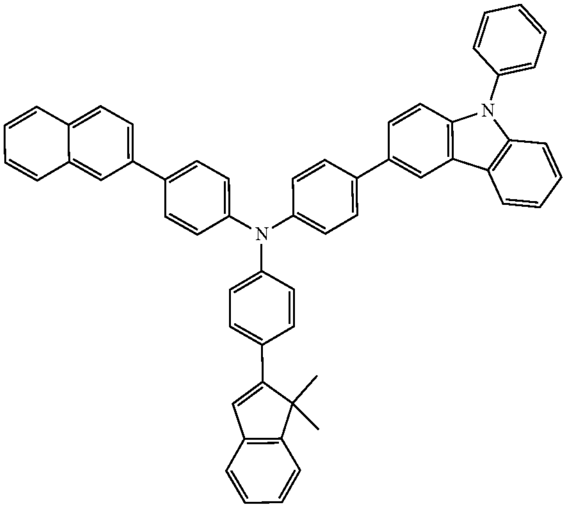
337
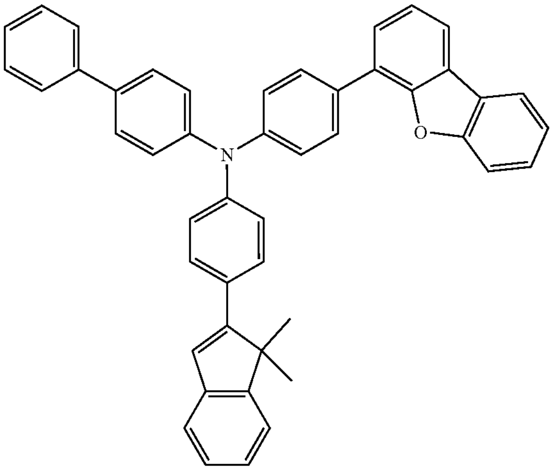
338
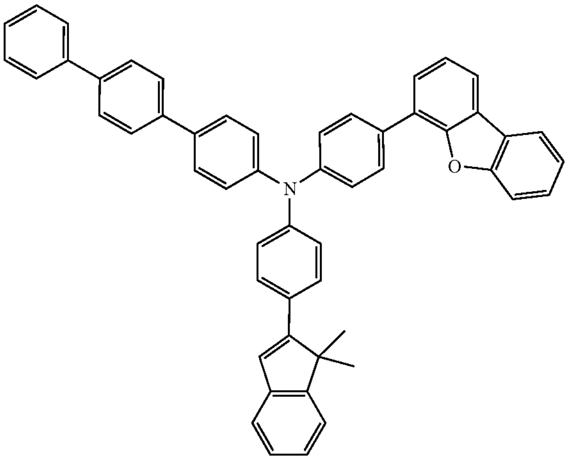
339
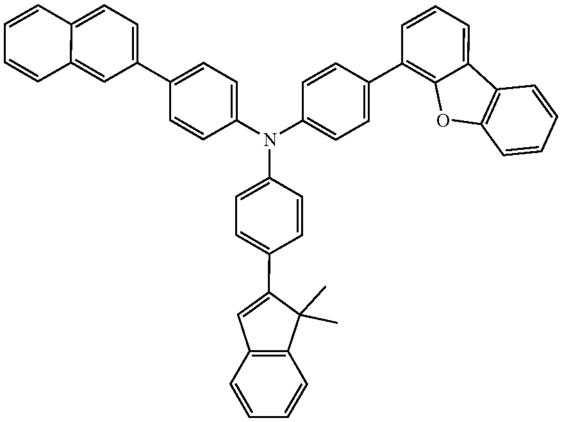
340
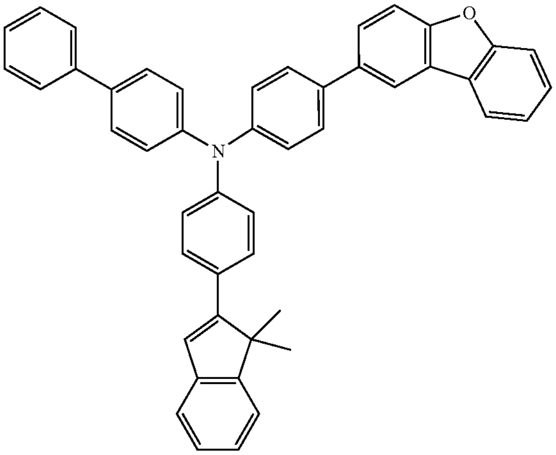

-continued
341
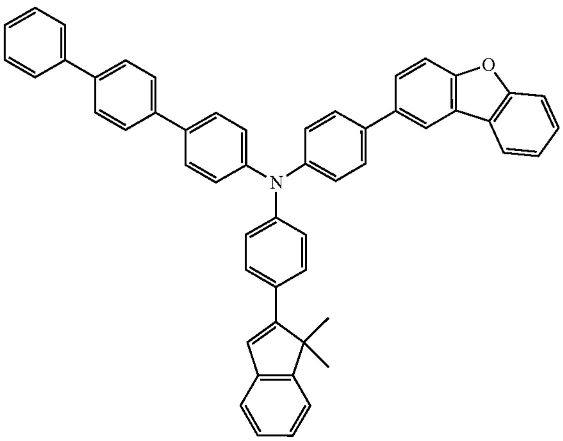
342
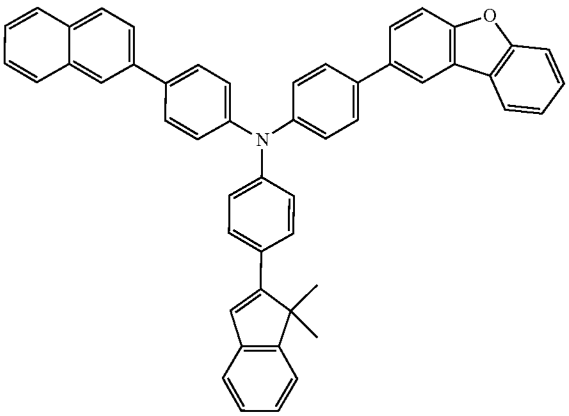
343
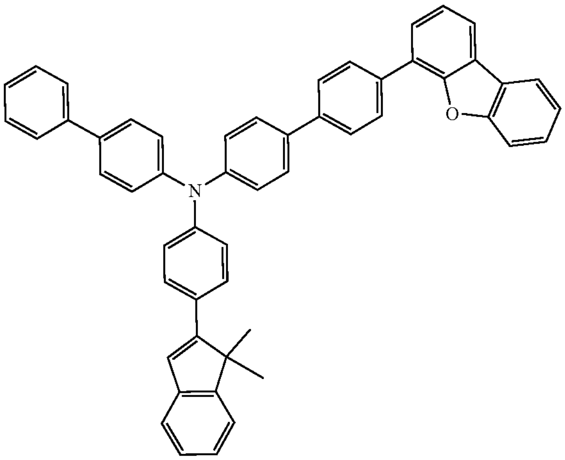
344
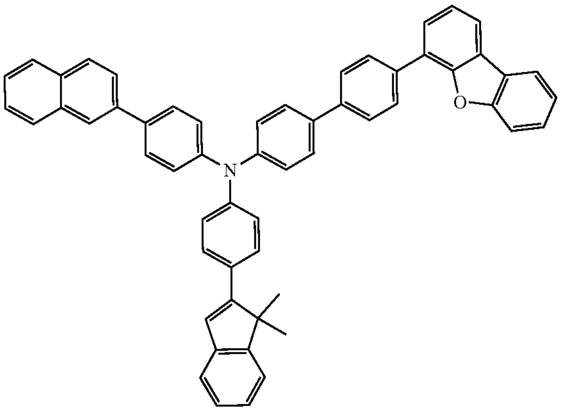
346
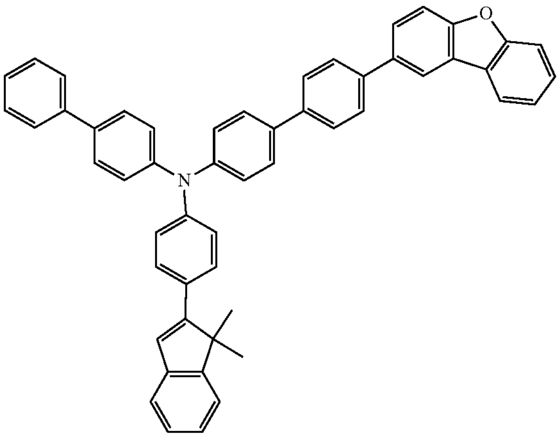
345
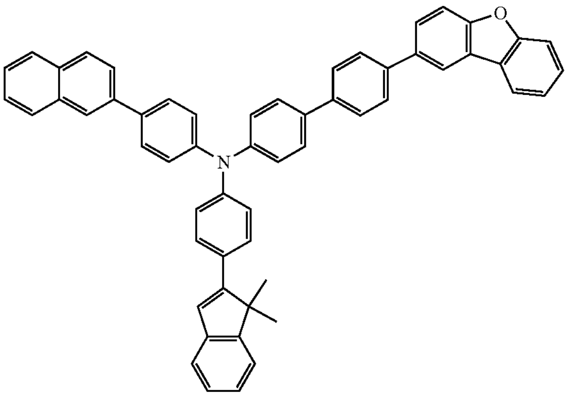

-continued
348
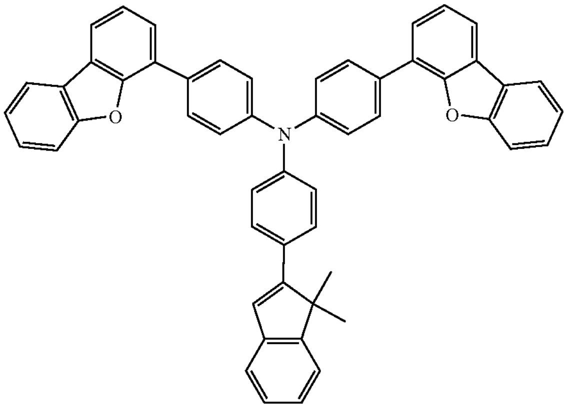
347
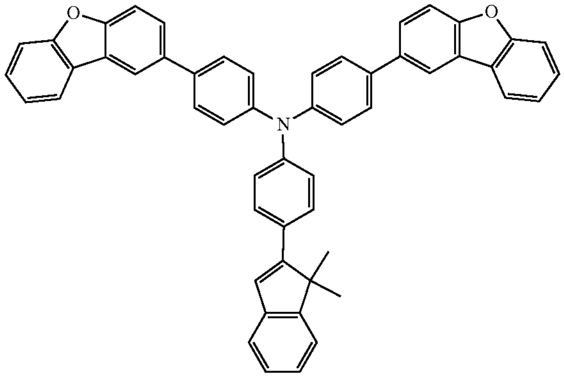
349
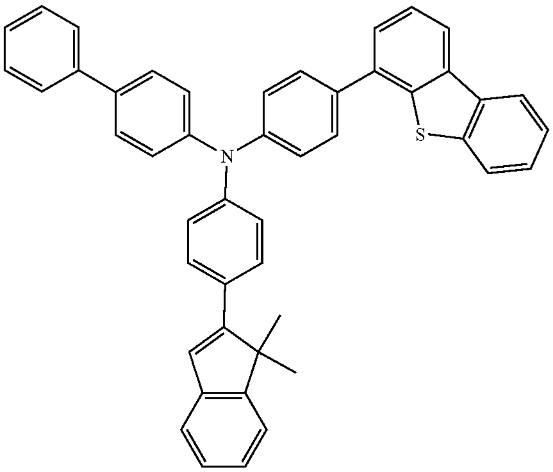
350
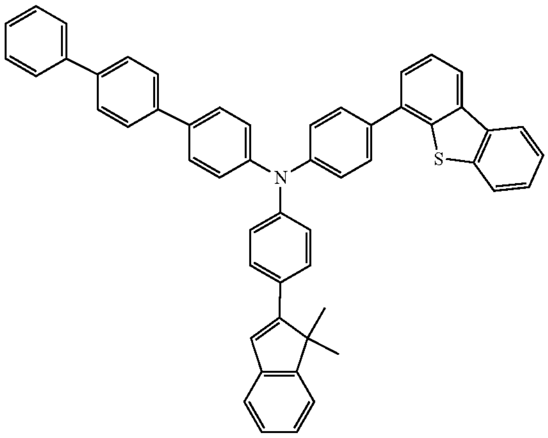
351
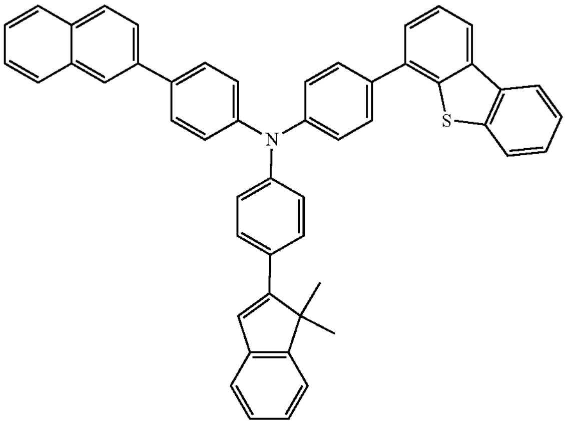
352
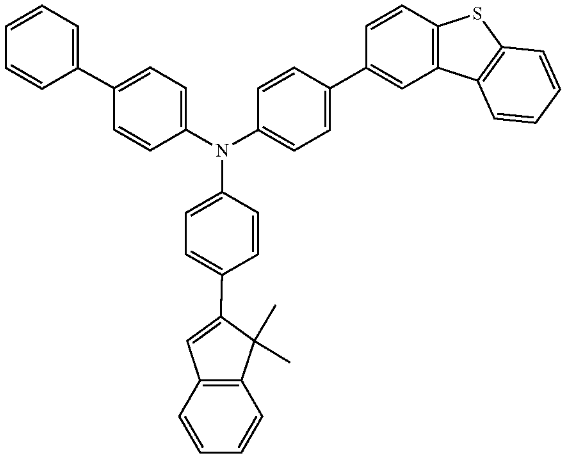

-continued
354
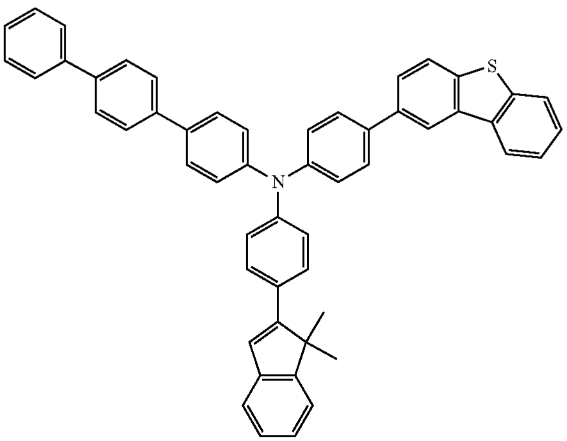
353
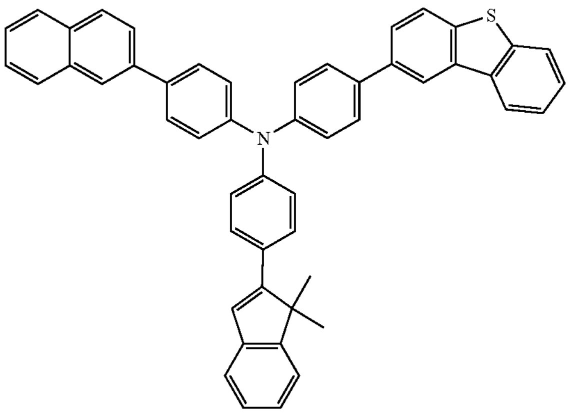
355
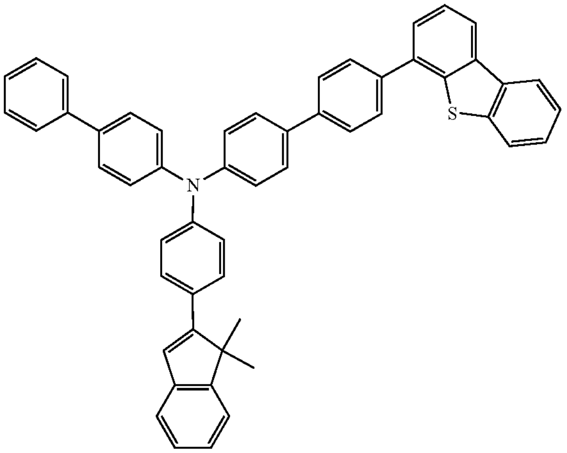
356
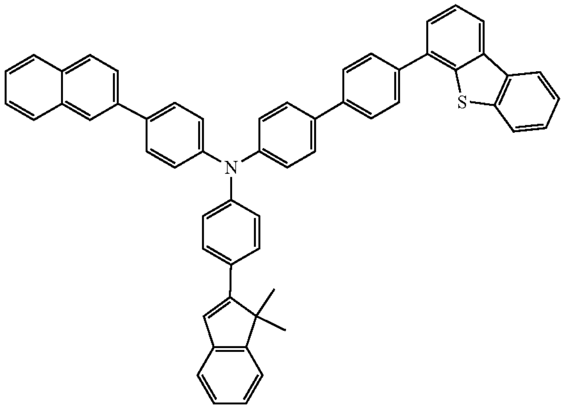
358
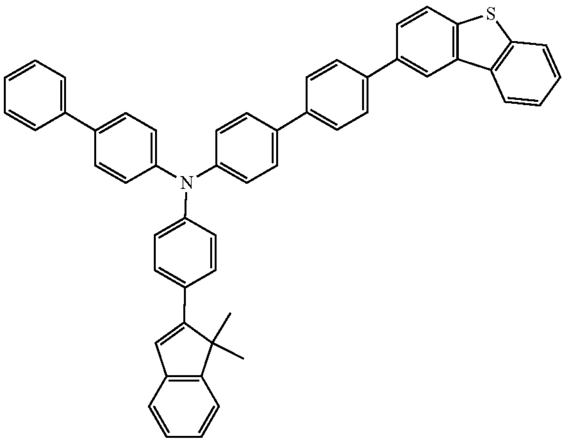
357
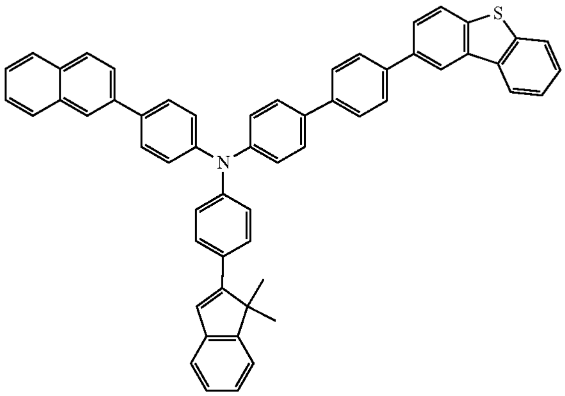

-continued
359
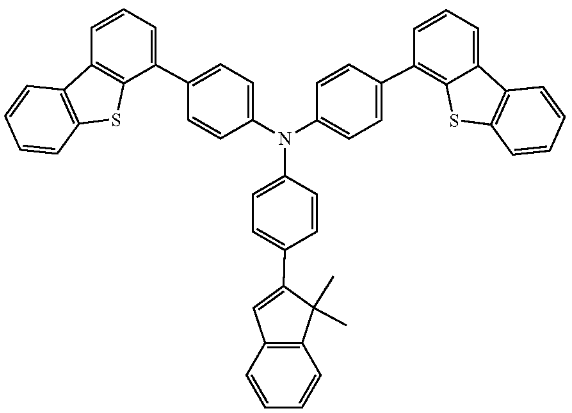
360
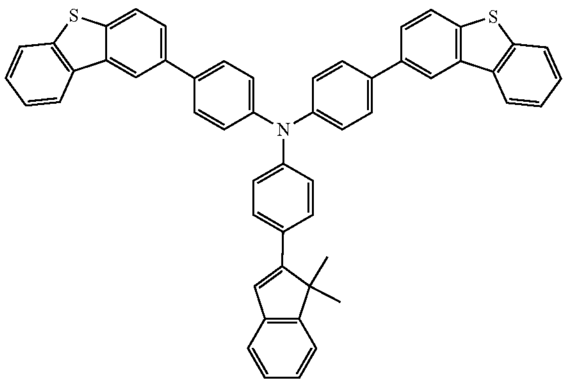
361
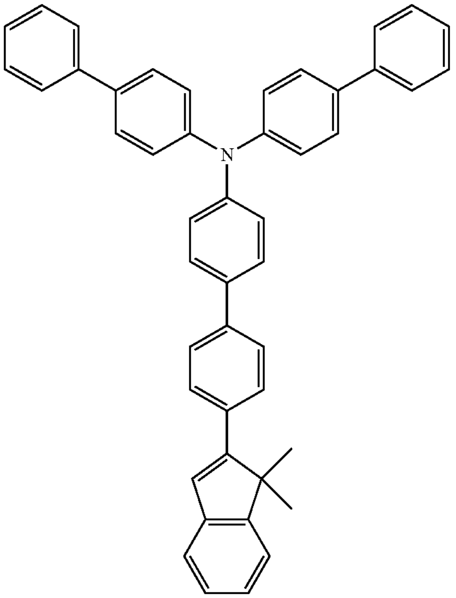
362
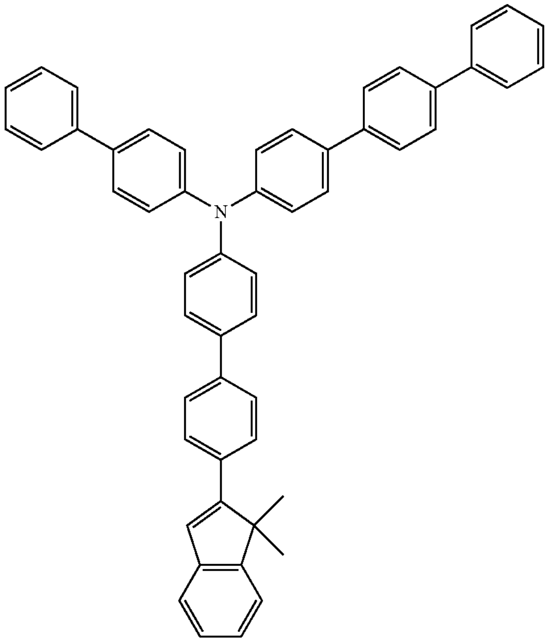

-continued
363
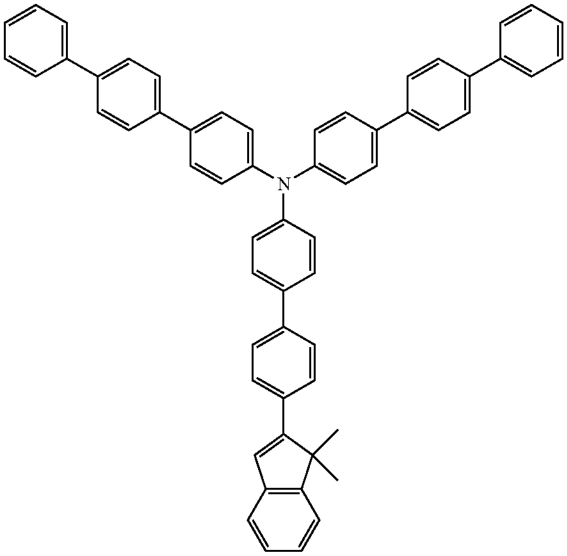
364
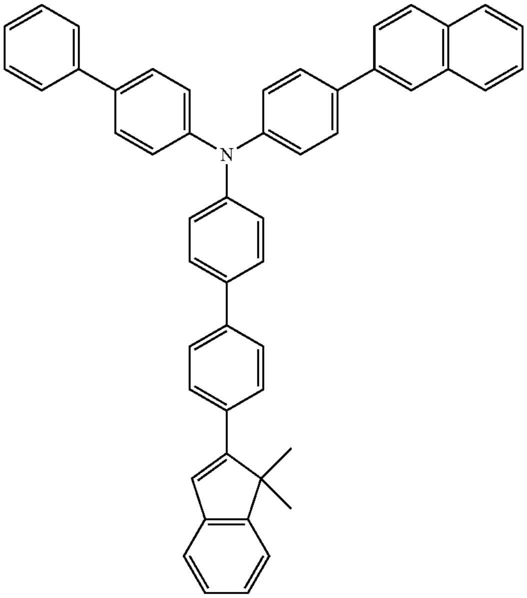
365
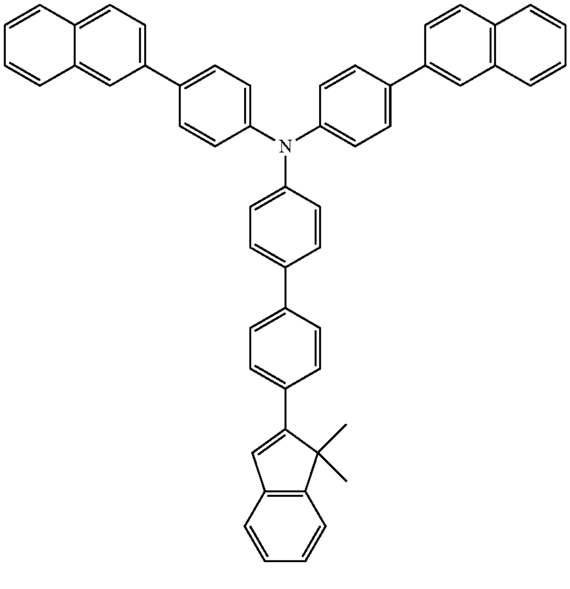
366
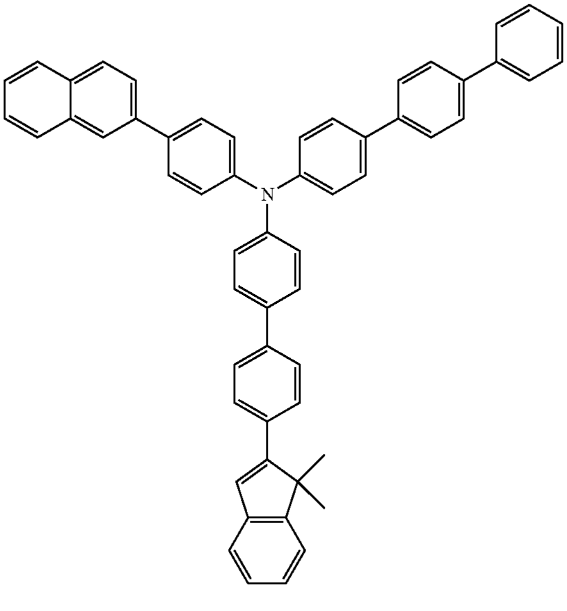

-continued
367
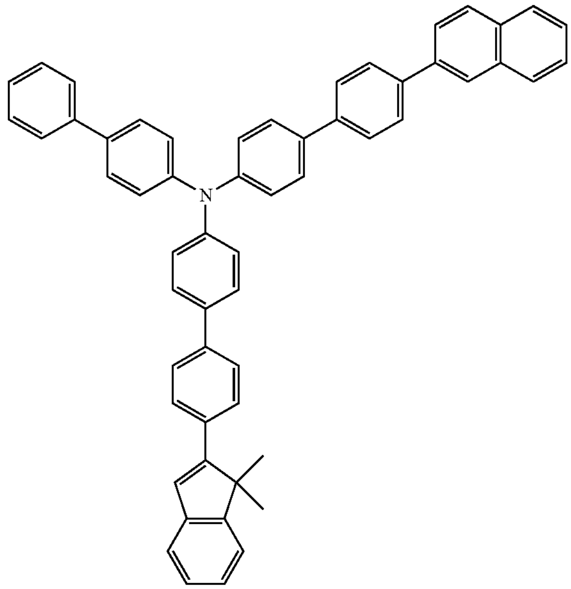
368
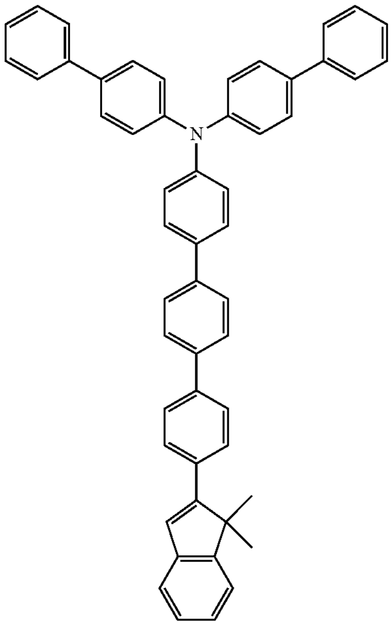
369
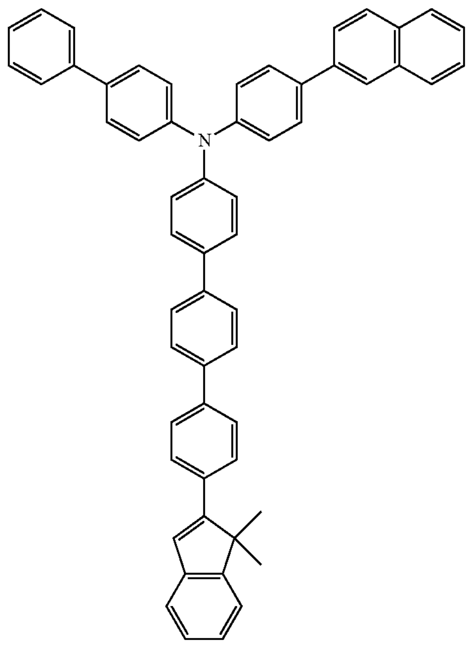
370
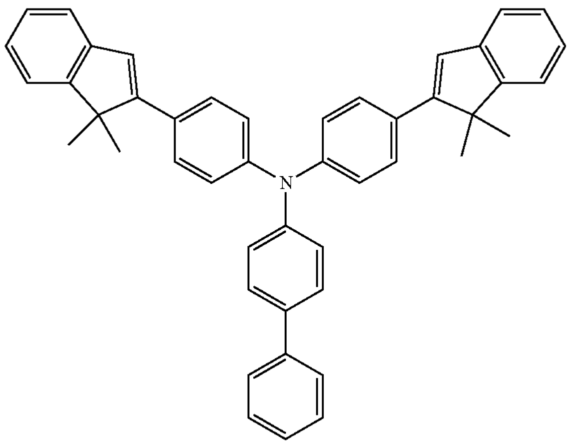

-continued
371
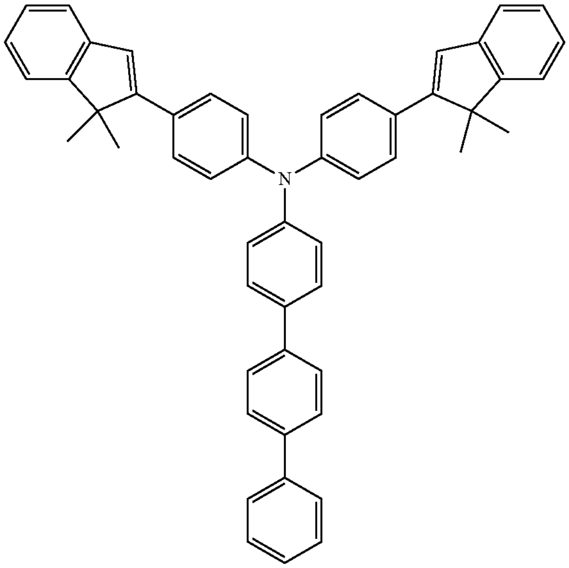
372
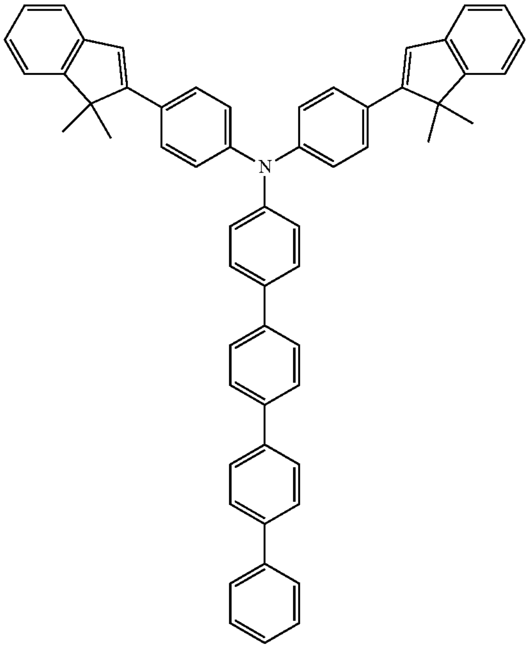
373
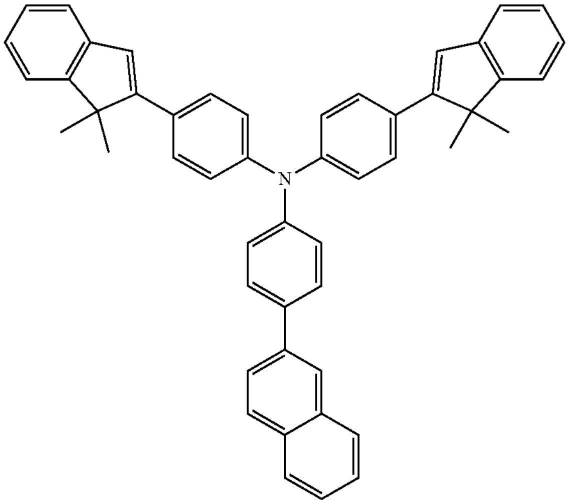
374
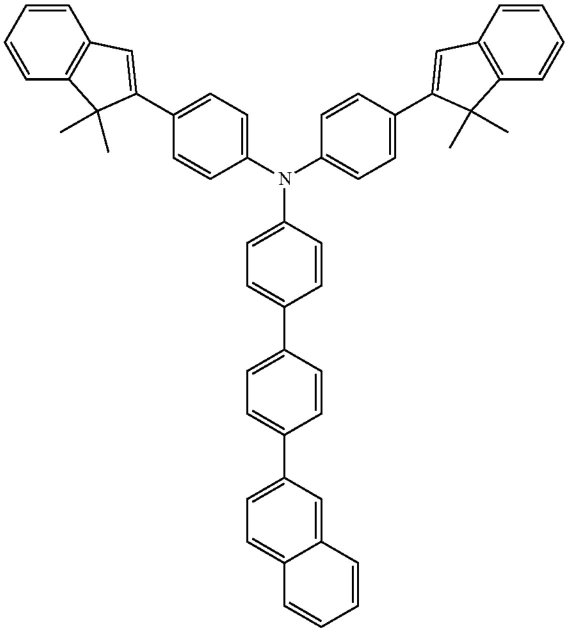

-continued
375
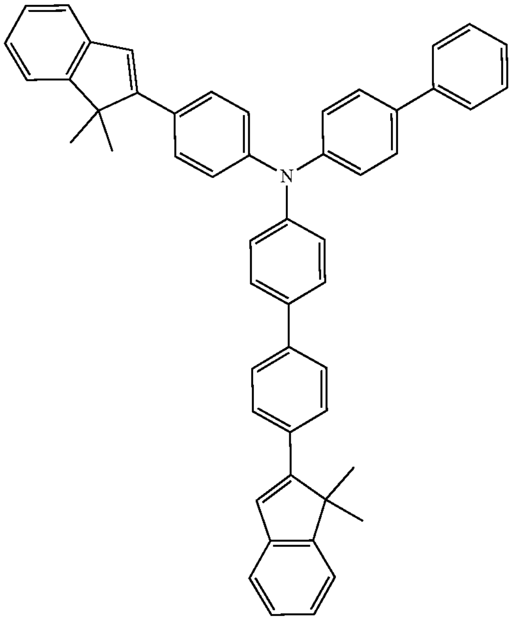
376
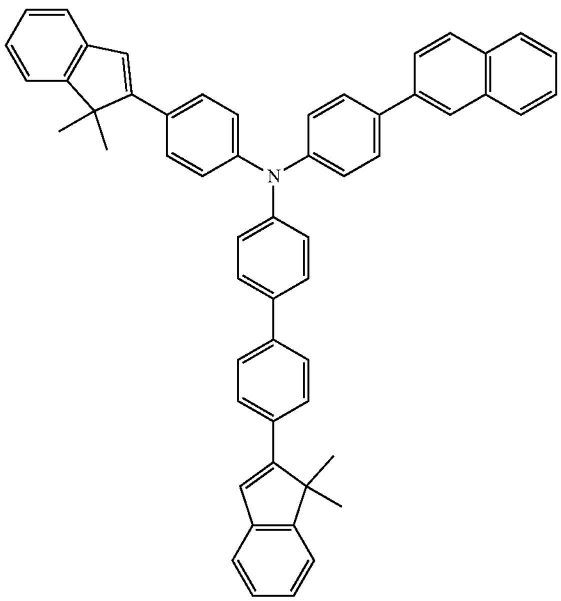
377
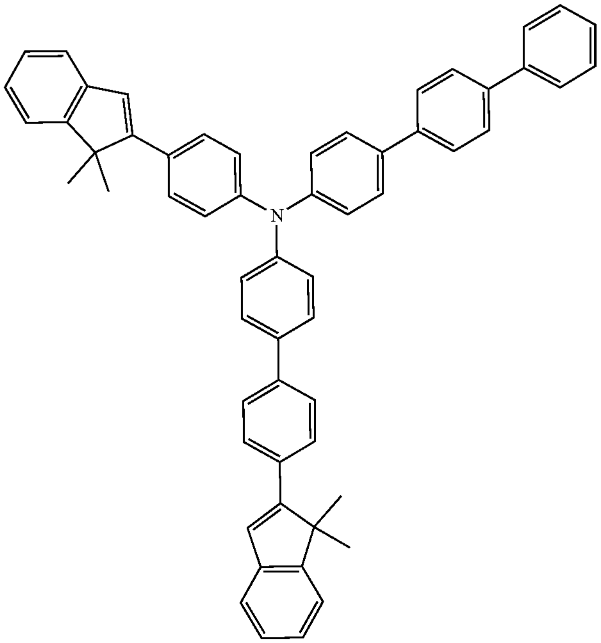
378
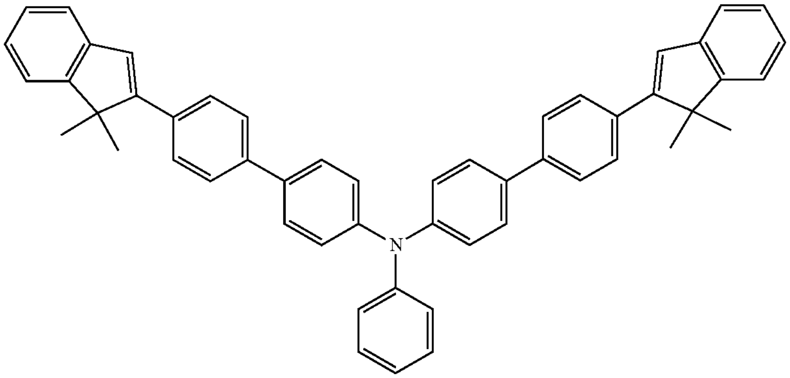

-continued
379
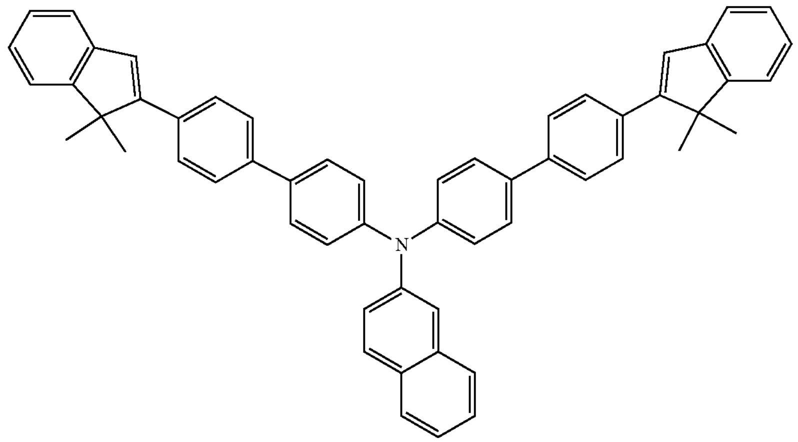
380
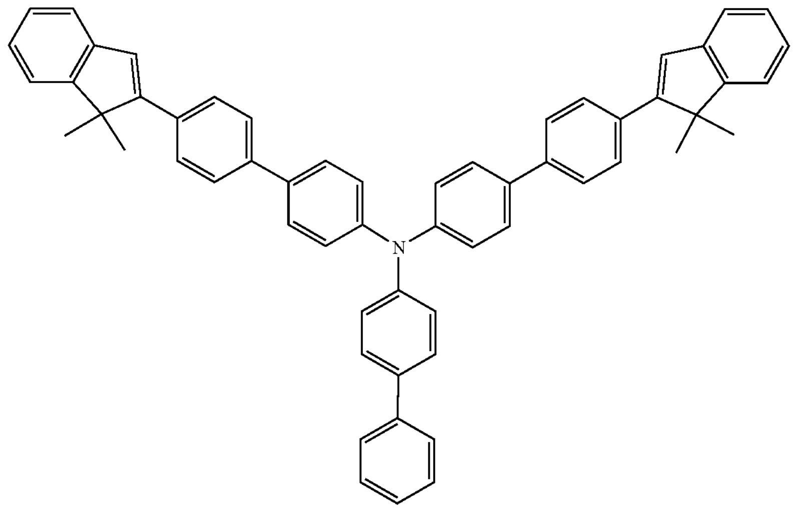
381
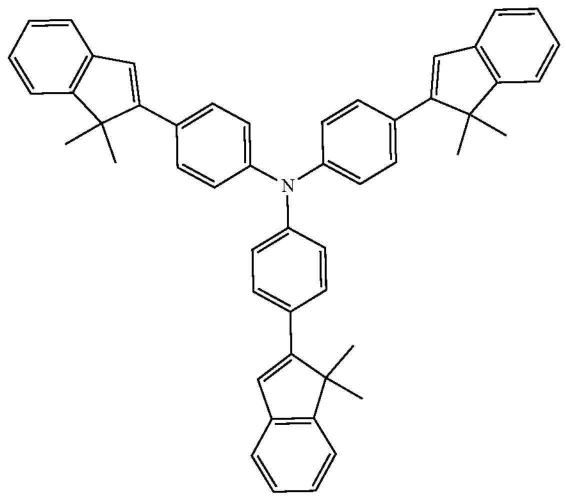
382
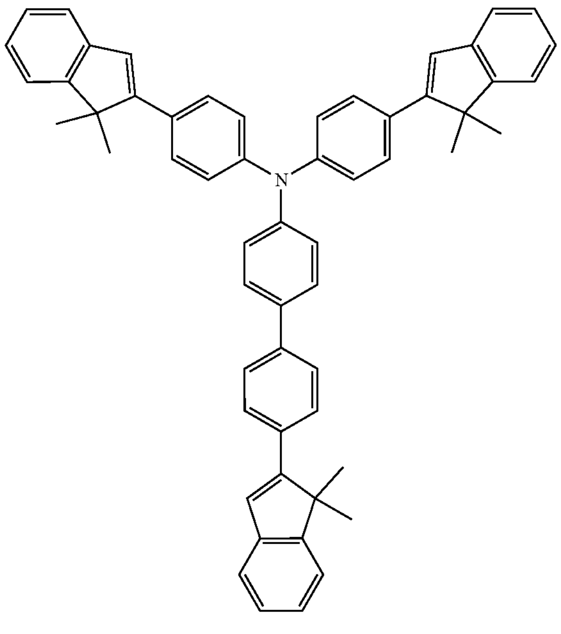

-continued
383
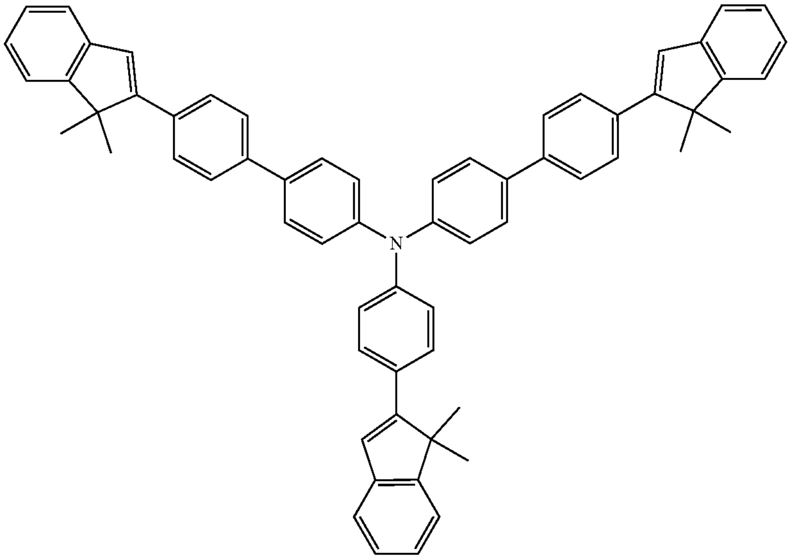
384
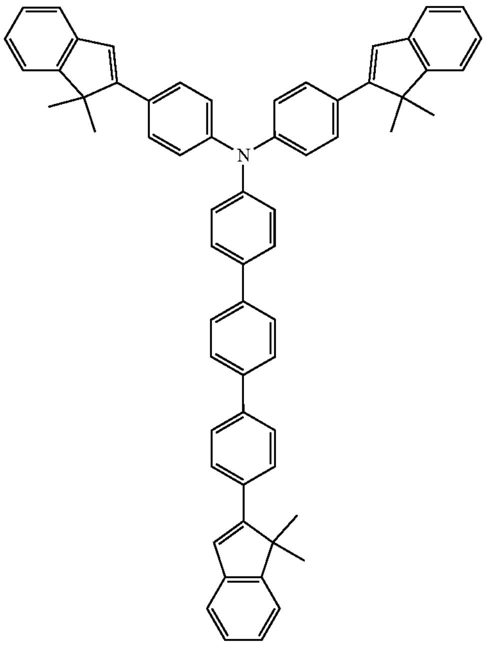

-continued
405
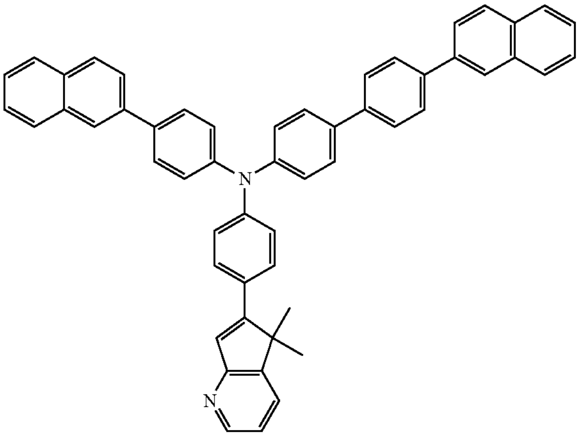
406
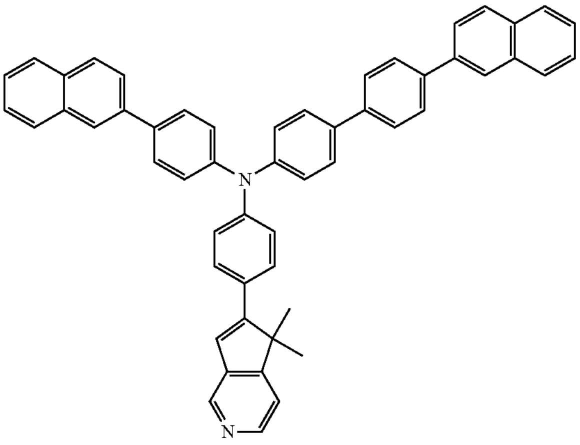
407
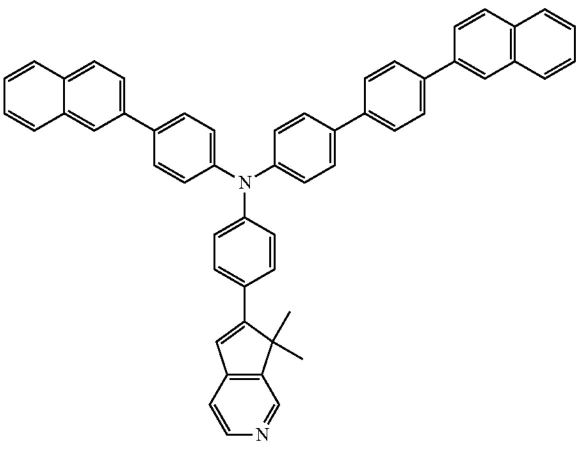
408
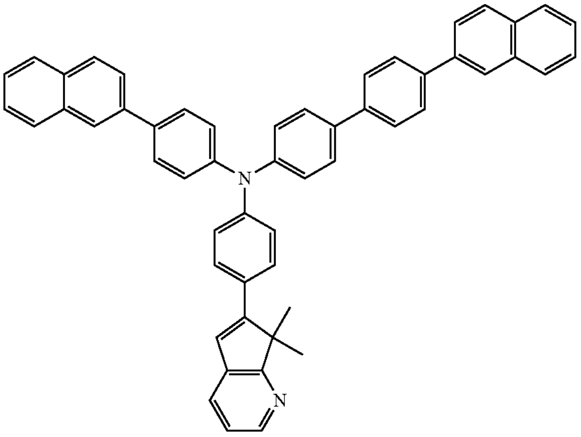
409
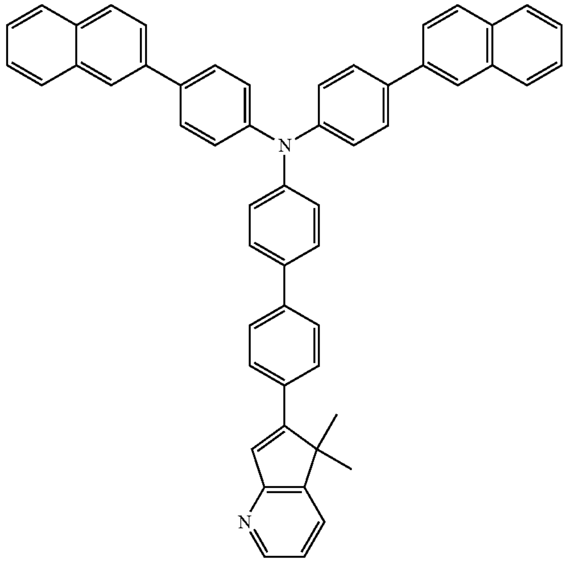
410
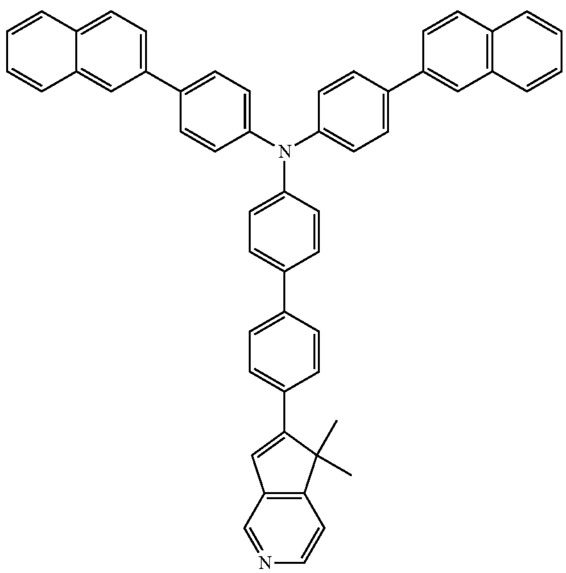

-continued
411
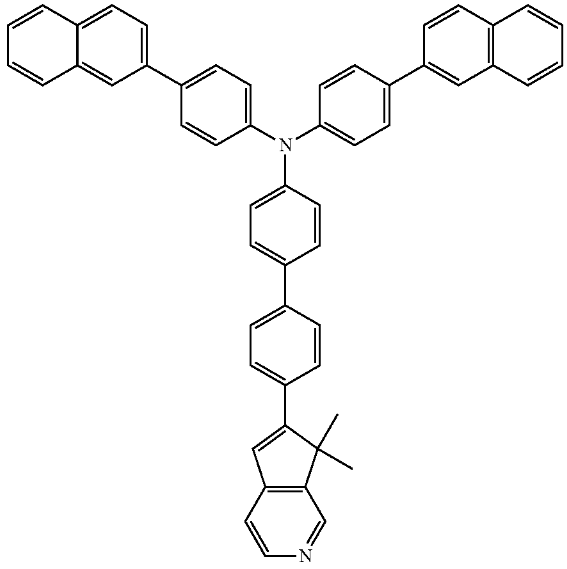
412
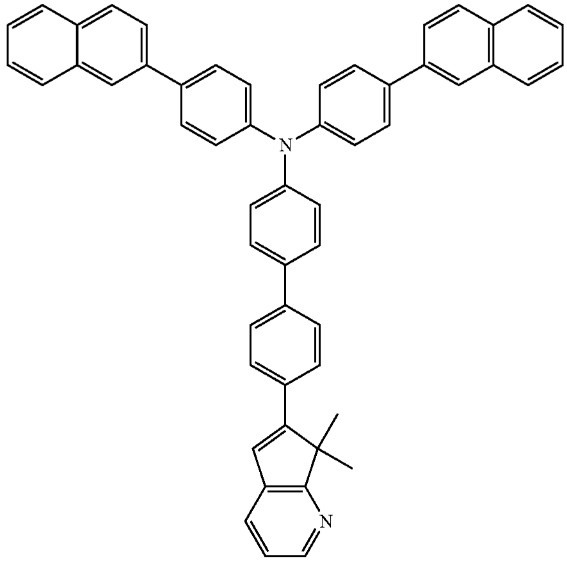
-continued
424
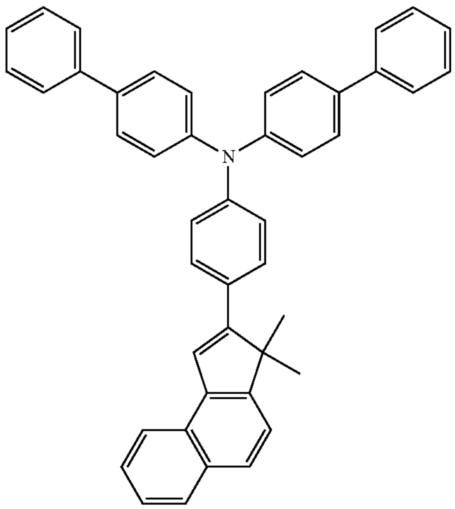
425
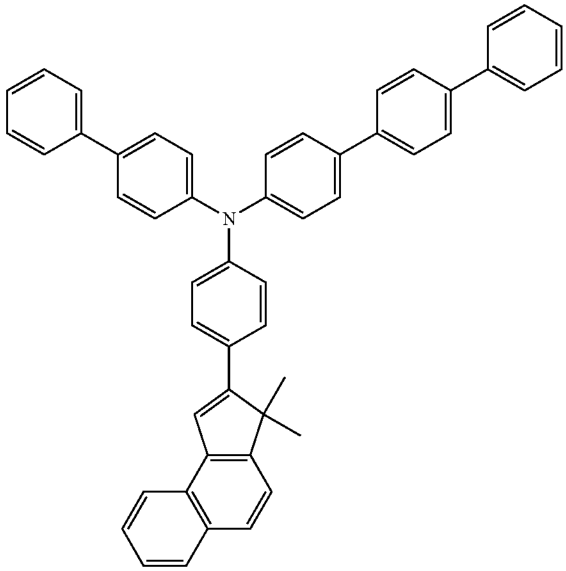
426
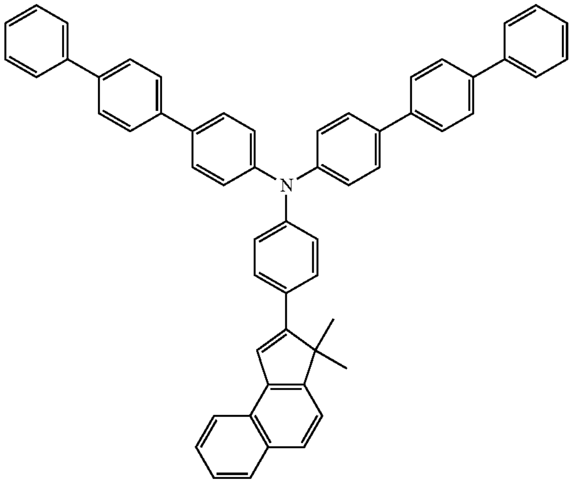

-continued
427
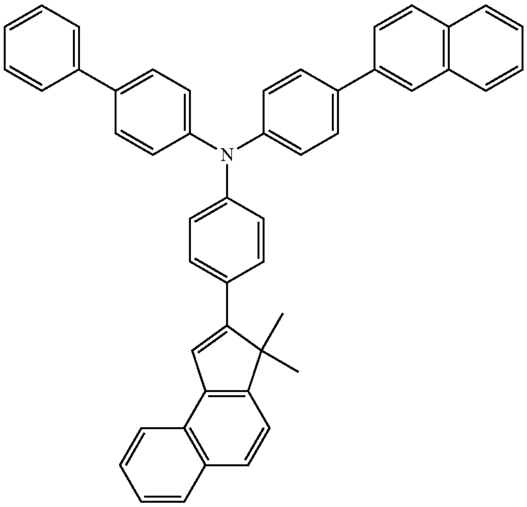
428
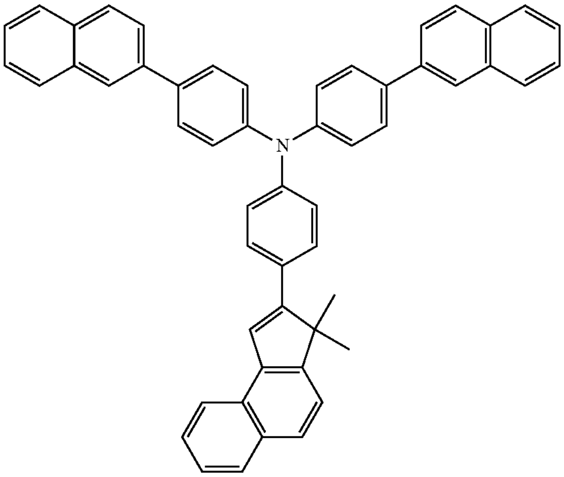
429
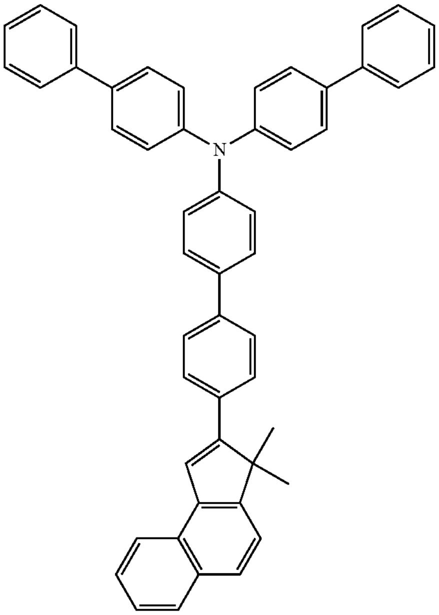
-continued
430
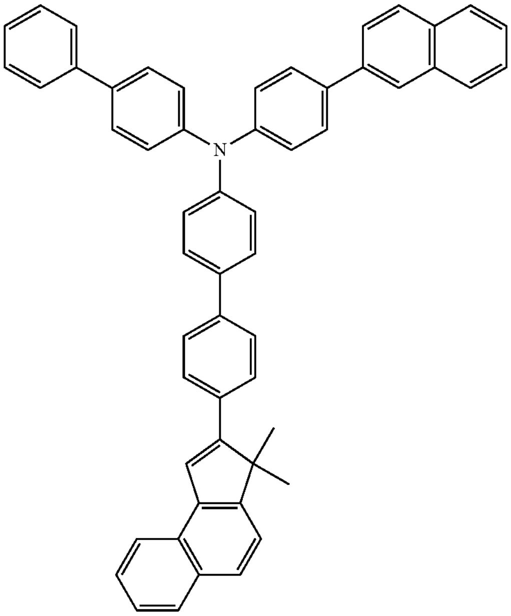
431
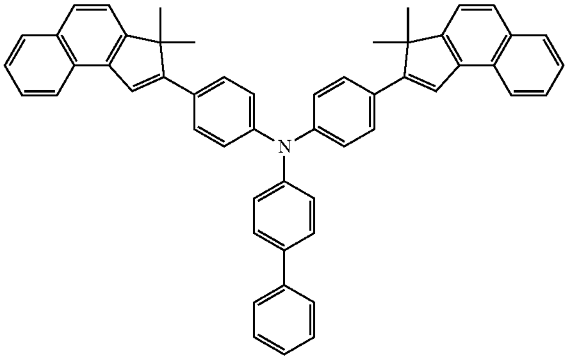
432
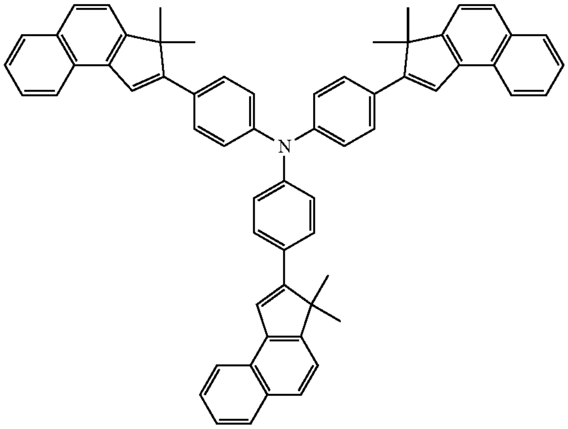

-continued
436
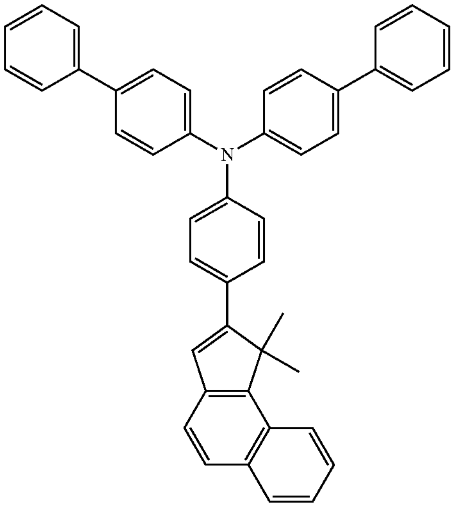
437
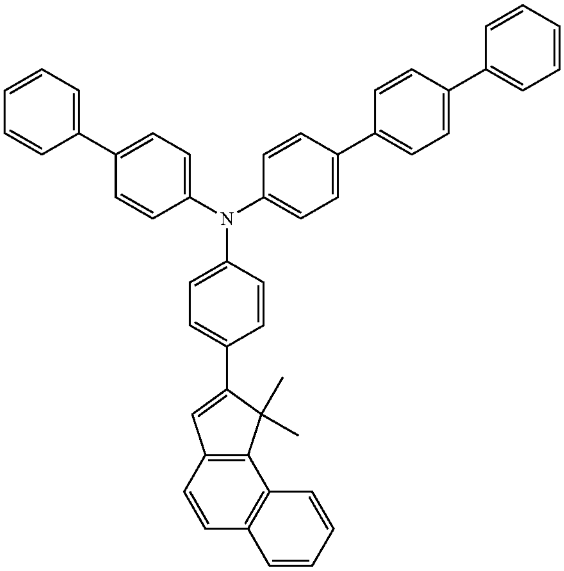
438
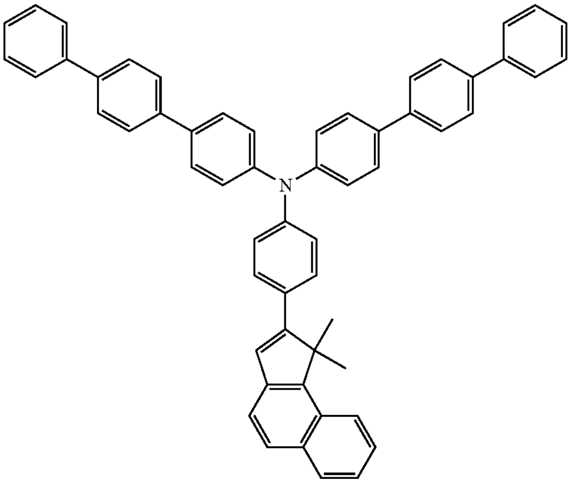
-continued
439
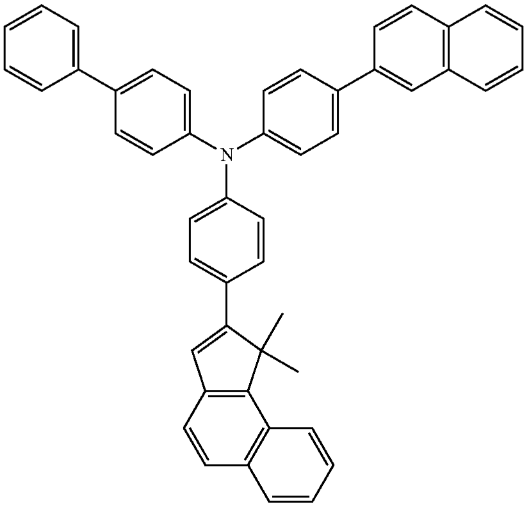
440
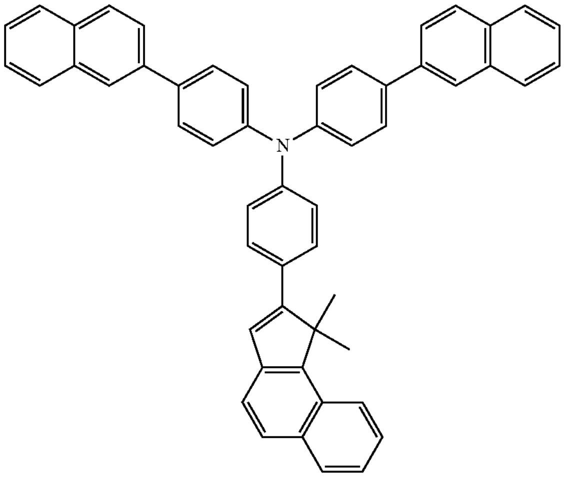
441
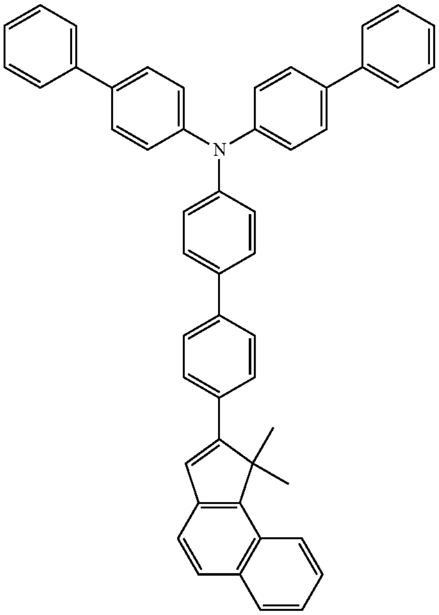

-continued
442
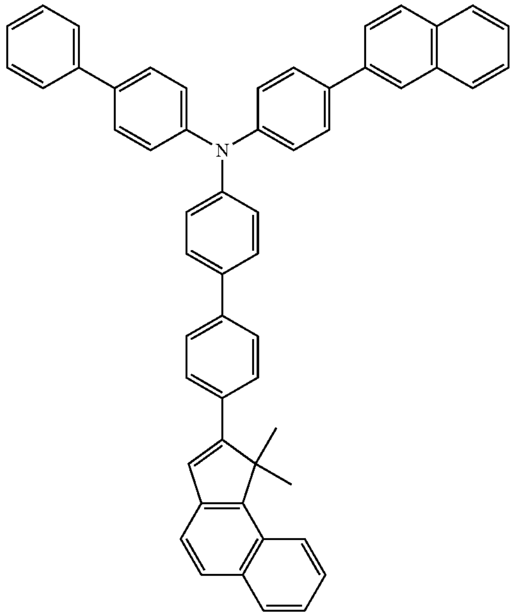
443
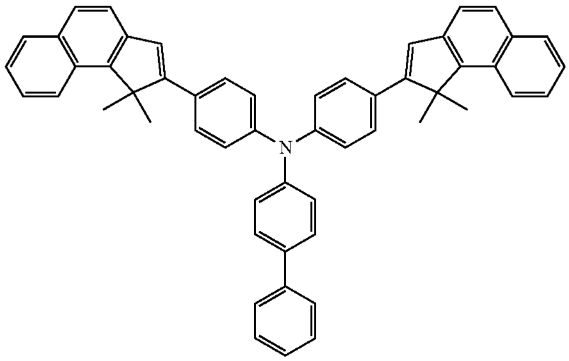
444
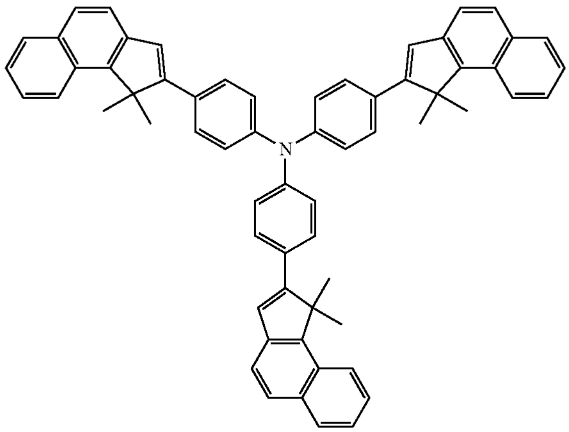
-continued
448
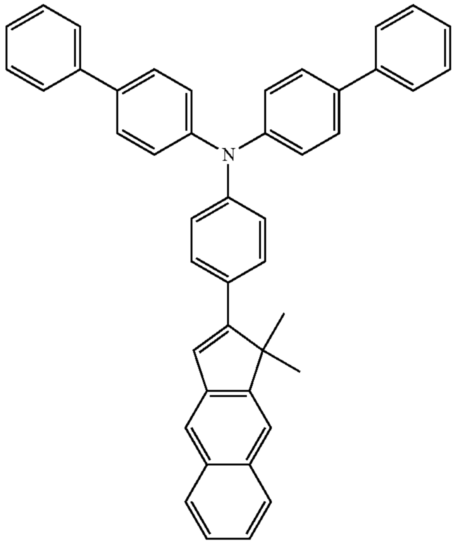
449
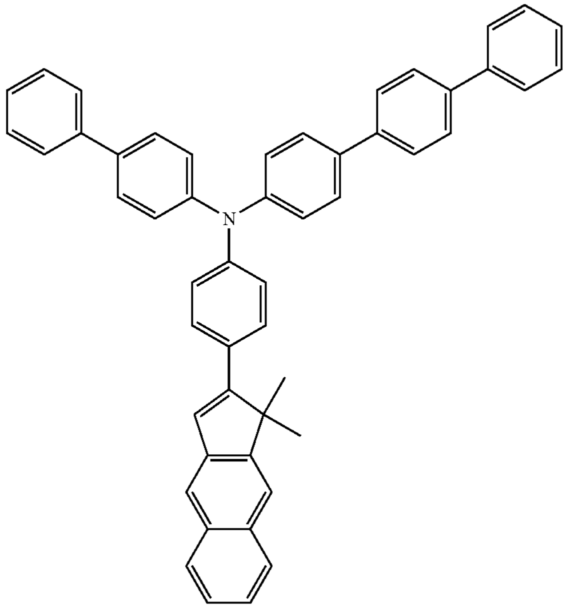

-continued
450
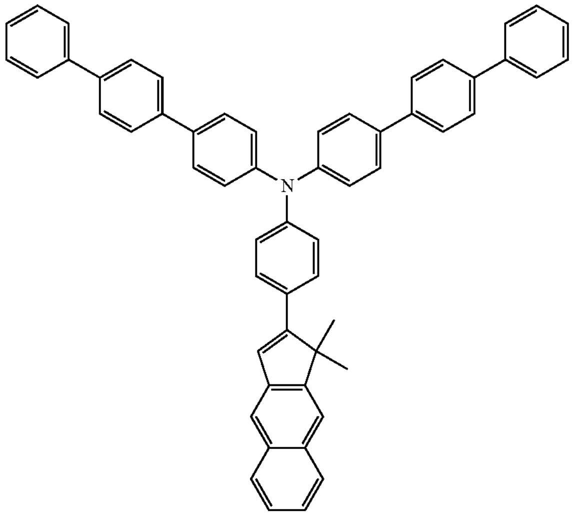
451
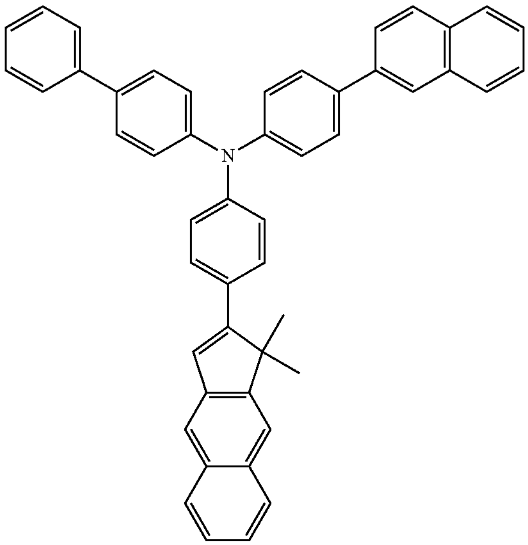
452
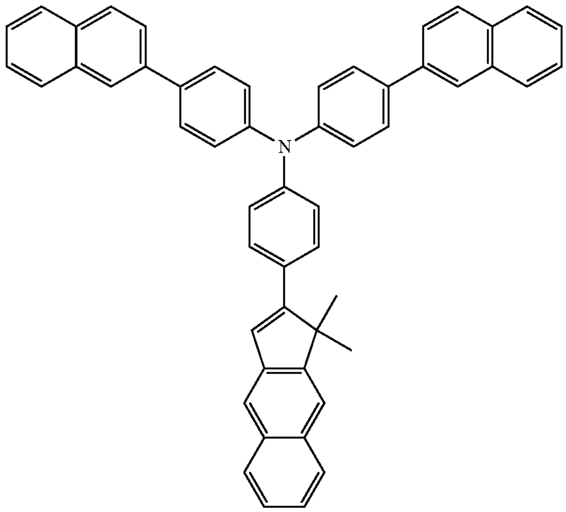
-continued
453
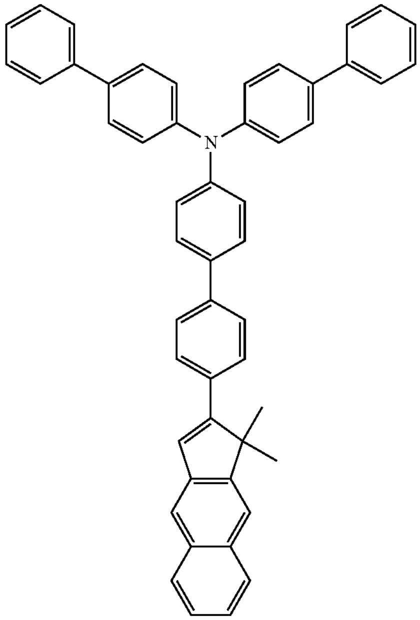
454
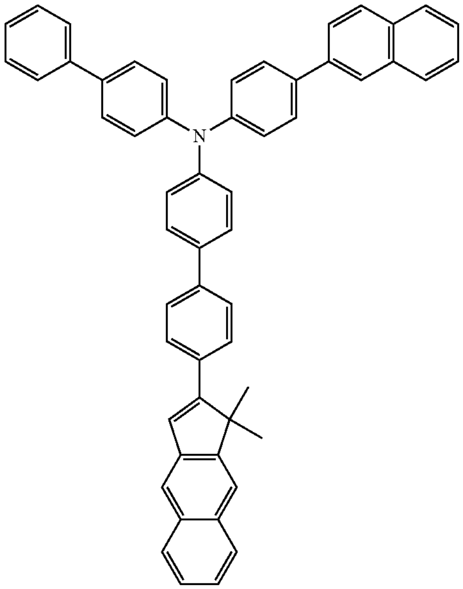
455
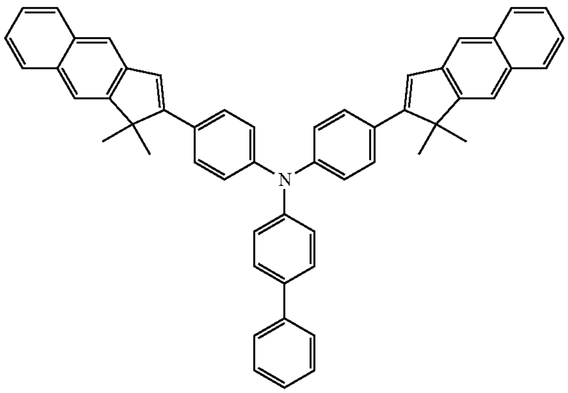

-continued
456
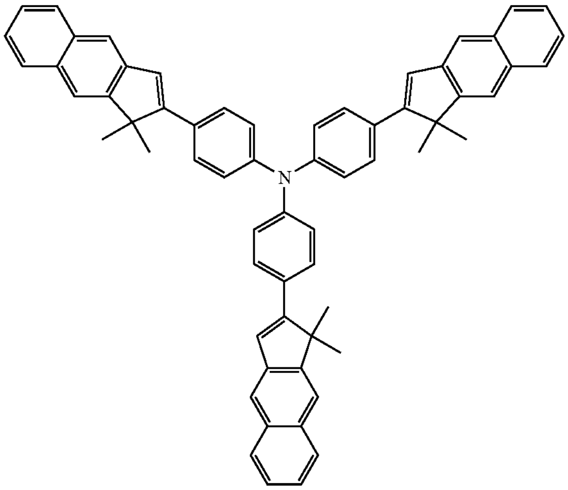
460
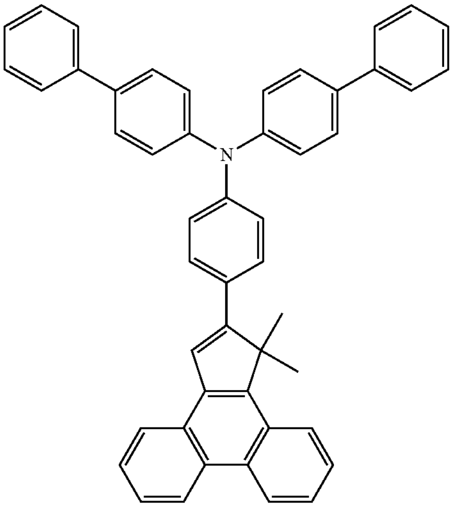
461
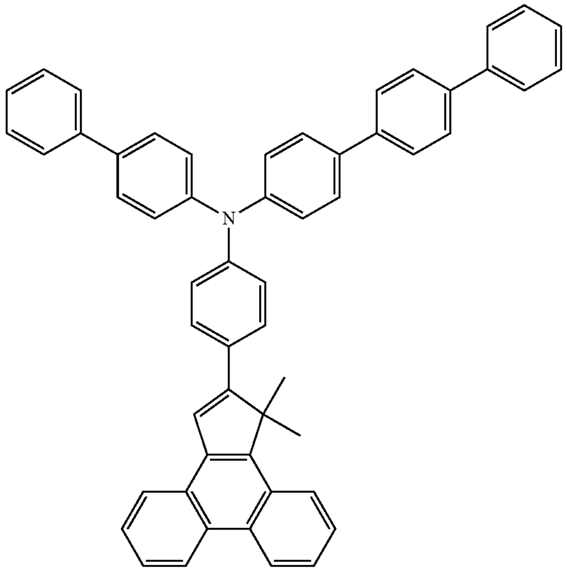
-continued
462
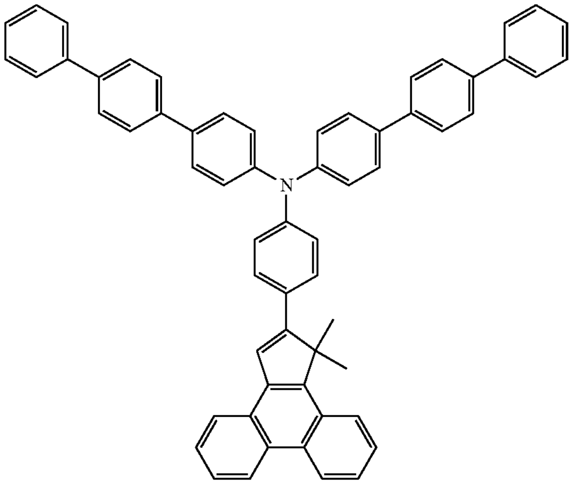
463
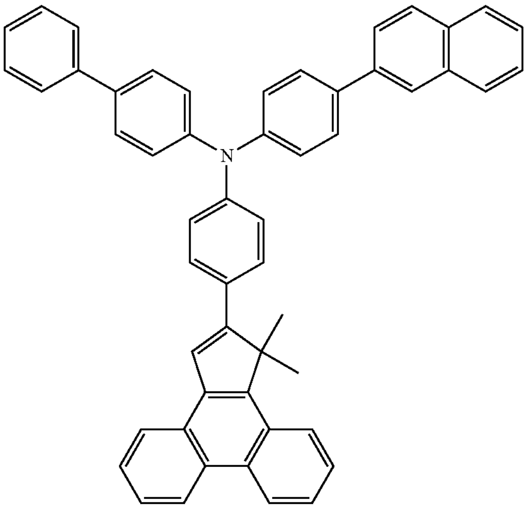
464
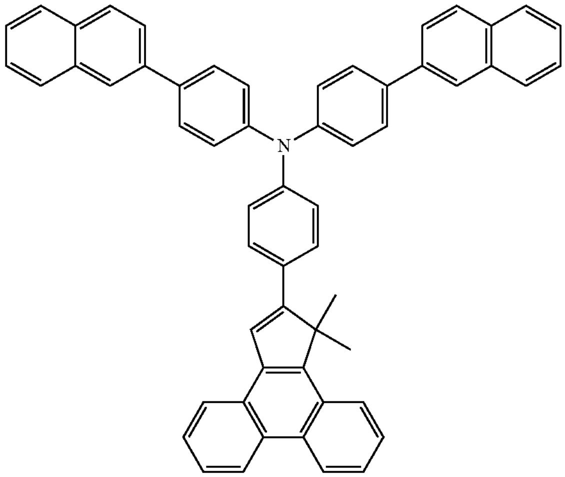

-continued
465
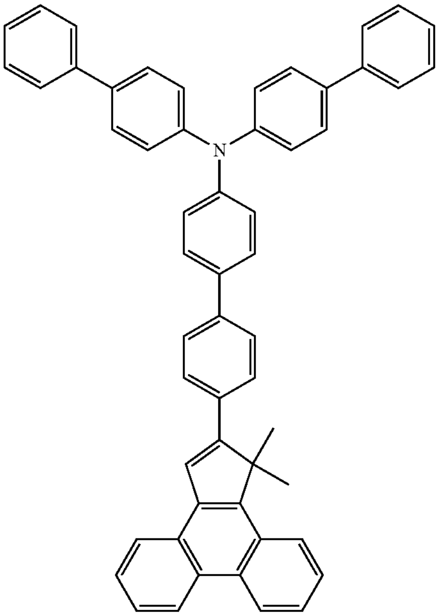
466
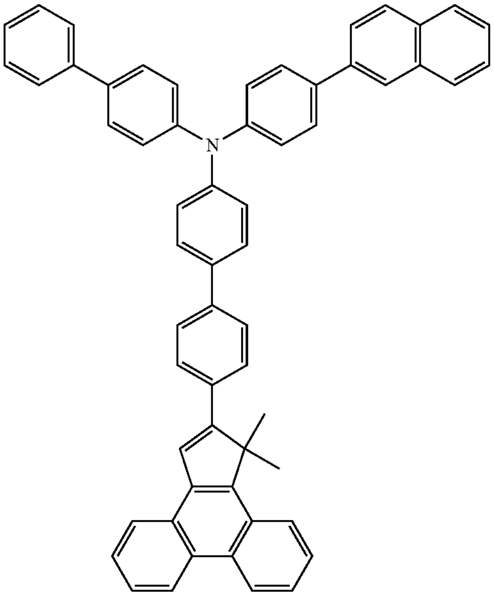
467
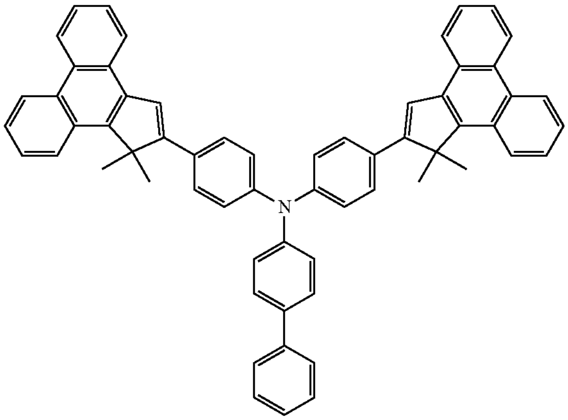
-continued
468
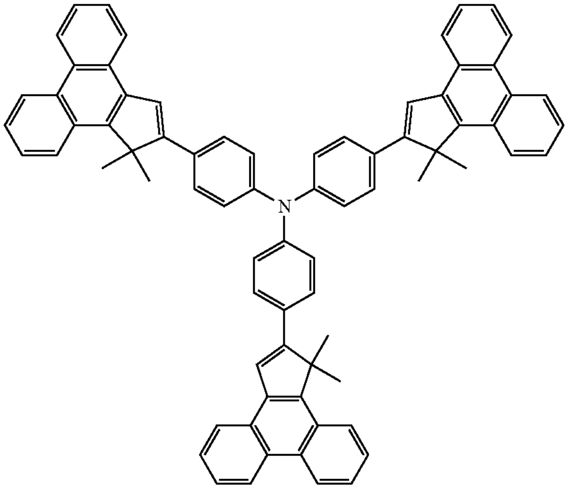
472
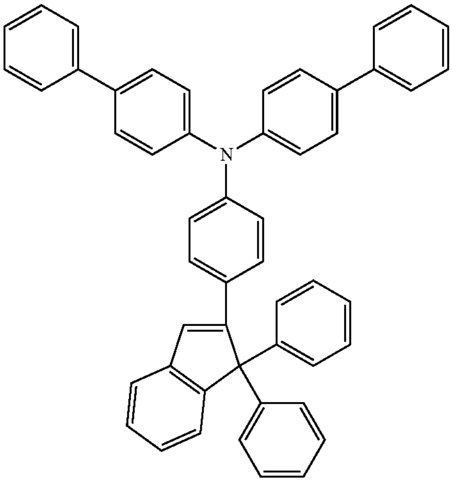
473
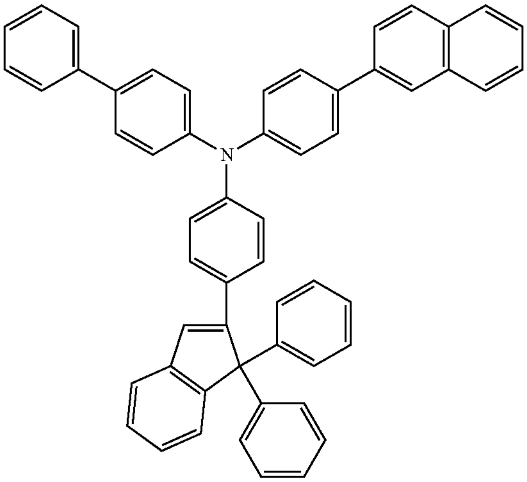

-continued
474
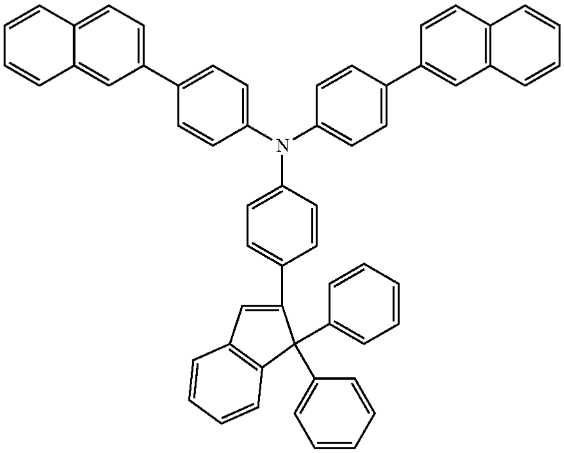
475
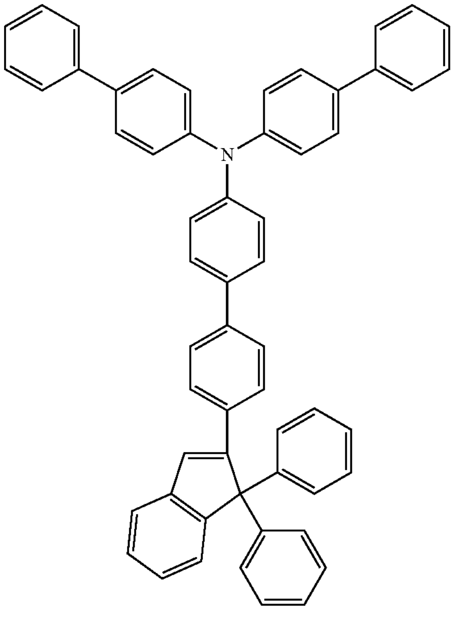
-continued
476
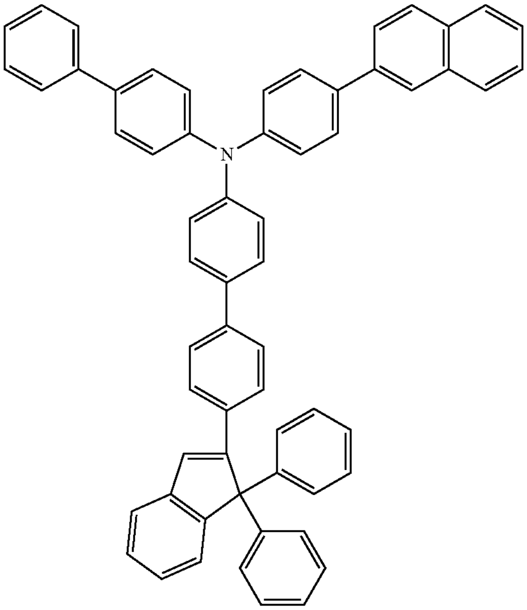
477
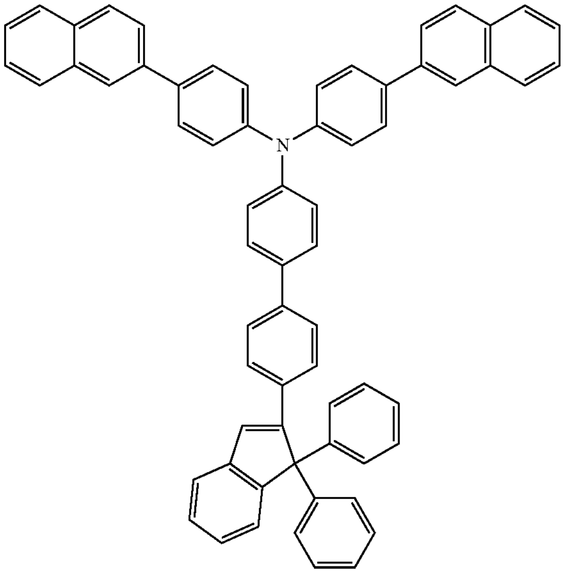
478
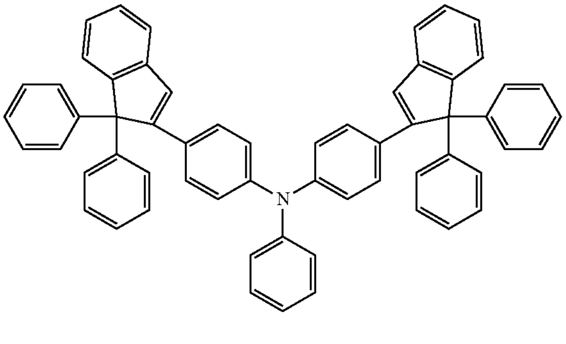

-continued
479
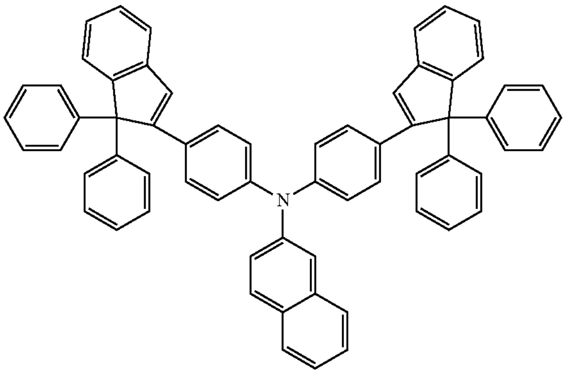
480
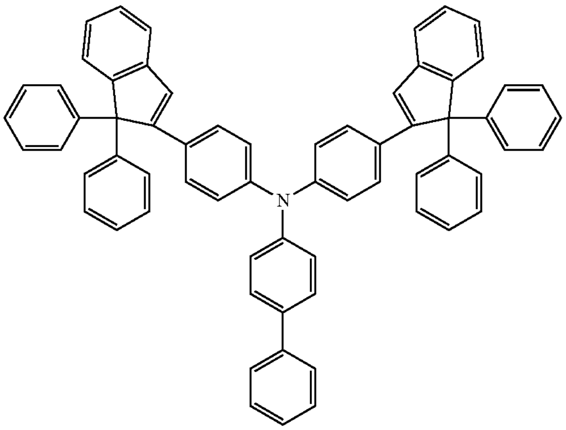
484
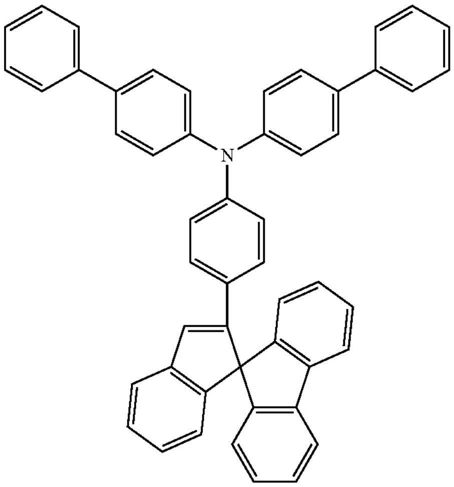
-continued
485
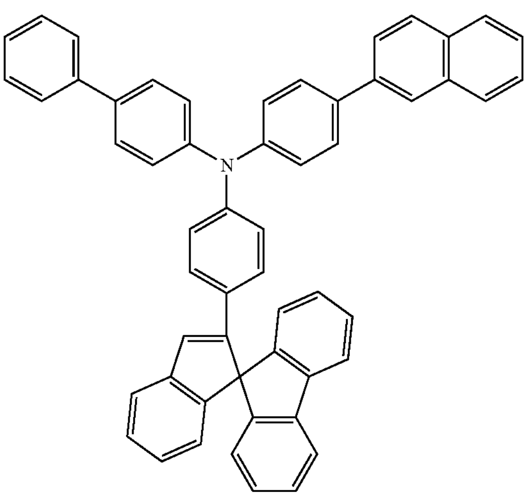
486
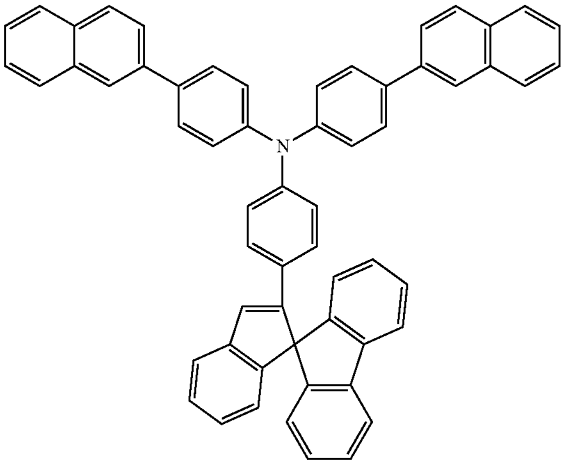
487
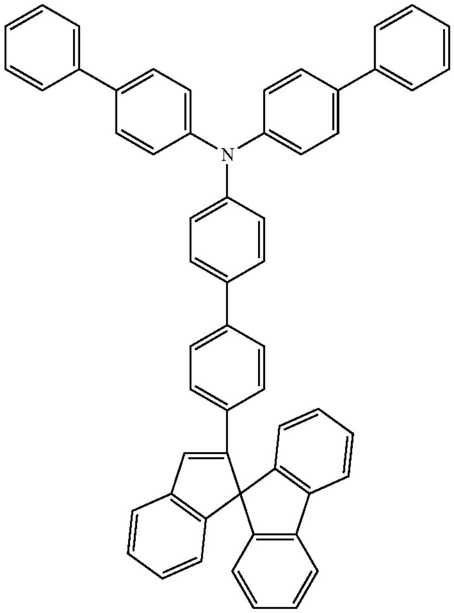

-continued

488

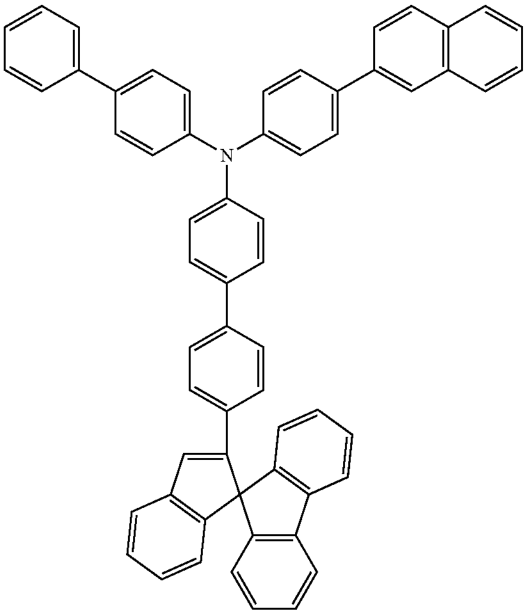

489

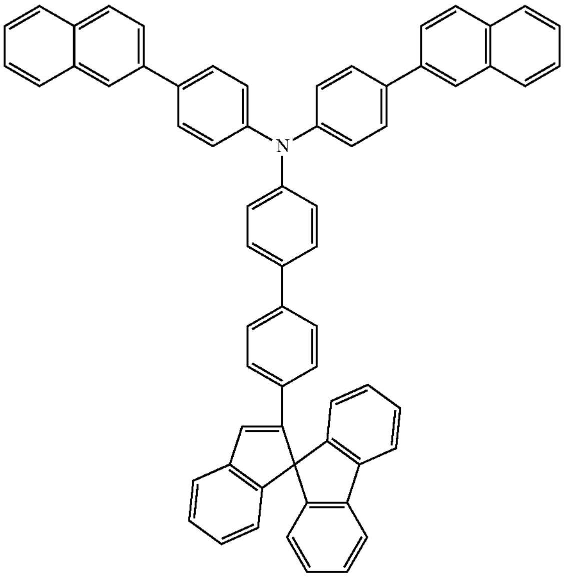

490

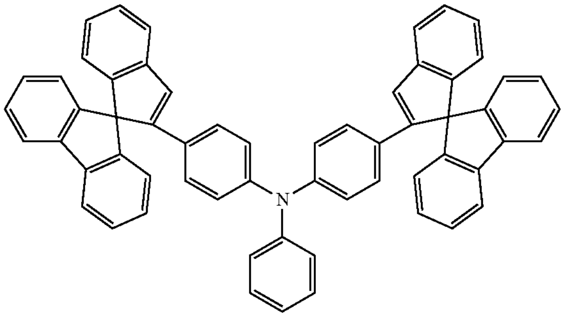

-continued

491

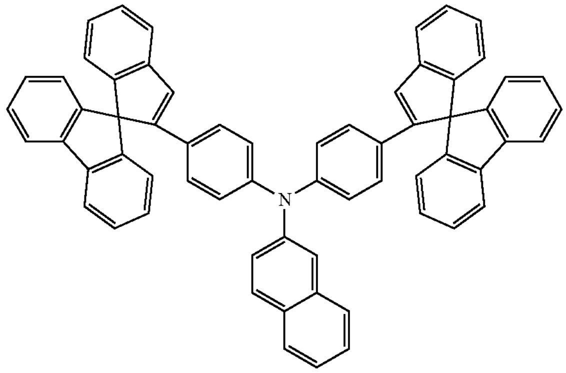

492

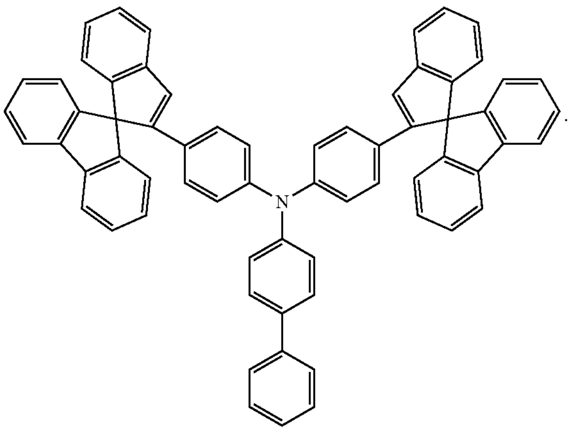

13. An organic light emitting device comprising:

a first electrode;

a second electrode;

an organic light material layer interposed between the first electrode and the second electrode; and the capping layer of claim 1 disposed on an outer surface of either the first electrode or the second electrode.

14. The organic light emitting device of claim 13, wherein the capping layer has a thickness in a range of from 300 Å to 1000 Å.

15. The organic light emitting device of claim 13, wherein the capping layer has a refractive index of 2.23 or more for a wavelength of 450 nm.

* * * * *